United States Patent
Paz et al.

(10) Patent No.: US 12,179,011 B2
(45) Date of Patent: Dec. 31, 2024

(54) METHOD AND APPARATUS FOR TRANSCUTANEOUS FACIAL NERVE STIMULATION AND APPLICATIONS THEREOF

(71) Applicant: NEUROTRIGGER LTD., Tel-Aviv (IL)

(72) Inventors: Shachar Paz, Modiin (IL); Assaf Deutsch, Zafaria (IL); Erez Marks, Zafaria (IL); Michal Marks, Zafaria (IL)

(73) Assignee: NEUROTRIGGER LTD., Tel-Aviv (IL)

( * ) Notice: Subject to any disclaimer, the term of this patent is extended or adjusted under 35 U.S.C. 154(b) by 851 days.

(21) Appl. No.: 17/258,524

(22) PCT Filed: Jul. 22, 2019

(86) PCT No.: PCT/IL2019/050819
§ 371 (c)(1),
(2) Date: Jan. 7, 2021

(87) PCT Pub. No.: WO2020/035852
PCT Pub. Date: Feb. 20, 2020

(65) Prior Publication Data
US 2021/0138232 A1 May 13, 2021

Related U.S. Application Data

(60) Provisional application No. 62/718,773, filed on Aug. 14, 2018.

(51) Int. Cl.
*A61N 1/04* (2006.01)
*A61N 1/36* (2006.01)

(52) U.S. Cl.
CPC ....... *A61N 1/0456* (2013.01); *A61N 1/36021* (2013.01); *A61N 1/36031* (2017.08); *A61N 1/36034* (2017.08)

(58) Field of Classification Search
None
See application file for complete search history.

(56) References Cited

U.S. PATENT DOCUMENTS

| 4,243,631 A | 1/1981 | Ryerson |
| 4,769,881 A | 9/1988 | Belovich et al. |

(Continued)

FOREIGN PATENT DOCUMENTS

| WO | 2007055726 A3 | 5/2007 |
| WO | 2014110575 A1 | 7/2014 |

OTHER PUBLICATIONS

International Search Report of PCT/IL2019/050819 dated Feb. 4, 2020.

(Continued)

*Primary Examiner* — Catherine M Voorhees
*Assistant Examiner* — James Moss
(74) *Attorney, Agent, or Firm* — Greenberg Traurig, LLP

(57) ABSTRACT

A system, device, and method for transcutaneous nerve stimulation such as facial nerve stimulation, and in particular, to using transcutaneous nerve stimulation for artificially eliciting eye blink, such as with humans with acute facial paralysis (Bell's palsy or Dry Eye syndrome), is disclosed. A battery-operated wearable device may employ a pulse generator for periodically and automatically In generating bursts train of asymmetrical Bi-Phasic square pulses. The output pulses are fed to two electrodes that are attached to the skin of the treated person to stimulate the facial nerve for eliciting blinking at a rate that mimics normal blinking operation. The device may include a sensor and a wireless (Continued)

connection, and the parameters of, or the activation of, the generated bursts may be controlled by the sensor output, by human user control, or by data received from the wireless network. Further, the device may transmit status to the wireless network.

8 Claims, 11 Drawing Sheets

(56) References Cited

U.S. PATENT DOCUMENTS

| | | | |
|---|---|---|---|
| 4,853,884 | A | 8/1989 | Brown et al. |
| 4,857,273 | A | 8/1989 | Stewart |
| 4,905,176 | A | 2/1990 | Schulz |
| 5,069,211 | A | 12/1991 | Bartelt et al. |
| 5,105,087 | A | 4/1992 | Jagielinski |
| 5,511,547 | A | 4/1996 | Markle |
| 5,578,877 | A | 11/1996 | Tiemann |
| 5,832,218 | A | 11/1998 | Gibbs et al. |
| 6,081,832 | A | 6/2000 | Gilchrist et al. |
| 6,208,115 | B1 | 3/2001 | Binder |
| 6,329,160 | B1 | 12/2001 | Schneider et al. |
| 6,747,258 | B2 | 6/2004 | Benz et al. |
| 7,124,157 | B2 | 10/2006 | Ikake |
| 7,136,901 | B2 | 11/2006 | Chung et al. |
| 7,145,933 | B1 | 12/2006 | Szajnowski |
| 7,256,466 | B2 | 8/2007 | Lieber et al. |
| 7,605,714 | B2 | 10/2009 | Thompson et al. |
| 7,688,036 | B2 | 3/2010 | Yarger et al. |
| 7,692,320 | B2 | 4/2010 | Lemieux |
| 7,818,383 | B2 | 10/2010 | Kodama |
| 7,847,421 | B2 | 12/2010 | Gardner et al. |
| 7,863,859 | B2 | 1/2011 | Soar |
| 7,863,861 | B2 | 1/2011 | Cheng et al. |
| 7,872,445 | B2 | 1/2011 | Hui |
| 7,876,067 | B2 | 1/2011 | Greenfeld et al. |
| 7,906,936 | B2 | 3/2011 | Azancot et al. |
| 8,060,208 | B2 | 11/2011 | Kilgore |
| 8,508,472 | B1 | 3/2013 | Wieder |
| 8,560,075 | B2 | 10/2013 | Covalin |
| 8,843,188 | B2 | 9/2014 | Kilgore |
| 8,948,832 | B2 | 2/2015 | Hong et al. |
| 8,948,876 | B2 | 2/2015 | Gozani et al. |
| 8,957,988 | B2 | 2/2015 | Wexler et al. |
| 8,983,614 | B2 | 3/2015 | Kilgore |
| 9,008,800 | B2 | 4/2015 | Ackermann |
| 9,119,966 | B2 | 9/2015 | Franke |
| 9,625,251 | B2 | 4/2017 | Heaton et al. |
| 9,757,584 | B2 | 9/2017 | Burnett |
| 2003/0023297 | A1 | 1/2003 | Byers et al. |
| 2005/0021104 | A1 | 1/2005 | DiLorenzo |
| 2005/0234525 | A1 | 10/2005 | Phillips |
| 2005/0247573 | A1 | 11/2005 | Nakamura et al. |
| 2006/0149337 | A1 | 7/2006 | John |
| 2006/0164383 | A1 | 7/2006 | Machin et al. |
| 2007/0025608 | A1 | 2/2007 | Armstrong |
| 2007/0052672 | A1 | 3/2007 | Ritter et al. |
| 2007/0179557 | A1 | 8/2007 | Maschino et al. |
| 2007/0210580 | A1 | 9/2007 | Robets et al. |
| 2007/0249063 | A1 | 10/2007 | Deshong et al. |
| 2007/0264623 | A1 | 11/2007 | Wang et al. |
| 2008/0082131 | A1 | 4/2008 | Llanos |
| 2009/0118808 | A1 | 5/2009 | Belacazar |
| 2010/0110368 | A1 | 5/2010 | Chaum |
| 2010/0217341 | A1 | 8/2010 | John |
| 2010/0234716 | A1* | 9/2010 | Engel .................. A61B 5/6833 600/459 |
| 2011/0045523 | A1 | 2/2011 | Strano et al. |
| 2011/0106220 | A1* | 5/2011 | DeGiorgio ......... A61N 1/36171 607/72 |
| 2011/0264167 | A1 | 10/2011 | Poletto |
| 2011/0275544 | A1 | 11/2011 | Zhou et al. |
| 2012/0050144 | A1 | 3/2012 | Morlock |
| 2012/0050668 | A1 | 3/2012 | Howell et al. |
| 2013/0023951 | A1 | 1/2013 | Greenspan |
| 2013/0158612 | A1 | 6/2013 | Lindenthaler |
| 2013/0169513 | A1 | 7/2013 | Heinrich et al. |
| 2013/0201316 | A1 | 8/2013 | Binder et al. |
| 2014/0045547 | A1 | 2/2014 | Singamsetty et al. |
| 2014/0070613 | A1 | 3/2014 | Garb et al. |
| 2014/0081353 | A1 | 3/2014 | Cook et al. |
| 2014/0148872 | A1* | 5/2014 | Goldwasser ....... A61N 1/36034 607/45 |
| 2014/0159877 | A1 | 6/2014 | Huang |
| 2015/0005841 | A1* | 1/2015 | Pal ...................... A61N 1/0456 607/45 |
| 2015/0126834 | A1 | 5/2015 | Wang |
| 2015/0138556 | A1 | 5/2015 | LeBoeuf |
| 2015/0142082 | A1 | 5/2015 | Simon et al. |
| 2015/0174402 | A1 | 6/2015 | Thomas |
| 2015/0238762 | A1* | 8/2015 | Pal ..................... A61N 1/36034 607/45 |
| 2015/0277559 | A1 | 10/2015 | Vescovi et al. |
| 2015/0349556 | A1 | 12/2015 | Mercando et al. |
| 2015/0373443 | A1 | 12/2015 | Carroll |
| 2016/0022992 | A1 | 1/2016 | Franke et al. |
| 2016/0310739 | A1 | 10/2016 | Burdick |
| 2016/0346545 | A1 | 12/2016 | Pal |
| 2017/0182285 | A1 | 6/2017 | Tyler et al. |
| 2017/0197081 | A1* | 7/2017 | Charlesworth .... A61N 1/36034 |
| 2017/0259063 | A1 | 9/2017 | DeGiorgio |
| 2018/0161579 | A1 | 6/2018 | Franke et al. |
| 2019/0022383 | A1 | 1/2019 | Hadlock et al. |

OTHER PUBLICATIONS

International Preliminary Report on Patentability (IPRP) of PCT/IL2019/050819 dated Aug. 26, 2020.
"FreeRTOS™ Modules" published in the www,freertos.org website dated Nov. 26, 2006 (112 pages).
Rich Goyette of Carleton University as part of 'SYSC5701: Operating System Methods for Real-Time Applications', entitled: "An Analysis and Description of the Inner Workings of the FreeRTOS Kernel", published Apr. 1, 2007 (46 pages).
Zetex Semiconductors PLC application note "AN39—Current measurement applications handbook" Issue 5, Jan. 2008 (42 pages).
The manual "80186/80188 High-Integration 16-Bit Microprocessors" by Intel Corporation (34 pages).
The manual "MC68360 Quad Integrated Communications Controller—User's Manual" by Motorola, Inc. (962 pages).
Data sheet [DS-TM4C123GH6PM-15842.2741, SPMS376E, Revision 15842.2741 Jun. 2014], "Tiva™ TM4C123GH6PM Microcontroller—Data Sheet", published 2015 by Texas Instruments Incorporated (1409 pages).
Book entitled: "Practical Design Techniques for Sensor Signal Conditioning", by Analog Devices, Inc., 1999 (ISBN-0-916550-20-6) (366 pages).
Sabrie Soloman, "Sensors and Control Systems in manufacturing", The McGraw-Hill Companies, ISBN: 978-0-07-160573-1, Second Edition 2010 (625 pages).
William C. Dunn, : "Fundamentals of Industrial Instrumentation and Process Control", 2005, The McGraw-Hill Companies, ISBN: 0-07-145735-6 (337 pages).
Jon Wilson, "Sensor technology Handbook", Newnes-Elsevier 2005, ISBN:0-7506-7729-5 (702 pages).
Alice Frigerio, M.D., Ph.D., James T. Heaton, Ph.D., Paolo Cavallari, M.D., Ph.D., Chris Knox, B.S., Marc H. Hohman, M.D., and Tessa A. Hadlock, M.D., "Electrical Stimulation of Eye Blink in Individuals with Acute Facial Palsy: Progress toward a Bionic Blink", published Oct. 2015 in Plastic and Reconstructive Surgery Journal [DOI: 10.1097/PRS.0000000000001639], presented in part at the 2013 International Facial Nerve Symposium, in Boston, Massachusetts, Jun. 28 through Jul. 2, 2013 (9 pages).
Nate Jowett, M.D., Robert E. Kearney, Ph.D., Christopher J. Knox, B.S., and Tessa A. Hadlock, M.D., "Toward the Bionic Face: A Novel Neuroprosthetic Device Paradigm for Facial Reanimation Consisting of Neural Blockade and Functional Electrical Stimulation", published in vol. 143, No. 1 of the Plastic and Reconstructive

(56) References Cited

OTHER PUBLICATIONS

Surgery Journal [DOI: 10.1097/PRS.0000000000005164], presented in part at the 2016 Annual Meeting of the American Society for Peripheral Nerve, in Scottsdale, Arizona (15 pages).
Datasheet Form No. EBC—4407cp-Z entitled: "Energizer A76—ZEROMERCURY Miniature Alkaline" (downloaded from the Internet Mar. 2016) (1 page).
Datasheet Form No. EBC—4120M entitled: "Energizer CR2032—Lithium Coin" (downloaded from the Internet Mar. 2016) (2 pages).
Data-sheet No. DS-CPC1006N-R05, 60V Normally-Open Single-Pole 4-Pin SOP OptoMOS™ Reply, published Jan. 30, 2018 (6 pages).
DS-CPC1965Y-R08 entitled: "CPC1965Y AC Solid State Relay", 2018 (6 pages).
Data sheet "BTA06 T/D/S/A BTB06 T/D/S/A—Sensitive Gate Triacs" published by SGS-Thomson Microelectronics Mar. 1995 (7 pages).
Product Specifications from Philips Semiconductors "TrenchMOS™ transistor Standard level FET BUK7524-55" Rev 1.000 dated Jan. 1997 (9 pages).
Pragyaditya Das. and S. Pragadeesh, "A Microcontroller Based Car-Safety System: Implementing Drowsiness Detection And Vehicle-Vehicle Distance Detection In Parallel", published 2015 in International Journal of Scientific & Technology Research vol. 4, Issue 12, Dec. 2015 ISSN 2277-8616 161 IJSTR© 2015 (3 pages).
Alice Frigerio, Tessa A. Hadlock, Elizabeth H Murray, and James T Heaton, "Infrared-Based Blink Detecting Glasses for Facial Pacing: Towards a Bionic Blink", published 2014 [JAMA Facial Plast Surg. 2014; 16(3): 211-218. doi:10.1001/jamafacial.2014.1] (19 pages).
Abhi R. Varma, Seema V. Arote, Chetna Bharti, and Kuldeep Singh (all of Pravara Rural Engineering College, Loni), "Accident Prevention Using Eye Blinking and Head Movement", published 2012 in "Emerging Trends in Computer Science and Information Technology -2012(ETCSIT2012) Proceedings published in International Journal of Computer Applications (IJCA)" (5 pages).
Application Note entitled: "Keysight Technologies—Impedance Measurement Handbook—A guide to measurement technology and techniques—6th Edition", published Nov. 2, 2016 by Keysight Technologies, Inc. [5950-3000] (140 pages).
Dr. Richard Wall entitled: "Carebot PIC32 MX7ck implementation of Free RTOS", (dated Sep. 23, 2013) (18 pages).
Chen et al., "Closed-Loop Eyelid Reanimation System with Real-Time Blink Detection and Electrochemical Stimulation for Facial Nerve Paralysis", 2009 IEEE International Symposium on Circuits and Systems. IEEE, pp. 549-552, 2009.
Nicholas Alexander Sachs, Electrical Simulation of the Orbicularis Oculi to Restore Eye Blink, Aug. 2007 (276 pages).
Kin Yi et al., A Blink Restoration System With Contralateral EMG Triggered Stimulation and Real-Time Artifact Blanking, IEEE Transactions on Biomedical Circuits and Systems, vol. 7 no. 2, Apr. 2013, pp. 140-148 (9 pages).
Roscoe Medical Inc. (of Middleburg Heights, OH, U.S.A.), instruction manual entitled: "Instruction Manual for the TENS 3000" (26 pages).
Roscoe Medical Inc. (of Middleburg Heights, OH, U.S.A.), instruction manual entitled: "Instruction Manual for the TENS 7000" (Document No. 42-DT7202_01), downloaded from the Internet on May 2019 (16 pages).
Takao Someya of the University of Tokyo, Japan, "Bionic Skin for a Cyborg You—Flexible electronics allow us to cover robots and humans with stretchy sensors", published Aug. 26, 2013 in IEEE Spectrum (downloaded May 2019 from spectrum.ieee.org/biomedical/bionics/bionic-skin-for-a-cyborg-you - preceded by https://) (17 pages).
M., Rabinovich D., Brandes B., and Hanein Y. (all of Tel-Aviv University, Tel-Aviv, Israel), "Temporary-tattoo for long-term high fidelity biopotential recordings", published May 12, 2016 on Scientific Reports [6:25727, DOI: 10.1038/srep25727] (7 pages).
Presentation entitled: "Implantable Neural Electrodes—Implantable Electronics Session" by Dr. Martin Schuettler (of the Laboratory for Biomedical Microtechnology Department of Microsystem Engineering University of Freiburg, Germany) dated Mar. 30, 2012 (24 pages).
Margaret I. Babb, Ph. D. and Anthony M. Dymond, Ph. D. (of Brain Information Service—Brain Research Institute, University of California, Los Angeles, California, U.S.A.), "Electrode Implantation in the Human Body", published 1974 (100 pages).
Katarzyna Blinowska and Piotr Durka of Warshow University, Waszawa, Poland, "Electroencephalography (EEG)", published 2006 in Wiley Encyclopedia of Biomedical Engineering.
M. Teplan, "Fundamentals of EEG Measurement", Measurement Science Review (vol. 2, Section 2, 2002) (12 pages).
M. Kabiraj, "EEG Course—Workshop 1—Basic principles and interpretations of electroencephalography", Neurosciences 2003; vol. 8 Supplement 2 (16 pages).
Chapter 20: "Wireless Technologies" of the publication No. 1-587005-001-3 by Cisco Systems, Inc. (7/99) "Internetworking Technologies Handbook" (42 pages).
Book published 2005 by Pearson Education, Inc. William Stallings [ISBN: 0-13-191835-4] "Wireless Communications and Networks—second Edition" (569 pages).
Telecom Regulatory Authority, "WiFi Technology", published on Jul. 2003 (60 pages).
Bluetooth SIG published Dec. 2, 2014 standard Covered Core Package version: 4.2, "Master Table of Contents & Compliance Requirements—Specification vol. 0" (2772 pages).
Carles Gomez et al., "Overview and Evaluation of Bluetooth Low Energy: An Emerging Low-Power Wireless Technology", published 2012 in Sensors [ISSN 1424-8220] [Sensors 2012, 12, 11734-11753; doi:10.3390/s120211734] (20 pages).
ECMA International white paper Ecma/TC32-TG19/2005/012 "Near Field Communication—White paper" (12 pages).
Rohde&Schwarz White Paper 1MA182_4e "Near Field Communication (NFC) Technology and Measurements White Paper", (26 pages).
Jan Kremer Consulting Services (JKCS) white paper "NFC—Near Field Communication—White paper" (44 pages).
RFC 1750, "Randomness Recommendations for Security", Dec. 1994 (31 pages).
Data sheet 'Physical Random No. generator RPG100.RPG100B' Rev. 08 publication No. HM-RAE106-0812 (4 pages).
Book by Wikipedia entitled: "Electronics" downloaded from en.wikibooks.org dated Mar. 15, 2015 (401 pages).
User Guide, "iPhone User Guide For iOS 8.4 Software", dated 2015 (019-00155/2015-06) by Apple Inc. (196 pages).
iPhone 6 technical specification (retrieved Oct. 2015 from www.apple.com/iphone-6/specs/) (32 pages).
User manual numbered English (EU), "SM-G925F SM-G925FQ SM-G9251 User Manual" Mar. 2015 (Rev. 1.0) (145 pages).
Galaxy S6 Edge—Technical Specification (retrieved Oct. 2015 from www.samsung.com/us/explore/galaxy-s-6-features-and-specs) (1 page).
Thesis by Tim van Lokven, "Review and Comparison of Instant Messaging Protocols", Jan. 23, 2011 (52 pages).
3GPP technical specification 3GPP TS 23.140, "3rd Generation Partnership Project; Technical Specification Group Core Network and Terminals; Multimedia Messaging Service (MMS); Functional description; Stage 2 (Release 6)", (V6.16.0, Mar. 2009) (224 pages).
3GPP Technical Specification 3GPP TS 22.011 entitled: "3rd Generation Partnership Project; Technical Specification Group Services and System Aspects; Service accessibility (Release 14)", (v143.0.0, Sep. 2015) (28 pages).
American Majority organization entitled:"facebook—A Beginner's Guide", retrieved Oct. 2015 from http://cmrw.org/ (28 pages).
Guide by Twitter, Inc., entitled: "Twitter for Small Business—a Guide to Get Started", retrieved 10/15 from https://g.twimg.com/business/pdfs/Twitter_Smallbiz_Guide.pdf (22 pages).
Karen Church and Rodrigo de Oliveira, "What's up with WhatsApp? Comparing Mobile Instant—Messaging Behaviors with Traditional SMS", published (Aug. 30, 2013) on Mobile HCI 2013—Collaboration and Communication (10 pages).
IETF RFC 5598 entitled: "Internet Mail Architecture", Jul. 2009 (40 pages).

(56) References Cited

OTHER PUBLICATIONS

IETF RFC 5321 entitled: "Simple Mail Transfer Protocol", Oct. 2008 (95 pages).
IETF RFC 7504 entitled: "SMTP 521 and 556 Reply Codes", Jun. 2015 (7 pages).
Craig Partridge, "The technical Development of Internet Mail", IEEE Annals of the History of Computing paper published 2008 by the IEEE Computer Society [1058-6180/08] (27 pages).
Pocket Consultant' book [ISBN: 978-0-7356-8168-2] entitled: "Microsoft Exchange Server 2013—Configuration & Clients", published 2013 by Microsoft Press (384 pages).
IETF RFC 1939 entitled: "Post Office Protocol", May 1996 (23 pages).
IETF RFC 2449 entitled: "POP3 Extension Mechanism", Nov. 1998 (19 pages).
IETF RFC 1734 entitled: "POP3 AUTHentication command", Dec. 1994 (5 pages).
IETF RFC 3501 entitled: "Internet Message Access Protocol—Version 4rev1", Mar. 2003 (108 pages).
IETF RFC 4314 entitled: "IMAP4 Access Control List (ACL) Extension", Dec. 2005 (27 pages).
IETF RFC 6914 entitled: "Simple Made Simple: An Overview of the IETF Specifications for Instant Messaging and Presence Using the Session Initiation Protocol (SIP)", Apr. 2013 (15 pages).
Texas Instrument 2015 publication # SWRT022 entitled: "SimpleLink™ Ultra-Low Power—Wireless Microcontroller Platform" (3 pages).
Datasheet # SWRS158A entitled: "CC2650 SimpleLink™ Multistandard Wireless MCU", by Texas Instrument, published Feb. 2015, Revised Oct. 2015 (59 pages).
National Institute on Deafness and Other Communication Disorders (NIDCD) publication No. 99-4340 entitled: "NIDCD Fact Sheet | Hearing and Balance", Sep. 2013 Reprinted Jul. 2015 (6 pages).
"iOS Tutorial", downloaded from tutorialspoint.com on Jul. 2014 (185 pages).
Application Note No. RES05B00008-0100/Rec. 1.00 by Renesas Technology Corp. entitled: "R8C Family—General RTOS Concepts", published Jan. 2010 (20 pages).
Walter Cedeno et al., "An Overview of Real-Time Operating Systems", The Association for Laboratory Automation, Feb. 2007 (6 pages).
Springer Science + Business Media B.V. entitled: "Hardware-Dependent Software—Principles and Practice", Chapter 2 entitled: "Basic Concepts of Real Time Operating Systems" of a book published 2009 [ISBN—978-1-4020-9435-4] (304 pages).
Nicolas Melot, "Study of an operating system: FreeRTOS—Operating systems for embedded devices", (downloaded Jul. 2015) (39 pages).

* cited by examiner

METHOD AND APPARATUS FOR TRANSCUTANEOUS FACIAL NERVE STIMULATION AND APPLICATIONS THEREOF

RELATED APPLICATIONS

This patent application is a national phase application of a PCT Application No. PCT/IL2019/050819, filed on Jul. 22, 2019 and which claims the benefit of U.S. Provisional Application Ser. No. 62/718,773 entitled: "comprehensive eye solution for functional impairment of the eye due to facial paralysis" that was filed on Aug. 14, 2018, which are all hereby incorporated herein by reference.

TECHNICAL FIELD

This disclosure relates generally to an apparatus and method for transcutaneous nerve stimulation such as facial nerve stimulation, and in particular, but not exclusive, to using non-invasive nerve stimulation for artificially eliciting eye blink, such as with humans with acute facial paralysis.

BACKGROUND

Unless otherwise indicated herein, the materials described in this section are not prior art to the claims in this application and are not admitted to be prior art by inclusion in this section.

Facial nerve. The facial nerve is the seventh cranial nerve, or simply CN VII. It emerges from the pons of the brainstem, controls the muscles of facial expression, and functions in the conveyance of taste sensations from the anterior two-thirds of the tongue. The nerve typically travels from the pons through the facial canal in the temporal bone and exits the skull at the stylomastoid foramen. It arises from the brainstem from an area posterior to the cranial nerve VI (abducens nerve) and anterior to cranial nerve VIII (vestibulocochlear nerve). The facial nerve also supplies preganglionic parasympathetic fibers to several head and neck ganglia. The facial and intermediate nerves can be collectively referred to as the nervus intermediofacialis.

The path of the facial nerve can be divided into six segments: intracranial (cisternal) segment, meatal (canalicular) segment (within the internal auditory canal), labyrinthine segment (internal auditory canal to geniculate ganglion), tympanic segment (from geniculate ganglion to pyramidal eminence), mastoid segment (from pyramidal eminence to stylomastoid foramen), and extratemporal segment (from stylomastoid foramen to post parotid branches). The motor part of the facial nerve arises from the facial nerve nucleus in the pons while the sensory and parasympathetic parts of the facial nerve arise from the intermediate nerve. From the brain stem, the motor and sensory parts of the facial nerve join together and traverse the posterior cranial fossa before entering the petrous temporal bone via the internal auditory meatus. Upon exiting the internal auditory meatus, the nerve then runs a tortuous course through the facial canal, which is divided into the labyrinthine, tympanic, and mastoid segments.

The labyrinthine segment is very short, and ends where the facial nerve forms a bend known as the geniculum of the facial nerve ("genu" meaning knee), which contains the geniculate ganglion for sensory nerve bodies. The first branch of the facial nerve, the greater superficial petrosal nerve, arises here from the geniculate ganglion. The greater petrosal nerve runs through the pterygoid canal and synapses at the pterygopalatine ganglion. Post synaptic fibers of the greater petrosal nerve innervate the lacrimal gland. In the tympanic segment, the facial nerve runs through the tympanic cavity, medial to the incus. The pyramidal eminence is the second bend in the facial nerve, where the nerve runs downward as the mastoid segment. In the temporal part of the facial canal, the nerve gives rise to the stapedius and chorda tympani. The chorda tympani supplies taste fibers to the anterior two thirds of the tongue, and also synapses with the submandibular ganglion. Postsynaptic fibers from the submandibular ganglion supply the sublingual and submandibular glands.

Upon emerging from the stylomastoid foramen, the facial nerve gives rise to the posterior auricular branch. The facial nerve then passes through the parotid gland, which it does not innervate, to form the parotid plexus, which splits into five branches innervating the muscles of facial expression (temporal, zygomatic, buccal, marginal mandibular, cervical). Facial expression. The main function of the facial nerve is motor control of all of the muscles of facial expression. It also innervates the posterior belly of the digastric muscle, the stylohyoid muscle, and the stapedius muscle of the middle ear. All of these muscles are striated muscles of branchiomeric origin developing from the 2nd pharyngeal arch.

Facial sensation. In addition, the facial nerve receives taste sensations from the anterior two-thirds of the tongue via the chorda tympani. Taste sensation is sent to the gustatory portion (superior part) of the solitary nucleus. General sensation from the anterior two-thirds of tongue are supplied by afferent fibers of the third division of the fifth cranial nerve (V-3). These sensory (V-3) and taste (VII) fibers travel together as the lingual nerve briefly before the chorda tympani leaves the lingual nerve to enter the tympanic cavity (middle ear) via the petrotympanic fissure. It joins the rest of the facial nerve via the canaliculus for chorda tympani. The facial nerve then forms the geniculate ganglion, which contains the cell bodies of the taste fibers of chorda tympani and other taste and sensory pathways. From the geniculate ganglion, the taste fibers continue as the intermediate nerve which goes to the upper anterior quadrant of the fundus of the internal acoustic meatus along with the motor root of the facial nerve. The intermediate nerve reaches the posterior cranial fossa via the internal acoustic meatus before synapsing in the solitary nucleus. The facial nerve also supplies a small amount of afferent innervation to the oropharynx below the palatine tonsil. There is also a small amount of cutaneous sensation carried by the nervus intermedius from the skin in and around the auricle (outer ear).

Facial nerve paralysis. Facial nerve paralysis is a common problem that involves the paralysis of any structures innervated by the facial nerve. The pathway of the facial nerve is long and relatively convoluted, so there are a number of causes that may result in facial nerve paralysis. The most common is Bell's palsy, a disease of unknown cause that may only be diagnosed by exclusion of identifiable serious causes. Facial nerve paralysis is characterized by facial weakness, usually only in one side of the face, with other symptoms possibly including loss of taste, hyperacusis and decreased salivation and tear secretion. Other signs may be linked to the cause of the paralysis, such as vesicles in the ear, which may occur if the facial palsy is due to shingles. Symptoms may develop over several hours.

Facial nerve paralysis may be divided into supranuclear and infranuclear lesions. Central facial palsy can be caused by a lacunar infarct affecting fibers in the internal capsule going to the nucleus. The facial nucleus itself can be affected by infarcts of the pontine arteries. These are corticobulbar fibers travelling in internal capsule. Infranuclear lesions refer to the majority of causes of facial palsy Bell's palsy. Bell's palsy is a type of facial paralysis that results in an inability to control the facial muscles on the affected side. Symptoms can vary from mild to severe. They may include muscle twitching, weakness, or total loss of the ability to move one or rarely both sides of the face. Other symptoms include drooping of the eyelid, a change in taste, pain around the ear, and increased sensitivity to sound. Typically, symptoms progress over 48 hours. The symptoms of Bell's palsy are schematically illustrated in the drawing 10 shown in FIG. 1 depicting a person's face, showing a droopy eyelid 11, a chick or facial paralysis or twitching 12, and a drooping corner 13 of the mouth.

The condition normally gets better by itself with most achieving normal or near-normal function. Corticosteroids have been found to improve outcomes, while antiviral medications may be of a small additional benefit. The eye should be protected from drying up with the use of eye drops or an eyepatch. Surgery is generally not recommended. Often signs of improvement begin within 14 days, with complete recovery within six months. A few may not recover completely or have a recurrence of symptoms. Bell's palsy is the most common cause of one-sided facial nerve paralysis (70%). It occurs in 1 to 4 per 10,000 people per year. About 1.5% of people are affected at some point in their life. It most commonly occurs in people between ages 15 and 60. Males and females are affected equally.

Bell's palsy is characterized by a one-sided facial droop that progresses within 72 hours. In rare cases (<1%), it can occur on both sides resulting in total facial paralysis. The facial nerve controls a number of functions, such as blinking and closing the eyes, smiling, frowning, lacrimation, salivation, flaring nostrils and raising eyebrows. It also carries taste sensations from the anterior two-thirds of the tongue, via the chorda tympani nerve (a branch of the facial nerve). Because of this, people with Bell's palsy may present with loss of taste sensation in the anterior ⅔ of the tongue on the affected side. Although the facial nerve innervates the stapedius muscle of the middle ear (via the tympanic branch), sound sensitivity, causing normal sounds to be perceived as very loud, and dysacusis are possible but hardly ever clinically evident.

Although defined as a mononeuritis (involving only one nerve), people diagnosed with Bell's palsy may have "myriad neurological symptoms" including "facial tingling, moderate or severe headache/neck pain, memory problems, balance problems, ipsilateral limb paresthesia, ipsilateral limb weakness, and a sense of clumsiness" that are "unexplained by facial nerve dysfunction".

Bell's palsy occurs due to a malfunction of the facial nerve (cranial nerve VII), which controls the muscles of the face. Facial palsy is typified by inability to control movement in the muscles of facial expression. The paralysis is of the infranuclear/lower motor neuron type. It is thought that as a result of inflammation of the facial nerve, pressure is produced on the nerve where it exits the skull within its bony canal (the stylomastoid foramen), blocking the transmission of neural signals or damaging the nerve. Patients with facial palsy for which an underlying cause can be found are not considered to have Bell's palsy per se. Possible causes include tumor, meningitis, stroke, diabetes mellitus, head trauma and inflammatory diseases of the cranial nerves (sarcoidosis, brucellosis, etc.). In these conditions, the neurologic findings are rarely restricted to the facial nerve.

Eye blink. Blinking is a bodily function involving a semi-autonomic rapid closing of the eyelid. A single blink is determined by the forceful closing of the eyelid or inactivation of the levator palpebrae superioris and the activation of the palpebral portion of the orbicularis oculi, not the full open and close. It is an essential function of the eye that helps spread tears across and remove irritants from the surface of the cornea and conjunctiva. Blinking may have other functions since it occurs more often than necessary just to keep the eye lubricated. Blink speed can be affected by elements such as fatigue, eye injury, medication, and disease. The blinking rate is determined by the body itself, but it can also be affected by external stimulus. Blinking provides moisture to the eye by irrigation using tears and a lubricant the eyes secrete. The eyelid provides suction across the eye from the tear duct to the entire eyeball to keep it from drying out. Blinking also protects the eye from irritants. Eyelashes are hairs attached to the upper and lower eyelids that create a line of defense against dust and other elements to the eye. The eyelashes catch most of these irritants before they reach the eyeball.

There are multiple muscles that control reflexes of blinking. The main muscles, in the upper eyelid, that control the opening and closing are the orbicularis oculi and levator palpebrae superioris muscle. The orbicularis oculi closes the eye, while the contraction of the levator palpebrae muscle opens the eye. The Muller's muscle, or the superior tarsal muscle, in the upper eyelid and the inferior palpebral muscle in the lower 3 eyelid are responsible for widening the eyes. These muscles are not only imperative in blinking, but they are also important in many other functions such as squinting and winking. The inferior palpebral muscle is coordinated with the inferior rectus to pull down the lower lid when one looks down.

Though one may think that the stimulus triggering blinking is dry or irritated eyes, it is most likely that it is controlled by a "blinking center" of the globus pallidus of the lenticular nucleus—a body of nerve cells between the base and outer surface of the brain. Nevertheless, external stimuli can contribute. The orbicularis oculi is a facial muscle; therefore its actions are translated by the facial nerve root. The levator palpebrae superioris' action is sent through the oculomotor nerve. The duration of a blink is on average 100-150 milliseconds according to UCL researcher and between 100-400 ms according to the Harvard Database of Useful Biological Numbers. Closures in excess of 1000 ms were defined as microsleeps. Greater activation of dopaminergic pathways dopamine production in the striatum is associated with a higher rate of spontaneous eye blinking. Conditions in which there is reduced dopamine availability such as Parkinson's disease have reduced eye blink rate, while conditions in which it is raised such as schizophrenia have an increased rate There are three types of eye blink. Spontaneous blinking which is done without external stimuli and internal effort. This type of blinking is conducted in the pre-motor brain stem and happens without conscious effort, like breathing and digestion. A reflex blink occurs in response to an external stimulus, such as contact with the cornea or objects that appear rapidly in front of the eye. A reflex blink is not necessarily a conscious blink either; however it does happen faster than a spontaneous blink. Reflex blink may occur in response to tactile stimuli (e.g. corneal, eyelash, skin of eyelid, contact with eyebrow), optical stimuli (e.g., dazzle reflex, or menace reflex) or auditory stimuli (e.g., menace reflex). Voluntary blink is larger amplitude than Reflex blink, with the use of all 3 divisions of the orbicularis oculi muscle.

Dry Eye Syndrome (DES). Dry eye syndrome (DES), also known as keratoconjunctivitis sicca (KCS), is the condition of having dry eyes. Other associated symptoms include irritation, redness, discharge, and easily fatigued eyes. Blurred vision may also occur. The symptoms can range from mild and occasional to severe and continuous. Scarring of the cornea may occur in some cases without treatment. Dry eye occurs when either the eye does not produce enough tears or when the tears evaporate too quickly. This can result from contact lens use, meibomian gland dysfunction, allergies, pregnancy, Sjögren's syndrome, vitamin A deficiency, LASIK surgery, and certain medications such as antihistamines, some blood pressure medication, hormone replacement therapy, and antidepressants. Chronic conjunctivitis such as from tobacco smoke exposure or infection may also lead to the condition. Diagnosis is mostly based on the symptoms, though a number of other tests may be used. Treatment depends on the underlying cause. Artificial tears are the usual first line treatment. Wrap around glasses that fit close to the face may decrease tear evaporation. Stopping or changing certain medications may help. The medication ciclosporin or steroid eye drops may be used in some cases. Another option is lacrimal plugs that prevent tears from draining from the surface of the eye. Dry eye syndrome occasionally makes wearing contact lenses impossible.

Dry eye syndrome is a common eye disease. It affects 5-34% of people to some degree depending on the population looked at. Among older people it affects up to 70%. In China it affects about 17% of people. Typical symptoms of dry eye syndrome are dryness, burning sensation, and a sandy-gritty eye irritation that gets worse as the day goes on. Symptoms may also be described as itchy, scratchy, stinging or tired eyes. Other symptoms are pain, redness, a pulling sensation, and pressure behind the eye. There may be a feeling that something, such as a speck of dirt, is in the eye. The resultant damage to the eye surface increases discomfort and sensitivity to bright light. Both eyes usually are affected. There may also be a stringy discharge from the eyes. Although it may seem strange, dry eye can cause the eyes to water. This can happen because the eyes are irritated. One may experience excessive tearing in the same way as one would if something got into the eye. These reflex tears will not necessarily make the eyes feel better. This is because they are the watery type that are produced in response to injury, irritation, or emotion. They do not have the lubricating qualities necessary to prevent dry eye.

Because blinking coats the eye with tears, symptoms are worsened by activities in which the rate of blinking is reduced due to prolonged use of the eyes. These activities include prolonged reading, computer usage, driving, or watching television. Symptoms increase in windy, dusty or smoky (including cigarette smoke) areas, in dry environments high altitudes including airplanes, on days with low humidity, and in areas where an air conditioner (especially in a car), fan, heater, or even a hair dryer is being used. Symptoms reduce during cool, rainy, or foggy weather and in humid places, such as in the shower.

Most people who have dry eyes experience mild irritation with no long-term effects. However, if the condition is left untreated or becomes severe, it can produce complications that can cause eye damage, resulting in impaired vision or (rarely) in the loss of vision. Symptom assessment is a key component of dry eye diagnosis—to the extent that many believe dry eye syndrome to be a symptom-based disease.

Several questionnaires have been developed to determine a score that would allow for dry eye diagnosis. Having dry eyes for a while can lead to tiny abrasions on the surface of the eyes. In advanced cases, the epithelium undergoes pathologic changes, namely squamous metaplasia and loss of goblet cells. Some severe cases result in thickening of the corneal surface, corneal erosion, punctate keratopathy, epithelial defects, corneal ulceration (sterile and infected), corneal neovascularization, corneal scarring, corneal thinning, and even corneal perforation. Another contributing factor may be lacritin monomer deficiency. Lacritin monomer, active form of lacritin, is selectively decreased in aqueous deficient dry eye, Sjögren's syndrome dry eye, contact lens-related dry eye and in blepharitis.

Dry eyes can usually be diagnosed by the symptoms alone. Tests can determine both the quantity and the quality of the tears. A slit lamp examination can be performed to diagnose dry eyes and to document any damage to the eye. A Schirmer's test can measure the amount of moisture bathing the eye. This test is useful for determining the severity of the condition. A five-minute Schirmer's test with and without anesthesia using a Whatman #41 filter paper 5 mm wide by 35 mm long is performed. For this test, wetting under 5 mm with or without anesthesia is considered diagnostic for dry eyes. If the results for the Schirmer's test are abnormal, a Schirmer II test can be performed to measure reflex secretion. In this test, the nasal mucosa is irritated with a cotton-tipped applicator, after which tear production is measured with a Whatman #41 filter paper. For this test, wetting under 15 mm after five minutes is considered abnormal.

A tear breakup time (TBUT) test measures the time it takes for tears to break up in the eye. The tear breakup time can be determined after placing a drop of fluorescein in the cul-de-sac. A tear protein analysis test measures the lysozyme contained within tears. In tears, lysozyme accounts for approximately 20 to 40 percent of total protein content. A lactoferrin analysis test provides good correlation with other tests. The presence of the recently described molecule Ap4A, naturally occurring in tears, is abnormally high in different states of ocular dryness. This molecule can be quantified biochemically simply by taking a tear sample with a plain Schirmer test. Utilizing this technique it is possible to determine the concentrations of Ap4A in the tears of patients and in such way diagnose objectively if the samples are indicative of dry eye.

TENS. Transcutaneous Electrical Nerve Stimulation (TENS or TNS) is the use of electric current produced by a device to stimulate the nerves for therapeutic purposes. TENS, by definition, covers the complete range of transcutaneously applied currents used for nerve excitation although the term is often used with a more restrictive intent, namely to describe the kind of pulses produced by portable stimulators used to treat pain. The unit is usually connected to the skin using two or more electrodes. A typical battery-operated TENS unit is able to modulate pulse width, frequency and intensity. Generally TENS is applied at high frequency (>50 Hz) with an intensity below motor contraction (sensory intensity) or low frequency (<10 Hz) with an intensity that produces motor contraction.

TENS devices available to the domestic market are used as a non-invasive nerve stimulation intended to reduce both acute and chronic pain. In principle, an adequate intensity of stimulation is necessary to achieve pain relief with TENS. An analysis of treatment fidelity (meaning that the delivery of TENS in a trial was in accordance with current clinical advice, such as using "a strong but comfortable sensation"

and suitable, frequent treatment durations) showed that higher fidelity trials tended to have a positive outcome. A few studies have shown objective evidence that TENS may modulate or suppress pain signals in the brain.

Various commercial off-the-shelf TENS devices are available in the market, primarily for providing non-invasive, drug-free method for controlling pain, by using electrical impulses sent through the skin to nerves to modify pain perception. Examples for commercially available TENS devices are the TENS 3000 model sold by Roscoe Medical Inc. (of Middleburg Heights, OH, U.S.A.), described in the instruction manual entitled: "Instruction Manual for the TENS 3000", and the TENS 7000 model sold by Roscoe Medical Inc. (of Middleburg Heights, OH, U.S.A.), described in the instruction manual entitled: "Instruction Manual for the TENS 7000" (Document Number 42-DT7202_01), downloaded from the Internet on May 2019, which are both incorporated in their entirety for all purposes as if fully set forth herein.

Methods for treating neuropathy and apparatus for use in the methods are described in U.S. Patent Application No. 2005/0234525 to Phillips entitled: "Electric stimulation for treating neuropathy using asymmetric biphasic signals", which is incorporated in its entirety for all purposes as if fully set forth herein. The apparatus may include a controller configured to output an asymmetric biphasic signal. The apparatus can also include a first container and a second container. The first and the second containers can be configured to hold a fluid. The apparatus may also include a first electrode and a second electrode. The first electrode and the second electrode can be configured to be in electrical contract with the fluid held by the container, and can be configured to be coupled to the controller. The electrodes may be configured to receive the asymmetric biphasic signal output from the controller.

A transcutaneous electrical nerve-stimulation therapy apparatus and method having absolute protection for the patient from shock and automatic operation are described in U.S. Pat. No. 4,769,881 to Pedigo et al. entitled: "High precision tens apparatus and method of use", which is incorporated in its entirety for all purposes as if fully set forth herein. The apparatus may operate in three modes, either controlled by timer, operating continuously or put in an automatic mode where the timer is automatically reset when the probe is removed from the patient and then recontacted. A circuit is provided for checking the continuity between the patient and the probes before each and every stimulation pulse. These pulses are generated at the same frequency and with a constant phase shift from the stimulation pulses. At the start of each set of stimulation pulses, the pulses are slowly ramped up over a 4-5 second interval so as to prevent any initial jolt to the patient. The device may also be used to locate appropriate application points on the patient's body. The pulses applied are variable current pulses having a fixed voltage.

Apparatus for transcutaneous electrical nerve stimulation in humans is described in U.S. Pat. No. 8,948,876 to Gozani et al. entitled: "Apparatus and method for relieving pain using transcutaneous electrical nerve stimulation", which is incorporated in its entirety for all purposes as if fully set forth herein. The apparatus comprising a housing; stimulation means mounted within the housing for electrically stimulating nerves; an electrode array releasably mounted to the housing, connectable to the stimulation means, and comprising electrodes for electrical stimulation of nerves; control means mounted to the housing and electrically connected to the stimulation means for controlling the stimulation means; monitoring means mounted to the housing and electrically connected to the stimulation means for monitoring the stimulation means; user interface means mounted to the housing and electrically connected to the control means for controlling the stimulation means; display means mounted to the housing and electrically connected to the control means and the monitoring means for displaying the status of the stimulations means; and a strap attached to the housing and configured to hold the housing, stimulation means and electrode array at a specific anatomical location to treat pain.

An electronic stimulating device is disclosed, with the stimulating device particularly illustrated being a transcutaneous nerve stimulating (TENS) device for effecting suppression of pain by nerve fiber stimulation, is described in U.S. Pat. No. 5,069,211 to Bartelt et al. entitled: "Microprocessor controlled electronic stimulating device having biphasic pulse output", which is incorporated in its entirety for all purposes as if fully set forth herein. Biphasic constant current output pulses are applied to a user through electrode pairs noninvasively positioned at the skin of the user. Microprocessor generated control pulses control generation of the biphasic output pulses at a biphasic output stage associated with each electrode pair, and the generated biphasic output pulses are capacitively coupled from each output stage which also includes a bleeder network for effecting capacitor discharge. Stimulation may be continuously applied at a level selected by the user or may be applied in timed varying intensities the maximum level of which is selectable, and displays of intensity and sensed faults, including low battery voltage, are also provided.

EMS. Electrical muscle stimulation (EMS), also known as neuromuscular electrical stimulation (NMES) or electromyostimulation, is the elicitation of muscle contraction using electric impulses. EMS has received an increasing amount of attention in the last few years for many reasons: it can be utilized as a strength training tool for healthy subjects and athletes; it could be used as a rehabilitation and preventive tool for partially or totally immobilized patients; it could be utilized as a testing tool for evaluating the neural and/or muscular function in vivo; it could be used as a post-exercise recovery tool for athletes. The impulses are generated by a device and are delivered through electrodes on the skin near to the muscles being stimulated. The electrodes are generally pads that adhere to the skin. The impulses mimic the action potential that comes from the central nervous system, causing the muscles to contract.

In medicine, EMS is used for rehabilitation purposes, for instance in physical therapy in the prevention muscle atrophy due to inactivity or neuromuscular imbalance, which can occur for example after musculoskeletal injuries (damage to bones, joints, muscles, ligaments and tendons). This is distinct from Transcutaneous Electrical Nerve Stimulation (TENS), in which an electric current is used for pain therapy.

Skin electrodes. An electrode is an electrical conductor used to make contact with a nonmetallic part of a circuit (e.g. a semiconductor, an electrolyte, a vacuum or air). Skin electrodes are the actual conductive pads attached to the body surface.] Any pair of electrodes can measure the electrical potential difference between the two corresponding locations of attachment. Commonly, 10 electrodes attached to the body are used to form 12 ECG leads, with each lead measuring a specific electrical potential difference (as listed in the table below). Two types of electrodes in common use are a flat paper-thin sticker and a self-adhesive circular pad. The former are typically used in a single ECG recording while the latter are for continuous recordings as they stick longer. Each electrode consists of an electrically conductive electrolyte gel and a silver/silver chloride conductor. The gel typically contains potassium chloride—sometimes silver chloride as well—to permit electron conduction from the skin to the wire and to the electrocardiogram.

'Electronic skin' electrodes. Flexible, stretchable printed circuits electrodes (referred to herein as "electronic skin" electrodes) shaped as miniature tattoos are described in an article entitled: "*Bionic Skin for a Cyborg You—Flexible electronics allow us to cover robots and humans with stretchy sensors*" by Takao Someya of the University of Tokyo, Japan, published August 2013 in IEEE Spectrum (downloaded May 2019 from spectrum.ieee.org/biomedical/bionics/bionic-skin-for-a-cyborg-you—preceded by https://), which is incorporated in its entirety for all purposes as if fully set forth herein. Such electrodes typically consist of a patterned conductive material printed on an adhesive film that attaches to the skin.

Electromyography is a non-invasive method widely used to map muscle activation. For decades, it was commonly accepted that dry metallic electrodes establish poor electrode-skin contact, making them impractical for skin electromyography applications. Gelled electrodes are therefore the standard in electromyography with their use confined, almost entirely, to laboratory settings. The tattoo electrodes are made of a conductive material laminated between adhesive polymer films, leaving the electrode ends exposed to be attached to the skin and the connector end to be attached to a slim connector (ZIF—Zero force connector, used to connect flexible printed circuits). This slim ZIF connector is wired to a signal generator by a flexible cable. Novel dry electrodes, exhibiting outstanding electromyography recording along with excellent user comfort, are presented in an article entitled: "*Temporary-tattoo for long-term high fidelity biopotential recordings*" by Bareket L., Inzelberg L., Rand D., David-Pur M., Rabinovich D., Brandes B., and Hanein Y. (all of Tel-Aviv University, Tel-Aviv, Israel), published 12 May 2016 on Scientific Reports [6:25727, DOI: 10.1038/srep25727], which is incorporated in its entirety for all purposes as if fully set forth herein. The electrodes were realized using screen-printing of carbon ink on a soft support. The conformity of the electrodes helps establish direct contact with the skin, making the use of a gel superfluous. Plasma polymerized 3,4-ethylenedioxythiophene was used to enhance the impedance of the electrodes. Cyclic voltammetry measurements revealed an increase in electrode capacitance by a factor of up to 100 in wet conditions. Impedance measurements show a reduction factor of 10 in electrode impedance on human skin. The suitability of the electrodes for long-term electromyography recordings from the hand and from the face is demonstrated. The presented electrodes are ideally suited for many applications, such as brain-machine interfacing, muscle diagnostics, post-injury rehabilitation, and gaming.

An example of an electrode assembly 20 is shown in FIG. 2. The assembly 20 includes two electrodes 24a and 24b serving as skin patches to be affixed to a treated human body, connected via respective isolated leads 21a and 21b to respective exposed leads 23a and 23b of the ZIF connector 22.

EEG Electrodes. EEG electrodes, placed on the scalp, can be either "passive" or "active". Passive electrodes, which are metallic, are connected to an amplifier, e.g., by a cable. Active electrodes may have an inbuilt preamplifier to make them less sensitive to environmental noise and cable movements. Some types of electrodes may need gel or saline liquid to operate, in order to reduce the skin-electrode contact impedance. While other types of EEG electrodes can operate without a gel or saline and are considered "dry electrodes". There are various brain activity patterns that may be measured by EEG. Some of the popular ones often used in affective computing include: Event Related Desynchronization/Synchronization, Event Related Potentials (e.g., P30 wave and error potentials), and Steady State Evoked Potentials. Measurements of EEG electrodes are typically subjected to various feature extraction techniques which aim to represent raw or preprocessed EEG signals by an ideally small number of relevant values, which describe the task-relevant information contained in the signals. For example, these features may be the power of the EEG over selected channels, and specific frequency bands.

Implantable electrodes. Implantable electrodes are described in a presentation entitled: "*Implantable Neural Electrodes—Implantable Electronics Session*" by Dr. Martin Schuettler (of the Laboratory for Biomedical Microtechnology Department of Microsystem Engineering University of Freiburg, Germany) dated 2012 Mar. 30, and in an article entitled: "*ELECTRODE IMPLANTATION IN THE HUMAN BODY*" by Margaret I. Babb, Ph. D. and Anthony M. Dymond, Ph. D. (of Brain Information Service—Brain Research Institute, University of California, Los Angeles, California, U.S.A.) published 1974, which are both incorporated in their entirety for all purposes as if fully set forth herein.

EEG. Electroencephalography (EEG) is an electrophysiological monitoring method to record electrical activity of the brain, which is typically noninvasive, with the electrodes placed along the scalp, although invasive electrodes are sometimes used in specific applications. EEG measures voltage fluctuations resulting from ionic current within the neurons of the brain. In clinical contexts, EEG refers to the recording of the brain's spontaneous electrical activity over a period, as recorded from multiple electrodes placed on the scalp. Diagnostic applications generally focus on the spectral content of EEG, that is, the type of neural oscillations (popularly called "brain waves") that can be observed in EEG signals. Despite limited spatial resolution, EEG continues to be a valuable tool for research and diagnosis, especially when millisecond-range temporal resolution (not possible with CT or MRI) is required. Derivatives of the EEG technique include evoked potentials (EP), which involves averaging the EEG activity time-locked to the presentation of a stimulus of some sort (visual, somatosensory, or auditory). Event-related potentials (ERPs) refer to averaged EEG responses that are time-locked to more complex processing of stimuli; this technique is used in cognitive science, cognitive psychology, and psychophysiological research. EEG and measuring EEG are described in an article published 2006 in Wiley Encyclopedia of Biomedical Engineering by Katarzyna Blinowska and Piotr Durka of Warshow University, Waszawa, Poland entitled: "*ELECTROENCEPHALOGRAPHY (EEG)*", in an article in Measurement Science Review (Volume 2, Section 2, 2002) by M. Teplan entitled: "Fundamentals of EEG Measurement", and in a presentation by M. Kabiraj in Neuroscoences 2003; Vol. 8 Supplement 2, entitled: "*EEG COURSE—Workshop 1—'Basic principles and interpretations of electroencephalography'*", which are all incorporated in their entirety for all purposes as if fully set forth herein.

In conventional scalp EEG, the recording is obtained by placing electrodes on the scalp with a conductive gel or paste, usually after preparing the scalp area by light abrasion to reduce impedance due to dead skin cells. Many systems typically use electrodes, each of which is attached to an individual wire. Some systems use caps or nets into which electrodes are embedded; this is particularly common when high-density arrays of electrodes are needed. Electrode locations and names are specified by the International 10-20 system for most clinical and research applications (except when high-density arrays are used). This system ensures that the naming of electrodes is consistent across laboratories. In most clinical applications, 19 recording electrodes (plus ground and system reference) are used. A smaller number of electrodes are typically used when recording EEG from neonates. Additional electrodes can be added to the standard set-up when a clinical or research application demands increased spatial resolution for a particular area of the brain. High-density arrays (typically via cap or net) can contain up to 256 electrodes more-or-less evenly spaced around the scalp. Each electrode is connected to one input of a differential amplifier (one amplifier per pair of electrodes); a common system reference electrode is connected to the other input of each differential amplifier. These amplifiers amplify the voltage between the active electrode and the reference (typically 1,000-100,000 times, or 60-100 dB of voltage gain). In analog EEG, the signal is then filtered (next paragraph), and the EEG signal is output as the deflection of pens as paper passes underneath. Most EEG systems these days, however, are digital, and the amplified signal is digitized via an analog-to-digital converter, after being passed through an anti-aliasing filter. Analog-to-digital sampling typically occurs at 256-512 Hz in clinical scalp EEG; sampling rates of up to 20 kHz are used in some research applications.

During the recording, a series of activation procedures may be used. These procedures may induce normal or abnormal EEG activity that might not otherwise be seen. These procedures include hyperventilation, photic stimulation (with a strobe light), eye closure, mental activity, sleep and sleep deprivation. During (inpatient) epilepsy monitoring, a patient's typical seizure medications may be withdrawn. The digital EEG signal is stored electronically and can be filtered for display. Typical settings for the high-pass filter and a low-pass filter are 0.5-1 Hz and 35-70 Hz, respectively. The high-pass filter typically filters out slow artifact, such as electrogalvanic signals and movement artifact, whereas the low-pass filter filters out high-frequency artifacts, such as electromyographic signals. An additional notch filter is typically used to remove artifact caused by electrical power lines (60 Hz in the United States and 50 Hz in many other countries). The EEG signal can be processed by freely available EEG software such as EEGLAB or the Neurophysiological Biomarker Toolbox.

As part of an evaluation for epilepsy surgery, it may be necessary to insert electrodes near the surface of the brain, under the surface of the dura mater. This is accomplished via burr hole or craniotomy. This is referred to variously as "electrocorticography (ECoG)", "intracranial EEG (I-EEG)" or "subdural EEG (SD-EEG)". Depth electrodes may also be placed into brain structures, such as the amygdala or hippocampus, structures, which are common epileptic foci and may not be "seen" clearly by scalp EEG. The electrocorticographic signal is processed in the same manner as digital scalp EEG (above), with a couple of caveats. ECoG is typically recorded at higher sampling rates than scalp EEG because of the requirements of Nyquist theorem—the subdural signal is composed of a higher predominance of higher frequency components. In addition, many of the artifacts that affect scalp EEG do not affect ECoG, and therefore display filtering is often not needed.

A typical adult human EEG signal is about 10 µV to 100 µV in amplitude when measured from the scalp and is about 10-20 mV when measured from subdural electrodes. Since an EEG voltage signal represents a difference between the voltages at two electrodes, the display of the EEG for the reading encephalographer may be set up in one of several ways. The representation of the EEG channels is referred to as a montage.

Internet. The Internet is a global system of interconnected computer networks that use the standardized Internet Protocol Suite (TCP/IP), including Transmission Control Protocol (TCP) and the Internet Protocol (IP), to serve billions of users worldwide. It is a network of networks that consists of millions of private, public, academic, business, and government networks, of local to global scope, that are linked by a broad array of electronic and optical networking technologies. The Internet carries a vast range of information resources and services, such as the interlinked hypertext documents on the World Wide Web (WWW) and the infrastructure to support electronic mail. The Internet backbone refers to the principal data routes between large, strategically interconnected networks and core routers on the Internet. These data routers are hosted by commercial, government, academic, and other high-capacity network centers, the Internet exchange points and network access points that interchange Internet traffic between the countries, continents and across the oceans of the world. Traffic interchange between Internet service providers (often Tier 1 networks) participating in the Internet backbone exchange traffic by privately negotiated interconnection agreements, primarily governed by the principle of settlement-free peering.

The Transmission Control Protocol (TCP) is one of the core protocols of the Internet Protocol suite (IP) described in RFC 675 and RFC 793, and the entire suite is often referred to as TCP/IP. TCP provides reliable, ordered and error-checked delivery of a stream of octets between programs running on computers connected to a local area network, intranet or the public Internet. It resides at the transport layer. Web browsers typically use TCP when they connect to servers on the World Wide Web, and is used to deliver email and transfer files from one location to another. HTTP, HTTPS, SMTP, POP3, IMAP, SSH, FTP, Telnet and a variety of other protocols are encapsulated in TCP. As the transport layer of TCP/IP suite, the TCP provides a communication service at an intermediate level between an application program and the Internet Protocol (IP). Due to network congestion, traffic load balancing, or other unpredictable network behavior, IP packets may be lost, duplicated, or delivered out-of-order. TCP detects these problems, requests retransmission of lost data, rearranges out-of-order data, and even helps minimize network congestion to reduce the occurrence of the other problems. Once the TCP receiver has reassembled the sequence of octets originally transmitted, it passes them to the receiving application. Thus, TCP abstracts the application's communication from the underlying networking details. The TCP is utilized extensively by many of the Internet's most popular applications, including the World Wide Web (WWW), E-mail, File Transfer Protocol, Secure Shell, peer-to-peer file sharing, and some streaming media applications.

While IP layer handles actual delivery of the data, TCP keeps track of the individual units of data transmission, called segments, which are divided smaller pieces of a message, or data for efficient routing through the network. For example, when an HTML file is sent from a web server, the TCP software layer of that server divides the sequence of octets of the file into segments and forwards them individually to the IP software layer (Internet Layer). The Internet Layer encapsulates each TCP segment into an IP packet by adding a header that includes (among other data) the destination IP address. When the client program on the destination computer receives them, the TCP layer (Transport Layer) reassembles the individual segments and ensures they are correctly ordered and error-free as it streams them to an application.

The TCP protocol operations may be divided into three phases. First, the connections must be properly established in a multi-step handshake process (connection establishment) before entering the data transfer phase. After data transmission is completed, the connection termination closes established virtual circuits and releases all allocated resources. A TCP connection is typically managed by an operating system through a programming interface that represents the local end-point for communications, the Internet socket. The local end-point undergoes a series of state changes throughout the duration of a TCP connection.

The Internet Protocol (IP) is the principal communications protocol used for relaying datagrams (packets) across a network using the Internet Protocol Suite. It is considered as the primary protocol that establishes the Internet, and is responsible for routing packets across the network boundaries. IP is the primary protocol in the Internet Layer of the Internet Protocol Suite and has the task of delivering datagrams from the source host to the destination host based on their addresses. For this purpose, IP defines addressing methods and structures for datagram encapsulation. Internet Protocol Version 4 (IPv4) is the dominant protocol of the Internet. IPv4 is described in Internet Engineering Task Force (IETF) Request for Comments (RFC) 791 and RFC 1349, and the successor, Internet Protocol Version 6 (IPv6), is currently active and in growing deployment worldwide. IPv4 uses 32-bit addresses (providing 4 billion: $4.3 \times 10^9$ addresses), while IPv6 uses 128-bit addresses (providing 340 undecillion or $3.4 \times 10^{38}$ addresses), as described in RFC 2460.

The Internet architecture employs a client-server model, among other arrangements. The terms 'server' or 'server computer' relates herein to a device or computer (or a plurality of computers) connected to the Internet, and is used for providing facilities or services to other computers or other devices (referred to in this context as 'clients') connected to the Internet. A server is commonly a host that has an IP address and executes a 'server program', and typically operates as a socket listener. Many servers have dedicated functionality such as web server, Domain Name System (DNS) server (described in RFC 1034 and RFC 1035), Dynamic Host Configuration Protocol (DHCP) server (described in RFC 2131 and RFC 3315), mail server, File Transfer Protocol (FTP) server and database server. Similarly, the term 'client' is used herein to include, but not limited to, a program or a device, or a computer (or a series of computers) executing this program, which accesses a server over the Internet for a service or a resource. Clients commonly initiate connections that a server may accept. For non-limiting example, web browsers are clients that connect to web servers for retrieving web pages, and email clients connect to mail storage servers for retrieving mails.

Wireless. Any embodiment herein may be used in conjunction with one or more types of wireless communication signals and/or systems, for example, Radio Frequency (RF), Infra Red (IR), Frequency-Division Multiplexing (FDM), Orthogonal FDM (OFDM), Time-Division Multiplexing (TDM), Time-Division Multiple Access (TDMA), Extended TDMA (E-TDMA), General Packet Radio Service (GPRS), extended GPRS, Code-Division Multiple Access (CDMA), Wideband CDMA (WCDMA), CDMA 2000, single-carrier CDMA, multi-carrier CDMA, Multi-Carrier Modulation (MDM), Discrete Multi-Tone (DMT), Bluetooth®, Global Positioning System (GPS), Wi-Fi, Wi-Max, ZigBee™, Ultra-Wideband (UWB), Global System for Mobile communication (GSM), 2G, 2.5G, 3G, 3.5G, Enhanced Data rates for GSM Evolution (EDGE), or the like. Any wireless network or wireless connection herein may be operating substantially in accordance with existing IEEE 802.11, 802.11a, 802.11b, 802.11g, 802.11k, 802.11n, 802.11r, 802.16, 802.16d, 802.16e, 802.20, 802.21 standards and/or future versions and/or derivatives of the above standards. Further, a network element (or a device) herein may consist of, be part of, or include, a cellular radio-telephone communication system, a cellular telephone, a wireless telephone, a Personal Communication Systems (PCS) device, a PDA device that incorporates a wireless communication device, or a mobile/portable Global Positioning System (GPS) device. Further, a wireless communication may be based on wireless technologies that are described in Chapter 20: "*Wireless Technologies*" of the publication number 1-587005-001-3 by Cisco Systems, Inc. (July 1999) entitled: "*Internetworking Technologies Handbook*", which is incorporated in its entirety for all purposes as if fully set forth herein. Wireless technologies and networks are further described in a book published 2005 by Pearson Education, Inc. William Stallings [ISBN: 0-13-191835-4] entitled: "*Wireless Communications and Networks—second Edition*", which is incorporated in its entirety for all purposes as if fully set forth herein.

Wireless networking typically employs an antenna (a.k.a. aerial), which is an electrical device that converts electric power into radio waves, and vice versa, connected to a wireless radio transceiver. In transmission, a radio transmitter supplies an electric current oscillating at radio frequency to the antenna terminals, and the antenna radiates the energy from the current as electromagnetic waves (radio waves). In reception, an antenna intercepts some of the power of an electromagnetic wave in order to produce a low voltage at its terminals that is applied to a receiver to be amplified. Typically an antenna consists of an arrangement of metallic conductors (elements), electrically connected (often through a transmission line) to the receiver or transmitter. An oscillating current of electrons forced through the antenna by a transmitter will create an oscillating magnetic field around the antenna elements, while the charge of the electrons also creates an oscillating electric field along the elements. These time-varying fields radiate away from the antenna into space as a moving transverse electromagnetic field wave. Conversely, during reception, the oscillating electric and magnetic fields of an incoming radio wave exert force on the electrons in the antenna elements, causing them to move back and forth, creating oscillating currents in the antenna. Antennas can be designed to transmit and receive radio waves in all horizontal directions equally (omnidirectional antennas), or preferentially in a particular direction (directional or high gain antennas). In the latter case, an antenna may also include additional elements or surfaces with no electrical connection to the transmitter or receiver, such as parasitic elements, parabolic reflectors or horns, which serve to direct the radio waves into a beam or other desired radiation pattern.

ISM. The Industrial, Scientific and Medical (ISM) radio bands are radio bands (portions of the radio spectrum) reserved internationally for the use of radio frequency (RF) energy for industrial, scientific and medical purposes other than telecommunications. In general, communications equipment operating in these bands must tolerate any interference generated by ISM equipment, and users have no regulatory protection from ISM device operation. The ISM bands are defined by the ITU-R in 5.138, 5.150, and 5.280 of the Radio Regulations. Individual countries use of the bands designated in these sections may differ due to variations in national radio regulations. Because communication devices using the ISM bands must tolerate any interference from ISM equipment, unlicensed operations are typically permitted to use these bands, since unlicensed operation typically needs to be tolerant of interference from other devices anyway. The ISM bands share allocations with unlicensed and licensed operations; however, due to the high likelihood of harmful interference, licensed use of the bands is typically low. In the United States, uses of the ISM bands are governed by Part 18 of the Federal Communications Commission (FCC) rules, while Part 15 contains the rules for unlicensed communication devices, even those that share ISM frequencies. In Europe, the ETSI is responsible for governing ISM bands.

Commonly used ISM bands include a 2.45 GHz band (also known as 2.4 GHz band) that includes the frequency band between 2.400 GHz and 2.500 GHz, a 5.8 GHz band that includes the frequency band 5.725-5.875 GHz, a 24 GHz band that includes the frequency band 24.000-24.250 GHz, a 61 GHz band that includes the frequency band 61.000-61.500 GHz, a 122 GHz band that includes the frequency band 122.000-123.000 GHz, and a 244 GHz band that includes the frequency band 244.000-246.000 GHz.

ZigBee. ZigBee is a standard for a suite of high-level communication protocols using small, low-power digital radios based on an IEEE 802 standard for Personal Area Network (PAN). Applications include wireless light switches, electrical meters with in-home-displays, and other consumer and industrial equipment that require a short-range wireless transfer of data at relatively low rates. The technology defined by the ZigBee specification is intended to be simpler and less expensive than other WPANs, such as Bluetooth. ZigBee is targeted at Radio-Frequency (RF) applications that require a low data rate, long battery life, and secure networking. ZigBee has a defined rate of 250 kbps suited for periodic or intermittent data or a single signal transmission from a sensor or input device.

ZigBee builds upon the physical layer and medium access control defined in IEEE standard 802.15.4 (2003 version) for low-rate WPANs. The specification further discloses four main components: network layer, application layer, ZigBee Device Objects (ZDOs), and manufacturer-defined application objects, which allow for customization and favor total integration. The ZDOs are responsible for a number of tasks, which include keeping of device roles, management of requests to join a network, device discovery, and security. Because ZigBee nodes can go from a sleep to active mode in 30 ms or less, the latency can be low and devices can be responsive, particularly compared to Bluetooth wake-up delays, which are typically around three seconds. ZigBee nodes can sleep most of the time, thus the average power consumption can be lower, resulting in longer battery life.

There are three defined types of ZigBee devices: ZigBee Coordinator (ZC), ZigBee Router (ZR), and ZigBee End Device (ZED). ZigBee Coordinator (ZC) is the most capable device and forms the root of the network tree and might bridge to other networks. There is exactly one defined ZigBee coordinator in each network, since it is the device that started the network originally. It is able to store information about the network, including acting as the Trust Center & repository for security keys. ZigBee Router (ZR) may be running an application function as well as may be acting as an intermediate router, passing on data from other devices. ZigBee End Device (ZED) contains functionality to talk to a parent node (either the coordinator or a router). This relationship allows the node to be asleep a significant amount of the time, thereby giving long battery life. A ZED requires the least amount of memory, and therefore can be less expensive to manufacture than a ZR or ZC.

The protocols build on recent algorithmic research (Ad-hoc On-demand Distance Vector, neuRFon) to automatically construct a low-speed ad-hoc network of nodes. In most large network instances, the network will be a cluster of clusters. It can also form a mesh or a single cluster. The current ZigBee protocols support beacon and non-beacon enabled networks. In non-beacon-enabled networks, an unslotted CSMA/CA channel access mechanism is used. In this type of network, ZigBee Routers typically have their receivers continuously active, requiring a more robust power supply. However, this allows for heterogeneous networks in which some devices receive continuously, while others only transmit when an external stimulus is detected.

In beacon-enabled networks, the special network nodes called ZigBee Routers transmit periodic beacons to confirm their presence to other network nodes. Nodes may sleep between the beacons, thus lowering their duty cycle and extending their battery life. Beacon intervals depend on the data rate; they may range from 15.36 milliseconds to 251.65824 seconds at 250 Kbit/s, from 24 milliseconds to 393.216 seconds at 40 kbit/s, and from 48 milliseconds to 786.432 seconds at 20 kbit/s. In general, the ZigBee protocols minimize the time the radio is on to reduce power consumption. In beaconing networks, nodes only need to be active while a beacon is being transmitted. In non-beacon-enabled networks, power consumption is decidedly asymmetrical: some devices are always active while others spend most of their time sleeping. Except for the Smart Energy Profile 2.0, current ZigBee devices conform to the IEEE 802.15.4-2003 Low-Rate Wireless Personal Area Network (LR-WPAN) standard. The standard specifies the lower protocol layers—the PHYsical layer (PHY), and the Media Access Control (MAC) portion of the Data Link Layer (DLL). The basic channel access mode is "Carrier Sense, Multiple Access/Collision Avoidance" (CSMA/CA), that is, the nodes talk in the same way that people converse; they briefly check to see that no one is talking before they start. There are three notable exceptions to the use of CSMA. Beacons are sent on a fixed time schedule, and do not use CSMA. Message acknowledgments also do not use CSMA. Finally, devices in Beacon Oriented networks that have low latency real-time requirement, may also use Guaranteed Time Slots (GTS), which by definition do not use CSMA.

Z-Wave. Z-Wave is a wireless communications protocol by the Z-Wave Alliance (http://www.z-wave.com) designed for home automation, specifically for remote control applications in residential and light commercial environments. The technology uses a low-power RF radio embedded or retrofitted into home electronics devices and systems, such as lighting, home access control, entertainment systems and household appliances. Z-Wave communicates using a low-power wireless technology designed specifically for remote control applications. Z-Wave operates in the sub-gigahertz frequency range, around 900 MHz. This band competes with some cordless telephones and other consumer electronics devices, but avoids interference with WiFi and other systems that operate on the crowded 2.4 GHz band. Z-Wave is designed to be easily embedded in consumer electronics products, including battery-operated devices such as remote controls, smoke alarms, and security sensors.

Z-Wave is a mesh networking technology where each node or device on the network is capable of sending and receiving control commands through walls or floors, and use intermediate nodes to route around household obstacles or radio dead spots that might occur in the home. Z-Wave devices can work individually or in groups, and can be programmed into scenes or events that trigger multiple devices, either automatically or via remote control. The Z-wave radio specifications include bandwidth of 9,600 bit/s or 40 kbit/s, fully interoperable, GFSK modulation, and a range of approximately 100 feet (or 30 meters) assuming "open air" conditions, with reduced range indoors depending on building materials, etc. The Z-Wave radio uses the 900 MHz ISM band: 908.42 MHz (United States); 868.42 MHz (Europe); 919.82 MHz (Hong Kong); and 921.42 MHz (Australia/New Zealand).

Z-Wave uses a source-routed mesh network topology and has one or more master controllers that control routing and security. The devices can communicate to another by using intermediate nodes to actively route around, and circumvent household obstacles or radio dead spots that might occur. A message from node A to node C can be successfully delivered even if the two nodes are not within range, providing that a third node B can communicate with nodes A and C. If the preferred route is unavailable, the message originator will attempt other routes until a path is found to the "C" node. Therefore, a Z-Wave network can span much farther than the radio range of a single unit; however, with several of these hops, a delay may be introduced between the control command and the desired result. In order for Z-Wave units to be able to route unsolicited messages, they cannot be in sleep mode. Therefore, most battery-operated devices are not designed as repeater units. A Z-Wave network can consist of up to 232 devices with the option of bridging networks if more devices are required.

WWAN. Any wireless network herein may be a Wireless Wide Area Network (WWAN) such as a wireless broadband network, and the WWAN port may be an antenna and the WWAN transceiver may be a wireless modem. The wireless network may be a satellite network, the antenna may be a satellite antenna, and the wireless modem may be a satellite modem. The wireless network may be a WiMAX network such as according to, compatible with, or based on, IEEE 802.16-2009, the antenna may be a WiMAX antenna, and the wireless modem may be a WiMAX modem. The wireless network may be a cellular telephone network, the antenna may be a cellular antenna, and the wireless modem may be a cellular modem. The cellular telephone network may be a Third Generation (3G) network, and may use UMTS W-CDMA, UMTS HSPA, UMTS TDD, CDMA2000 1×RTT, CDMA2000 EV-DO, or GSM EDGE-Evolution. The cellular telephone network may be a Fourth Generation (4G) network and may use or be compatible with HSPA+, Mobile WiMAX, LTE, LTE-Advanced, MBWA, or may be compatible with, or based on, IEEE 802.20-2008.

WLAN. Wireless Local Area Network (WLAN), is a popular wireless technology that makes use of the Industrial, Scientific and Medical (ISM) frequency spectrum. In the US, three of the bands within the ISM spectrum are the A band, 902-928 MHz; the B band, 2.4-2.484 GHz (a.k.a. 2.4 GHz); and the C band, 5.725-5.875 GHz (a.k.a. 5 GHz). Overlapping and/or similar bands are used in different regions such as Europe and Japan. In order to allow interoperability between equipment manufactured by different vendors, few WLAN standards have evolved, as part of the IEEE 802.11 standard group, branded as WiFi (www.wi-fi.org). IEEE 802.11b describes a communication using the 2.4 GHz frequency band and supporting communication rate of 11 Mb/s, IEEE 802.11a uses the 5 GHz frequency band to carry 54 MB/s and IEEE 802.11g uses the 2.4 GHz band to support 54 Mb/s. The WiFi technology is further described in a publication entitled: "WiFi Technology" by Telecom Regulatory Authority, published on July 2003, which is incorporated in its entirety for all purposes as if fully set forth herein. The IEEE 802 defines an ad-hoc connection between two or more devices without using a wireless access point: the devices communicate directly when in range. An ad hoc network offers peer-to-peer layout and is commonly used in situations such as a quick data exchange or a multiplayer LAN game, because the setup is easy and an access point is not required.

A node/client with a WLAN interface is commonly referred to as STA (Wireless Station/Wireless client). The STA functionality may be embedded as part of the data unit, or alternatively be a dedicated unit, referred to as bridge, coupled to the data unit. While STAs may communicate without any additional hardware (ad-hoc mode), such network usually involves Wireless Access Point (a.k.a. WAP or AP) as a mediation device. The WAP implements the Basic Stations Set (BSS) and/or ad-hoc mode based on Independent BSS (IBSS). STA, client, bridge and WAP will be collectively referred to hereon as WLAN unit. Bandwidth allocation for IEEE 802.11g wireless in the U.S. allows multiple communication sessions to take place simultaneously, where eleven overlapping channels are defined spaced 5 MHz apart, spanning from 2412 MHz as the center frequency for channel number 1, via channel 2 centered at 2417 MHz and 2457 MHz as the center frequency for channel number 10, up to channel 11 centered at 2462 MHz. Each channel bandwidth is 22 MHz, symmetrically (+/−11 MHz) located around the center frequency. In the transmission path, first the baseband signal (IF) is generated based on the data to be transmitted, using 256 QAM (Quadrature Amplitude Modulation) based OFDM (Orthogonal Frequency Division Multiplexing) modulation technique, resulting a 22 MHz (single channel wide) frequency band signal. The signal is then up converted to the 2.4 GHz (RF) and placed in the center frequency of required channel, and transmitted to the air via the antenna. Similarly, the receiving path comprises a received channel in the RF spectrum, down converted to the baseband (IF) wherein the data is then extracted.

In order to support multiple devices and using a permanent solution, a Wireless Access Point (WAP) is typically used. A Wireless Access Point (WAP, or Access Point—AP) is a device that allows wireless devices to connect to a wired network using Wi-Fi, or related standards. The WAP usually connects to a router (via a wired network) as a standalone device, but can also be an integral component of the router itself. Using Wireless Access Point (AP) allows users to add devices that access the network with little or no cables. A WAP normally connects directly to a wired Ethernet connection, and the AP then provides wireless connections using radio frequency links for other devices to utilize that wired connection. Most APs support the connection of multiple wireless devices to one wired connection. Wireless access typically involves special security considerations, since any device within a range of the WAP can attach to the network. The most common solution is wireless traffic encryption. Modern access points come with built-in encryption such as Wired Equivalent Privacy (WEP) and Wi-Fi Protected Access (WPA), typically used with a pass-word or a passphrase. Authentication in general, and a WAP authentication in particular, is used as the basis for authorization, which determines whether a privilege may be granted to a particular user or process, privacy, which keeps information from becoming known to non-participants, and non-repudiation, which is the inability to deny having done something that was authorized to be done based on the authentication. An authentication in general, and a WAP authentication in particular, may use an authentication server that provides a network service that applications may use to authenticate the credentials, usually account names and passwords of their users. When a client submits a valid set of credentials, it receives a cryptographic ticket that it can subsequently be used to access various services. Authentication algorithms include passwords, Kerberos, and public key encryption.

Prior art technologies for data networking may be based on single carrier modulation techniques, such as AM (Amplitude Modulation), FM (Frequency Modulation), and PM (Phase Modulation), as well as bit encoding techniques such as QAM (Quadrature Amplitude Modulation) and QPSK (Quadrature Phase Shift Keying). Spread spectrum technologies, to include both DSSS (Direct Sequence Spread Spectrum) and FHSS (Frequency Hopping Spread Spectrum) are known in the art. Spread spectrum commonly employs Multi-Carrier Modulation (MCM) such as OFDM (Orthogonal Frequency Division Multiplexing). OFDM and other spread spectrum are commonly used in wireless communication systems, particularly in WLAN networks.

BAN. A wireless network may be a Body Area Network (BAN) according to, or based on, IEEE 802.15.6 standard, and communicating devices may comprise a BAN interface that may include a BAN port and a BAN transceiver. The BAN may be a Wireless BAN (WBAN), and the BAN port may be an antenna and the BAN transceiver may be a WBAN modem. Bluetooth. Bluetooth is a wireless technology standard for exchanging data over short distances (using short-wavelength UHF radio waves in the ISM band from 2.4 to 2.485 GHz) from fixed and mobile devices, and building personal area networks (PANs). It can connect several devices, overcoming problems of synchronization. A Personal Area Network (PAN) may be according to, compatible with, or based on, Bluetooth™ or IEEE 802.15.1-2005 standard. A Bluetooth controlled electrical appliance is described in U.S. Patent Application No. 2014/0159877 to Huang entitled: "Bluetooth Controllable Electrical Appliance", and an electric power supply is described in U.S. Patent Application No. 2014/0070613 to Garb et al. entitled: "Electric Power Supply and Related Methods", which are both incorporated in their entirety for all purposes as if fully set forth herein. Any Personal Area Network (PAN) may be according to, compatible with, or based on, Bluetooth™ or IEEE 802.15.1-2005 standard. A Bluetooth controlled electrical appliance is described in U.S. Patent Application No. 2014/0159877 to Huang entitled: "Bluetooth Controllable Electrical Appliance", and an electric power supply is described in U.S. Patent Application No. 2014/0070613 to Garb et al. entitled: "Electric Power Supply and Related Methods", which are both incorporated in their entirety for all purposes as if fully set forth herein.

Bluetooth operates at frequencies between 2402 and 2480 MHz, or 2400 and 2483.5 MHz including guard bands 2 MHz wide at the bottom end and 3.5 MHz wide at the top. This is in the globally unlicensed (but not unregulated) Industrial, Scientific and Medical (ISM) 2.4 GHz short-range radio frequency band. Bluetooth uses a radio technology called frequency-hopping spread spectrum. Bluetooth divides transmitted data into packets, and transmits each packet on one of 79 designated Bluetooth channels. Each channel has a bandwidth of 1 MHz. It usually performs 800 hops per second, with Adaptive Frequency-Hopping (AFH) enabled. Bluetooth low energy uses 2 MHz spacing, which accommodates 40 channels. Bluetooth is a packet-based protocol with a master-slave structure. One master may communicate with up to seven slaves in a piconet. All devices share the master's clock. Packet exchange is based on the basic clock, defined by the master, which ticks at 312.5 μs intervals. Two clock ticks make up a slot of 625 μs, and two slots make up a slot pair of 1250 μs. In the simple case of single-slot packets the master transmits in even slots and receives in odd slots. The slave, conversely, receives in even slots and transmits in odd slots. Packets may be 1, 3 or 5 slots long, but in all cases the master's transmission begins in even slots and the slave's in odd slots.

A master Bluetooth device can communicate with a maximum of seven devices in a piconet (an ad-hoc computer network using Bluetooth technology), though not all devices reach this maximum. The devices can switch roles, by agreement, and the slave can become the master (for example, a headset initiating a connection to a phone necessarily begins as master—as initiator of the connection—but may subsequently operate as slave). The Bluetooth Core Specification provides for the connection of two or more piconets to form a scatternet, in which certain devices simultaneously play the master role in one piconet and the slave role in another. At any given time, data can be transferred between the master and one other device (except for the little-used broadcast mode). The master chooses which slave device to address; typically, it switches rapidly from one device to another in a round-robin fashion. Since it is the master that chooses which slave to address, whereas a slave is supposed to listen in each receive slot, being a master is a lighter burden than being a slave. Being a master of seven slaves is possible; being a slave of more than one master is difficult.

Bluetooth Low Energy. Bluetooth low energy (Bluetooth LE, BLE, marketed as Bluetooth Smart) is a wireless personal area network technology designed and marketed by the Bluetooth Special Interest Group (SIG) aimed at novel applications in the healthcare, fitness, beacons, security, and home entertainment industries. Compared to Classic Bluetooth, Bluetooth Smart is intended to provide considerably reduced power consumption and cost while maintaining a similar communication range. Bluetooth low energy is described in a Bluetooth SIG published Dec. 2, 2014 standard Covered Core Package version: 4.2, entitled: *"Master Table of Contents & Compliance Requirements—Specification Volume 0"*, and in an article published 2012 in Sensors [ISSN 1424-8220] by Caries Gomez et al. [Sensors 2012, 12, 11734-11753; doi:10.3390/s120211734] entitled: *"Overview and Evaluation of Bluetooth Low Energy: An Emerging Low-Power Wireless Technology"*, which are both incorporated in their entirety for all purposes as if fully set forth herein.

Bluetooth Smart technology operates in the same spectrum range (the 2.400 GHz-2.4835 GHz ISM band) as Classic Bluetooth technology, but uses a different set of channels. Instead of the Classic Bluetooth 79 1-MHz channels, Bluetooth Smart has 40 2-MHz channels. Within a channel, data is transmitted using Gaussian frequency shift modulation, similar to Classic Bluetooth's Basic Rate scheme. The bit rate is 1 Mbit/s, and the maximum transmit power is 10 mW. Bluetooth Smart uses frequency hopping to counteract narrowband interference problems. Classic Bluetooth also uses frequency hopping but the details are different; as a result, while both FCC and ETSI classify Bluetooth technology as an FHSS scheme, Bluetooth Smart is classified as a system using digital modulation techniques or a direct-sequence spread spectrum. All Bluetooth Smart devices use the Generic Attribute Profile (GATT). The application programming interface offered by a Bluetooth Smart aware operating system will typically be based around GATT concepts.

WMN. A Wireless Mesh Network (WMN) and Wireless Distribution Systems (WDS) are known in the art to be a communication network made up of clients, mesh routers and gateways organized in a mesh topology and connected using radio. Such wireless networks may be based on DSR as the routing protocol. WMNs are standardized in IEEE 802.11s and described in a slide-show by W. Steven Conner, Intel Corp. et al. entitled: "*IEEE 802.11s Tutorial*" presented at the IEEE 802 Plenary, Dallas on Nov. 13, 2006, in a slide-show by Eugen Borcoci of University Politehnica Bucharest, entitled: "*Wireless Mesh Networks Technologies: Architectures, Protocols, Resource Management and Applications*", presented in INFOWARE Conference on Aug. 22-29, 2009 in Cannes, France, and in an IEEE Communication magazine paper by Joseph D. Camp and Edward W. Knightly of Electrical and Computer Engineering, Rice University, Houston, TX, USA, entitled: "*The IEEE 802.11s Extended Service Set Mesh Networking Standard*", which are incorporated in their entirety for all purposes as if fully set forth herein. The arrangement described herein can be equally applied to such wireless networks, wherein two clients exchange information using different paths by using mesh routers as intermediate and relay servers. Commonly in wireless networks, the routing is based on MAC addresses. Hence, the above discussion relating to IP addresses applies in such networks to using the MAC addresses for identifying the client originating the message, the mesh routers (or gateways) serving as the relay servers, and the client serving as the ultimate destination computer.

Cellular. Cellular telephone network may be according to, compatible with, or may be based on, a Third Generation (3G) network that uses UMTS W-CDMA, UMTS HSPA, UMTS TDD, CDMA2000 1×RTT, CDMA2000 EV-DO, or GSM EDGE-Evolution. The cellular telephone network may be a Fourth Generation (4G) network that uses HSPA+, Mobile WiMAX, LTE, LTE-Advanced, MBWA, or may be based on or compatible with IEEE 802.20-2008.

NFC. Any wireless communication herein may be partly or in full in accordance with, or based on, short-range communication such as Near Field Communication (NFC), having a theoretical working distance of 20 centimeters and a practical working distance of about 4 centimeters, and commonly used with mobile devices, such as smartphones. The NFC typically operates at 13.56 MHz as defined in IS O/IEC 18000-3 air interface, and at data rates ranging from 106 kbit/s to 424 kbit/s. NFC commonly involves an initiator and a target; the initiator actively generates an RF field that may power a passive target. NFC peer-to-peer communication is possible, provided both devices are powered.

The NFC typically supports passive and active modes of operation. In passive communication mode, the initiator device provides a carrier field and the target device answers by modulating the existing field, and the target device may draw its operating power from the initiator-provided electromagnetic field, thus making the target device a transponder. In active communication mode, both devices typically have power supplies, and both initiator and target devices communicate by alternately generating their own fields, where a device deactivates its RF field while it is waiting for data. NFC typically uses Amplitude-Shift Keying (ASK), and employs two different schemes to transfer data. At the data transfer rate of 106 kbit/s, a modified Miller coding with 100% modulation is used, while in all other cases Manchester coding is used with a modulation ratio of 10%.

The NFC communication may be partly or in full in accordance with, or based on, NFC standards ISO/IEC 18092 or ECMA-340 entitled: "Near Field Communication Interface and Protocol-1 (NFCIP-1)", and ISO/IEC 21481 or ECMA-352 standards entitled: "*Near Field Communication Interface and Protocol-2 (NFCIP-2)*". The NFC technology is described in ECMA International white paper Ecma/TC32-TG19/2005/012 entitled: "*Near Field Communication—White paper*", in Rohde&Schwarz White Paper 1MA182_4e entitled: "*Near Field Communication (NFC) Technology and Measurements White Paper*", and in Jan Kremer Consulting Services (JKCS) white paper entitled: "*NFC—Near Field Communication—White paper*", which are all incorporated in their entirety for all purposes as if fully set forth herein.

Random. Randomness is commonly implemented by using random numbers, defined as a sequence of numbers or symbols that lack any pattern and thus appear random, are often generated by a random number generator. Randomness for security is also described in IETF RFC 1750 "*Randomness Recommendations for Security*" (December 1994), which is incorporated in its entirety for all purposes as if fully set forth herein. A random number generator (having either analog or digital output) can be hardware based, using a physical process such as thermal noise, shot noise, nuclear decaying radiation, photoelectric effect or other quantum phenomena. Alternatively, or in addition, the generation of the random numbers can be software based, using a processor executing an algorithm for generating pseudo-random numbers which approximates the properties of random numbers.

The term 'random' herein is intended to cover not only pure random, non-deterministically and non-predicted generated signals, but also pseudo-random, deterministic signals such as the output of a shift-register arrangement provided with a feedback circuit as used to generate pseudo-random binary signals or as scramblers, and chaotic signals, and where a randomness factor may be used.

A digital random signal generator (known as random number generator) wherein numbers in binary form replaces the analog voltage value output may be used for any randomness. One approach to random number generation is based on using linear feedback shift registers. An example of random number generators is disclosed in U.S. Pat. No. 7,124,157 to Ikake entitled: "Random Number Generator", in U.S. Pat. No. 4,905,176 to Schulz entitled: "Random Number Generator Circuit", in U.S. Pat. No. 4,853,884 to Brown et al. entitled: "Random Number Generator with Digital Feedback" and in U.S. Pat. No. 7,145,933 to Szajnowski entitled: "Method and Apparatus for generating Random signals", which are incorporated in its entirety for all purposes as if fully set forth herein.

A digital random signal generator may be based on 'True Random Number Generation IC RPG100/RPG100B' available from FDK Corporation and described in the data sheet 'Physical Random number generator RPG100. RPG100B' REV. 08 publication number HM-RAE106-0812, which is incorporated in its entirety for all purposes as if fully set forth herein. The digital random signal generator can be hardware based, generating random numbers from a natural physical process or phenomenon, such as the thermal noise of semiconductor which has no periodicity. Typically, such hardware random number generators are based on microscopic phenomena such as thermal noise, shot noise, nuclear decaying radiation, photoelectric effect or other quantum phenomena, and typically contain a transducer to convert some aspect of the physical phenomenon to an electrical signal, an amplifier and other electronic to bring the output into a signal that can be converted into a digital representation by an analog to digital converter. In the case where digitized serial random number signals are generated, the output is converted to parallel, such as 8 bits data, with 256 values of random numbers (values from 0 to 255). Alternatively, a digital random signal generator may be software (or firmware) based, such as pseudo-random number generators. Such generators include a processor for executing software that includes an algorithm for generating numbers, which approximates the properties of random numbers. The random signal generator (either analog or digital) may output a signal having uniform distribution, in which there is a substantially or purely equal probability of a signal falling between two defined limits, having no appearance outside these limits. However, Gaussian and other distribution may be equally used.

Electronic circuits and components are described in a book by Wikipedia entitled: "Electronics" downloaded from en.wikibooks.org dated Mar. 15, 2015, which is incorporated in its entirety for all purposes as if fully set forth herein.

Smartphone. A mobile phone (also known as a cellular phone, cell phone, smartphone, or hand phone) is a device which can make and receive telephone calls over a radio link whilst moving around a wide geographic area, by connecting to a cellular network provided by a mobile network operator. The calls are to and from the public telephone network, which includes other mobiles and fixed-line phones across the world. The Smartphones are typically hand-held and may combine the functions of a personal digital assistant (PDA), and may serve as portable media players and camera phones with high-resolution touchscreens, web browsers that can access, and properly display, standard web pages rather than just mobile-optimized sites, GPS navigation, Wi-Fi and mobile broadband access. In addition to telephony, the Smartphones may support a wide variety of other services such as text messaging, MMS, email, Internet access, short-range wireless communications (infrared, Bluetooth), business applications, gaming and photography.

An example of a contemporary smartphone is model iPhone 6 available from Apple Inc., headquartered in Cupertino, California, U.S.A. and described in iPhone 6 technical specification (retrieved October 2015 from www.apple.com/iphone-6/specs/), and in a User Guide dated 2015 (019-00155/2015-06) by Apple Inc. entitled: "*iPhone User Guide For iOS 8.4 Software*", which are both incorporated in their entirety for all purposes as if fully set forth herein. Another example of a smartphone is Samsung Galaxy S6 available from Samsung Electronics headquartered in Suwon, South-Korea, described in the user manual numbered English (EU), March 2015 (Rev. 1.0) entitled: "*SM-G925F SM-G925FQ SM-G925I User Manual*" and having features and specification described in "*Galaxy S6 Edge—Technical Specification*" (retrieved October 2015 from www.samsung.com/us/explore/galaxy-s-6-features-and-specs), which are both incorporated in their entirety for all purposes as if fully set forth herein.

Instant Messaging. Instant Messaging (IM) is a type of online chat, which offers real-time text transmission over the Internet. Short messages are typically transmitted bi-directionally between two parties, when each user chooses to complete a thought and select "send". Some IM applications can use push technology to provide real-time text, which transmits messages character by character, as they are composed. More advanced instant messaging can add file transfer, clickable hyperlinks, Voice over IP, or video chat. Instant messaging systems typically facilitate connections between specified known users (often using a contact list also known as a "buddy list" or "friend list"). Depending on the IM protocol, the technical architecture can be peer-to-peer (direct point-to-point transmission) or client-server (a central server retransmits messages from the sender to the communication device).

Instant messaging is a set of communication technologies used for text-based communication between two or more participants over the Internet or other types of networks. IM-chat happens in real-time. Of importance is that online chat and instant messaging differ from other technologies such as email due to the perceived quasi-synchrony of the communications by the users. Some systems permit messages to be sent to users not then 'logged on' (offline messages), thus removing some differences between IM and email (often done by sending the message to the associated email account). Various IP technologies are described in a thesis by Tim van Lokven (Jan. 23, 2011) entitled: "*Review and Comparison of Instant Messaging Protocols*", which is incorporated in its entirety for all purposes as if fully set forth herein.

Text Messaging. Text messaging, or texting, is the act of composing and sending brief, electronic messages between two or more mobile phones, or fixed or portable devices over a phone network. The term commonly refers to messages sent using the Short Message Service (SMS), but may include messages containing image, video, and sound content (known as MMS messages). The sender of a text message is known as a texter, while the service itself has different colloquialisms depending on the region. Text messages can be used to interact with automated systems, for example, to order products or services, or to participate in contests. Advertisers and service providers use direct text marketing to message mobile phone users about promotions, payment due dates, et cetera instead of using mail, e-mail or voicemail. In a straight and concise definition for the purposes of this English language article, text messaging by phones or mobile phones should include all 26 letters of the alphabet and 10 numerals, i.e., alpha-numeric messages, or text, to be sent by texter or received by the textee. SMS messaging gateway providers can provide gateway-to-mobile (Mobile Terminated—MT) services. Some suppliers can also supply mobile-to-gateway (text-in or Mobile Originated/MO services).

SMS. Short Message Service (SMS) is a text messaging service component of phone, Web, or mobile communication systems. It uses standardized communications protocols to allow fixed line or mobile phone devices to exchange short text messages. SMS as used on modern handsets as part of the Global System for Mobile Communications (GSM) series of standards as a means of sending messages of up to 160 characters to and from GSM mobile handsets. Though most SMS messages are mobile-to-mobile text messages, support for the service has expanded to include other mobile technologies, such as ANSI CDMA networks and Digital AMPS, as well as satellite and landline networks. The Short Message Service-Point to Point (SMS-PP) is standardized by the 3GPP as TS 23.040 and 3GPP TS 23.041, which define the Short Message Service-Cell Broadcast (SMS-CB), which allows messages (advertising, public information, etc.) to be broadcast to all mobile users in a specified geographical area.

Messages are sent to a Short Message Service Center (SMSC), which provides a "store and forward" mechanism. It attempts to send messages to the SMSC recipients, and if a recipient is not reachable, the SMSC queues the message for later retry. Some SMSCs also provide a "forward and forget" option where transmission is tried only once. Both Mobile Terminated (MT, for messages sent to a mobile handset) and Mobile Originating (MO, for those sent from the mobile handset) operations are supported, and the message delivery is "best effort" scheme, so there are no guarantees that a message will actually be delivered to its recipient, but delay or complete loss of a message is uncommon. SMS is a stateless communication protocol in which every SMS message is considered entirely independent of other messages. Enterprise applications using SMS as a communication channel for stateful dialogue (where an MO reply message is paired to a specific MT message) requires that session management be maintained external to the protocol through proprietary methods as Dynamic Dialogue Matrix (DDM).

The Short Message Service is realized by the use of the Mobile Application Part (MAP) of the SS #7 protocol, with Short Message protocol elements being transported across the network as fields within the MAP messages. These MAP messages may be transported using 'traditional' TDM based signaling, or over IP using SIGTRAN and an appropriate adaptation layer. The Short Message protocol itself is defined by 3GPP TS 23.040 for the Short Message Service-Point-to-Point (SMS-PP), and 3GPP TS 23.041 for the Cell Broadcast Service (CBS). SMS is further described in a 3GPP Technical Specification 3GPP TS 22.011 (v143.0.0, 2015 September) entitled: "3rd Generation Partnership Project; Technical Specification Group Services and System Aspects; Service accessibility (Release 14)", which is incorporated in its entirety for all purposes as if fully set forth herein.

MMS. Multimedia Messaging Service (MMS) is an Open Mobile Alliance (OMA) standard way to send messages that include multimedia content to and from mobile phones over a cellular network. It extends the core SMS (Short Message Service) capability that allowed exchange of text messages only up to 160 characters in length. The most popular use is to send photographs from camera-equipped handsets, and is used on a commercial basis by media companies as a method of delivering news and entertainment content and by retail brands as a tool for delivering scannable coupon codes, product images, videos and other information. Unlike text only SMS, commercial MMS can deliver a variety of media including up to forty seconds of video, one image, multiple images via slideshow, or audio plus unlimited characters.

MMS messages are delivered differently from SMS. The first step is for the sending device to encode the multimedia content in a fashion similar to sending a MIME e-mail (MIME content formats are defined in the MMS Message Encapsulation specification). The message is then forwarded to the carrier MMS store and forward server, known as the MMSC (Multimedia Messaging Service Centre). If the receiver is on another carrier, then the MMSC acts as a relay, and forwards the message to the MMSC of the recipient's carrier using the Internet.

Once the recipient MMSC has received a message, it first determines whether the receiver's handset is "MMS capable", that it supports the standards for receiving MMS. If so, the content is extracted and sent to a temporary storage server with an HTTP front-end. An SMS "control message" (ping) containing the URL of the content is then sent to the recipient's handset to trigger the receiver's WAP browser to open and receive the content from the embedded URL. Several other messages are exchanged to indicate status of the delivery attempt. Before delivering content, some MMSCs also include a conversion service known as "content adaptation" that will attempt to modify the multimedia content into a format suitable for the receiver. E-mail and web-based gateways to the MMS (and SMS) system are common. On the reception side, the content servers can typically receive service requests from both WAPs and normal HTTP browsers, so delivery via the web is simple. For sending from external sources to handsets, most carriers allow MIME encoded message to be sent to the receiver's phone number with a special domain. MMS is described in a 3GPP technical specification 3GPP TS 23.140 V6.16.0 (2009 March) entitled: "3rd Generation Partnership Project; Technical Specification Group Core Network and Terminals; Multimedia Messaging Service (MMS); Functional description; Stage 2 (Release 6)", which is incorporated in its entirety for all purposes as if fully set forth herein.

Facebook. Facebook Messenger is an instant messaging service and software application which provides text and voice communication. Integrated with Facebook web-based Chat feature and built on the open MQTT protocol, Messenger lets Facebook users chat with friends both on mobile and on the main website. Facebook is described in a guide by American Majority organization (retrieved October 2015 from http://cmrw.org/) entitled: "facebook—A Beginner's Guide", which is incorporated in its entirety for all purposes as if fully set forth herein.

Twitter. Twitter is an online social networking service by Twitter Inc. (headquartered in San Francisco) that enables users to send and read short 140-character messages called "tweets". Registered users can read and post tweets, but unregistered users can only read them. Users access Twitter through the website interface, SMS, or mobile device applications. Tweets are publicly visible by default, but senders can restrict message delivery to just their followers. Users can tweet via the Twitter website, compatible external applications (such as for smartphones), or by Short Message Service (SMS) available in certain countries. The action of forwarding a tweet via Twitter is referred to as Retweeting. Both tweets and retweets can be tracked to see which ones are most popular. Users may subscribe to other users tweets—this is known as "following" and subscribers are known as "followers" or "tweeps", a portmanteau of Twitter and peeps. Users can check the people who are unsubscribing them on Twitter ("unfollowing") via various services. In addition, users can block those who have followed them. As a social network, Twitter revolves around the principle of followers. When you choose to follow another Twitter user that user's tweets appear in reverse chronological order on your main Twitter page. Individual tweets are registered under unique IDs using software called snowflake, and geolocation data is added using 'Rockdove'. The URL t.co then checks for a spam link and shortens the URL. Next, the tweets are stored in a MySQL database using Gizzard, and the user receives acknowledgement that the tweets were sent. Tweets are then sent to search engines via the Firehose API. The process itself is managed by FlockDB and takes an average of 350 ms, and the service's Application Programming Interface (API) allows other web services and applications to integrate with Twitter. Twitter is described in a guide (retrieved October 15 from https://g.twimg.com/business/pdfs/Twitter_Smallbiz_Guide.pdf) by Twitter, Inc., entitled: "*Twitter for Small Business—A GUIDE TO GET STARTED*", which is incorporated in its entirety for all purposes as if fully set forth herein.

WhatsApp. WhatsApp is an instant messaging app developed by WhatsApp Inc. (headquartered in Mountain View, California) for smartphones that operates under a subscription business model. The proprietary, cross-platform app uses the Internet to send text messages, images, video, user location, and audio media messages. WhatsApp uses a customized version of the open standard Extensible Messaging and Presence Protocol (XMPP). Upon installation, it creates a user account using one's phone number as the username (Jabber ID: [phone number]@ s.whatsapp.net) WhatsApp software automatically compares all the phone numbers from the device's address book with its central database of WhatsApp users to automatically add contacts to the user's WhatsApp contact list.

Multimedia messages are sent by uploading the image, audio or video to be sent to an HTTP server and then sending a link to the content along with its Base64 encoded thumbnail (if applicable). WhatsApp follows a 'store and forward' mechanism for exchanging messages between two users. When a user sends a message, it first travels to the WhatsApp server where it is stored. Then the server repeatedly requests the receiver acknowledge receipt of the message. As soon as the message is acknowledged, the server drops the message; it is no longer available in database of server. The WhatsApp service is described in an article published (Aug. 30, 2013) on MOBILE HCI 2013—COLLABORATION AND COMMUNICATION by Karen Church and Rodrigo de Oliveira (both of Telefonica Research) entitled: "*What's up with WhatsApp? Comparing Mobile Instant-Messaging Behaviors with Traditional SMS*", which is incorporated in its entirety for all purposes as if fully set forth herein.

Viber. Viber is an instant messaging and Voice over IP (VoIP) app for smartphones developed by Viber Media, where in addition to instant messaging, users can exchange images, video and audio media messages. Viber works on both 3G/4G and Wi-Fi networks. Viber includes text, picture and video messaging across all platforms, with voice calling available only to iPhone, Android and Microsoft's Windows Phone. The application user interface includes tab bar on the bottom, giving access to messages, recent calls, contact, the keypad and a button for accessing more options. Upon installation, it creates a user account using one's phone number as username. Viber synchronizes with the phone's address book, so users do not need to add contacts in a separate book. Since all users are registered with their phone number, the software returns all Viber users among the user contacts.

Mail Server. Mail server (a.k.a. Email server, Electronic Mail server, Mail Exchanger—MX) refer to a server operating as an electronic post office for email exchanging across networks, commonly performing the server-side of an MTA function. A Message Transfer Agent (or Mail Transfer Agent—MTA), or mail relay is a software that transfers electronic mail messages from one computer to another using a client-server application architecture. An MTA typically implements both the client (sending) and server (receiving) portions of the Simple Mail Transfer Protocol (SMTP). The Internet mail architecture is described in IETF RFC 5598 entitled: "*Internet Mail Architecture*", and the SMTP protocol is described in IETF RFC 5321 entitled: "*Simple Mail Transfer Protocol*" and in IETF RFC 7504 entitled: "*SMTP 521 and 556 Reply Codes*", which are all incorporated in their entirety for all purposes as if fully set forth herein.

The Domain Name System (DNS) typically associates a mail server to a domain with mail exchanger (MX) resource records, containing the domain name of a host providing MTA services. A message transfer agent receives mail from either another MTA, a Mail Submission Agent (MSA), or a Mail User Agent (MUA). The transmission details are specified by the Simple Mail Transfer Protocol (SMTP). When a recipient mailbox of a message is not hosted locally, the message is relayed, that is, forwarded to another MTA. Every time an MTA receives an email message, it adds a 'Received' trace header field to the top of the header of the message, thereby building a sequential record of MTAs handling the message. The process of choosing a target MTA for the next hop is also described in SMTP, but can usually be overridden by configuring the MTA software with specific routes. Internet mail schemes are described in IEEE Annals of the History of Computing paper published 2008 by the IEEE Computer Society [1058-6180/08], authored by Craig Partridge of BBN Technologies entitled: "The technical Development of Internet Mail", which is incorporated in its entirety for all purposes as if fully set forth herein.

A mail server infrastructure consists of several components that work together to send, relay, receive, store, and deliver email, and typically uses various Internet standard protocols for sending and retrieving email, such as the Internet standard protocol Simple Mail Transfer Protocol (SMTP) for sending email, the Internet standard protocols for retrieving email Post Office Protocol (POP), and Internet Message Access Protocol version 4 (IMAPv4). An example of a mail server software is 'Microsoft Exchange Server 2013' (available from Microsoft Corporation, headquartered in Redmond, Washington, U.S.A.), described in 'Pocket Consultant' book [ISBN: 978-0-7356-8168-2] published 2013 by Microsoft Press and entitled: "*Microsoft Exchange Server* 2013—*Configuration & Clients*", which is incorporated in its entirety for all purposes as if fully set forth herein.

The POP is specified in IETF RFC 1939 entitled: "*Post Office Protocol*", and updated specification with an extension mechanism is described in IETF RFC 2449 entitled: "*POP3 Extension Mechanism*", and an authentication mechanism is described in IETF RFC 1734 entitled: "*POP3 AUTHentication command*", which are all incorporated in their entirety for all purposes as if fully set forth herein. IMAP4 clients can create, rename, and/or delete mailboxes (usually presented to the user as folders) on the mail server, and copy messages between mailboxes, and this multiple mailbox support also allows servers to access shared and public folders. IMAP4 is described in IETF RFC 3501 entitled: "*INTERNET MESSAGE ACCESS PROTOCOL—VERSION 4rev1*", and the IMAP4 Access Control List (ACL) Extension may be used to regulate access rights, and is described in IETF RFC 4314 entitled: "*IMAP4 Access Control List (ACL) Extension*", which are both incorporated in their entirety for all purposes as if fully set forth herein.

Mail servers may be operated, or used by mailbox providers, and mail servers are described in U.S. Pat. No. 5,832,218 to Gibbs et al. entitled: "Client/server Electronic Mail System for Providing Off-Line Client Utilization and Seamless Server Resynchronization", in U.S. Pat. No. 6,081,832 to Gilchrist et al. entitled: "Object Oriented Mail Server Framework Mechanism", in U.S. Pat. No. 7,136,901 to Chung et al. entitled: "Electronic Mail Server", and in U.S.

Pat. No. 7,818,383 to Kodama entitled: "E-Mail Server", which are all incorporated in their entirety for all purposes as if fully set forth herein.

XMPP. Extensible Messaging and Presence Protocol (XMPP) is an open standard communications protocol for message-oriented middleware based on XML (Extensible Markup Language) that enables the near-real-time exchange of structured yet extensible data between any two or more network entities. Designed to be extensible, the protocol has also been used for publish-subscribe systems, signaling for VoIP, video, file transfer, gaming, Internet of Things (IoT) applications such as the smart grid, and social networking services. The XMPP network uses a client-server architecture where clients do not talk directly to one another. The model is decentralized and anyone can run a server. By design, there is no central authoritative. Every user on the network has a unique XMPP address, called JID (for historical reasons, XMPP addresses are often called Jabber IDs). The JID is structured like an email address with a username and a domain name (or IP address) for the server where that user resides, separated by an at sign (@), such as username@example.com. Since a user may wish to log in from multiple locations, they may specify a resource. A resource identifies a particular client belonging to the user (for example home, work, or mobile). This may be included in the JID by appending a slash followed by the name of the resource. For example, the full JID of a user's mobile account could be username@example.com/mobile. Each resource may have specified a numerical value called priority. Messages simply sent to username@example.com will go to the client with highest priority, but those sent to username@example.com/mobile will go only to the mobile client. The highest priority is the one with largest numerical value. JIDs without a username part are also valid, and may be used for system messages and control of special features on the server. A resource remains optional for these JIDs as well. XMPP is described in IETF RFC 6120 entitled: "*Extensible Messaging and Presence Protocol (XMPP): Core*", which describes client-server messaging using two open-ended XML streams, in IETF RFC 6121 entitled: "*Extensible Messaging and Presence Protocol (XMPP): Instant Messaging and Presence*", which describes instant messaging (IM), the most common application of XMPP, and in IETF RFC 6122 entitled: "*Extensible Messaging and Presence Protocol (XMPP): Address Format*", which describes the rules for XMPP addresses, also called JabberIDs or JIDs.

SIMPLE. The Session Initiation Protocol (SIP) for Instant Messaging and Presence Leveraging Extensions (SIMPLE) is an open standard Instant Messaging (IM) and presence protocol suite based on Session Initiation Protocol (SIP) managed by the Internet Engineering Task Force. The SIMPLE presence use the core protocol machinery that provides the actual SIP extensions for subscriptions, notifications and publications. IETF RFC 6665 defines the SUBSCRIBE and NOTIFY methods, where SUBSCRIBE allows to subscribe to an event on a server, and the server responds with NOTIFY whenever the event come up. IETF RFC 3856 defines how to make use of SUBSCRIBE/NOTIFY for presence. Two models are defined: an end-to-end model in which each User Agent handles presence subscriptions itself, and a centralized model. The message PUBLISH (IETF RFC 3903) allows User Agents to inform the presence server about their subscription states.

SIP defines two modes of instant messaging: The Page Mode makes use of the SIP method MESSAGE, as defined in IETF RFC 3428. This mode establishes no sessions, and the Session Mode. The Message Session Relay Protocol (RFC 4975, RFC 4976) is a text-based protocol for exchanging arbitrarily-sized content between users, at any time. An MSRP session is set up by exchanging certain information, such as an MSRP URI, within SIP and SDP signaling. SIMPLE is described in IETF RFC 6914 entitled: "SIMPLE Made Simple: An Overview of the IETF Specifications for Instant Messaging and Presence Using the Session Initiation Protocol (SIP)", which is incorporated in its entirety for all purposes as if fully set forth herein.

Wearables. As used herein, the term "wearable device" (or "wearable") includes a body-borne device (or item) designed or intended to be worn by a human. Such devices are typically comfortably worn on, and are carried or transported by, the human body, and are commonly used to create constant, convenient, seamless, portable, and mostly hands-free access to electronics and computers. The wearable devices may be in direct contact with the human body (such as by touching, or attaching to, the body skin), or may be releasably attachable to clothes or other items intended or designed to be worn on the human body. In general, the goal of wearable technologies is to smoothly incorporate functional, portable electronics and computers into individuals' daily lives. Wearable devices may be releasably attached to the human body using attaching means such as straps, buckles, belts, or clasps. Alternatively or in addition, wearable devices may be shaped, structured, or having a form factor to be body releasably mountable or attachable, such as using eye-glass frames or headphones. Further, wearable devices may be worn under, with, or on top of, clothing.

Wearable devices may interact as sensors or actuators with an organ or part of the human body, such as a head mounted wearable device may include a screen suspended in front of a user's eye, without providing any aid to the user's vision. Examples of wearable devices include watches, glasses, contact lenses, pedometers, chest straps, wristbands, head bands, arm bands, belt, head wear, hats, glasses, watches, sneakers, clothing, pads, e-textiles and smart fabrics, headbands, beanies, and caps, as well as jewelry such as rings, bracelets, and hearing aid-like devices that are designed to look like earrings. A wearable device may be structured, designed, or have a form factor that is identical to, substantially similar to, or is at least in part substitute to, a traditional wearable item.

A wearable device may be a headwear that may be structured, designed, or have a form factor that is identical to, substantially similar to, or is at least in part substitute to, any headwear item. The headwear may be attached to, or be in contact with, a head part, such as a face, nose, right nostril, left nostril, right cheek, left cheek, right eye, left eye, right ear, or left ear, nose, mouth, lip, forehead, or chin. A wearable device may be structured, designed, or have a form factor that is identical to, substantially similar to, or is at least in part substitute to, a bonnet, a cap, a crown, a fillet, a hair cover, a hat, a helmet, a hood, a mask, a turban, a veil, or a wig.

A headwear device may be an eyewear that may be structured, designed, or have a form factor that is identical to, substantially similar to, or is at least in part substitute to, any eyewear item, such as glasses, sunglasses, a contact lens, a blindfold, or a goggle. A headwear device may be an earpiece that may be structured, designed, or have a form factor that is identical to, substantially similar to, or is at least in part substitute to, any earpiece item, such as a hearing aid, a headphone, a headset, or an earplug.

A wearable device may be releasably or permanently attach to, or be part of, a clothing article such as a tie, sweater, jacket, or hat. The attachment may use taping, gluing, pinning, enclosing, encapsulating, or any other method of attachment or integration known in the art. Furthermore, in some embodiments, there may be an attachment element such as a pin or a latch and hook system, of portion thereof (with the complementary element on the item to which it is to be affixed) or clip. In a non-limiting example, the attachment element has a clip-like design to allow attachment to pockets, belts, watches, bracelets, broaches, rings, shoes, hats, bike handles, necklaces, ties, spectacles, collars, socks, bags, purses, wallets, or cords.

A wearable device may be releasably or permanently attach to, or be part of, a top underwear such as a bra, camisole, or undershirt, a bottom underwear such as a diaper, panties, plastic pants, slip, thong, underpants, boxer briefs, boxer shorts, or briefs, or a full-body underwear such as bodysuit, long underwear, playsuit, or teddy. Similarly, a wearable device may be releasably or permanently attach to, or be part of, a headwear such as a Baseball cap, Beret, Cap, Fedora, hat, helmet, hood, knit cap, toque, turban, or veil. Similarly, a wearable device may be releasably or permanently attach to, or be part of, a footwear such as an athletic shoe, boot, court shoe, dress shoe, flip-flops, hosiery, sandal, shoe, spats, slipper, sock, or stocking. Further, a wearable device may be releasably or permanently attach to, or be part of, an accessory such as a bandana, belt, bow tie, coin purse, cufflink, cummerbund, gaiters, glasses, gloves, headband, handbag, handkerchief, jewellery, muff, necktie, pocket protector, pocketwatch, sash, scarf, sunglasses, suspenders, umbrella, wallet, or wristwatch.

A wearable device may be releasably or permanently attach to, or be part of, an outwear such as an apron, blazer, British warm, cagoule, cape, chesterfield, coat, covert coat, cut-off, duffle coat, flight jacket, gilet, goggle jacket, guards coat, Harrington jacket, hoodie, jacket, leather jacket, mess jacket, opera coat, overcoat, parka, paletot, pea coat, poncho, raincoat, robe, safari jacket, shawl, shrug, ski suit, sleeved blanket, smoking jacket, sport coat, trench coat, ulster coat, waistcoat, or windbreaker. Similarly, a wearable device may be releasably or permanently attach to, or be part of, a suit (or uniform) such as an academic dress, ball dress, black tie, boilersuit, cleanroom suit, clerical clothing, court dress, gymslip, jumpsuit, kasaya, lab coat, military uniform, morning dress, onesie, pantsuit, red sea rig, romper suit, school uniform, scrubs, stroller, tuxedo, or white tie. Further, a wearable device may be releasably or permanently attach to, or be part of, a dress such as a ball gown, bouffant gown, coatdress, cocktail dress, debutante dress, formal wear, frock, evening gown, gown, house dress, jumper, little black dress, princess line, sheath dress, shirtdress, slip dress, strapless dress, sundress, wedding dress, or wrap dress. Furthermore, a wearable device may be releasably or permanently attach to, or be part of, a skirt such as an A-line skirt, ballerina skirt, denim skirt, men's skirts, miniskirt, pencil skirt, prairie skirt, rah-rah skirt, sarong, Skort, tutu, or wrap. In one example, a wearable device may be releasably or permanently attach to, or be part of, a trousers (or shorts) such as bell-bottoms, bermuda shorts, bondage pants, capri pants, cargo pants, chaps, cycling shorts, dress pants, high water pants, lowrise pants, Jeans, jodhpurs, leggings, overall, Palazzo pants, parachute pants, pedal pushers, phat pants, shorts, slim-fit pants, sweatpants, windpants, or yoga pants. In one example, a wearable device may be releasably or permanently attach to, or be part of, a top such as a blouse, crop top, dress shirt, guayabera, guernsey, halterneck, henley shirt, hoodie, jersey, polo shirt, shirt, sleeveless shirt, sweater, sweater vest, t-shirt, tube top, turtleneck, or twinset.

A wearable device may be structured, designed, or have a form factor that is identical to, substantially similar to, or is at least in part substitute to, a fashion accessory. These accessories may be purely decorative, or have a utility beyond aesthetics. Examples of these accessories include, but are not limited to, rings, bracelets, necklaces, watches, watch bands, purses, wallets, earrings, body rings, headbands, glasses, belts, ties, tie bars, tie tacks, wallets, shoes, pendants, charms and bobbles. For example, wearable devices may also be incorporated into pockets, steering wheels, keyboards, pens, and bicycle handles.

In one example, the wearable device may be shaped as, or integrated with, a device that includes an annular member defining an aperture therethrough that is sized for receipt therein of a human body part. The body part may be part of a human hand such as upper arm, elbow, forearm, wrist (such as a wrist-band), or a finger (such as a ring). Alternatively or in addition, the body part may be part of a human head or neck, such as a forehead, ear, skull, or face. Alternatively or in addition, the body part may be part of a human thorax or abdomen, such as waist or hip. Alternatively or in addition, the body part may be part of a human leg or foot, such as thigh, calf, ankle, instep, knee, or toe.

In one example, the wearable device may be shaped as, or integrated with, a ring. The ring may comprise, consist essentially of or consist of a shank, which is the location that provides an opening for a finger, and a head, which comprises, consists essentially or consists of ornamental features of the ring and in some embodiments houses the signaling assembly of the present device. The head may be of any shape, e.g., a regular sphere, truncated sphere, cube, rectangular prism, cylinder, triangular prism, cone, pyramid, barrel, truncated cone, domed cylinder, truncated cylinder, ellipsoid, regular polygon prism or truncated three-dimensional polygon of e.g., 4-16 sides, such as a truncated pyramid (trapezoid), or combination thereof or it may be an irregular shape. Further, the head may comprise an upper face that contains and is configured to show one or more jewels and/or ornamental designs.

A mobile communication device configured to be worn on an index finger of a user's hand is described in U.S. Patent Application Publication No. 2015/0373443 to Carroll entitled: "Finger-wearable mobile communication device", which is incorporated in its entirety for all purposes as if fully set forth herein. The device includes a case, a microphone, a switch, and a power source. The microphone and the switch are strategically located along a shape of the case so that as worn on the user's index finger and when the switch is activated by the thumb of the user's hand, the hand naturally cups about the microphone to form a barrier to ambient noise. Further, the microphone can readily be located near a corner of the user's mouth for optimal speech-receiving conditions and to provide more private audio input.

A user controls an external electronic device with a finger-ring-mounted touchscreen is described in U.S. Patent Application Publication No. 2015/0277559 to Vescovi et al. entitled: "Devices and Methods for a Ring Computing Device", which is incorporated in its entirety for all purposes as if fully set forth herein. The device includes a computer processor, wireless transceiver, and rechargeable power source; the ring is worn on a first finger receives an input from a second finger, selects one of a plurality of touch events associated with the input, and wirelessly transmits a command associated with the touch event to the external electronic device.

A mobile communication device that comprises a fashion accessory and a signaling assembly is described in U.S. Patent Application Publication No. 2015/0349556 to Mercando et al. entitled: "Mobile Communication Devices", which is incorporated in its entirety for all purposes as if fully set forth herein. The signaling assembly may be configured to provide sensory stimuli such as a flashing LED light and a vibration. These stimuli may vary depending on the signal received from a remote communication device or from gestures made by a user or from information stored in the mobile communication device.

A wearable fitness-monitoring device is described in U.S. Pat. No. 8,948,832 to Hong et al. entitled: "Wearable Heart Rate Monitor", which is incorporated in its entirety for all purposes as if fully set forth herein. The device includes a motion sensor and a photoplethysmographic (PPG) sensor. The PPG sensor includes (i) a periodic light source, (ii) a photo detector, and (iii) circuitry determining a user's heart rate from an output of the photo detector. Some embodiments provide methods for operating a heart rate monitor of a wearable fitness-monitoring device to measure one or more characteristics of a heartbeat waveform. Some embodiments provide methods for operating the wearable fitness monitoring device in a low power state when the device determines that the device is not worn by a user. Some embodiments provide methods for operating the wearable fitness-monitoring device in a normal power state when the device determines that the device is worn by a user.

A wearable device and method for processing mages to prolong battery life are described in U.S. Pat. No. 8,957,988 to Wexler et al. entitled: "Apparatus for processing images to prolong battery life", which is incorporated in its entirety for all purposes as if fully set forth herein. In one implementation, a wearable apparatus may include a wearable image sensor configured to capture a plurality of images from an environment of a user. The wearable apparatus may also include at least one processing device configured to, in a first processing-mode, process representations of the plurality of images to determine a value of at least one capturing parameter for use in capturing at least one subsequent image, and in a second processing-mode, process the representations of the plurality of images to extract information. In addition, the at least one processing device may operate in the first processing-mode when the wearable apparatus is powered by a mobile power source included in the wearable apparatus and may operate in the second processing-mode when the wearable apparatus is powered by an external power source.

A wearable device may be used for notifying a person, such as by using tactile, visual, or audible stimulus, as described for example in U.S. Patent Application No. 2015/0341901 to RYU et al. entitled: "Method and apparatus for providing notification", which is incorporated in its entirety for all purposes as if fully set forth herein, describing an electronic device that includes: a transceiver configured to communicate with at least one wearable device and receive, from the at least one wearable device, status information indicating whether the at least one wearable device is currently being worn; and a processor configured to determine whether to send a notification request to the at least one wearable device based on the status information received by the transceiver.

A communication device, system and method are described for example in U.S. Patent Application No. 2007/0052672 to Ritter et al. entitled: "Communication device, system and method", which is incorporated in its entirety for all purposes as if fully set forth herein. It is discloses comprising a Virtual Retinal Display (VRD) in form of glasses (1), at least one haptic sensor (12) mounted on the frame of said glasses or connected by a short range communication interface (13) to said glasses (1), wherein it is possible to navigate by means of a cursor through an image displayed by the Virtual Retinal Display (VRD) with the at least one haptic sensor (12). A central control unit controls (11) the Virtual Retinal Display (VRD) and the at least one haptic sensor (12). When the Virtual Retinal Display (VRD) is connected to an external device (2, 9) by a short range communication interface (13), the user can navigate through the content of the external device (2, 9) by easy use of the haptic sensor (12).

Wearable communication devices, e.g. implemented in a watch, using short range communication to a cell phone, and facilitating natural and intuitive user interface with low-power implementation are described for example in U.S. Patent Application No. 2014/0045547 to Singamsetty et al. entitled: "Wearable Communication Device and User Interface", which is incorporated in its entirety for all purposes as if fully set forth herein. The devices allow a user to easily access all features of the phone, all while a phone is nearby but not visible. Notification is performed with vibration, an LED light and OLED text display of incoming calls, texts, and calendar events. It allows communicating hands-free. This allows using the communication device as "remote control" for home devices, etc. via voice and buttons. The device comprises interfaces motion sensors such as accelerometers, magnetometer and gyroscope, infrared proximity sensors, vibrator motor, and/or voice recognition. Low power consumption is achieved by dynamical configuration of sensor parameters to support only the necessary sensor functions at any given state of the device.

A wearable electronic device that is configured to control and command a variety of wireless devices within its proximity is described in U.S. Pat. No. 7,605,714 to Thompson et al. entitled: "System and method for command and control of wireless devices using a wearable device", which is incorporated in its entirety for all purposes as if fully set forth herein. The wearable device dynamically generates a user interface corresponding to the services of a particular wireless device. Through the user interface, the wireless device surface content to a user and allows a user select interactions with the wireless devices using the wearable device.

An apparatus and method for the remote control and/or interaction-with electronic-devices such as computers; home-entertainment-systems; media-centers; televisions; DVD-players; VCR-players; music systems; appliances; security systems; toys/games; and/or displays are described in U.S. Pat. No. 8,508,472 to Wieder entitled: "Wearable remote control with a single control button", which is incorporated in its entirety for all purposes as if fully set forth herein. A user may orient a pointer (e.g., laser pointer) to place a pointer-spot on/near object(s) on an active-display(s); and/or a fixed-display(s); and/or on real-world object(s) within a display region or pointer-spot detection-region. Detectors, imager(s) and/or camera(s) may be connected/attached to the display region and/or a structure that is connected/attached to display region. When the user initiates a "select", the detectors/cameras may detect the location of the pointer-spot within the display region. Corresponding to the user's selection(s); control action(s) may be performed on the device(s) being controlled/interacted-with and additional selection-menus may be optionally presented on an active-display.

A hand-worn controller consisting of a housing having a central opening sized to permit the controller to be worn as ring on the index finger of a human hand is described in U.S. Patent Application Publication No. 2006/0164383 to Machin et al. entitled: "Remote controller ring for user interaction", which is incorporated in its entirety for all purposes as if fully set forth herein. A joystick lever projects outwardly from said housing and is positioned to be manipulated by the user's thumb. The joystick operates on or more control devices, such as switches or potentiometers, that produce control signals. A wireless communications device, such as a Bluetooth module, mounted in said housing transmits command signals to a remote utilization device, which are indicative of the motion or position of said joystick lever.

A wearable augmented reality computing apparatus with a display screen, a reflective device, a computing device and a head mounted harness to contain these components is described in U.S. Patent Application Publication No. 2012/0050144 to Morlock entitled: "Wearable augmented reality computing apparatus", which is incorporated in its entirety for all purposes as if fully set forth herein. The display device and reflective device are configured such that a user can see the reflection from the display device superimposed on the view of reality. An embodiment uses a switchable mirror as the reflective device. One usage of the apparatus is for vehicle or pedestrian navigation. The portable display and general purpose computing device can be combined in a device such as a smartphone. Additional components consist of orientation sensors and non-handheld input devices.

In one example, a wearable device may use, or may be based on, a processor or a microcontroller that is designed for wearable applications, such as the CC2650 SimpleLink™ Multistandard Wireless MCU available from Texas Instruments Incorporated (headquartered in Dallas, Texas, U.S.A.) and described in a Texas Instrument 2015 publication #SWRT022 entitled: "*SimpleLink™ Ultra-Low Power—Wireless Microcontroller Platform*", and in a Texas Instrument 2015 datasheet #SWRS158A (published February 2015, Revised October 2015) entitled: "*CC2650 SimpleLink™ Multistandard Wireless MCU*", which are both incorporated in their entirety for all purposes as if fully set forth herein.

An example of a personal multimedia electronic device, and more particularly to a head-worn device such as an eyeglass frame, is described in U.S. Patent Application No. 2010/0110368 to Chaum entitled: "System and apparatus for eyeglass appliance platform", which is incorporated in its entirety for all purposes as if fully set forth herein. The device is having a plurality of interactive electrical/optical components. In one embodiment, a personal multimedia electronic device includes an eyeglass frame having a side arm and an optic frame; an output device for delivering an output to the wearer; an input device for obtaining an input; and a processor comprising a set of programming instructions for controlling the input device and the output device. The output device is supported by the eyeglass frame and is selected from the group consisting of a speaker, a bone conduction transmitter, an image projector, and a tactile actuator. The input device is supported by the eyeglass frame and is selected from the group consisting of an audio sensor, a tactile sensor, a bone conduction sensor, an image sensor, a body sensor, an environmental sensor, a global positioning system receiver, and an eye tracker. In one embodiment, the processor applies a user interface logic that determines a state of the eyeglass device and determines the output in response to the input and the state.

An example of an eyewear for a user is described in U.S. Patent Application No. 2012/0050668 Howell et al. entitled: "Eyewear with touch-sensitive input surface", which is incorporated in its entirety for all purposes as if fully set forth herein. The eyewear includes an eyewear frame, electrical circuitry at least partially in the eyewear frame, and a touch sensitive input surface on the eyewear frame configured to provide an input to the electrical circuitry to perform a function via touching the touch sensitive input surface. In another embodiment, the eyewear includes a switch with at least two operational states. The operational states of the switch can be configured to be changed by sliding a finger across the touch sensitive input surface of the frame.

An example of a wearable computing device is described in U.S. Patent Application No. 2013/0169513 to Heinrich et al. entitled: "Wearable computing device", which is incorporated in its entirety for all purposes as if fully set forth herein. The device includes a bone conduction transducer, an extension arm, a light pass hole, and a flexible touch pad input circuit. When a user wears the device, the transducer contacts the user's head. A display is attached to a free end of an extension arm. The extension arm is pivotable such that a distance between the display and the user's eye is adjustable to provide the display at an optimum position. The light pass hole may include a light emitting diode and a flash. The touch pad input circuit may be adhered to at least one side arm such that parting lines are not provided between edges of the circuit and the side arm.

Hearing aid. A hearing aid is a small electronic device this wear in or behind a human ear to make some sounds louder so that a person with hearing loss can listen, communicate, and participate more fully in daily activities. A hearing aid can help people hear more in both quiet and noisy situations. A hearing aid has three basic parts: a microphone, amplifier, and speaker. The hearing aid receives sound through a microphone, which converts the sound waves to electrical signals and sends them to an amplifier. The amplifier increases the power of the signals and then sends them to the ear through a speaker.

As described by U.S. DEPARTMENT OF HEALTH AND HUMAN SERVICES, National Institutes of Health (NIH), National Institute on Deafness and Other Communication Disorders (NIDCD) publication No. 99-4340 September 2013 Reprinted July 2015 entitled: "*NIDCD Fact Sheet|Hearing and Balance*", which is incorporated in its entirety for all purposes as if fully set forth herein, there are three basic styles of hearing aids, two of which shown in FIG. 2a. The styles differ by size, their placement on or inside the ear, and the degree to which they amplify sound.

Behind-the-ear (BTE) hearing aids shown in a view 25 in FIG. 2a consist of a hard plastic case worn behind the ear and connected to a plastic earmold that fits inside the outer ear. The electronic parts are held in the case behind the ear. Sound travels from the hearing aid through the earmold and into the ear. A new kind of BTE aid ('Mini' BTE) is an open-fit hearing aid. Small, open-fit aids fit behind the ear completely, with only a narrow tube inserted into the ear canal, enabling the canal to remain open. For this reason, open-fit hearing aids may be a good choice for people who experience a buildup of earwax, since this type of aid is less likely to be damaged by such substances. In addition, some people may prefer the open-fit hearing aid because their perception of their voice does not sound "plugged up."

In-The-Ear (ITE) hearing aids shown in a view 26 in FIG. 2a fit completely inside the outer ear and are used for mild to severe hearing loss. The case holding the electronic components is made of hard plastic. Some ITE aids may have certain added features installed, such as a telecoil. A telecoil is a small magnetic coil that allows users to receive sound through the circuitry of the hearing aid, rather than through its microphone. This makes it easier to hear conversations over the telephone. A telecoil also helps people hear in public facilities that have installed special sound systems, called induction loop systems. Induction loop systems can be found in many churches, schools, airports, and auditoriums. ITE aids usually are not worn by young children because the casings need to be replaced often as the ear grows.

The term 'client' typically refers to an application (or a device executing the application) used for retrieving or rendering resources, or resource manifestations, such as a web browser, an e-mail reader, or a Usenet reader, while the term 'server' typically refers to an application (or a device executing the application) used for supplying resources or resource manifestations, and typically offers (or hosts) various services to other network computers and users. These services are usually provided through ports or numbered access points beyond the server's network address. Each port number is usually associated with a maximum of one running program, which is responsible for handling requests to that port. A daemon, being a user program, can in turn access the local hardware resources of that computer by passing requests to the operating system kernel.

A mobile operating system (also referred to as mobile OS), is an operating system that operates a smartphone, tablet, PDA, or another mobile device. Modern mobile operating systems combine the features of a personal computer operating system with other features, including a touchscreen, cellular, Bluetooth, Wi-Fi, GPS mobile navigation, camera, video camera, speech recognition, voice recorder, music player, near field communication and infrared blaster. Currently, the popular mobile OSs include Android, Symbian, Apple iOS, BlackBerry, MeeGo, Windows Phone, and Bada. Mobile devices with mobile communications capabilities (e.g. smartphones) typically contain two mobile operating systems: a main user-facing software platform is supplemented by a second low-level proprietary real-time operating system that operates the radio and other hardware.

Android is a Linux-based, open source mobile operating system (OS) based on the Linux kernel that is currently offered by Google. With a user interface based on direct manipulation, Android is designed primarily for touchscreen mobile devices such as smartphones and tablet computers with specialized user interfaces for televisions (Android TV), cars (Android Auto), and wrist watches (Android Wear). The OS uses touch inputs that loosely correspond to real-world actions, such as swiping, tapping, pinching, and reverse pinching to manipulate on-screen objects, and a virtual keyboard. Despite being primarily designed for touchscreen input, it also has been used in game consoles, digital cameras, and other electronics. The response to user input is designed to be immediate and provides a fluid touch interface, often using the vibration capabilities of the device to provide haptic feedback to the user. Internal hardware such as accelerometers, gyroscopes, and proximity sensors are used by some applications to respond to additional user actions. For example, adjusting the screen from portrait to landscape depending on the device orientation, or allowing the user to steer a vehicle in a racing game by rotating the device, a process that simulates control of a steering wheel.

Android devices boot to the homescreen, the primary navigation and information point on the device, which is similar to the desktop found on PCs. The homescreens on Android are typically made up of app icons and widgets. App icons launch the associated app, whereas widgets display live, auto-updating content such as the weather forecast, the user's email inbox, or a news ticker directly on the homescreen. A homescreen may be made up of several pages that the user can swipe back and forth between pages. A heavily-customizable Android homescreen interface allows the user to adjust the look and feel of the device to their liking. Third-party apps available on Google Play and other app stores can extensively re-theme the homescreen, and even mimic the look of other operating systems, such as Windows Phone. The Android OS is described in a publication entitled: "*Android Tutorial*", downloaded from tutorialspoint.com on July 2014, which is incorporated in its entirety for all purposes as if fully set forth herein.

iOS (previously iPhone OS) from Apple Inc. (headquartered in Cupertino, California, U.S.A.) is a mobile operating system distributed exclusively for Apple hardware. The user interface of the iOS is based on the concept of direct manipulation, using multi-touch gestures. Interface control elements consist of sliders, switches, and buttons. Interaction with the OS includes gestures such as swipe, tap, pinch, and reverse pinch, all of which have specific definitions within the context of the iOS operating system and its multi-touch interface. Internal accelerometers are used by some applications to respond to shaking the device (one common result is the undo command), or rotating it in three dimensions (one common result is switching from portrait to landscape mode). The iOS is described in a publication entitled: "*IOS Tutorial*", downloaded from tutorialspoint.com on July 2014, which is incorporated in its entirety for all purposes as if fully set forth herein.

RTOS. A Real-Time Operating System (RTOS) is an Operating System (OS) intended to serve real-time applications that process data as it comes in, typically without buffer delays. Processing time requirements (including any OS delay) are typically measured in tenths of seconds or shorter increments of time, and is a time bound system which has well defined fixed time constraints. Processing is commonly to be done within the defined constraints, or the system will fail. They either are event driven or time sharing, where event driven systems switch between tasks based on their priorities while time sharing systems switch the task based on clock interrupts. A key characteristic of an RTOS is the level of its consistency concerning the amount of time it takes to accept and complete an application's task; the variability is jitter. A hard real-time operating system has less jitter than a soft real-time operating system. The chief design goal is not high throughput, but rather a guarantee of a soft or hard performance category. An RTOS that can usually or generally meet a deadline is a soft real-time OS, but if it can meet a deadline deterministically it is a hard real-time OS. An RTOS has an advanced algorithm for scheduling, and includes a scheduler flexibility that enables a wider, computer-system orchestration of process priorities. Key factors in a real-time OS are minimal interrupt latency and minimal thread switching latency; a real-time OS is valued more for how quickly or how predictably it can respond than for the amount of work it can perform in a given period of time.

Common designs of RTOS include event-driven, where tasks are switched only when an event of higher priority needs servicing; called preemptive priority, or priority scheduling, and time-sharing, where task are switched on a regular clocked interrupt, and on events; called round robin. Time sharing designs switch tasks more often than strictly needed, but give smoother multitasking, giving the illusion that a process or user has sole use of a machine. In typical designs, a task has three states: Running (executing on the CPU); Ready (ready to be executed); and Blocked (waiting for an event, I/O for example). Most tasks are blocked or ready most of the time because generally only one task can run at a time per CPU. The number of items in the ready queue can vary greatly, depending on the number of tasks the system needs to perform and the type of scheduler that the system uses. On simpler non-preemptive but still multitasking systems, a task has to give up its time on the CPU to other tasks, which can cause the ready queue to have a greater number of overall tasks in the ready to be executed state (resource starvation).

RTOS concepts and implementations are described in an Application Note No. RES05B00008-0100/Rec. 1.00 published January 2010 by Renesas Technology Corp. entitled: "*R8C Family—General RTOS Concepts*", in JAJA Technologfy Review article published February 2007 [1535-5535/$32.00] by The Association for Laboratory Automation [doi:10.1016/j.jala.2006.10.016] entitled: "*An Overview of Real-Time Operating Systems*", and in Chapter 2 entitled: "*Basic Concepts of Real Time Operating Systems*" of a book published 2009 [ISBN—978-1-4020-9435-4] by Springer Science+Business Media B.V. entitled: "*Hardware-Dependent Software—Principles and Practice*", which are all incorporated in their entirety for all purposes as if fully set forth herein.

QNX. One example of RTOS is QNX, which is a commercial Unix-like real-time operating system, aimed primarily at the embedded systems market. QNX was one of the first commercially successful microkernel operating systems and is used in a variety of devices including cars and mobile phones. As a microkernel-based OS, QNX is based on the idea of running most of the operating system kernel in the form of a number of small tasks, known as Resource Managers. In the case of QNX, the use of a microkernel allows users (developers) to turn off any functionality they do not require without having to change the OS itself; instead, those services will simply not run.

FreeRTOS. FreeRTOS™ is a free and open-source Real-Time Operating system developed by Real Time Engineers Ltd., designed to fit on small embedded systems and implements only a very minimalist set of functions: very basic handle of tasks and memory management, and just sufficient API concerning synchronization. Its features include characteristics such as preemptive tasks, support for multiple microcontroller architectures, a small footprint (4.3 Kbytes on an ARM7 after compilation), written in C, and compiled with various C compilers. It also allows an unlimited number of tasks to run at the same time, and no limitation about their priorities as long as used hardware can afford it.

FreeRTOS™ provides methods for multiple threads or tasks, mutexes, semaphores and software timers. A tick-less mode is provided for low power applications, and thread priorities are supported. Four schemes of memory allocation are provided: allocate only; allocate and free with a very simple, fast, algorithm; a more complex but fast allocate and free algorithm with memory coalescence; and C library allocate and free with some mutual exclusion protection. While the emphasis is on compactness and speed of execution, a command line interface and POSIX-like IO abstraction add-ons are supported. FreeRTOS™ implements multiple threads by having the host program call a thread tick method at regular short intervals.

The thread tick method switches tasks depending on priority and a round-robin scheduling scheme. The usual interval is $\frac{1}{1000}$ of a second to $\frac{1}{100}$ of a second, via an interrupt from a hardware timer, but this interval is often changed to suit a particular application. FreeRTOS™ is described in a paper by Nicolas Melot (downloaded July 2015) entitled: "*Study of an operating system: FreeRTOS—Operating systems for embedded devices*", in a paper (dated Sep. 23, 2013) by Dr. Richard Wall entitled: "*Carebot PIC32 MX7ck implementation of Free RTOS*", FreeRTOS™ modules are described in web pages entitled: "*FreeRTOS™ Modules*" published in the www,freertos.org web-site dated 26 Nov. 2006, and FreeRTOS kernel is described in a paper published 1 April 7 by Rich Goyette of Carleton University as part of 'SYSC5701: Operating System Methods for Real-Time Applications', entitled: "*An Analysis and Description of the Inner Workings of the FreeRTOS Kernel*", which are all incorporated in their entirety for all purposes as if fully set forth herein.

SafeRTOS. SafeRTOS was constructed as a complementary offering to FreeRTOS, with common functionality but with a uniquely designed safety-critical implementation. When the FreeRTOS functional model was subjected to a full HAZOP, weakness with respect to user misuse and hardware failure within the functional model and API were identified and resolved. Both SafeRTOS and FreeRTOS share the same scheduling algorithm, have similar APIs, and are otherwise very similar, but they were developed with differing objectives. SafeRTOS was developed solely in the C language to meet requirements for certification to IEC61508. SafeRTOS is known for its ability to reside solely in the on-chip read only memory of a microcontroller for standards compliance. When implemented in hardware memory, SafeRTOS code can only be utilized in its original configuration, so certification testing of systems using this OS need not re-test this portion of their designs during the functional safety certification process.

VxWorks. VxWorks is an RTOS developed as proprietary software and designed for use in embedded systems requiring real-time, deterministic performance and, in many cases, safety and security certification, for industries, such as aerospace and defense, medical devices, industrial equipment, robotics, energy, transportation, network infrastructure, automotive, and consumer electronics. VxWorks supports Intel architecture, POWER architecture, and ARM architectures. The VxWorks may be used in multicore asymmetric multiprocessing (AMP), symmetric multiprocessing (SMP), and mixed modes and multi-OS (via Type 1 hypervisor) designs on 32- and 64-bit processors. VxWorks comes with the kernel, middleware, board support packages, Wind River Workbench development suite and complementary third-party software and hardware technologies. In its latest release, VxWorks 7, the RTOS has been re-engineered for modularity and upgradeability so the OS kernel is separate from middleware, applications and other packages. Scalability, security, safety, connectivity, and graphics have been improved to address Internet of Things (IoT) needs.

μC/OS. Micro-Controller Operating Systems (MicroC/OS, stylized as μC/OS) is a real-time operating system (RTOS) that is a priority-based preemptive real-time kernel for microprocessors, written mostly in the programming language C, and is intended for use in embedded systems. MicroC/OS allows defining several functions in C, each of which can execute as an independent thread or task. Each task runs at a different priority, and runs as if it owns the central processing unit (CPU). Lower priority tasks can be preempted by higher priority tasks at any time. Higher priority tasks use operating system (OS) services (such as a delay or event) to allow lower priority tasks to execute. OS services are provided for managing tasks and memory, communicating between tasks, and timing.

Electrical sensor. Electrical sensor is a component, device or a circuit used to measure electrical quantities. Such an electrical sensor may be conductively connected to measure the electrical parameter, or may be non-conductively coupled to measure an electric-related phenomenon, such as magnetic field or heat. Further, the average or RMS value may be measured.

Ampermeter. An electrical sensor may be an ampermeter (a.k.a. ammeter) that is a current sensor that measures the magnitude of the electric current in a circuit or in a conductor such as a wire. Electric current is commonly measured in Amperes, milliampers, microamperes, or kiloampers. The sensor may be an integrating ammeter (a.k.a. watt-hour meter) where the current is summed over time, providing a current/time product, which is proportional to the energy transferred. The measured electric current may be an Alternating Current (AC) such as a sinewave, a Direct Current (DC), or an arbitrary waveform. A galvanometer is a type of ampermeter for detecting or measuring low current, typically by producing a rotary deflection of a coil in a magnetic field. Some ampermeters use a resistor (shunt), whose voltage is directly proportional to the current flowing through, requiring the current to pass through the meter. A hot-wire ampermeter involves passing the current through a wire which expands as it heats, and the expansion is measured. A non-conductive or non-contact current sensor may be based on 'Hall effect' magnetic field sensor, measuring the magnetic field generated by the current to be measured. Other non-conductive current sensors involve a current clamp or current probe, which has two jaws that open to allow clamping around an electrical conductor, allowing for measuring of the electric current properties (commonly AC), without making a physical contact or disconnecting the circuit. Such current clamp commonly comprises a wire coil wounded around a split ferrite ring, acting as the secondary winding of a current transformer, with the current-carrying conductor acting as the primary winding. Other current sensors and related circuits are described in Zetex Semiconductors PLC application note "*AN39—Current measurement application handbook*" Issue 5, January 2008, which is incorporated in its entirety for all purposes as if fully set forth herein.

Voltmeter. An electrical sensor may be a voltmeter, commonly used for measuring the magnitude of the electric potential difference between two points. Electric voltage is commonly measured in volts, millivolts, microvolts, or kilovolts. The measured electric voltage may be an Alternating Current (AC) such as a sinewave, a Direct Current (DC), or an arbitrary waveform. Similarly, an electrometer may be used for measuring electric charge (commonly in Coulomb units—C) or electrical potential difference, with very low leakage current. The voltmeter commonly works by measuring the current through a fixed resistor, which, according to Ohm's Law, is proportional to the voltage across the resistor. A potentiometer-based voltmeter works by balancing the unknown voltage against a known voltage in a bridge circuit. A multimeter (a.k.a. VOM—Volt-Ohm-Milliameter) as well as Digital MultiMeter (DMM), typically includes a voltmeter, an ampermeter and an ohmmeter.

Wattmeter. An electrical sensor may be a wattmeter measuring the magnitude of the active power (or the supply rate of electrical energy), commonly using watts (W), milliwatts, kilowatts, or megawatts units. A wattmeter may be based on measuring the voltage and the current, and multiplying to calculate the power P=VI. In AC measurement, the true power is P=VIcos($\phi$). The wattmeter may be a bolometer, used for measuring the power of incident electromagnetic radiation via the heating of a material with a temperature-dependent electrical resistance. A sensor may be an electricity meter (or electrical energy meter) that measures the amount of electrical energy consumed by a load. Commonly, an electricity meter is used to measure the energy consumed by a single load, an appliance, a residence, a business, or any electrically powered device, and may provide or be the basis for the electricity cost or billing. The electricity meter may be an AC (single or multi-phase) or DC type, and the common unit of measurement is kilowatt-hour, however any energy related unit may be used such as Joules. Some electricity meters are based on wattmeters, which accumulate or average the readings, or may be based on induction.

Ohmeter. An electrical sensor may be an ohmmeter measuring the electrical resistance, commonly measured in ohms ($\Omega$), milliohms, kiloohms or megohms, or conductance measured in Siemens (S) units. Low-resistance measurements commonly use micro-ohmmeter, while megohmmeter (a.k.a. Megger) measures large value of resistance. Common ohmmeter passes a constant known current through the measured unknown resistance (or conductance), while measuring the voltage across the resistance, and deriving the resistance (or conductance) value from Ohm's law (R=V/I). A Wheatstone bridge may also be used as a resistance sensor, by balancing two legs of a bridge circuit, where one leg includes the unknown resistance (or conductance) component. Variations of Wheatstone bridge may be used to measure capacitance, inductance, impedance, and other electrical or non-electrical quantities.

Capacitance meter. An electrical sensor may be a capacitance meter for measuring capacitance, commonly using units of picofarads, nanofarads, microfarads, and Farads (F). A sensor may be an inductance meter for measuring inductance, commonly using SI units of Henry (H), such as microHenry, milliHenry, and Henry. Further, a sensor may be an impedance meter for measuring an impedance of a device or a circuit. A sensor may be an LCR meter, used to measure inductance (L), capacitance (C), and resistance (R). A meter may use sourcing an AC voltage, and use the ratio of the measured voltage and current (and their phase difference) through the tested device according to Ohm's law to calculate the impedance. Alternatively or in addition, a meter may use a bridge circuit (Similar to Wheatstone bridge concept), where variable calibrated elements are adjusted to detect a null. The measurement may be in a single frequency, or over a range of frequencies.

Magnetometer. An electrical sensor may be a magnetometer for measuring a local H or B magnetic fields. The B-field (a.k.a. magnetic flux density or magnetic induction) is measured in Tesla (T) in SI units and Gauss in cgs units, and magnetic flux is measured in Weber (Wb) units. The H-field (a.k.a. magnetic field intensity or magnetic field strength) is measured in ampere-turn per meter (A/m) in SI units, and in Oersteds (Oe) in cgs units. Many Smartphones contain magnetometers serving as compasses. A magnetometer may be a scalar magnetometer, measuring the total strength, or may be a vector magnetometer, providing both magnitude and direction (relative to the spatial orientation) of the magnetic field. Common magnetometers include Hall effect sensor, magneto-diode, magneto-transistor, AMR magnetometer, GMR magnetometer, magnetic tunnel junction magnetometer, magneto-optical sensor, Lorentz force based MEMS sensor (a.k.a. Nuclear Magnetic Resonance—NMR), Electron Tunneling based MEMS sensor, MEMS compasses, Nuclear precession magnetic field sensor, optically pumped magnetic field sensor, fluxgate magnetometer, search coil magnetic field sensor, and Superconducting Quantum Interference Device (SQUID) magnetometer. 'Hall effect' magnetometers are based on 'Hall probe', which contains an indium compound semiconductor crystal such as indium antimonide, mounted on an aluminum backing plate, and provides a voltage a voltage in response to the measured B-field. A fluxgate magnetometer makes use of the non-linear magnetic characteristics of a probe or sensing element that has a ferromagnetic core. NMR and Proton Precession Magnetometers (PPM) measure the resonance frequency of protons in the magnetic field to be measured. SQUID meters are very sensitive vector magnetometers, based on superconducting loops containing Josephson junctions. The magnetometer may be Lorentz-force-based MEMS sensor, relying on the mechanical motion of the MEMS structure due to the Lorentz force acting on the current-carrying conductor in the magnetic field.

Signal generator. A signal generator (a.k.a. frequency generator) is an electronic device or circuit devices that can generate repeating or non-repeating electronic signals (typically voltage or current), having an analog output (analog signal generator) or a digital output (digital signal generator). The output signal may be based on an electrical circuit, or may be based on a generated or stored digital data. A function generator is typically a signal generator which produces simple repetitive waveforms. Such devices contain an electronic oscillator, a circuit that is capable of creating a repetitive waveform, or may use digital signal processing to synthesize waveforms, followed by a digital to analog converter, or DAC, to produce an analog output. Common waveforms are a sine wave, a saw-tooth, a step (pulse), a square, and a triangular waveforms. The generator may include some sort of modulation functionality such as Amplitude Modulation (AM), Frequency Modulation (FM), or Phase Modulation (PM). An Arbitrary Waveform Generators (AWGs) are sophisticated signal generators which allow the user to generate arbitrary waveforms, within published limits of frequency range, accuracy, and output level. Unlike function generators, which are limited to a simple set of waveforms; an AWG allows the user to specify a source waveform in a variety of different ways. Logic signal generator (a.k.a. data pattern generator and digital pattern generator) is a digital signal generator that produces logic types of signals—that is logic 1's and 0's in the form of conventional voltage levels. The usual voltage standards are: LVTTL, LVCMOS.

Processor. The term "processor" is used herein to include, but not limited to, any integrated circuit or any other electronic device (or collection of electronic devices) capable of performing an operation on at least one instruction, including, without limitation, a microprocessor (µP), a microcontroller (µC), a Digital Signal Processor (DSP), or any combination thereof. A processor may further be a Reduced Instruction Set Core (RISC) processor, a Complex Instruction Set Computing (CISC) microprocessor, a Microcontroller Unit (MCU), or a CISC-based Central Processing Unit (CPU). The hardware of the processor may be integrated onto a single substrate (e.g., silicon "die"), or distributed among two or more substrates.

A non-limiting example of a processor may be 80186 or 80188 available from Intel Corporation located at Santa Clara, California, USA. The 80186 and its detailed memory connections are described in the manual "80186/80188 High-Integration 16-Bit Microprocessors" by Intel Corporation, which is incorporated in its entirety for all purposes as if fully set forth herein. Other non-limiting example of a processor may be MC68360 available from Motorola Inc. located at Schaumburg, Illinois, USA. The MC68360 and its detailed memory connections are described in the manual "*MC68360 Quad Integrated Communications Controller—User's Manual*" by Motorola, Inc., which is incorporated in its entirety for all purposes as if fully set forth herein. While exampled above regarding an address bus having an 8-bit width, other widths of address buses are commonly used, such as the 16-bit, 32-bit and 64-bit. Similarly, while exampled above regarding a data bus having an 8-bit width, other widths of data buses are commonly used, such as 16-bit, 32-bit and 64-bit width. In one example, the processor consists of, comprises, or is part of, Tiva™ TM4C123GH6PM Microcontroller available from Texas Instruments Incorporated (Headquartered in Dallas, Texas, U.S.A.), described in a data sheet published 2015 by Texas Instruments Incorporated [DS-TM4C123GH6PM-15842.2741, SPMS376E, Revision 15842.2741 June 2014], entitled: "*Tiva™ TM4C123GH6PM Microcontroller—Data Sheet*", which is incorporated in its entirety for all purposes as if fully set forth herein, and is part of Texas Instrument's Tiva™ C Series microcontrollers family that provide designers a high-performance ARM® Cortex™-M-based architecture with a broad set of integration capabilities and a strong ecosystem of software and development tools. Targeting performance and flexibility, the Tiva™ C Series architecture offers an 80 MHz Cortex-M with FPU, a variety of integrated memories and multiple programmable GPIO. Tiva™ C Series devices offer consumers compelling cost-effective solutions by integrating application-specific peripherals and providing a comprehensive library of software tools which minimize board costs and design-cycle time. Offering quicker time-to-market and cost savings, the Tiva™ C Series microcontrollers are the leading choice in high-performance 32-bit applications. Targeting performance and flexibility, the Tiva™ C Series architecture offers an 80 MHz Cortex-M with FPU, a variety of integrated memories and multiple programmable GPIO. Tiva™ C Series devices offer consumers compelling cost-effective solutions.

Sensor. Any element capable of measuring or responding to a physical phenomenon may be used as a sensor. An appropriate sensor may be adapted for a specific physical phenomenon, such as a sensor responsive to temperature, humidity, pressure, audio, vibration, light, motion, sound, proximity, flow rate, electrical voltage, and electrical current. A sensor may be an analog sensor having an analog signal output such as analog voltage or current, or may have continuously variable impedance. Alternatively on in addition, a sensor may have a digital signal output. A sensor may serve as a detector, notifying only the presence of a phenomenon, such as by a switch, and may use a fixed or settable threshold level. A sensor may measure time-dependent or space-dependent parameters of a phenomenon. A sensor may measure time-dependencies or a phenomenon such as the rate of change, time-integrated or time-average, duty-cycle, frequency or time period between events. A sensor may be a passive sensor, or an active sensor requiring an external source of excitation. A sensor may be semiconductor-based, and may be based on MEMS technology.

A sensor may measure the amount of a property or of a physical quantity or the magnitude relating to a physical phenomenon, body or substance. Alternatively or in addition, a sensor may be used to measure the time derivative thereof, such as the rate of change of the amount, the quantity or the magnitude. In the case of space related quantity or magnitude, a sensor may measure the linear density, surface density, or volume density, relating to the amount of property per volume. Alternatively or in addition, a sensor may measure the flux (or flow) of a property through a cross-section or surface boundary, the flux density, or the current. In the case of a scalar field, a sensor may measure the quantity gradient. A sensor may measure the amount of property per unit mass or per mole of substance. A single sensor may be used to measure two or more phenomena.

A sensor may provide an electrical output signal in response to a physical, chemical, biological or any other phenomenon, serving as a stimulus to the sensor. A sensor may serve as, or be, a detector, for detecting the presence of the phenomenon. Alternatively or in addition, a sensor may measure (or respond to) a parameter of a phenomenon or a magnitude of the physical quantity thereof. For example, a sensor may be a thermistor or a platinum resistance temperature detector, a light sensor, a pH probe, a microphone for audio receiving, or a piezoelectric bridge. Similarly, a sensor may be used to measure pressure, flow, force or other mechanical quantities. A sensor output may be amplified by an amplifier connected to the sensor output. Other signal conditioning may also be applied in order to improve the handling of the sensor output or adapting it to the next stage or manipulating, such as attenuation, delay, current or voltage limiting, level translation, galvanic isolation, impedance transformation, linearization, calibration, filtering, amplifying, digitizing, integration, derivation, and any other signal manipulation. Some sensors conditioning involves connecting them in a bridge circuit. In the case of conditioning, the conditioning circuit may added to manipulate the sensor output, such as filter or equalizer for frequency related manipulation such as filtering, spectrum analysis or noise removal, smoothing or de-blurring in case of image enhancement, a compressor (or de-compressor) or coder (or decoder) in the case of a compression or a coding/decoding schemes, modulator or demodulator in case of modulation, and extractor for extracting or detecting a feature or parameter such as pattern recognition or correlation analysis. In case of filtering, passive, active or adaptive (such as Wiener or Kalman) filters may be used. The conditioning circuits may apply linear or non-linear manipulations. Further, the manipulation may be time-related such as analog or digital delay-lines, integrators, or rate-based manipulation. A sensor may have analog output, requiring an A/D to be connected thereto, or may have digital output. Further, the conditioning may be based on the book entitled: "*Practical Design Techniques for Sensor Signal Conditioning*", by Analog Devices, Inc., 1999 (ISBN-0-916550-20-6), which is incorporated in its entirety for all purposes as if fully set forth herein.

Alternatively or in addition, any sensor herein, any sensor technology herein, any sensor conditioning herein or handling circuits, or any sensor application herein, may be according to the book entitled: "*Sensors and Control Systems in manufacturing*", Second Edition 2010, by Sabrie Soloman, The McGraw-Hill Companies, ISBN: 978-0-07-160573-1, according to the book entitled: "*Fundamentals of Industrial Instrumentation and Process Control*", by William C. Dunn, 2005, The McGraw-Hill Companies, ISBN: 0-07-145735-6, or according to the book entitled: "*Sensor technology Handbook*", Edited by Jon Wilson, by Newnes-Elsevier 2005, ISBN:0-7506-7729-5, which are all incorporated in their entirety for all purposes as if fully set forth herein. Further, a sensor may be any sensor described in U.S. Patent Application Publication No. 2013/0201316 to Binder et al., entitled: "*System and Method for Server Based Control*", which is incorporated in its entirety for all purposes as if fully set forth herein.

A sensor may directly or indirectly measure the rate of change of the physical quantity (gradient) versus the direction around a particular location, or between different locations. For example, a temperature gradient may describe the differences in the temperature between different locations. Further, a sensor may measure time-dependent or time-manipulated values of the phenomenon, such as time-integrated, average or Root Mean Square (RMS or rms), relating to the square root of the mean of the squares of a series of discrete values (or the equivalent square root of the integral in a continuously varying value). Further, a parameter relating to the time dependency of a repeating phenomenon may be measured, such as the duty-cycle, the frequency (commonly measured in Hertz—Hz) or the period. A sensor may be based on the Micro Electro-Mechanical Systems—MEMS (a.k.a. Micro-mechanical electrical systems) technology. A sensor may respond to environmental conditions such as temperature, humidity, noise, vibration, fumes, odors, toxic conditions, dust, and ventilation.

A sensor may be an active sensor, requiring an external source of excitation. For example, resistor-based sensors such as thermistors and strain gages are active sensors, requiring a current to pass through them in order to determine the resistance value, corresponding to the measured phenomenon. Similarly, a bridge circuit based sensors are active sensors depending or external electrical circuit for their operation. Alternatively or in addition, a sensor may be a passive sensor, generating an electrical output without requiring any external circuit or any external voltage or current. Thermocouples and photodiodes are examples or passive sensors.

A sensor may measure the amount of a property or of a physical quantity or the magnitude relating to a physical phenomenon, body or substance. Alternatively or in addition, a sensor may be used to measure the time derivative thereof, such as the rate of change of the amount, the quantity or the magnitude. In the case of space related quantity or magnitude, a sensor may measure the linear density, relating to the amount of property per length, a sensor may measure the surface density, relating to the amount of property per area, or a sensor may measure the volume density, relating to the amount of property per volume. Alternatively or in addition, a sensor may measure the amount of property per unit mass or per mole of substance. In the case of a scalar field, a sensor may further measure the quantity gradient, relating to the rate of change of property with respect to position. Alternatively or in addition, a sensor may measure the flux (or flow) of a property through a cross-section or surface boundary. Alternatively or in addition, a sensor may measure the flux density, relating to the flow of property through a cross-section per unit of the cross-section, or through a surface boundary per unit of the surface area. Alternatively or in addition, a sensor may measure the current, relating to the rate of flow of property through a cross-section or a surface boundary, or the current density, relating to the rate of flow of property per unit through a cross-section or a surface boundary. A sensor may include or consists of a transducer, defined herein as a device for converting energy from one form to another for the purpose of measurement of a physical quantity or for information transfer. Further, a single sensor may be used to measure two or more phenomena. For example, two characteristics of the same element may be measured, each characteristic corresponding to a different phenomenon.

A sensor output may have multiple states, where the sensor state is depending upon the measured parameter of the sensed phenomenon. A sensor may be based on a two state output (such as '0' or '1', or 'true' and 'false'), such as an electric switch having two contacts, where the contacts can be in one of two states: either "closed" meaning the contacts are touching and electricity can flow between them, or "open", meaning the contacts are separated and the switch is non-conducting. A sensor may be a threshold switch, where the switch changes its state upon sensing that the magnitude of the measured parameter of a phenomenon exceeds a certain threshold. For example, a sensor may be a thermostat is a temperature-operated switch used to control a heating process. Another example is a voice operated switch (a.k.a. VOX), which is a switch that operates when sound over a certain threshold is detected. It is usually used to turn on a transmitter or recorder when someone speaks and turn it off when they stop speaking. Another example is a mercury switch (also known as a mercury tilt switch), which is a switch whose purpose is to allow or interrupt the flow of electric current in an electrical circuit in a manner that is dependent on the switch's physical position or alignment relative to the direction of the "pull" of earth's gravity, or other inertia. The threshold of a threshold based switch may be fixed or settable. Further, an actuator may be used in order to locally or remotely set the threshold level.

In some cases, a sensor operation may be based on generating a stimulus or an excitation to generate influence or create a phenomenon. The entire or part of the generating or stimulating mechanism may be in this case an integral part of the sensor, or may be regarded as independent actuators, and thus may be controlled by the controller. Further, a sensor and an actuator, independent or integrated, may be cooperatively operating as a set, for improving the sensing or the actuating functionality. For example, a light source, treated as an independent actuator, may be used to illuminate a location, in order to allow an image sensor to faithfully and properly capture an image of that location. In another example, where a bridge is used to measure impedance, the excitation voltage of the bridge may be supplied from a power supply treated and acting as an actuator.

A sensor may be a piezoelectric sensor, where the piezoelectric effect is used to measure pressure, acceleration, strain or force. Depending on how the piezoelectric material is cut, there are three main modes of operation: transverse longitudinal and shear. In the transverse effect mode, a force applied along an axis generates charges in a direction perpendicular to the line of force, and in the longitudinal effect mode, the amount of charge produced is proportional to the applied force and is independent of size and shape of the piezoelectric element. When using as a pressure sensor, commonly a thin membrane is used to transfer the force to the piezoelectric element, while in accelerometer use, a mass is attached to the element, and the load of the mass is measured. A piezoelectric sensor element material may be a piezoelectric ceramics (such as PZT ceramic) or a single crystal material. A single crystal material may be gallium phosphate, quartz, tourmaline, or Lead Magnesium Niobate-Lead Titanate (PMN-PT).

A sensor may be a solid state sensor, which is typically a semiconductor device and which have no mobile parts, and commonly enclosed as a chip. The sensor may be according to, or based on, the sensor described in U.S. Pat. No. 5,511,547 to Markle, entitled: "Solid State Sensors", in U.S. Pat. No. 6,747,258 to Benz et al., entitled: "Intensified Hybrid Solid-State Sensor with an Insulating Layer", in U.S. Pat. No. 5,105,087 to Jagielinski, entitled: "Large Solid State Sensor Assembly Formed from Smaller Sensors", or in U.S. Pat. No. 4,243,631 to Ryerson, entitled: "Solid State Sensor", which are all incorporated in their entirety for all purposes as if fully set forth herein.

A sensor may be a nanosensor, which is a biological, chemical or physical sensor constructed using nanoscale components, usually microscopic or submicroscopic in size. A nanosensor may be according to, or based on, the sensor described in U.S. Pat. No. 7,256,466 to Lieber et al., entitled: "Nanosensors", in U.S. Patent Application Publication No. 2007/0264623 to Wang et al., entitled: "Nanosensors", in U.S. Patent Application Publication No. 2011/0045523 to Strano et al., entitled: "Optical Nenosensors Comprising Photoluminescent Nanostructures", or in U.S. Patent Application Publication No. 2011/0275544 to Zhou et al., entitled: "Microfluidic Integration with Nanosensor Platform", which are all incorporated in their entirety for all purposes as if fully set forth herein.

A sensor may include one or more sensors, each providing an electrical output signal (such as voltage or current), or changing a characteristic (such as resistance or impedance) in response to a measured or detected phenomenon. The sensors may be identical, similar or different from each other, and may measure or detect the same or different phenomena. Two or more sensors may be connected in series or in parallel. In the case of a changing characteristic sensor or in the case of an active sensor, the unit may include an excitation or measuring circuits (such as a bridge) to generate the sensor electrical signal. The sensor output signal may be conditioned by a signal conditioning circuit. The signal conditioner may involve time, frequency, or magnitude related manipulations. The signal conditioner may be linear or non-linear, and may include an operation or an instrument amplifier, a multiplexer, a frequency converter, a frequency-to-voltage converter, a voltage-to-frequency converter, a current-to-voltage converter, a current loop converter, a charge converter, an attenuator, a sample-and-hold circuit, a peak-detector, a voltage or current limiter, a delay line or circuit, a level translator, a galvanic isolator, an impedance transformer, a linearization circuit, a calibrator, a passive or active (or adaptive) filter, an integrator, a deviator, an equalizer, a spectrum analyzer, a compressor or a de-compressor, a coder (or decoder), a modulator (or demodulator), a pattern recognizer, a smoother, a noise remover, an average or RMS circuit, or any combination thereof. In the case of analog sensor, an analog to digital (A/D) converter may be used to convert the conditioned sensor output signal to a digital sensor data. The unit may include a computer for controlling and managing the unit operation, processing the digital sensor data and handling the unit communication. The unit may include a modem or transceiver coupled to a network port (such as a connector or antenna), for interfacing and communicating over a network.

Methods and devices are provided for electrical neural blockade and stimulation of dysfunctional or transferred nerves and are described in U.S. Patent Application Publication No. 2019/0022383 to Hadlock et al. entitled: "Electrical Neural Blockade and Functional Stimulation of Dysfunctional or Transferred Nerves", which is incorporated in its entirety for all purposes as if fully set forth herein. For example, a method is provided including identifying a dysfunctional or transferred nerve, attaching an electrode array to the dysfunctional or transferred nerve proximal to the target musculature, delivering an electrical neural blockade signal, and stimulating the dysfunctional or transferred nerve distal to the point of neural blockade. A system is also provided with an electrode array configured to attach proximally to a dysfunctional or transferred nerve and deliver an electrical neural blockade signal with a neuromuscular stimulating electrode array placed distal to the point of neural blockade, and a processor in communication with the electrode arrays and configured to provide stimulation instructions based on the detected activity of the other neuromusculature. A method is further provided for identifying and treating dysfunction arising from aberrant neural regeneration for which contralateral paired neuromusculature exists.

Elicitation of eye closure and other movements via electrical stimulation may provide effective treatment for facial paralysis. A survey performed on a human feasibility study to determine whether transcutaneous neural stimulation can elicit a blink in individuals with acute facial palsy and to obtain feedback from participants regarding the tolerability of surface electrical stimulation for daily blink restoration. The survey results are provided in an article entitled: "*Electrical Stimulation of Eye Blink in Individuals with Acute Facial Palsy: Progress toward a Bionic Blink*" by Alice Frigerio, M.D., Ph.D., James T. Heaton, Ph.D., Paolo Cavallari, M.D., Ph.D., Chris Knox, B.S., Marc H. Hohman, M.D., and Tessa A. Hadlock, M.D. (Milan, Italy; and Boston, Mass.), and published October 2015 in Plastic and Reconstructive Surgery Journal [DOI: 10.1097/PRS.0000000000001639] and presented in part at the 2013 International Facial Nerve Symposium, in Boston, Massachusetts, Jun. 28 through Jul. 2, 2013, which is incorporated in its entirety for all purposes as if fully set forth herein. The Method included forty individuals with acute unilateral facial paralysis, HB grades 4 through 6, that were prospectively studied between 6 and 60 days of onset. Unilateral stimulation of zygomatic facial nerve branches to elicit eye blink was achieved with brief bipolar, charge-balanced pulse trains, delivered transcutaneously by adhesive electrode placement; results were recorded on a high-speed video camera. The relationship between stimulation parameters and cutaneous sensation was analyzed using the Wong-Baker Faces Pain Rating Scale. Complete eye closure was achieved in 55 percent of participants using stimulation parameters reported as tolerable. In those individuals, initial eye twitch was observed at an average current of 4.6 mA ($\pm 1.7$; average pulse width of 0.7 ms, 100 to 150 Hz), with complete closure requiring a mean of 7.2 mA ($\pm 2.6$). Conclusions: Transcutaneous facial nerve stimulation may artificially elicit eye blink in a majority of patients with acute facial paralysis. Although individuals varied widely in their reported degrees of discomfort from blink-eliciting stimulation, most of them indicated that such stimulation would be tolerable if it could restore eye closure. These patients would therefore benefit from a biomimetic device to facilitate eye closure until the recovery process is complete.

Facial palsy is a devastating condition potentially amenable to rehabilitation by functional electrical stimulation. A novel paradigm for unilateral facial reanimation using an implantable neuroprosthetic device is proposed and its feasibility demonstrated in a live rodent model as described in an article entitled: "*Toward the Bionic Face: A Novel Neuroprosthetic Device Paradigm for Facial Reanimation Consisting of Neural Blockade and Functional Electrical Stimulation*" by Nate Jowett, M.D., Robert E. Kearney, Ph.D., Christopher J. Knox, B.S., and Tessa A. Hadlock, M.D. (of Boston, Mass., U.S.A. and Montreal, Quebec, Canada) that was published in Volume 143, Number 1 of the Plastic and Reconstructive Surgery Journal [DOI: 10.1097/PRS.0000000000005164] and Presented as part at the 2016 Annual Meeting of the American Society for Peripheral Nerve, in Scottsdale, Arizona, which is incorporated in its entirety for all purposes as if fully set forth herein. The paradigm comprises use of healthy-side electromyographic activity as control inputs to a system whose outputs are neural stimuli to effect symmetric facial displacements. The vexing issue of suppressing undesirable activity resulting from aberrant neural regeneration (synkinesis) or nerve transfer procedures is addressed using proximal neural blockade. Methods: Epimysial and nerve cuff electrode arrays were implanted in the faces of Wistar rats. Stimuli were delivered to evoke blinks and whisks of various durations and amplitudes. The dynamic relation between electromyographic signals and facial displacements was modeled, and model predictions were compared against measured displacements. Optimal parameters to achieve facial nerve blockade by means of high-frequency alternating current were determined, and the safety of continuous delivery was assessed. Results: Electrode implantation was well tolerated. Blinks and whisks of tunable amplitudes and durations were evoked by controlled variation of neural stimuli parameters. Facial displacements predicted from electromyographic input modelling matched those observed with a variance-accounted-for exceeding 96 percent. Effective and reversible facial nerve blockade in awake behaving animals was achieved, without detrimental effect noted from long-term continual use. Conclusions: Proof-of-principle of rehabilitation of hemifacial palsy by means of a neuroprosthetic device has been demonstrated. The use of proximal neural blockade coupled with distal functional electrical stimulation may have relevance to rehabilitation of other peripheral motor nerve deficits.

Systems and methods for detecting a user's facial movement and expression are featured in U.S. Pat. No. 9,625,251 to Heaton et al. entitled: "Facial movement and expression detection and stimulation", which is incorporated in its entirety for all purposes as if fully set forth herein. The systems and methods include a plurality of radiation sources, a plurality of radiation detectors, where each radiation detector is paired with a different one of the radiation sources and configured to detect radiation emitted by its paired radiation source, and a controller connected to the radiation detectors and configured to receive signals corresponding to measurements of emitted radiation from each of the radiation detectors, determine, for each radiation source-detector pair, information about whether a radiation path between the source and detector is blocked by a portion of the user's face, and determine a facial movement or expression of the user based on the information.

A system and method of treating hyperactivity of an eyelid closing muscle in a subject after facial nerve paralysis is described in U.S. Patent Application Publication No. 2013/0158612 to Lindenthaler entitled: "System and Method for Eyelid Simulation", which is incorporated in its entirety for all purposes as if fully set forth herein. The method or system includes providing a stimulation system and selectively stimulating eyelid opening muscle(s) or innervating nerves, eyelid opening reflexes, or eyelid opening reflexes in non-muscular tissue, using the stimulation system, without substantially activating the eyelid closing muscle. The system and method evokes eyelid movement in the subject.

A method that includes evoking and recording the response of a trigeminal reflex in the presence and absence of occipital nerve stimulation (ONS) is described in U.S. Patent Application Publication No. 2011/0264167 to Poletto entitled: "Modulation of trigeminal reflex strength", which is incorporated in its entirety for all purposes as if fully set forth herein. The method is used to determine whether, and to what extent, ONS modulates the trigeminal reflex. If the ONS modulates the trigeminal reflex, e.g. to a sufficient degree, the subject may be considered a candidate for ONS for treatment of headache.

The Facial Nerve Stimulator (FNS) is a headset type device used to treat patients with mild or severe Bell's Palsy and other facial nerve problems, and is described in U.S. Patent Application Publication No. 2008/0082131 to Llanos entitled: "Facial Nerve Stimulator (FNS)", which is incorporated in its entirety for all purposes as if fully set forth herein. The Facial Nerve Stimulator (FNS) is worn comfortably by resting one end on the ear lobe and inserting the Oral Electrode casing inside the mouth. The exterior Electrode casing rests just over the mandibular condyle. With the Oral Electrode casing inside the mouth and the exterior Electrode casing resting on the mandibular condyle, the FNS system is activated from a TENS unit to allow small electric pulses to stimulate both the 2nd branch (Maxillary) and the 3rd branch (mandibular) of the Trigeminal nerve as well as the mandibular condyle.

In certain variations, systems and/or methods for electromagnetic induction therapy are disclosed in U.S. Pat. No. 9,757,584 to BURNETT entitled: "Methods and devices for performing electrical stimulation to treat various conditions", which is incorporated in its entirety for all purposes as if fully set forth herein. One or more ergonomic or body contoured applicators may be included. The applicators include one or more conductive coils configured to generate an electromagnetic or magnetic field focused on a target nerve, muscle or other body tissues positioned in proximity to the coil. One or more sensors may be utilized to detect stimulation and to provide feedback about the efficacy of the applied electromagnetic induction therapy. A controller may be adjustable to vary a current through a coil to adjust the magnetic field focused upon the target nerve, muscle or other body tissues based on the feedback provide by a sensor or by a patient. In certain systems or methods, pulsed magnetic fields may be intermittently applied to a target nerve, muscle or tissue without causing habituation.

Electrical stimulation patterns and methods of use thereof for treating dry eye disease, tired eye, or other forms of ocular discomfort are described in in U.S. Patent Application Publication No. 2016/0022992 to Franke et al. entitled: "Stimulation patterns for treating dry eye", which is incorporated in its entirety for all purposes as if fully set forth herein. The methods generally include applying patterned stimulation to an anatomical structure located in an ocular region or a nasal region to increase tear production.

A battery-operated transcutaneous electrical nerve stimulator (TENS) to treat headache pain in an abortive and/or preventive manner is described in in U.S. Pat. No. 8,560,075 to Covalin entitled: "Apparatus and method for the treatment of headache", which is incorporated in its entirety for all purposes as if fully set forth herein. The TENS unit and its electrodes are built into a unitary device which facilitates a self-administered treatment. In some embodiments, the pulses are monophasic. In other embodiments, pairs of biphasic pulses are provided, wherein each pair of biphasic pulses includes a first pulse having a first polarity separated by a gap in time from a second pulsed having an opposite polarity. In some embodiments, each pulse in each biphasic pair is of a duration equal to that of the other pulse of the pair. In some embodiments, the duration of each pulse is between about 50 microseconds and about 400 microseconds, and the gap in time between pulses of a pair is between about 50 and 100 microseconds.

A method, apparatus, and system for affecting neuromodulation based upon an evoking signal applied to a patient's body are disclosed in U.S. Patent Application Publication No. 2007/0179557 to Maschino et al. entitled: "Controlling neuromodulation using stimulus modalities", which is incorporated in its entirety for all purposes as if fully set forth herein. An internal and/or external evoking and/or therapeutic signal is applied to a first target portion of a patient's body. Data relating to a physiological response resulting from the internal and/or external evoking and/or therapeutic signal is received. A neurotransmission characteristic of the patient's body is determined based upon the data relating to the physiological response. At least one parameter defining an electrical therapeutic signal provided by an implantable medical device is controlled based upon the determined neurotransmission characteristic to treat a disorder.

An implantable miniature eyelid electrode apparatus that causes a paralyzed eyelid to close or open by passing an electrical stimulating current to a nerve or muscle is described in U.S. Patent Application Publication No. 2003/0023297 to Byers et al. entitled: "Miniature implantable array and stimulation system suitable for eyelid stimulation", which is incorporated in its entirety for all purposes as if fully set forth herein. The apparatus is comprised of a longitudinally flexible, nonconductive body containing electrodes that pass an electrical signal to the nearby nerve or muscle, which closes or opens the eyelid. The apparatus is electrically actuated by a source that may be located remotely from the apparatus. The electrical signal passes along wires from the source to the apparatus. The apparatus is biocompatible with the environment in the living tissue and is electrically insulated from the surrounding tissue, except where the electrodes contact the living tissue. The apparatus is very small and is not obvious to visual inspection when implanted A system for trigeminal nerve stimulation is disclosed in U.S. Patent Application Publication No. 2014/0081353 to Cook et al. entitled: "Pulse generator for cranial nerve stimulation", which is incorporated in its entirety for all purposes as if fully set forth herein. In one embodiment, the system includes a storage medium, a pulse generator in communication with the storage medium, a power source coupled to the pulse generator, and at least one electrode communicatively coupled to the pulse generator. The pulse generator includes a microcontroller which executes instructions from the storage medium and the microcontroller is configured to perform at least one of the following operations: produce electrical pulses having defined characteristics, record a log of use and anomalous events, restrict use to a specified individual, interface with electrodes, provide a signal to the specified individual indicating operational conditions and trouble conditions, and provide a signal to the specified individual indicating an end of a treatment period.

See for example U.S. Pat. No. 8,060,208 entitled "Action potential conduction prevention," U.S. Pat. No. 8,843,188 entitled "Adjustable nerve electrode," U.S. Pat. No. 8,983,614 entitled "Onset-mitigating high-frequency nerve block," U.S. Pat. No. 9,008,800 entitled "Separated-interface nerve electrode," and U.S. Pat. No. 9,119,966 entitled "Systems and methods that provide an electrical waveform for neural stimulation or nerve block," all of which are incorporated herein by reference in their entirety.

In consideration of the foregoing, it would be an advancement in the art to provide a method, device, or a system for transcutaneous nerve stimulation such as facial nerve stimulation, and in particular, for using transcutaneous nerve stimulation for artificially eliciting eye blink, a smile, or other facial muscle activity, such as with humans with acute facial paralysis, such as Bell's palsy, or with Dry eye syndrome. Preferably, such methods, devices, or systems may be providing an improved elicitation of eye closure and are discomfort or pain tolerable, simple, secure, cost-effective, reliable, easy to install, use or monitor, has a minimum part count, enclosed in a small housing, minimum hardware, and/or using existing and available components, protocols, programs and applications, that enable better control, security (or additional functionalities), and providing a better user experience.

SUMMARY

A device may be used for artificially stimulating a nerve in a human body, and maybe used with a network over a medium. Any device herein may comprise a controllable pulse generator for generating a bursts train signal; a sensor that may output a sensor signal in response to a physical phenomenon; a port for coupling to the medium; a transceiver coupled to the port for transmitting digital data to, and for receiving digital data from, the network; two electrodes attachable to a human body and connected to the pulse generator for coupling bursts train signal to the human body for periodically stimulating the nerve; software and a processor for executing the software, the processor is coupled to the sensor for receiving the sensor signal therefrom, to the transceiver for receiving the digital data from the network therefrom, and to control and activate the controllable pulse generator; a power source for supplying Direct Current (DC) power to the controllable pulse generator, the sensor, the transceiver, and the processor; and a single wearable enclosure housing the pulse generator, the sensor, the transceiver, the port, the processor, and the power source. Any pulse generator herein may be controlled or activated in response to the sensor signal or the received digital data from the network.

Any device herein may further be integrated with, may be attached to, may be part of, may be used with, may be the basis of, or may be included in, a commercial available off-the-shelf Transcutaneous Electrical Nerve Stimulation (TENS) device. Any commercial available off-the-shelf TENS device may integrate, may be attached to, may be part of, or may comprises, any device herein. Any sensor herein may comprise, or may consist of, an eye blink detector. Any nerve herein may be a facial nerve, and any electrodes herein may be attachable to the human body scalp, so that when attached, may elicit eye blinking by stimulating the facial nerve. Any device herein may be used for overcoming facial nerve paralysis or Bell's palsy, for Dry eye syndrome, or for Electrical Muscle Stimulation (EMS).

Any power source herein may consist of, or may comprise, a primary or a rechargeable battery, and any device herein may further comprise a battery compartment for housing the battery. Any power source herein may consist of, or may comprise, a rechargeable battery, and any device herein may further comprise a battery charger for charging the rechargeable battery. Any device herein may be operative to contactless charging the rechargeable battery, the contactless charging may be based on induction, and any battery charger herein may further comprise an induction coil for receiving AC power and charging the rechargeable battery when the device is disposed in an electromagnetic field. Any device herein may be operative to be powered by kinetic energy, and any battery charger herein may include a kinetic energy to an electrical energy converter. Any converter herein may comprise a coil and a magnetic field, and a relative movement of the coil and the magnetic field may generate power in response to the device motion.

Any device herein may further comprise an electric sensor that may be connectable to the electrodes for measuring an electrical parameter by the electrodes. Any electric sensor herein may comprise, may consist of, or may be based on, an impedance meter for measuring an impedance between the electrodes. Any the impedance meter may comprise, may consist of, or may be based on, an ohmmeter measuring an electrical resistance, wherein the impedance meter comprises, consists of, or is based on, a capacitance meter for measuring capacitance, wherein the impedance meter comprises, consists of, or is based on, an inductance meter for measuring inductance, or any combination thereof. Any pulse generator may be activated or deactivated in response to the measured electrical parameter. Alternatively or in addition, any parameter or any characteristic of the bursts train signal may be set in response to any measured electrical parameter, such as the peak-to-peak amplitude, the amplitude nominal value, the amplitude effective value, the signal frequency in at least one of, or in all of, the bursts, the duration of at least one of, or in all of, the bursts, or the period between at least two consecutive bursts, or between any two consecutive bursts, of the bursts train signal. Any electric sensor herein may be periodically connected to the electrodes for measuring the electrical parameter by the electrodes, and any electric sensor herein may be connected to the electrodes between two consecutive bursts. Any device herein may further comprise a switch having two states, and any switch herein may be coupled to be controlled by the processor and may be operative to be in distinct first and second states. In the first state, the electrodes may be connected to the pulse generator for receiving the bursts train signal therefrom, and in the first state the electrodes may be connected to the electric sensor for measuring the electric parameter. Any switch herein may comprise, or may consist of, a single pole double throw (SPDT) switch.

Any device herein may operative for operating of an operating system that is included in the software. Any operating system herein may be is a mobile operating system, such as Android version 2.2 (Froyo), Android version 2.3 (Gingerbread), Android version 4.0 (Ice Cream Sandwich), Android Version 4.2 (Jelly Bean), Android version 4.4 (KitKat), Apple iOS version 3, Apple iOS version 4, Apple iOS version 5, Apple iOS version 6, Apple iOS version 7, Microsoft Windows® Phone version 7, Microsoft Windows® Phone version 8, Microsoft Windows® Phone version 9, or Blackberry® operating system. Any operating system herein may be Real-Time Operating System (RTOS), such as FreeRTOS, SafeRTOS, QNX, VxWorks, or Micro-Controller Operating Systems (μC/OS).

Any of the bursts in the signal herein may comprise, or may consist of, one or more asymmetrical Bi-Phasic square current or voltage pulses. Any controllable pulse generator herein may comprise, or may consist of, a continuous signal generator and an electrically controlled switch connected in series with the continuous signal generator output. Any switch herein may comprise a control port that may be coupled to be controlled by the processor.

Any electrically controlled switch herein may be based on, may comprise, or may consist of, an electrical circuit that may comprise a relay, an open collector transistor, an open drain transistor, a thyristor, a TRIAC, or an opto-isolator.

Any electrically controlled switch herein may be based on, may comprise, or may consist of, an electrical circuit or a transistor. Any transistor herein may be a field-effect power transistor, and any switch herein may be formed between a 'drain' and a 'source' pins, and the control port is a 'gate' pin. Any field-effect power transistor herein may be an N-channel or a P-channel field-effect power transistor. Any relay herein may be a solenoid-based electromagnetic relay or a reed relay, a solid-state or semiconductor based relay, or an AC Solid State Relay (SSR).

Any pulse generator herein may be a current generator, and the peak-to-peak amplitude, the nominal value, or the effective value, of at least one burst may be above 0.1 milliamper (mA), 0.2 mA, 0.5 mA, 0.8 mA, 1 mA, 1.2 mA, 1.5 mA, 1.8 mA, 2 mA, 2.5 mA, 3 mA, 3.5 mA, 4 mA, 4.5 mA, 5 mA, 5.5 mA, 6 mA, 7 mA, 8 mA, 9 mA, 10 mA, 11 ma, 12 mA, 15 mA, 18 mA, 20 mA, 22 mA, 25 mA, 30 mA, 35 mA, 40 mA, 45 mA, 50 mA, 55 mA, 60 mA, 65 mA, 70 mA, 75 mA, 80 mA, or 100 mA. Alternatively or in addition, any pulse generator herein may be a current generator, and the peak-to-peak amplitude, the nominal value, or the effective value, of at least one burst may be below 0.1 milliamper (mA), 0.2 mA, 0.5 mA, 0.8 mA, 1 mA, 1.2 mA, 1.5 mA, 1.8 mA, 2 mA, 2.5 mA, 3 mA, 3.5 mA, 4 mA, 4.5 mA, 5 mA, 5.5 mA, 6 mA, 7 mA, 8 mA, 9 mA, 10 mA, 11 ma, 12 mA, 15 mA, 18 mA, 20 mA, 22 mA, 25 mA, 30 mA, 35 mA, 40 mA, 45 mA, 50 mA, 55 mA, 60 mA, 65 mA, 70 mA, 75 mA, 80 mA, or 100 mA. Any pulse generator herein may be a voltage generator, and the peak-to-peak amplitude, the nominal value, or the effective value, of at least one burst may be above 0.1 millivolt (mV), 0.2 mV, 0.5 mV, 0.8 mV, 1 mV, 1.2 mV, 1.5 mV, 1.8 mV, 2 mV, 2.5 mV, 3 mV, 3.5 mV, 4 mV, 4.5 mV, 5 mV, 5.5 mV, 6 mV, 7 mV, 8 mV, 9 mV, 10 mV, 11 mV, 12 mV, 15 mV, 18 mV, 20 mV, 22 mV, 25 mV, 30 mV, 35 mV, 40 mV, 45 mV, 50 mV, 55 mV, 60 mV, 65 mV, 70 mV, 75 mV, 80 mV, or 100 mV. Alternatively or in addition, any pulse generator herein may be a voltage generator, and the peak-to-peak amplitude, the nominal value, or the effective value, of at least one burst may be below 0.1 millivolt (mV), 0.2 mV, 0.5 mV, 0.8 mV, 1 mV, 1.2 mV, 1.5 mV, 1.8 mV, 2 mV, 2.5 mV, 3 mV, 3.5 mV, 4 mV, 4.5 mV, 5 mV, 5.5 mV, 6 mV, 7 mV, 8 mV, 9 mV, 10 mV, 11 mV, 12 mV, 15 mV, 18 mV, 20 mV, 22 mV, 25 mV, 30 mV, 35 mV, 40 mV, 45 mV, 50 mV, 55 mV, 60 mV, 65 mV, 70 mV, 75 mV, 80 mV, or 100 mV.

Alternatively or in addition, any pulse generator herein may be a voltage generator, and the peak-to-peak amplitude, the nominal value, or the effective value, of at least one burst may be more than 0.1 Volts (V), 0.2 V, 0.5 V, 0.8 V, 1 V, 1.2 V, 1.5 V, 1.8 V, 2 V, 2.5 V, 3 V, 3.5 V, 4 V, 4.5 V, 5 V, 5.5 V, 6 V, 7 V, 8 V, 9 V, 10 V, 11 V, 12 V, 15 V, 18V, 20 V, 22 V, 25 V, 30 V, 35 V, 40 V, 45 V, 50 V, 55 V, 60 V, 65 V, 70 V, 75 V, 80 V, or 100 V. Alternatively or in addition, any pulse generator herein may be a voltage generator, and the peak-to-peak amplitude, the nominal value, or the effective value, of at least one burst may be less than 0.1 Volts (V), 0.2 V, 0.5 V, 0.8 V, 1 V, 1.2 V, 1.5 V, 1.8 V, 2 V, 2.5 V, 3 V, 3.5 V, 4 V, 4.5 V, 5 V, 5.5 V, 6 V, 7 V, 8 V, 9 V, 10 V, 11 V, 12 V, 15 V, 18V, 20 V, 22 V, 25 V, 30 V, 35 V, 40 V, 45 V, 50 V, 55 V, 60 V, 65 V, 70 V, 75 V, 80 V, or 100 V.

Any duration herein of at least one of, or in all of, the bursts of the bursts train signal may be more than 1 milliseconds (ms), 2 ms, 3 ms, 5 ms, 7 ms, 10 ms, 12 ms, 15 ms, 18 ms, 20 ms, 25 ms, 30 ms, 40 ms, 45 ms, 50 ms, 100 ms, 120 ms, 150 ms, 180 ms, 200 ms, 250 ms, 300 ms, 400 ms, 450 ms, or 500 ms. Alternatively or in addition, any duration of at least one of, or in all of, the bursts of the bursts train signal may be less than 1 milliseconds (ms), 2 ms, 3 ms, 5 ms, 7 ms, 10 ms, 12 ms, 15 ms, 18 ms, 20 ms, 25 ms, 30 ms, 40 ms, 45 ms, 50 ms, 100 ms, 120 ms, 150 ms, 180 ms, 200 ms, 250 ms, 300 ms, 400 ms, 450 ms, or 500 ms.

Any signal frequency herein in at least one of, or in all of, the bursts of the bursts train signal may be more than 1 Hertz (Hz), 2 Hz, 5 Hz, 8 Hz, 10 Hz, 12 Hz, 15 Hz, 18 Hz, 20 Hz, 22 Hz, 25 Hz, 30 Hz, 35 Hz, 50 Hz, 60 Hz, 70 Hz, 80 Hz, 100 Hz, 120 Hz, 150 Hz, 180 Hz, 200 Hz, 250 Hz, 300 Hz, 350 Hz, 400 Hz, or 500 Hz. Alternatively or in addition, any signal frequency herein in at least one of, or in all of, the bursts of the bursts train signal may be less than 1 Hertz (Hz), 2 Hz, 5 Hz, 8 Hz, 10 Hz, 12 Hz, 15 Hz, 18 Hz, 20 Hz, 22 Hz, 25 Hz, 30 Hz, 35 Hz, 50 Hz, 60 Hz, 70 Hz, 80 Hz, 100 Hz, 120 Hz, 150 Hz, 180 Hz, 200 Hz, 250 Hz, 300 Hz, 350 Hz, 400 Hz, or 500 Hz.

Any period herein between at least two consecutive bursts, or between any two consecutive bursts, may be more than 100 milliseconds (ms), 120 ms, 150 ms, 180 ms, 200 ms, 250 ms, 300 ms, 400 ms, 450 ms, 500 ms, 700 ms, 1,000 (ms), 1,200 ms, 1,500 ms, 1,800 ms, 2,000 ms, 2,500 ms, 3,000 ms, 3,500 ms, 4,000 ms, 4,500 ms, 5,000 ms, 6,000 ms, 6,500 ms, 7,000 ms, 7,500 ms, 8,000 ms, 8,500 ms, 9,000 ms, or 9,500 ms. Alternatively or in addition, any period herein between at least two consecutive bursts, or between any two consecutive bursts, may be less than 100 milliseconds (ms), 120 ms, 150 ms, 180 ms, 200 ms, 250 ms, 300 ms, 400 ms, 450 ms, 500 ms, 700 ms, 1,000 (ms), 1,200 ms, 1,500 ms, 1,800 ms, 2,000 ms, 2,500 ms, 3,000 ms, 3,500 ms, 4,000 ms, 4,500 ms, 5,000 ms, 6,000 ms, 6,500 ms, 7,000 ms, 7,500 ms, 8,000 ms, 8,500 ms, 9,000 ms, or 9,500 ms.

Any device herein any comprise a random number generator that may be coupled to the processor for producing a random number or signal, and any bursts train signal herein may be in response to the random number. Any random number generator herein may be hardware based, and may be using thermal noise, shot noise, nuclear decaying radiation, photoelectric effect, or quantum phenomena. Any random number generator herein may be software based, and may be based on executing an algorithm for generating pseudo-random numbers. Any pulse generator herein may be activated or deactivated in response to the random number. Any parameter or any characteristic herein of any bursts train signal may be set in response to the random number, and any parameter herein may comprise the peak-to-peak amplitude, the amplitude nominal value, the amplitude effective value, the signal frequency in at least one of, or in all of, the bursts, the duration of at least one of, or in all of, the bursts, or the period between at least two consecutive bursts, or between any two consecutive bursts, of the bursts train signal.

Any wearable enclosure herein may be wearable on the human body, such as wearable on an organ of the person head that may be an eye, ear, face, cheek, nose, mouth, lip, forehead, or chin. Any enclosure herein may be constructed to have a form substantially similar to, is constructed to have a shape allowing mounting or wearing identical or similar to, or is constructed to have a form to at least in part substitute for, headwear, eyewear, or earpiece. Any headwear herein may consist of, may be structured as, or may comprise, a bonnet, a cap, a crown, a fillet, a hair cover, a hat, a helmet, a hood, a mask, a turban, a veil, or a wig. Any eyewear herein may consist of, may be structured as, or may comprise, glasses, sunglasses, a contact lens, a blindfold, or a goggle. Any earpiece herein may consist of, may be structured as, or may comprise, a hearing aid, a headphone, a headset, or an earplug. Any enclosure herein may be permanently or releaseably attachable to, or may be part of, a clothing piece of a person, and the attaching may use taping, gluing, pinning, enclosing, encapsulating, a pin, or a latch and hook clip. Any clothing piece herein may be a top, a bottom, or full-body underwear, or a headwear, a footwear, an accessory, an outwear, a suit, a dress, or a skirt. Any device herein may further comprise an annular member defining an aperture therethrough that is sized for receipt therein of a part of a human body, and the human body part may be part of a human hand that may consist of, or may comprise, an upper arm, elbow, forearm, wrist, or a finger.

Any human body part herein may be part of a human head or neck that may consist of, or may comprise, a forehead, ear, skull, or face. Further, any human body part herein may be part of a human thorax or abdomen that may consist of, or may comprise, a waist or hip. Any human body part herein may be part of a human leg or foot that may consist of, or may comprise, a thigh, calf, ankle, instep, knee, or toe. Any single enclosure herein may be shaped or structured as Behind-the-ear (BTE), 'Mini' BTE, or In-The-Ear (ITE) enclosure. Any enclosure herein may be constructed to have a form substantially similar to that of a standard hearing aid; a wearable element substantially similar to those of a standard hearing aid; a shape allowing direct mounting in or on the external ear; or a form to at least in part substitute for a standard hearing aid. Further, any enclosure herein may be constructed to have a form substantially similar to that of a standard headphone or earplug; wearable elements substantially similar to those of a standard headphone or earplug; a shape allowing direct mounting in or on the head; or a form to at least in part substitute for a standard headphone or earplug.

Any electrodes herein may be EEG or ECG electrodes, or may be optimized or configured to primarily serve as Electroencephalography (EEG) or an Electrocardiography (ECG) electrodes. Any electrodes herein may be mechanically attached or coupled to each other, and any device herein may further comprise an electrodes assembly that may comprise a single structure attached to the two electrodes, the assembly may further comprise a connector for connecting to the wearable enclosure, and the assembly may further determine the distance between the electrodes. Any connector herein may comprise, or may consist of, a slim connector or a Zero Force connector (ZIF), and any device herein may further comprise a flexible cable for connecting the electrodes assembly to the enclosure. Each of the electrodes herein may be a skin electrode that may comprise a substantially flat and round conductive pad, having a surface area of the conductive pad that may be above 1 square millimeters ($mm^2$), 2 $mm^2$, 3 $mm^2$, 5 $mm^2$, 8 $mm^2$, 10 $mm^2$, 12 $mm^2$, 15 $mm^2$, 17 $mm^2$, 20 $mm^2$, 22 $mm^2$, 25 $mm^2$, 30 $mm^2$, or 50 $mm^2$, or the surface area of the conductive pad may be less than 2 square millimeters ($mm^2$), 3 $mm^2$, 5 $mm^2$, 8 $mm^2$, 10 $mm^2$, 12 $mm^2$, 15 $mm^2$, 17 $mm^2$, 20 $mm^2$, 22 $mm^2$, 25 $mm^2$, 30 $mm^2$, 50 $mm^2$, or 100 $mm^2$. Upon attaching to the scalp, the distance between the centers or edges of any two electrodes conductive pads herein may be less than 5 millimeter (mm), 7 mm, 10 mm, 12 mm, 15 mm, 20 mm, 25 mm, 30 mm, 40 mm, 50 mm, 70 mm, or 100 mm.

Upon attaching to the scalp, the distance between the centers or edges of any two electrodes conductive pads herein may be more than 4 millimeter (mm), 7 mm, 10 mm, 12 mm, 15 mm, 20 mm, 25 mm, 30 mm, 40 mm, 50 mm, 70 mm, or 90 mm. Each of the electrodes herein may be based on, may comprise, or may consist of, flexible, stretchable, printed circuit. Each of the electrodes herein may be based on, may comprise, or may consist of, a patterned conductive material printed on an adhesive film that is attachable to a human skin. Each of the electrodes herein may be based on, may comprise, or may consist of, a 'tattoo' electrode that may be based on, may comprise, or may consist of, a conductive material laminated between adhesive polymer films. Each of the electrodes herein may be based on, may comprise, or may consist of, an implantable electrode or an implanted electrode.

Any electrodes herein may be attached to a human face, such as to affect or stimulate a facial nerve in the human face, for example to affect or stimulate the Zygomatic branch, the Temporal Branch, or both. Each of the electrodes herein may include a conductive area that may be attached to the human face, and any conductive area herein may define a center point. Any device herein may be used with an imaginary line defined by the shortest path between a right eye and a right ear, or between a left eye and a left ear, of the human face, and one of the electrodes herein may be located so that part of, most of, or all of, the conductive area is above the imaginary line. Alternatively or in addition, any one of the electrodes herein may be located so that part of, most of, or all of, the conductive area is below the imaginary line. The center point of at least one of the electrodes may be above or below the imaginary line.

The center point of at least one of the electrodes herein may be at a distance from the imaginary line that may be at least 1 millimeter (mm), 2 mm, 3 mm, 5 mm, 7 mm, 10 mm, 12 mm, 15 mm, 20 mm, 15 mm, 30 mm, 40 mm, 50 mm, 70 mm, or 100 mm. Alternatively or in addition, the center point of the at least one of the electrodes herein may be at a distance from the imaginary line that may be less than 2 millimeter (mm), 3 mm, 5 mm, 7 mm, 10 mm, 12 mm, 15 mm, 20 mm, 25 mm, 30 mm, 40 mm, 50 mm, 70 mm, 100 mm, or 120 mm. Any device herein may be used with a first line that is perpendicular to the imaginary line and passes through the center point of one of the electrodes, and a second line that is perpendicular to the imaginary line and passes through the center point of the other electrode, and the distance between the first and second lines may be equal to, or less than, 1 millimeter (mm), 2 mm, 3 mm, 5 mm, 7 mm, 10 mm, 12 mm, 15 mm, 20 mm, 25 mm, 30 mm, 40 mm, 50 mm, 70 mm, or 100 mm, or the distance between the first and second lines may be equal to, or more than, 0 mm, 1 millimeter (mm), 2 mm, 3 mm, 5 mm, 7 mm, 10 mm, 12 mm, 15 mm, 20 mm, 25 mm, 30 mm, 40 mm, 50 mm, 70 mm, 100 mm, or 120 mm.

Any pulse generator herein may be activated or deactivated in response to digital data received from the network. Any parameter or any characteristic of any of the bursts train signal herein may be set in response to digital data received from the network. Any parameter herein may comprise the peak-to-peak amplitude, the amplitude nominal value, the amplitude effective value, the signal frequency in at least one of, or in all of, the bursts, the duration of at least one of, or in all of, the bursts, or the period between at least two consecutive bursts, or between any two consecutive bursts, of the bursts train signal.

Any pulse generator herein may be activated or deactivated in response to the sensor signal. Any device herein may be used with a minimum or maximum value, and any pulse generator may be activated or deactivated in response to the sensor signal being below the minimum value, or any pulse generator may be activated or deactivated in response to the sensor signal being above the maximum value. Any parameter or any characteristic of any bursts train signal herein may be set in response to the sensor signal. Any parameter herein may comprise the peak-to-peak amplitude, the amplitude nominal value, the amplitude effective value, the signal frequency in at least one of, or in all of, the bursts, the duration of at least one of, or in all of, the bursts, or the period between at least two consecutive bursts, or between any two consecutive bursts, of the bursts train signal.

Any device herein may be further operative to send a message to the network, and any network herein may be a wireless network, and any herein message may be sent over the Internet via the wireless network. Any message herein may be sent over the Internet via the wireless network to an Instant Messaging (IM) server for being sent to a client device as part of an IM service. The message or the communication with the IM server may be using, or may be based on, SMTP (Simple Mail Transfer Protocol), SIP (Session Initiation Protocol), SIMPLE (SIP for Instant Messaging and Presence Leveraging Extensions), APEX (Application Exchange), Prim (Presence and Instance Messaging Protocol), XMPP (Extensible Messaging and Presence Protocol), IMPS (Instant Messaging and Presence Service), RTMP (Real Time Messaging Protocol), STM (Simple TCP/IP Messaging) protocol, Azureus Extended Messaging Protocol, Apple Push Notification Service (APNs), or Hypertext Transfer Protocol (HTTP).

Any message herein may be a text-based message and the IM service may be a text messaging service. Any message herein may be according to, or may be based on, a Short Message Service (SMS) message and the IM service is a SMS service, the message is according to, or based on, an electronic-mail (e-mail) message and the IM service is an e-mail service, the message is according to, or based on, WhatsApp message and the IM service is a WhatsApp service, the message is according to, or based on, an Twitter message and the IM service is a Twitter service, or the message is according to, or based on, a Viber message and the IM service is a Viber service. Any message herein may be a Multimedia Messaging Service (MMS) or an Enhanced Messaging Service (EMS) message that may include an audio or video, and the IM service may be respectively a NMS or EMS service. Any device herein may be used with a minimum or maximum value, and any message may be sent in response to the sensor signal being below the minimum value, or the message may be sent in response to the sensor signal being above the maximum value.

Any device herein may be addressable in the network, such as in the Internet, using a digital address. Any digital address herein may be a MAC layer address that is MAC-48, EUI-48, or EUI-64 address type. Alternatively or in addition, any digital address herein may be a layer 3 address and is static or dynamic IP address that is IPv4 or IPv6 type address.

Any network herein may comprise, may use, or may consist of, a wireless network, any port herein may comprise, may use, or may consist of, an antenna for transmitting and receiving first Radio-Frequency (RF) signals over the air; and any transceiver herein may comprise, may use, or may consist of, a wireless transceiver coupled to the antenna for wirelessly transmitting and receiving the digital data over the air using the wireless network. Any wireless network herein may be a Wireless Wide Area Network (WWAN), such as wireless broadband network, any wireless transceiver herein may be a WWAN transceiver, and any antenna herein may be a WWAN antenna. Any wireless network herein may be a WiMAX network, any antenna herein may be a WiMAX antenna and any wireless transceiver herein may be a WiMAX modem, and the WiMAX network may be according to, or may be based on, IEEE 802.16-2009. Any wireless network herein may be a cellular telephone network, any antenna herein may be a cellular antenna, and any wireless herein transceiver may be a cellular modem, and any cellular telephone network herein may be a Third Generation (3G) network that uses UMTS W-CDMA, UMTS HSPA, UMTS TDD, CDMA2000 1×RTT, CDMA2000 EV-DO, or GSM EDGE-Evolution, or wherein the cellular telephone network is a Fourth Generation (4G) network that uses HSPA+, Mobile WiMAX, LTE, LTE-Advanced, MBWA, or is may be based on IEEE 802.20-2008.

Any wireless network herein may be a Wireless Personal Area Network (WPAN), any wireless transceiver herein may be a WPAN transceiver, and any antenna herein may be a WPAN antenna. Any WPAN herein may be according to, or may be based on, Bluetooth™ Bluetooth Low Energy (BLE), or IEEE 802.15.1-2005 standards, or any WPAN may be a wireless control network that may be according to, or may be based on, Zigbee™, IEEE 802.15.4-2003, or Z-Wave™ standards. Any wireless network herein may be a Body Area Network (BAN), such as according to, or based on, IEEE 802.15.6 standard, and any wireless transceiver herein may be a BAN transceiver, and any antenna herein may be a BAN antenna.

Any wireless network herein may be a Wireless Local Area Network (WLAN), such as according to, or based on, IEEE 802.11-2012, IEEE 802.11a, IEEE 802.11b, IEEE 802.11g, IEEE 802.11n, or IEEE 802.116ac, and any wireless transceiver herein may be a WLAN transceiver, and any antenna herein may be a WLAN antenna. Any wireless network herein may be over a licensed or unlicensed radio frequency band. Any wireless network herein may be in the unlicensed radio frequency band is an Industrial, Scientific and Medical (ISM) radio band. Any wireless transceiver herein may be operative to communicate in an ad-hok scheme. Any device herein may be used with an intermediary device, and the wireless transceiver may be operative to communicate with the intermediary device using an infrastructure scheme, and the intermediary device may be a Wireless Access Point (WAP), a wireless switch, or a wireless router.

Any sensor herein may be a physiological sensor that may respond to parameters associated with the human body, and may be external to the sensed body, implanted inside the sensed body, attached to the sensed body, or wearable on the sensed body. Any physiological sensor herein may be responding to body electrical signals and may be an EEG Electroencephalography (EEG) or an Electrocardiography (ECG) sensor, or may be responding to oxygen saturation, gas saturation, or a blood pressure in the sensed body.

Any sensor herein may be an electric sensor that responds to an electrical characteristics or electrical phenomenon quantity in an electrical circuit, and any sensor herein may be connected for measuring a parameter or characteristic the bursts train signal, such as being connected in series between the pulse generator and the electrodes, or connected in parallel to the electrodes. Any electrical sensor herein may be responsive to Alternating Current (AC) or Direct Current (DC). Any electrical sensor herein may be an ampermeter that responds to electrical current passing through a conductor or wire. Any ampermeter herein may consist of, or may comprise, a galvanometer, a hot-wire ampermeter, a current clamp, or a current probe. Any electrical sensor herein may be a voltmeter that responds to an electrical voltage, or a wattmeter that responds to active electrical power.

Any sensor herein may be a piezoelectric sensor that may use the piezoelectric effect, may include single crystal material or a piezoelectric ceramics, and may use transverse, longitudinal, or shear effect mode. Any sensor herein may be a thermoelectric sensor that responds to a temperature or a temperature gradient that may sense the temperature using conduction, convection, or radiation. Any thermoelectric sensor herein may consist of, or may comprise, a Positive Temperature Coefficient (PTC) thermistor, a Negative Temperature Coefficient (NTC) thermistor, a thermocouple, a quartz crystal, or a Resistance Temperature Detector (RTD). Any device herein may comprise multiple sensors arranged as a directional sensor array operative to estimate the number, magnitude, frequency, Direction-Of-Arrival (DOA), distance, or speed of the phenomenon impinging the sensor array, and the processor may be operative for processing of the sensor array outputs.

Any sensor herein may consist of, or may comprise, a nanosensor, a crystal, or a semiconductor, or wherein: the sensor is an ultrasonic based, the sensor is an eddy-current sensor, the sensor is a proximity sensor, the sensor is a bulk or surface acoustic sensor, or the sensor is an atmospheric or an environmental sensor. Any sensor herein may consist of, or may comprise a radiation sensor that responds to radioactivity, nuclear radiation, alpha particles, beta particles, or gamma rays, and is based on gas ionization. Any sensor herein may consist of, or may comprise a photoelectric sensor that responds to a visible or an invisible light, the invisible light is infrared, ultraviolet, X-rays, or gamma rays, and wherein the photoelectric sensor consists of, comprises, or is based on the photoelectric or photovoltaic effect, and consists of, or comprises, a semiconductor component that consists of, or comprises, a photodiode, a phototransistor, or a solar cell. Any photoelectric sensor herein may consist of, may comprise, or may be based on Charge-Coupled Device (CCD) or a Complementary Metal-Oxide Semiconductor (CMOS) element. Any sensor herein may consist of, or may comprise a photosensitive image sensor array comprising multiple photoelectric sensors, for capturing an image and producing electronic image information representing the image, and the device further comprising one or more optical lens for focusing the received light and to guide the image, and any image sensor herein may be disposed approximately at an image focal point plane of the one or more optical lens for properly capturing the image.

Any image processor herein may be coupled to the image sensor for providing a digital data video signal according to a digital video format, the digital video signal carrying digital data video based on the captured images, and the digital video format may be based on one out of: TIFF (Tagged Image File Format), RAW format, AVI, DV, MOV, WMV, MP4, DCF (Design Rule for Camera Format), ITU-T H.261, ITU-T H.263, ITU-T H.264, ITU-T CCIR 601, ASF, Exif (Exchangeable Image File Format), and DPOF (Digital Print Order Format) standards. Any device herein may further comprise a intraframe or interframe compression based video compressor coupled to the image sensor for lossy or non-lossy compressing the digital data video, and any compression herein may be based on a standard compression algorithm which may be one or more out of JPEG (Joint Photographic Experts Group) and MPEG (Moving Picture Experts Group), ITU-T H.261, ITU-T H.263, ITU-T H.264 and ITU-T CCIR 601.

Any sensor herein may consist of, or may comprise, an electrochemical sensor that responds to an object chemical structure, properties, composition, or reactions. Any electrochemical sensor herein may consist of, or may comprise, a pH meter or a gas sensor responding to a presence of radon, hydrogen, oxygen, or Carbon-Monoxide (CO), or wherein the electrochemical sensor consists of, comprises, or is based on optical detection or on ionization and is a smoke, a flame, or a fire detector, or is responsive to combustible, flammable, or toxic gas. Any sensor herein may consist of, or may comprise, an electroacoustic sensor that responds to an audible or inaudible sound. Any electroacoustic sensor herein may consist of, or may comprise, an omnidirectional, unidirectional, or bidirectional microphone that may consist of, may comprise, or may be based on the sensing the incident sound based motion of a diaphragm or a ribbon, and the microphone may consist of, or may comprise, a condenser, an electret, a dynamic, a ribbon, a carbon, or a piezoelectric microphone.

Any sensor herein may consist of, or may comprise an angular position sensor for measuring angular setting or a change of an angle. Any sensor herein may consist of, or may comprise an absolute-pressure sensor for measuring ranges from 50% to 500% of the earth's atmospheric pressure. Any sensor herein may be an electric sensor that may respond to an electrical characteristics or electrical phenomenon quantity in an electrical circuit, and may be conductively coupled to the electrical circuit, or may be a non-contact sensor that is non-conductively coupled to the electrical circuit. Any electrical sensor herein may be responsive to Alternating Current (AC) or Direct Current (DC), and may be an ampermeter that responds to electrical current passing through a conductor or wire, and may consist of, or may comprise, a galvanometer, a hot-wire ampermeter, a current clamp, or a current probe. Alternatively or in addition, any electrical sensor herein may be a voltmeter that responds to an electrical voltage, and may consist of, or may comprise, an electrometer, a resistor, a potentiometer, or a bridge circuit. Alternatively or in addition, any electrical sensor herein may be a wattmeter that responds to active electrical power.

Any device herein may be integrated with at least one of a wireless device, a notebook computer, a laptop computer, a media player, a Digital Still Camera (DSC), a Digital video Camera (DVC or digital camcorder), a Personal Digital Assistant (PDA), a cellular telephone, a digital camera, a video recorder, or a smartphone. Alternatively or in addition, any device herein may be integrated with a smartphone that may comprise, or may be based on, an Apple iPhone 6 or a Samsung Galaxy S6.

The above summary is not an exhaustive list of all aspects of the present invention. Indeed, the inventor contemplates that his invention includes all systems and methods that can be practiced from all suitable combinations and derivatives of the various aspects summarized above, as well as those disclosed in the detailed description below, and particularly pointed out in the claims filed with the application. Such combinations have particular advantages not specifically recited in the above summary.

BRIEF DESCRIPTION OF THE DRAWINGS

The invention is herein described, by way of non-limiting examples only, with reference to the accompanying drawings, wherein like designations denote like elements. Understanding that these drawings only provide information concerning typical embodiments of the invention and are not therefore to be considered limiting in scope.

DETAILED DESCRIPTION

Figure 1:
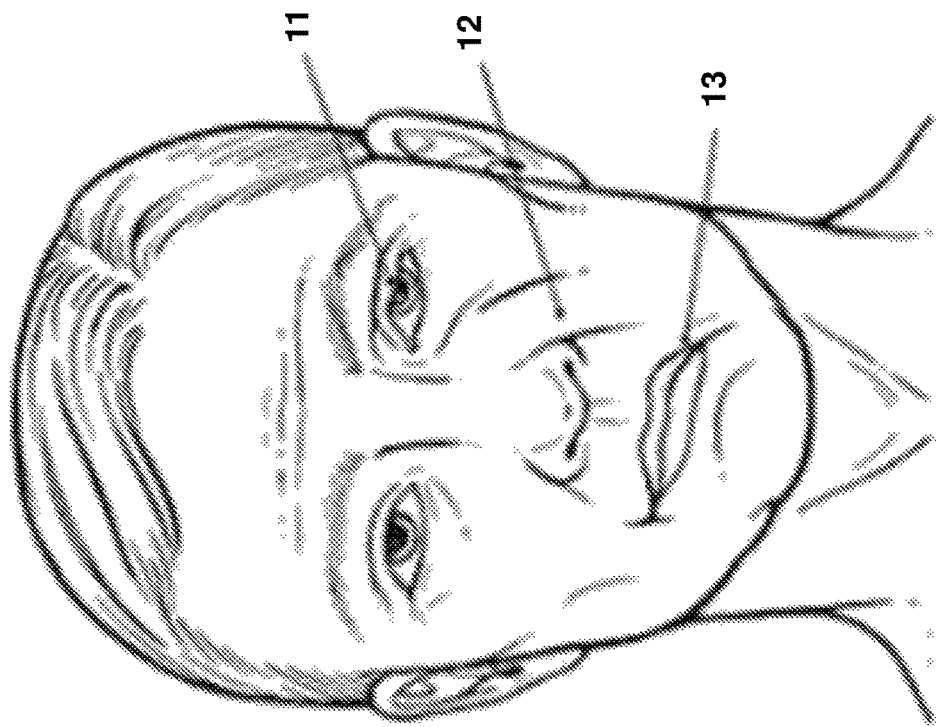
FIG. 1 depicts pictorially a person face showing Bell's palsy symptoms.

The principles and operation of an apparatus according to the present invention may be understood with reference to the figures and the accompanying description wherein similar components appearing in different figures are denoted by identical reference numerals. The drawings and descriptions are conceptual only. In actual practice, a single component can implement one or more functions; alternatively or in addition, each function can be implemented by a plurality of components and devices. In the figures and descriptions, identical reference numerals indicate those components that are common to different embodiments or configurations. Identical numerical references (even in the case of using different suffix, such as 5, 5a, 5b and 5c) refer to functions or actual devices that are either identical, substantially similar, or having similar functionality. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in the figures herein, is not intended to limit the scope of the invention, as claimed, but is merely the representative embodiments of the invention. It is to be understood that the singular forms "a," "an," and "the" herein include plural referents unless the context clearly dictates otherwise. Thus, for example, reference to "a component surface" includes reference to one or more of such surfaces. By the term "substantially" it is meant that the recited characteristic, parameter, or value need not be achieved exactly, but that deviations or variations, including for example, tolerances, measurement errors, measurement accuracy limitations and other factors known to those of skill in the art, may occur in amounts that do not preclude the effect the characteristic was intended to provide.

In one example, a stimulating device or apparatus is used to generate modulated pulse bursts, preferably enabling adjustment of the output signal parameters or characteristics, offering minimum energy consumption and minimal discomfort. The device is preferably located to effectively couple the output signal to a nerve, such as a facial nerve, via a coupling device. The device output may be controlled manually or automatically, and may be synchronized with the opposite eye or by a preset program. In one application, the stimulating device may be used to generate timed eye blinking preferably by inducing muscle action to close upper and preferably also lower eyelids, each independently or in combination, to result in complete eye closure, and with the correct physiological ratio between lower and upper eyelids. Further, the device may be used to stimulate or squeeze the tear gland.

Figure 3:
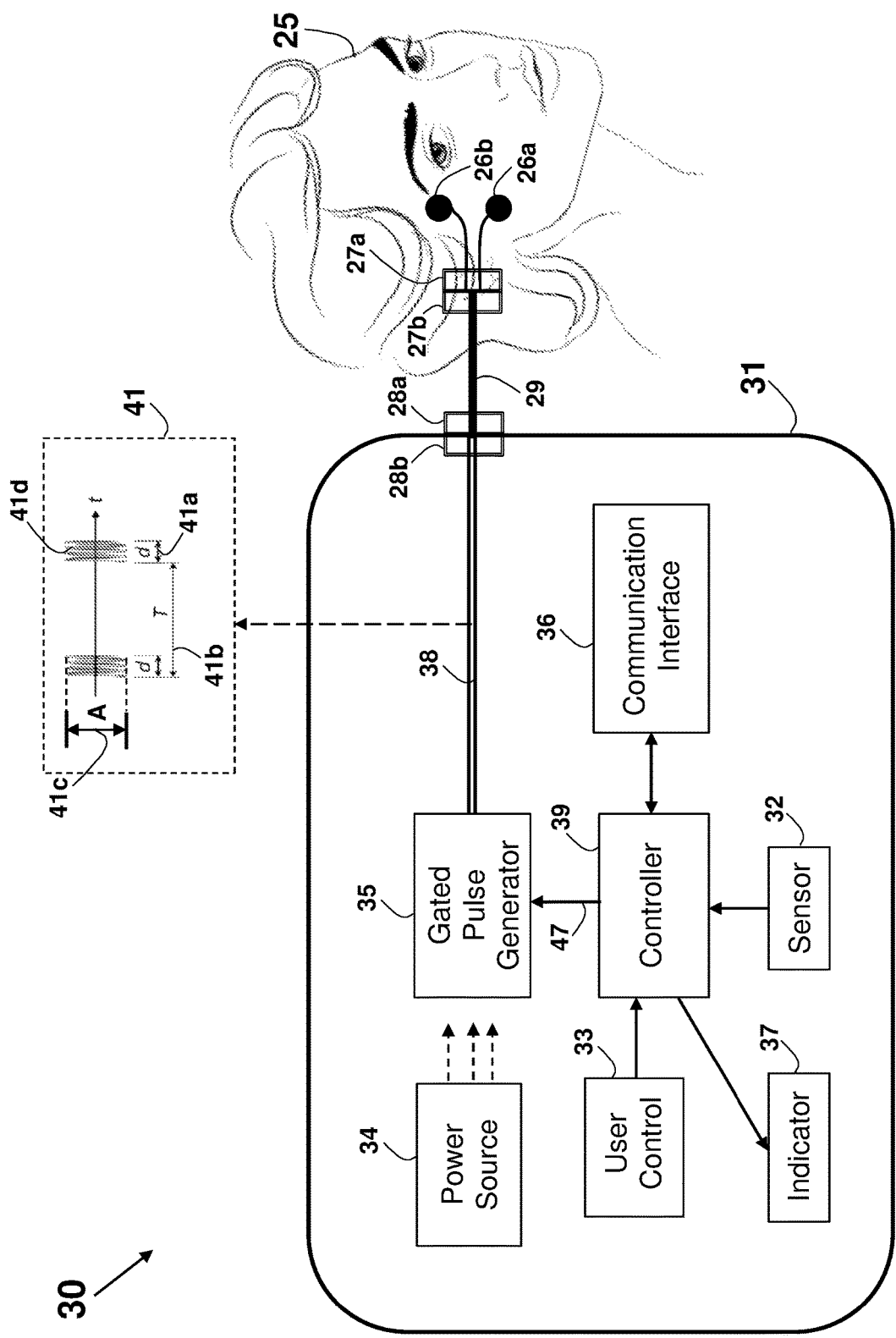
FIG. 3 illustrates schematically a block diagram of a general stimulating device.
Figure 4:
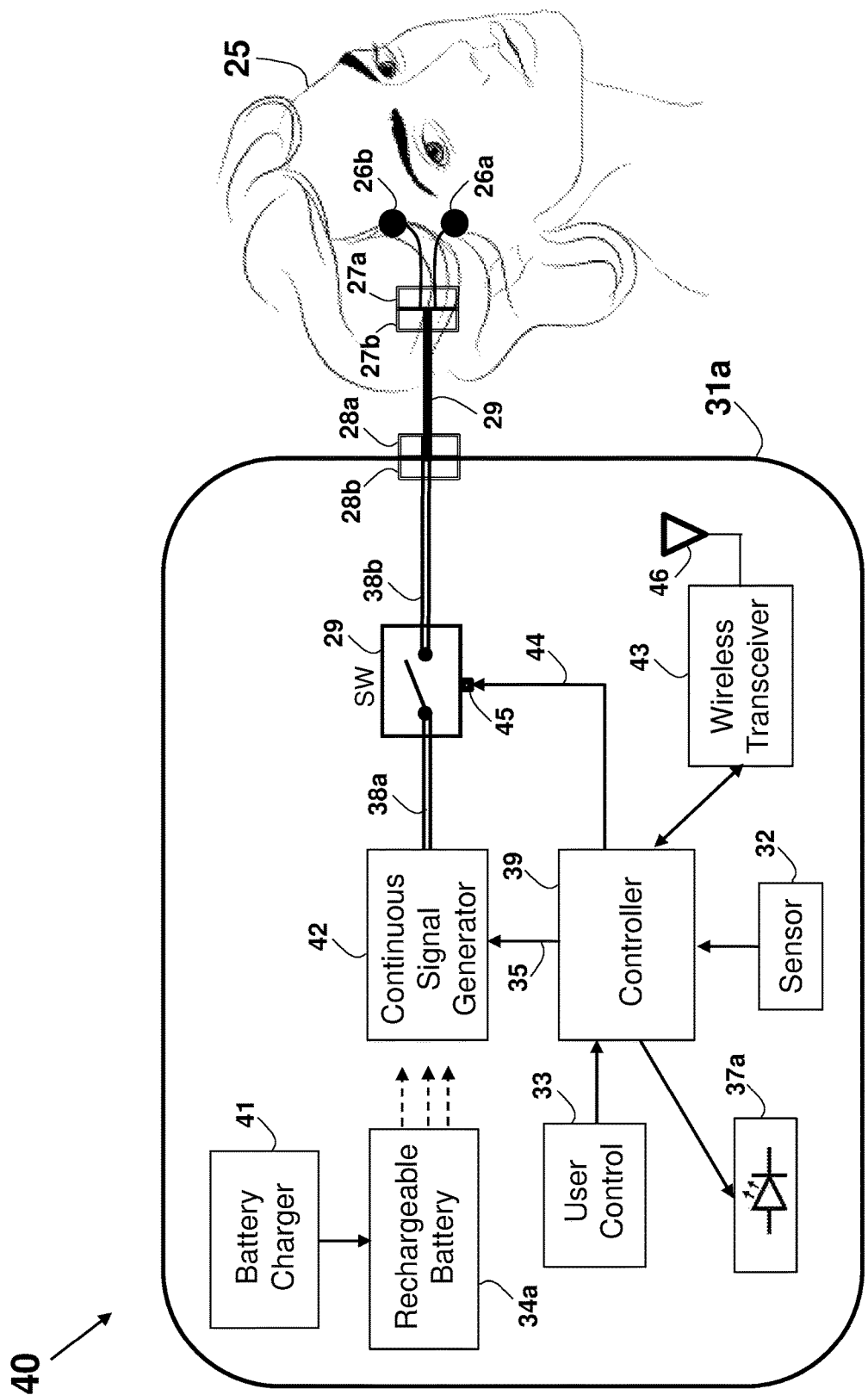
FIG. 4 illustrates schematically a block diagram of a battery-powered stimulating device using continuous pulse generator and providing wireless communication.

A general arrangement 30 of using a general stimulator device 31 is shown in FIG. 3, and a general arrangement 40 of using an examplary embodiment of a stimulator device 31a is shown in FIG. 4. The device 31 comprises a Gated Pulse Generator 35 that outputs via a connection or port 38 a gated symmetrical or asymmetrical Bi-Phasic square pulse signal 41. The signal 41 is comprised of train of square wave bursts 41d having a peak-to-peak amplitude 'A' 41c and a time duration d 41a. The pulses train 41 is periodically repeated every T 41b seconds, and in each burst 41d the square-wave frequency is 'f'. The generator 35 output signal 41 is carried over the connection 38 to a connector 28b in the enclosure of the device 31. The signal 41 reaches electrodes 26a and 26b that are attached to a scalp of a treated person 25. The electrodes 26a and 26b are connected via wires or conductors to a connector 27a. A cable 29 having end connectors 28a and 27b connects respectively to the device 31 connector 28a and electrodes structure connector 27b, thus forming a continuous connection from the generator 35 to the person 25 skin.

The device 31 operation is controlled by a controller block 39, which preferably comprises a software (or firmware) and a processor for executing the software (or firmware). The controller 39 further controls and set the signal 41 parameters, such as the burst duration 'd' 41a, the repetition period 'T' 41b, the amplitude A 41c, the burst internal frequency 41d, or any combination thereof, via a connection 47 between the controller 39 and the generator 35. The simulating device 31 may further comprise a sensor 32 that outputs sensor data, in response to a physical phenomenon, the sensor 32 may be coupled to transmit the sensor output data to the controller 39 for further handling and processing, and for acting in response to the value of the sensor 32 output.

The stimulating device 31 may further include an indicator 37 that is an output component for notifying or outputting information to a user, which may be the person 25 that is treated by the arrangement 30, or another person. For example, the indicator 37 may provide auditory or visual feedback to a human, such as to alert the user through auditory tones/beeps in advance of the presentation of information, or by changes in a display. Alternatively or in addition, the indicator 37 may include a vibrator for tactile interface with the user, such as the person 25 that may wear the device 31. The indicator 37 is coupled to be controlled or activated by the controller 39.

The stimulating device 31 may further include a user control functionality 33 that is an input component for receiving information or control commands from a user, which may be the person 25 that is treated by the arrangement 30, or another person. The user control block 33 may include an input component that may be a piece of computer hardware equipment used to provide data and control signals to an information processing system such as a computer or information appliance. Such input component may be an integrated or a peripheral input device (e.g., hard/soft keyboard, mouse, resistive or capacitive touch display, etc.). Examples of input components include keyboards, mouse, scanners, digital cameras and joysticks. An input components can be categorized based on the modality of input (e.g., mechanical motion, audio, visual, etc.), whether the input is discrete (e.g. pressing of key) or continuous (e.g., a mouse's position, though digitized into a discrete quantity, is fast enough to be considered continuous), the number of degrees of freedom involved (e.g., two-dimensional traditional mice, or three-dimensional navigators designed for CAD applications). Pointing devices (such as 'computer mouse'), which are input components used to specify a position in space, can further be classified according to whether the input is direct or indirect. With direct input, the input space coincides with the display space, i.e., pointing is done in the space where visual feedback or the pointer appears. Touchscreens and light pens involve direct input. Examples involving indirect input include the mouse and trackball, and whether the positional information is absolute (e.g., on a touch screen) or relative (e.g., with a mouse that can be lifted and repositioned). Direct input is almost necessarily absolute, but indirect input may be either absolute or relative. For example, digitizing graphics tablets that do not have an embedded screen involve indirect input and sense absolute positions and are often run in an absolute input mode, but they may also be set up to simulate a relative input mode like that of a touchpad, where the stylus or puck can be lifted and repositioned. Further, an input component in the user control block 33 may include dedicated hard controls for frequently used/accessed functions (e.g., repeat system message).

The stimulating device 31 may further include a communication interface 36 for transmitting data to, or for receiving data from, another device over a communication network. The communication interface 36 may consist of, be part of, or include, a transceiver or modem for communication with the network. In the case of wired networks, the communication interface 36 connects to the network via a port that may include a connector, and in the case of wireless network, the communication interface 36 connects to the network via the port that may include an antenna. The communication interface 36 is controlled and activated by the controller 39. Further, data received from an external device over the communication network is transferred to the controller 39 for further handling, and data to be sent to an external device over the communication network is received at the communication interface 36 from the controller 39. The electronic circuits and components in the stimulating device 31 are electrically powered from a power source 34, which typically supplies a Direct Current (DC) voltage (or current).

The controller 39 may be based on a discrete logic or an integrated device, such as a processor, microprocessor or microcomputer, and may include a general-purpose device or may be a special purpose processing device, such as an ASIC, PAL, PLA, PLD, Field Programmable Gate Array (FPGA), Gate Array, or other customized or programmable device. In the case of a programmable device as well as in other implementations, a memory is required. The controller 39 commonly includes a memory that may include a static RAM (random Access Memory), dynamic RAM, flash memory, ROM (Read Only Memory), or any other data storage medium. The memory may include data, programs, and/or instructions and any other software or firmware executable by the processor. Control logic can be implemented in hardware or in software, such as a firmware stored in the memory. The controller 39 controls and monitors the device operation, such as initialization, configuration, interface, and commands. Any step, method, or flow-chart herein may be performed by the processor in the controller 39 as directed by the software therein.

Battery. In one example, the power source 34 may comprise, may be based on, or may consist of, a battery. A battery may be a primary battery or cell, in which an irreversible chemical reaction that generates the electricity, and thus the cell is disposable and cannot be recharged, and need to be replaced after the battery is drained. Such battery replacement may be expensive and cumbersome. Alternatively or in addition, the battery may be a rechargeable battery 34a, illustrated as part of the stimulator device 31a shown in FIG. 4, such as a nickel-cadmium based battery. In such a case, a battery charger 41 is employed for charging the battery while it is in use or not in use. Various types of such battery chargers are known in the art, such as trickle chargers, pulse chargers and the like. The battery charger may be integrated with the field unit or be external to it. The battery may be a primary or a rechargeable (secondary) type, may include a single or few batteries, and may use various chemicals for the electro-chemical cells, such as lithium, alkaline and nickel-cadmium. Common batteries are manufactured in pre-defined standard output voltages (1.5, 3, 4.5, 9 Volts, for example), as well as defined standard mechanical enclosures (usually defined by letters such as "A", "AA", "B", "C" sizes), and 'coin' or 'button' type. In one embodiment, the battery (or batteries) is held in a battery holder or compartment, and thus can be easily replaced.

A battery may be a 'watch battery' (a.k.a. 'coin cell' or 'button cell'), which is a small single cell battery shaped as a squat cylinder typically 5 to 25 mm in diameter and 1 to 6 mm high. Button cells are typically used to power small portable electronics devices such as wrist watches, pocket calculators, artificial cardiac pacemakers, implantable cardiac defibrillators, and hearing aids. Most button cells have low self-discharge and hold their charge for a long time if not used. Higher-power devices such as hearing aids may use zinc-air cells that have much higher capacity for a given size, but discharge over a few weeks even if not used. Button cells are single cells, usually disposable primary cells. Common anode materials are zinc or lithium, and common cathode materials are manganese dioxide, silver oxide, carbon monofluoride, cupric oxide or oxygen from the air. A metal can forms the bottom body and positive terminal of the cell, where the insulated top cap is the negative terminal.

An example of a 'coin cell' is designated by the International Electrotechnical Commission (IEC) in the IEC 60086-3 standard (Primary batteries, part 3 Watch batteries) as LR44 type, which is an alkaline 1.5 volt button cell. The letter 'L' indicates the electrochemical system used: a zinc negative electrode, manganese dioxide depolarizer and positive electrode, and an alkaline electrolyte. R44 indicates a round cell 11.4±0.2 mm diameter and 5.2±0.2 mm height as defined by the IEC standard 60086. An example of LR44 type battery is Energizer A76 battery, available from Energizer Holdings, Inc., and described in a product datasheet Form No. EBC—4407cp-Z (downloaded from the Internet March 2016) entitled: "*Energizer A76—ZEROMERCURY Miniature Alkaline*", which is incorporated in its entirety for all purposes as if fully set forth herein. Another example of a 'coin cell' is a CR2032 battery, which is a button cell lithium battery rated at 3.0 volts. Nominal diameter is 20 mm, nominal height is 3.2 mm. CR2032 indicates a round cell 19.7-20 mm diameter and 2.9-3.2 mm height as defined by the IEC standard 60086. The battery weight typically ranges from 2.8 g to 3.9 g. The BR2032 battery has the same dimensions, a slightly lower nominal voltage and capacity, and an extended temperature range compared with the CR2032. It is rated for a temperature range of −30° C. to 85° C., while the CR2032 is specified over the range −20° C. to 70° C. BR2032 also has a much lower self-discharge rate. An example of CR2032 type battery is Energizer CR2032 Lithium Coin battery, available from Energizer Holdings, Inc., and described in a product datasheet Form No. EBC—4120M (downloaded from the Internet March 2016) entitled: "*Energizer CR2032—Lithium Coin*", which is incorporated in its entirety for all purposes as if fully set forth herein.

While the invention was exampled in FIG. 4 above with regard to a direct and conductive charging, thus may require a connector, a contactless charging may equally be used, such as by using inductive coupling where the energy is transferred using an electromagnetic field. In inductive coupling a charging station sends energy using a transmitter induction coil to the device to be charged, which includes a receiving induction coil inductively coupled to the transmitter coil. The received power is commonly used to charge the rechargeable battery 34a while enclosed within the device. In such a configuration there is no need for any connectors or for connector engagement, thus making it easy to use, impermeable to water and dirt and with improved shape and look. Such an arrangement of induction-based charging device 31b capable of inductive charging is shown in an arrangement 50 shown in FIG. 5. The receiving coil 56 internal to the device 31b is designed to receive energy when properly positioned in an electromagnetic field. The received signal is rectified by a rectifier and further processed or conditioned as required, as part of the battery charger 41a that is connected via the conductors or wires 57a and 57b to the coil 56. The electric power is then fed from the battery charger 41 to charge the secondary cell 34a. Contactless battery charging systems are described in U.S. Pat. No. 6,208,115 to Binder titled: "Battery Substitute Pack", in U.S. Pat. No. 7,863,859 to Soar titled: "Contactless Battery Charging Apparel", in U.S. Pat. No. 7,872,445 to Ron Hui titled: "Rechargeable Battery Powered Portable Electronic Device", in U.S. Pat. No. 7,906,936 to Azancot et al. titled: "Rechargeable Inductive Charger", in U.S. Pat. No. 7,863,861 to Cheng et al. titled: "Contact-Less Power Transfer" and in U.S. Pat. No. 7,876,067 to Greenfeld et al. titled: "High Frequency Connector-Less Charging Scheme", which are all incorporated in their entirety for all purposes as if fully set forth herein.

Figure 5:
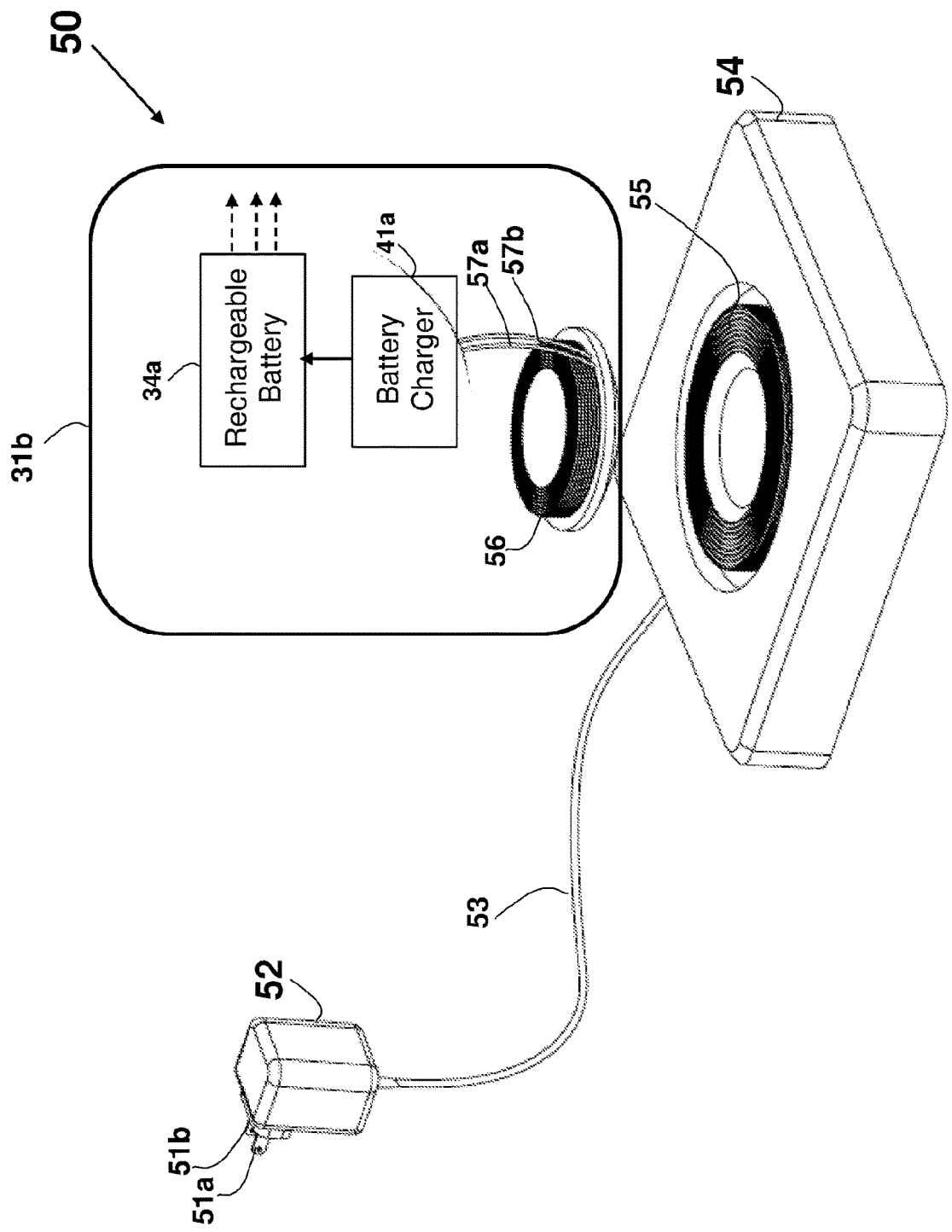
FIG. 5 depicts schematically a battery-powered stimulating device employing inductive battery charging.

As shown in the examplary arrangement 50 in FIG. 5, a device 31b that is capable of contactless inductive charging is used with a charging station 54 is shown. The device 31b comprises a receiving coil 56, connected via wires 57a and 57b, hence when the coil 56 is in the electromagnetic field generated by a coil 55 in the charger 54, the rechargeable battery 34a is charged. The coil 55 which generates the electromagnetic field, and is fed from the AC power by the AC/DC converter 52 having prongs 51a and 51b, feeding the inductive generator 54 via a cable 53.

In another example, the device 31a may be locally energized. The battery charger 41 may comprise an electrical energy generator to locally generate electrical power for charging the rechargeable battery 34a. Preferably, the generator may be integrated within the device 31a enclosure. Such generator may be based on converting kinetic energy harvested from the device 31a motion, which may be caused by a human or animal activity, to electrical energy. Such generator is described in U.S. Pat. No. 7,692,320 to Lemieux titled: "Electrical Energy Generator", in U.S. Pat. No. 5,578,877 to Tiemann titled: "Apparatus for Converting Vibratory Motion to Electrical Energy", in U.S. Pat. No. 7,847,421 to Gardner et al. titled: "System for Generating Electrical Energy from Ambient Motion" and in U.S. Patent Application 2007/0210580 to Robets et al. titled: "Electromechanical Generator for, and Method of Converting Mechanical Vibrational Energy into Electrical Energy", as well as a battery-shaped generator described in U.S. Pat. No. 7,688,036 to Yarger et al. titled: "System and Method for Storing Energy", which are all incorporated in their entirety for all purposes as if fully set forth herein.

Any part of, or whole of, any device, apparatus, block, or functionality described herein may be integrated with, attached to, part of, used with, be the basis of, or included in, any commercial available off-the-shelf TENS device, such as the TENS 3000 or TENS 7000 available from Roscoe Medical Inc. (of Middleburg Heights, OH, U.S.A.), or any other nerve stimulation device described as part of the 'BACKGROUND' section Similarly, any part of, or whole of, any device, apparatus, block, or functionality, of any commercial available off-the-shelf TENS device, such as the TENS 3000 or TENS 7000 available from Roscoe Medical Inc. (of Middleburg Heights, OH, U.S.A.), or any other nerve stimulation device described as part of the 'BACKGROUND' section, may be integrated with, attached to, part of, used with, be the basis of, or included in, any device or apparatus described herein.

The gated pulse generator 35 is a signal generator that serves as a current (or voltage) source for providing the bursts train 41 to the connector 28b of the stimulator device 31, for supplying via the cable 29 to the person 25. The activation of the generator 35, as well as the controlling and setting of the bursts train 41 parameters may be set by the controller 39 via the connection or port 47. Typically, the gated pulse generator 35 supplies asymmetrical Bi-Phasic square current pulse as the bursts train 41.

The burst train 41 parameters include the peak-to-peak amplitude 'A' 41c (or the nominal value, or effective value, of the signal 41), the burst duration d 41a, the frequency 'f' of the signal in the burst 41d, and the period T 41b. Each of the parameters may be implemented as fixed value, and as such cannot be changed during the device 31 operation. Alternatively or in addition, each of the parameters may be changed and controlled during operation, such as by the user using the user control 33, externally from the network via the communication interface 36, or in response to the sensor 32 output. Each of the changeable parameters may be variable over a range from a minimum value to a maximum value, as set by the controller 39 over the control connection or port 47.

The gated pulse generator 35 may be a voltage or current generator. The peak-to-peak amplitude 'A' 41c, the nominal value, or effective value, of the signal 41, in case of a current generator, (or the minimum or maximum settable value) may be above 0.1 milliamper (mA), 0.2 mA, 0.5 mA, 0.8 mA, 1 mA, 1.2 mA, 1.5 mA, 1.8 mA, 2 mA, 2.5 mA, 3 mA, 3.5 mA, 4 mA, 4.5 mA, 5 mA, 5.5 mA, 6 mA, 7 mA, 8 mA, 9 mA, 10 mA, 11 ma, 12 mA, 15 mA, 18 mA, 20 mA, 22 mA, 25 mA, 30 mA, 35 mA, 40 mA, 45 mA, 50 mA, 55 mA, 60 mA, 65 mA, 70 mA, 75 mA, 80 mA, or 100 mA. Alternatively or in addition, the peak-to-peak amplitude 'A' 41c, or the nominal or effective value, of the signal 41, in case of a current generator, (or the minimum or maximum settable value) may be below 0.2 milliamper (mA), 0.5 mA, 0.8 mA, 1 mA, 1.2 mA, 1.5 mA, 1.8 mA, 2 mA, 2.5 mA, 3 mA, 3.5 mA, 4 mA, 4.5 mA, 5 mA, 5.5 mA, 6 mA, 7 mA, 8 mA, 9 mA, 10 mA, 11 ma, 12 mA, 15 mA, 18 mA, 20 mA, 22 mA, 25 mA, 30 mA, 35 mA, 40 mA, 45 mA, 50 mA, 55 mA, 60 mA, 65 mA, 70 mA, 75 mA, 80 mA, 100 mA, or 150 mA. In case of a voltage generator, the peak-to-peak amplitude 'A' 41c, the nominal value, or the effective value, of the signal 41, in case of a current generator, (or the minimum or maximum settable value) may be above 0.1 millivolt (mV), 0.2 mV, 0.5 mV, 0.8 mV, 1 mV, 1.2 mV, 1.5 mV, 1.8 mV, 2 mV, 2.5 mV, 3 mV, 3.5 mV, 4 mV, 4.5 mV, 5 mV, 5.5 mV, 6 mV, 7 mV, 8 mV, 9 mV, 10 mV, 11 mV, 12 mV, 15 mV, 18 mV, 20 mV, 22 mV, 25 mV, 30 mV, 35 mV, 40 mV, 45 mV, 50 mV, 55 mV, 60 mV, 65 mV, 70 mV, 75 mV, 80 mV, or 100 mV.

Alternatively or in addition, in case of a voltage generator, the peak-to-peak amplitude 'A' 41c, the nominal value, or the effective value, of the signal 41, (or the minimum or maximum settable value) may be below 0.2 millivolt (mV), 0.5 mV, 0.8 mV, 1 mV, 1.2 mV, 1.5 mV, 1.8 mV, 2 mV, 2.5 mV, 3 mV, 3.5 mV, 4 mV, 4.5 mV, 5 mV, 5.5 mV, 6 mV, 7 mV, 8 mV, 9 mV, 10 mV, 11 mV, 12 mV, 15 mV, 18 mV, 20 mV, 22 mV, 25 mV, 30 mV, 35 mV, 40 mV, 45 mV, 50 mV, 55 mV, 60 mV, 65 mV, 70 mV, 75 mV, 80 mV, 100 mV, or 150 mV.

Alternatively or in addition, in case of a voltage generator, the peak-to-peak amplitude 'A' 41c, the nominal value, or the effective value, of the signal 41, in case of a current generator, (or the minimum or maximum settable value) may be above 0.1 Volts (V), 0.2 V, 0.5 V, 0.8 V, 1 V, 1.2 V, 1.5 V, 1.8 V, 2 V, 2.5 V, 3 V, 3.5 V, 4 V, 4.5 V, 5 V, 5.5 V, 6 V, 7 V, 8 V, 9 V, 10 V, 11 V, 12 V, 15 V, 18V, 20 V, 22 V, 25 V, 30 V, 35 V, 40 V, 45 V, 50 V, 55 V, 60 V, 65 V, 70 V, 75 V, 80 V, or 100 V. Alternatively or in addition, in case of a voltage generator, the peak-to-peak amplitude 'A' 41c, the nominal value, or the effective value, of the signal 41, (or the minimum or maximum settable value) may be below 0.2 Volts (V), 0.5 V, 0.8 V, 1 V, 1.2 V, 1.5 V, 1.8 V, 2 V, 2.5 V, 3 V, 3.5 V, 4 V, 4.5 V, 5 V, 5.5 V, 6 V, 7 V, 8 V, 9 V, 10 V, 11 V, 12 V, 15 V, 18V, 20 V, 22 V, 25 V, 30 V, 35 V, 40 V, 45 V, 50 V, 55 V, 60 V, 65 V, 70 V, 75 V, 80 V, 100V, or 150 V.

The burst duration d 41a at the gated pulse generator 35 output (or the minimum or maximum settable value) may be above 1 milliseconds (ms), 2 ms, 3 ms, 5 ms, 7 ms, 10 ms, 12 ms, 15 ms, 18 ms, 20 ms, 25 ms, 30 ms, 40 ms, 45 ms, 50 ms, 100 ms, 120 ms, 150 ms, 180 ms, 200 ms, 250 ms, 300 ms, 400 ms, 450 ms, or 500 ms. Alternatively or in addition, the burst duration d 41a (or the minimum or maximum settable value) may be below 2 milliseconds (ms), 2 ms, 3 ms, 5 ms, 7 ms, 10 ms, 12 ms, 15 ms, 18 ms, 20 ms, 25 ms, 30 ms, 40 ms, 45 ms, 50 ms, 100 ms, 120 ms, 150 ms, 180 ms, 200 ms, 250 ms, 300 ms, 400 ms, 450 ms, 500 ms, or 900 ms.

The frequency 'f' of the signal in the burst 41d (or the minimum or maximum settable value) may be above 1 Hertz (Hz), 2 Hz, 5 Hz, 8 Hz, 10 Hz, 12 Hz, 15 Hz, 18 Hz, 20 Hz, 22 Hz, 25 Hz, 30 Hz, 35 Hz, 50 Hz, 60 Hz, 70 Hz, 80 Hz, 100 Hz, 120 Hz, 150 Hz, 180 Hz, 200 Hz, 250 Hz, 300 Hz, 350 Hz, 400 Hz, or 500 Hz. Alternatively or in addition, the frequency 'f' of the signal in the burst 41d (or the minimum or maximum settable value) may be below 2 Hertz (Hz), 5 Hz, 8 Hz, 10 Hz, 12 Hz, 15 Hz, 18 Hz, 20 Hz, 22 Hz, 25 Hz, 30 Hz, 35 Hz, 50 Hz, 60 Hz, 70 Hz, 80 Hz, 100 Hz, 120 Hz, 150 Hz, 180 Hz, 200 Hz, 250 Hz, 300 Hz, 350 Hz, 400 Hz, 500 Hz, or 1,000 Hz.

The period T 41b of the signal between the bursts 41d (or the minimum or maximum settable value) may be above 100 milliseconds (ms), 120 ms, 150 ms, 180 ms, 200 ms, 250 ms, 300 ms, 400 ms, 450 ms, 500 ms, 700 ms, 1,000 ms, 1,200 ms, 1,500 ms, 1,800 ms, 2,000 ms, 2,500 ms, 3,000 ms, 3,500 ms, 4,000 ms, 4,500 ms, 5,000 ms, 6,000 ms, 6,500 ms, 7,000 ms, 7,500 ms, 8000 ms, 8500 ms, 9000 ms, or 9500 ms. Alternatively or in addition, The period T 41b of the signal between the bursts 41d (or the minimum or maximum settable value) may be below 120 ms, 150 ms, 180 ms, 200 ms, 250 ms, 300 ms, 400 ms, 450 ms, 500 ms, 700 ms, 1,000 (ms), 1,200 ms, 1,500 ms, 1,800 ms, 2,000 ms, 2,500 ms, 3,000 ms, 3,500 ms, 4,000 ms, 4,500 ms, 5,000 ms, 6,000 ms, 6,500 ms, 7,000 ms, 7,500 ms, 8,000 ms, 8,500 ms, 9,000 ms, 9,500 ms, or 10,000 ms.

In one example, the gated signal generator 35 is implemented using a continuous pulse generator 42, which generates an output signal not as the bursts train 41 but as continuous signal, together with a serially connected controlled switch 29, which switch the continuous signal to produce the required bursts train 41. In such a case, the peak-to-peak amplitude 'A' 41c (or the nominal value, or effective value, of the signal 41) and the frequency 'f' of the signal in the burst 41d are determined by the continuous signal generator 42, and may be controlled or set by the controller 39 via the control port or connection 35, while the period T 41b and the burst duration d 41a are determined by the controlled switch 29 actuation, which may be controlled by the controller 39 via the connection 44 connected to the switch 29 control port or connection 45. In one example, the switch 29 is an electromechanical device with one or more sets of electrical contacts having two or more states. The switch may be a 'normally open' type, requiring actuation for closing the contacts, may be 'normally closed' type, where actuation affects breaking the circuit, or may be a changeover switch, having both types of contacts arrangements. A changeover switch may be either a 'make-before-break' or a 'break-before-make' type. The switch contacts may have one or more poles and one or more throws. Common switch contacts arrangements include Single-Pole-Single-Throw (SPST), Single-Pole-Double-Throw (SPDT), Double-Pole-Double-Throw (DPDT), Double-Pole-Single-Throw (DPST), and Single-Pole-Changeover (SPCO). A switch may be electrically or mechanically actuated.

A relay is a non-limiting example of an electrically operated switch 29. A relay may be a latching relay, that has two relaxed states (bi-stable), and when the current is switched off, the relay remains in its last state. This is achieved with a solenoid operating a ratchet and cam mechanism, or by having two opposing coils with an over-center spring or permanent magnet to hold the armature and contacts in position while the coil is relaxed, or with a permanent core. A relay may be an electromagnetic relay, that typically consists of a coil of wire wrapped around a soft iron core, an iron yoke which provides a low reluctance path for magnetic flux, a movable iron armature, and one or more sets of contacts. The armature is hinged to the yoke and mechanically linked to one or more sets of moving contacts. It is held in place by a spring so that when the relay is de-energized there is an air gap in the magnetic circuit. In this condition, one of the two sets of contacts in the relay pictured is closed, and the other set is open. A reed relay is a reed switch enclosed in a solenoid, and the switch has a set of contacts inside an evacuated or inert gas-filled glass tube, which protects the contacts against atmospheric corrosion.

Alternatively or in addition, a relay may be a Solid State Relay (SSR), where a solid-state based component functioning as a relay, without having any moving parts.

In one example, the SSR may be Part Number CPC1006N—60V Normally-Open Single-Pole 4-Pin SOP OptoMOS® Relay—available from IXYS Integrated Circuits Division, headquartered in Beverly, MA, U.S.A., described in a data-sheet No. DS-CPC1006N-R05 published Jan. 30, 2018, which is incorporated in its entirety for all purposes as if fully set forth herein. The CPC1006N is a miniature single-pole, normally-open (1-Form-A) solid state relay in a 4-pin SOP package that employs optically coupled MOSFET technology to provide 1500 Vrms of input to output isolation. The relay outputs are constructed with efficient MOSFET switches and photovoltaic die that use IXYS Integrated Circuits Division's patented OptoMOS architecture while the input, a highly efficient infrared LED, provides the optically coupled control.

In another example, the SSR may be controlled by an optocoupler, such as a CPC1965Y AC Solid State Relay, available from IXYS Integrated Circuits Division (Headquartered in Milpitas, California, U.S.A.) which is an AC Solid State Relay (SSR) using waveguide coupling with dual power SCR outputs to produce an alternative to optocoupler and Triac circuits. The switches are robust enough to provide a blocking voltage of up to 600 VP, and are tightly controlled zero-cross circuitry ensures switching of AC loads without the generation of transients. The input and output circuits are optically coupled to provide 3750 Vrms of isolation and noise immunity between control and load circuits. The CPC1965Y AC Solid State Relay is described in an IXYS Integrated Circuits Division specification DS-CPC1965Y-R07 entitled: "*CPC1965Y AC Solid State Relay*", which is incorporated in its entirety for all purposes as if fully set forth herein.

Alternatively or in addition, the switch 29 may be implemented using an electrical circuit or component. For example, an open collector (or open drain) based circuit may be used. Further, an opto-isolator (a.k.a. optocoupler, photocoupler, or optical isolator) may be used to provide isolated power transfer. Further, a thyristor such as a Triode for Alternating Current (TRIAC) may be used for triggering the power. In one example, the switch 29 may be based on, or consists of, a TRIAC Part Number BTA06 available from SGS-Thomson Microelectronics is used, described in the data sheet "*BTA06 T/D/S/A BTB06 T/D/S/A—Sensitive Gate Triacs*" published by SGS-Thomson Microelectronics March 1995, which is incorporated in its entirety for all purposes as if fully set forth herein.

In addition, the switch 29 may be based on a transistor. The transistor may be a Metal-Oxide-Semiconductor Field-Effect Transistor (MOSFET, MOS-FET, or MOS FET), commonly used for amplifying or switching electronic signals. The MOSFET transistor is a four-terminal component with source (S), gate (G), drain (D), and body (B) terminals, where the body (or substrate) of the MOSFET is often connected to the source terminal, making it a three-terminal component like other field-effect transistors. In an enhancement mode MOSFETs, a voltage drop across the oxide induces a conducting channel between the source and drain contacts via the field effect. The term "enhancement mode" refers to the increase of conductivity with an increase in oxide field that adds carriers to the channel, also referred to as the inversion layer. The channel can contain electrons (called an nMOSFET or nMOS), or holes (called a pMOSFET or pMOS), opposite in type to the substrate, so nMOS is made with a p-type substrate, and pMOS with an n-type substrate. In one example, the switch 29 may be based on an N-channel enhancement mode standard level field-effect transistor that features very low on-state resistance. Such a transistor may be based on, or consists of, TrenchMOS transistor Part Number BUK7524-55 from Philips Semiconductors, described in the Product Specifications from Philips Semiconductors "*TrenchMOS™ transistor Standard level FET BUK7524-55*" Rev 1.000 dated January 1997, which is incorporated in its entirety for all purposes as if fully set forth herein.

Figure 2:
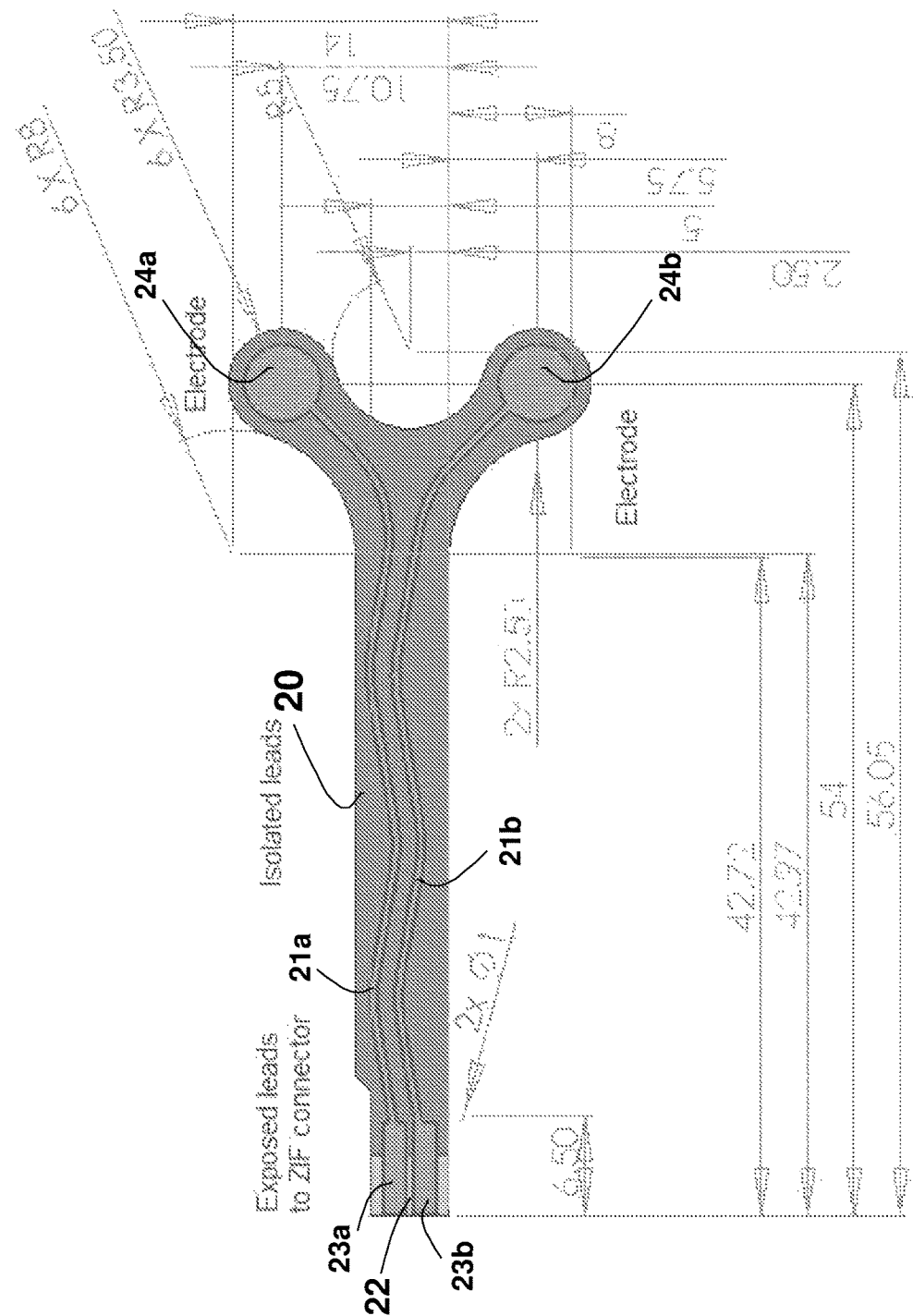
FIG. 2 depicts pictorially an electrodes assembly.
Figure 2A:
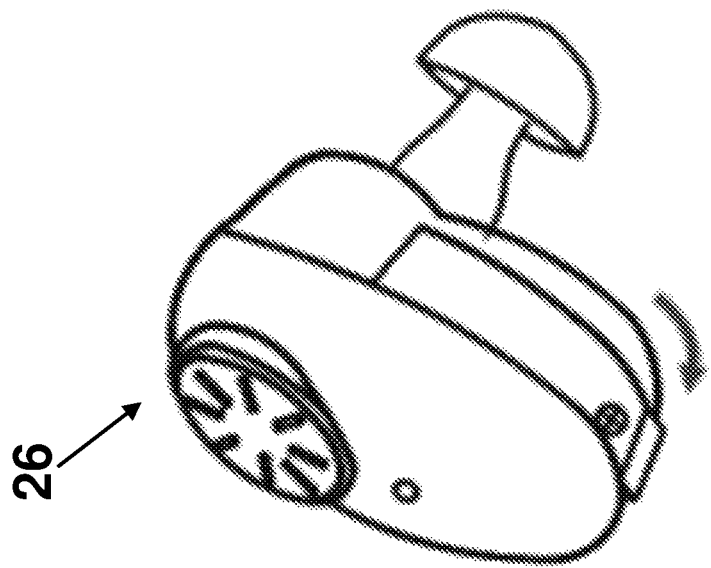
FIG. 2a depicts pictorially hearing aid enclosures.
Figure 2A:
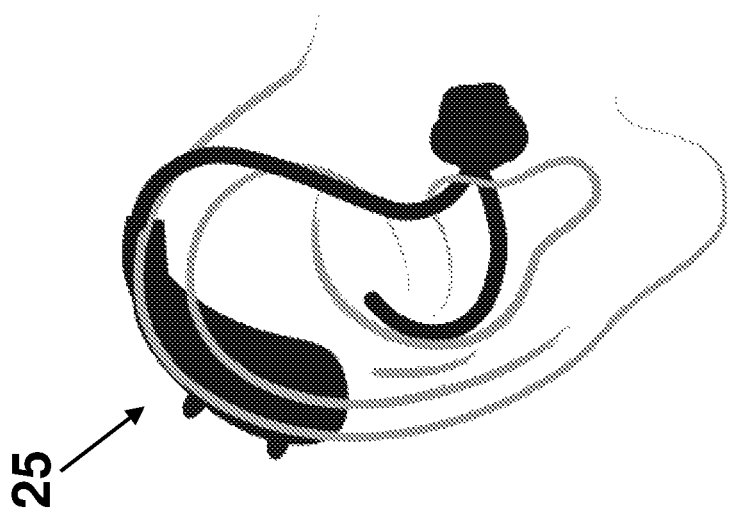

Electrodes. Any type of electrodes or skin electrodes known in the art may be used to implement electrodes 26a and 26b. Further, any electrodes assembly, in which the two electrodes are mechanically attached or coupled to each other and to a connector, such as the assembly 20 shown in FIG. 2 may be used, where the connector 27a is implemented by connector 22 of the assembly 20. Further, any type of electrodes or skin electrodes, and any type of electrodes assembly, known in the art to be used for Electroencephalography (EEG) or an Electrocardiography (ECG) may be used to implement the electrodes 26a and 26b, either as independent electrodes or as part of an electrodes assembly. Further, any type of electrodes or skin electrodes, and any type of electrodes assembly, described for any nerve stimulation as part of the 'BACKGROUND' section above may as well, be used, or may be the basis of, implementing the electrodes 26a and 26b, either as independent electrodes or as part of an electrodes assembly. Alternatively or in addition, the electrodes may be implantable electrodes. In one example, each of the skin electrodes is implemented as substantially flat and round conductive pad. The surface where the electrodes pads touch the skin, such as the scalp, may use a conductive material, such as gel or carbon nano-tubes conductive layer. Preferably, the skin surface area of each electrode is 15 $mm^2 \pm 2$ $mm^2$. In another example, the skin surface area of each electrode each of the electrodes may be above 1 square millimeters ($mm^2$), 2 $mm^2$, 3 $mm^2$, 5 $mm^2$, 8 $mm^2$, 10 $mm^2$, 12 $mm^2$, 15 $mm^2$, 17 $mm^2$, 20 $mm^2$, 22 $mm^2$, 25 $mm^2$, 30 $mm^2$, or 50 $mm^2$. Alternatively or in addition, the skin surface area of each electrode each of the electrodes may be less than 2 square millimeters ($mm^2$), 3 $mm^2$, 5 $mm^2$, 8 $mm^2$, 10 $mm^2$, 12 $mm^2$, 15 $mm^2$, 17 $mm^2$, 20 $mm^2$, 22 $mm^2$, 25 $mm^2$, 30 $mm^2$, 50 $mm^2$, or 100 $mm^2$.

The distance between the centers or edges of the two electrodes conductive pads as part of an electrodes assembly (such as the assembly 20 shown in FIG. 2), or the distance upon attaching to the scalp, may be less than 5 millimeter (mm), 7 mm, 10 mm, 12 mm, 15 mm, 20 mm, 25 mm, 30 mm, 40 mm, 50 mm, 70 mm, or 100 mm. Alternatively or in addition, the distance between the centers or edges of the two electrodes conductive pads may be more than 4 millimeter (mm), 7 mm, 10 mm, 12 mm, 15 mm, 20 mm, 25 mm, 30 mm, 40 mm, 50 mm, 70 mm, or 90 mm.

In one example, each electrode consists of an electrically conductive electrolyte gel and a silver/silver chloride conductor. Further, the electrodes may be based on flexible, stretchable printed circuits electrodes. Such electrodes typically consist of a patterned conductive material printed on an adhesive film that attaches to the skin. In addition, dry metallic electrodes or gelled electrodes may be used. Further, tattoo electrodes that are made of a conductive material laminated between adhesive polymer films may be used. The electrodes may be part of an electrodes assembly, which may include a connector, such as slim connector or Zero force connector (ZIF).

Wearable. Any device, component, or apparatus herein, such as the device 31 shown in FIG. 3 or the device 31a shown in FIG. 4, or any electrode or electrode assembly herein, may be structured as, may be shaped or configured to serve as, or may be integrated with, a wearable device. Any apparatus or device herein may be wearable on an organ such as on the person head, and the organ may be eye, ear, face, cheek, nose, mouth, lip, forehead, or chin. Alternatively or in addition, any apparatus or device herein may be constructed to have a form substantially similar to, may be constructed to have a shape allowing mounting or wearing identical or similar to, or may be constructed to have a form to at least in part substitute for, headwear, eyewear, or earpiece. Any headwear herein may consist of, may be structured as, or may comprise, a bonnet, a headband, a cap, a crown, a fillet, a hair cover, a hat, a helmet, a hood, a mask, a turban, a veil, or a wig. Any eyewear herein may consist of, may be structured as, or may comprise, glasses, sunglasses, a contact lens, a blindfold, or a goggle. Any earpiece herein may consist of, may be structured as, or may comprise, a hearing aid, a headphone, a headset, or an earplug. Alternatively or in addition, any enclosure herein may be permanently or releaseably attachable to, or may be part of, a clothing piece of a person. The attaching may use taping, gluing, pinning, enclosing, encapsulating, a pin, or a latch and hook clip, and the clothing piece may be a top, bottom, or full-body underwear, or a headwear, a footwear, an accessory, an outwear, a suit, a dress, a skirt, or a top. In one example, the device 31 enclosure may be shaped or structured as a Behind-the-ear (BTE), 'Mini' BTE, or In-The-Ear (ITE) enclosure.

The user control 33 may be an input component that comprises, or consists of, a piece of computer hardware equipment used to provide data and control signals to an information processing system such as a computer or information appliance. Such input component 33 may be an integrated or a peripheral input device (e.g., hard/soft keyboard, mouse, resistive or capacitive touch display, etc.). Examples of input components include keyboards, mouse, scanners, digital cameras and joysticks. Input component 33 can be categorized based on the modality of input (e.g., mechanical motion, audio, visual, etc.), whether the input is discrete (e.g. pressing of key) or continuous (e.g., a mouse's position, though digitized into a discrete quantity, is fast enough to be considered continuous), the number of degrees of freedom involved (e.g., two-dimensional traditional mice, or three-dimensional navigators designed for CAD applications). Pointing devices (such as 'computer mouse'), which are input components used to specify a position in space, can further be classified according to whether the input is direct or indirect. With direct input, the input space coincides with the display space, i.e., pointing is done in the space where visual feedback or the pointer appears. Touchscreens and light pens involve direct input. Examples involving indirect input include the mouse and trackball, and whether the positional information is absolute (e.g., on a touch screen) or relative (e.g., with a mouse that can be lifted and repositioned). Direct input is almost necessarily absolute, but indirect input may be either absolute or relative. For example, digitizing graphics tablets that do not have an embedded screen involve indirect input and sense absolute positions and are often run in an absolute input mode, but they may also be set up to simulate a relative input mode like that of a touchpad, where the stylus or puck can be lifted and repositioned. Further, the input component 33 may include dedicated hard controls for frequently used/accessed functions (e.g., repeat system message).

The indicator 37 may include a color display for displaying screen elements or for organizing on-screen items and controls for data entry. Further, the device may support the display of split-screen views. Many systems used re-configurable keys/buttons whose function change depending on the application. Typically, a switch is used to activate the voice recognition system and it may increase system reliability. The indicator 37 may provide auditory or visual feedback to confirm user inputs.

In one example, the sensor 32 may include a physiological sensor, for monitoring a live body such as a human body, for example the body of the treated person 25. Such physiological sensor output may be used, as part of "Sensor Output" step 64 shown in FIG. 6 to adapt or optimize the device 31 operation to the person physiological condition or state.

The physiological sensor 32 may be used to sense, log and monitor vital signs, such as of patients suffering from chronic diseases such as diabetes, asthma, and heart attack. The sensor may be ECG (Electrocardiography), involving interpretation of the electrical activity of the heart over a period of time, as detected by electrodes attached to the outer surface of the skin. The sensor 32 may be used to measure oxygen saturation (SO2), involving the measuring the percentage of hemoglobin binding sites in the bloodstream occupied by oxygen. A pulse oximeter relies on the light absorption characteristics of saturated hemoglobin to give an indication of oxygen saturation. Venous oxygen saturation (SvO2) is measured to see how much oxygen the body consumes, tissue oxygen saturation (StO2) can be measured by near infrared spectroscopy, and Saturation of peripheral oxygen (SpO2) is an estimation of the oxygen saturation level usually measured with a pulse oximeter device. Other sensors may be a blood pressure sensor, for measuring is the pressure exerted by circulating blood upon the walls of blood vessels, which is one of the principal vital signs, and may be based on a sphygmomanometer measuring the arterial pressure. An EEG (Electroencephalography) sensor may be used for the monitoring of electrical activity along the scalp. EEG measures voltage fluctuations resulting from ionic current flows within the neurons of the brain. The sensors (or the sensor units) may be a small bio-sensor implanted inside the human body, or may be worn at the human body, or as wearable, near, on or around a live body. Non-human applications may involve the monitoring of crops and animals. Such networks involving biological sensors may be part of a Body Area Network (BAN) or Body Sensor Network (BSN), and may be in accordance to, or based on, IEEE 802.15.6. The sensor may be a biosensor, and may be according to, or based on, the sensor described in U.S. Pat. No. 6,329,160 to Schneider et al., entitled: "Biosensors", in U.S. Patent Application Publication No. 2005/0247573 to Nakamura et al., entitled: "Biosensors", in U.S. Patent Application Publication No. 2007/0249063 to Deshong et al., entitled: "Biosensors", or in U.S. Pat. No. 4,857,273 to Stewart, entitled: "Biosensors", which are all incorporated in their entirety for all purposes as if fully set forth herein.

Alternatively or in addition, the sensor 32 may be effective to a measure of effective response of a user comprises, and/or is based on, a physiological signal of the user, which reflects a physiological state of the user, such as:

(a) Heart Rate (HR), Heart Rate Variability (HRV), and Blood-Volume Pulse (BVP), and/or other parameters relating to blood flow, which may be determined by various means such as electrocardiogram (ECG), photoplethysmogram (PPG), and/or impedance cardiography (ICG).

(b) Skin Conductance (SC), which may be measured via sensors for Galvanic Skin Response (GSR), which may also be referred to as Electrodermal Activity (EDA).

(c) Skin Temperature (ST) may be measured, for example, with various types of thermometers.

(d) Brain activity and/or brainwave patterns, which may be measured with electroencephalography (EEG), as described herein.

(e) Brain activity determined based on functional magnetic resonance imaging (fMRI).

(f) Brain activity based on Magnetoencephalography (MEG).
(g) Muscle activity, which may be determined via electrical signals indicative of activity of muscles, e.g., measured with electromyography (EMG). In one example, surface electromyography (sEMG) may be used to measure muscle activity of frontalis and corrugator supercilii muscles, indicative of eyebrow movement, and from which an emotional state may be recognized.
(h) Eye movement, e.g., measured with electrooculography (EOG).
(i) Blood oxygen levels that may be measured using hemoencephalography (HEG).
(j) CO2 levels in the respiratory gases that may be measured using capnography.
(k) Concentration of various volatile compounds emitted from the human body (referred to as the Volatome), which may be detected from the analysis of exhaled respiratory gasses and/or secretions through the skin using various detection tools that utilize nanosensors.
(l) Temperature of various regions of the body and/or face may be determined utilizing thermal Infra-Red (IR) cameras. For example, thermal measurements of the nose and/or its surrounding region may be utilized to estimate physiological signals such as respiratory rate and/or occurrence of allergic reactions.

Alternatively or in addition, the sensor 32 may be an electric sensor or electric meter 32a that responds to an electrical characteristics or electrical phenomenon quantity in an electrical circuit, and is used to measure electrical quantities or electrical properties. The electrical sensor 32a may be connected in series or in parallel between the generator 35 and the electrodes 26a and 26b, to measure the bursts train signal 41 carried thereon. Such meter 32a may be used as a safety measure to check that the power, current, voltage, or charge supplied or inserted to the human body via the electrodes 26a and 26b in within pre-defined safe limits. Alternatively or in addition, this meter 32a forms a closed control loop allowing the controller 39 to verify that the determined setting applied as part of an "Apply Settings" step 66 are indeed provided. Further, the meter 32a may be used to indicate whether the electrodes are indeed attached to a person body. For example, measuring the current flowing via the electrodes may indicate that the electrodes are not properly attached to the human body or there is a short circuit.

The meter 32a may be conductively coupled to the electrical circuit, or may be a non-contact sensor non-conductively to the electrical circuit. The electrical sensor may be responsive to Alternating Current (AC) or Direct Current (DC). The electrical sensor may be an ampermeter that responds to electrical current passing through a conductor or wire, and may consist of, or may comprise, a galvanometer, a hot-wire ampermeter, a current clamp, or a current probe. Alternatively or in addition, the electrical sensor may be a voltmeter that responds to an electrical voltage, and may consist of, or may comprise, an electrometer, a resistor, a potentiometer, or a bridge circuit. Alternatively or in addition, the electrical sensor may be a wattmeter that responds to active electrical power.

The electrical sensor 32a may be conductively connected to the measured element. Alternatively or in addition, the electrical sensor may use non-conductive or non-contact coupling to the measured element, such as measuring a phenomenon associated with the measured quantity or property. The electric sensor may be a current sensor or an ampmeter (a.k.a. ammeter) for measuring DC or AC (or any other waveform) electric current passing through a conductor or wire. The current sensor may be connected such that part or entire of the measured electric current may be passing through the ampermeter, such as a galvanometer or a hot-wire ampermeter. An ampermeter may be a current clamp or current probe, and may use the 'Hall effect' or a current transformer concept for non-contact or non-conductive current measurement. The electrical sensor may be a voltmeter for measuring the DC or AC (or any other waveform) voltage, or any potential difference between two points. The voltmeter may be based on the current passing a resistor using the Ohm's law, may be based on a potentiometer, or may be based on a bridge circuit. The sensor 32a may be a wattmeter measuring the magnitude of the active AC or DC power (or the supply rate of electrical energy). The wattmeter may be a bolometer, used for measuring the power of incident electromagnetic radiation via the heating of a material with a temperature-dependent electrical resistance. The electrical sensor 32a may be an ohmmeter for measuring the electrical resistance (or conductance), and may be a megohmmeter or a microohmmeter. The ohmmeter may use the Ohm's law to derive the resistance from voltage and current measurements, or may use a bridge such as a Wheatstone bridge. A sensor may be a capacitance meter for measuring capacitance. A sensor may be an inductance meter for measuring inductance. The sensor 32a may be an impedance meter for measuring an impedance of a device or a circuit. A sensor may be an LCR meter, used to measure inductance (L), capacitance (C), and resistance (R). A meter may use sourcing a DC or an AC voltage, and use the ratio of the measured voltage and current (and their phase difference) through the tested device according to Ohm's law to calculate the resistance, the capacitance, the inductance, or the impedance ($R=V/I$). Alternatively or in addition, a meter may use a bridge circuit (such as Wheatstone bridge), where variable calibrated elements are adjusted to detect a null. The measurement may be using DC, using a single frequency or over a range of frequencies.

The sensor 32a may be used to measure electrical quantities. An electrical sensor may be conductively connected to measure the electrical parameter, or may be non-conductively coupled to measure an electric-related phenomenon, such as magnetic field or heat. Further, the average or RMS value may be measured. An ampermeter (a.k.a. ammeter) is a current sensor that measures the magnitude of the electric current in a circuit or in a conductor such as a wire. Electric current is commonly measured in Amperes, milliampers, microamperes, or kiloampers. The sensor may be an integrating ammeter (a.k.a. watt-hour meter) where the current is summed over time, providing a current/time product, which is proportional to the energy transferred. The measured electric current may be an Alternating Current (AC) such as a sinewave, a Direct Current (DC), or an arbitrary waveform. A galvanometer is a type of ampermeter for detecting or measuring low current, typically by producing a rotary deflection of a coil in a magnetic field. Some ampermeters use a resistor (shunt), whose voltage is directly proportional to the current flowing through, requiring the current to pass through the meter. A hot-wire ampermeter involves passing the current through a wire which expands as it heats, and the expansion is measured. A non-conductive or non-contact current sensor may be based on 'Hall effect' magnetic field sensor, measuring the magnetic field generated by the current to be measured. Other non-conductive current sensors involve a current clamp or current probe, which has two jaws which open to allow clamping around an electrical conductor, allowing for measuring of the electric current properties (commonly AC), without making a physical contact or disconnecting the circuit. Such current clamp commonly comprises a wire coil wounded around a split ferrite ring, acting as the secondary winding of a current transformer, with the current-carrying conductor acting as the primary winding. Other current sensors and related circuits are described in Zetex Semiconductors PLC application note "AN39—Current measurement application handbook" Issue 5, January 2008, which is incorporated in its entirety for all purposes as if fully set forth herein.

The sensor 32*a* may be a voltmeter, commonly used for measuring the magnitude of the electric potential difference between two points. Electric voltage is commonly measured in volts, millivolts, microvolts, or kilovolts. The measured electric voltage may be an Alternating Current (AC) such as a sinewave, a Direct Current (DC), or an arbitrary waveform. Similarly, an electrometer may be used for measuring electric charge (commonly in Coulomb units—C) or electrical potential difference, with very low leakage current. The voltmeter commonly works by measuring the current through a fixed resistor, which, according to Ohm's Law, is proportional to the voltage across the resistor. A potentiometer-based voltmeter works by balancing the unknown voltage against a known voltage in a bridge circuit. A multimeter (a.k.a. VOM—Volt-Ohm-Millimeter) as well as Digital MultiMeter (DMM), typically includes a voltmeter, an ampermeter and an ohmmeter.

The sensor 32*a* may be a wattmeter measuring the magnitude of the active power (or the supply rate of electrical energy), commonly using watts (W), milliwatts, kilowatts, or megawatts units. A wattmeter may be based on measuring the voltage and the current, and multiplying to calculate the power $P=VI$. In AC measurement, the true power is $P=VI\cos(\phi)$. The wattmeter may be a bolometer, used for measuring the power of incident electromagnetic radiation via the heating of a material with a temperature-dependent electrical resistance. A sensor may be an electricity meter (or electrical energy meter) that measures the amount of electrical energy consumed by a load. Commonly, an electricity meter is used to measure the energy consumed by a single load, an appliance, a residence, a business, or any electrically powered device, and may provide or be the basis for the electricity cost or billing. The electricity meter may be an AC (single or multi-phase) or DC type, and the common unit of measurement is kilowatt-hour, however any energy related unit may be used such as Joules. Some electricity meters are based on wattmeters which accumulate or average the readings, or may be based on induction.

The sensor 32*a* may be an ohmmeter measuring the electrical resistance, commonly measured in ohms ($\Omega$), milliohms, kiloohms or megohms, or conductance measured in Siemens (S) units. Low-resistance measurements commonly use micro-ohmmeter, while megohmmeter (a.k.a. Megger) measures large value of resistance. Common ohmmeter passes a constant known current through the measured unknown resistance (or conductance), while measuring the voltage across the resistance, and deriving the resistance (or conductance) value from Ohm's law ($R=V/I$). A Wheatstone bridge may also be used as a resistance sensor, by balancing two legs of a bridge circuit, where one leg includes the unknown resistance (or conductance) component. Variations of Wheatstone bridge may be used to measure capacitance, inductance, impedance and other electrical or non-electrical quantities.

The sensor 32*a* may be a capacitance meter for measuring capacitance, commonly using units of picofarads, nanofarads, microfarads, and Farads (F). A sensor may be an inductance meter for measuring inductance, commonly using SI units of Henry (H), such as microHenry, milli-Henry, and Henry. Further, a sensor may be an impedance meter for measuring an impedance of a device or a circuit. The sensor 32*a* may be an LCR meter, used to measure inductance (L), capacitance (C), and resistance (R). A meter may use sourcing an AC voltage, and use the ratio of the measured voltage and current (and their phase difference) through the tested device according to Ohm's law to calculate the impedance. Alternatively or in addition, a meter may use a bridge circuit (Similar to Wheatstone bridge concept), where variable calibrated elements are adjusted to detect a null. The measurement may be in a single frequency or over a range of frequencies.

The electrical sensor 32*a* may be a magnetometer for measuring a local H or B magnetic fields. The B-field (a.k.a. magnetic flux density or magnetic induction) is measured in Tesla (T) in SI units and Gauss in cgs units, and magnetic flux is measured in Weber (Wb) units. The H-field (a.k.a. magnetic field intensity or magnetic field strength) is measured in ampere-turn per meter (A/m) in SI units, and in Oersteds (Oe) in cgs units. Many Smartphones contain magnetometers serving as compasses. A magnetometer may be a scalar magnetometer, measuring the total strength, or may be a vector magnetometer, providing both magnitude and direction (relative to the spatial orientation) of the magnetic field. Common magnetometers include Hall effect sensor, magneto-diode, magneto-transistor, AMR magnetometer, GMR magnetometer, magnetic tunnel junction magnetometer, magneto-optical sensor, Lorentz force based MEMS sensor (a.k.a. Nuclear Magnetic Resonance—NMR), Electron Tunneling based MEMS sensor, MEMS compasses, Nuclear precession magnetic field sensor, optically pumped magnetic field sensor, fluxgate magnetometer, search coil magnetic field sensor, and Superconducting Quantum Interference Device (SQUID) magnetometer. 'Hall effect' magnetometers are based on 'Hall probe', which contains an indium compound semiconductor crystal such as indium antimonide, mounted on an aluminum backing plate, and provides a voltage a voltage in response to the measured B-field. A fluxgate magnetometer makes use of the non-linear magnetic characteristics of a probe or sensing element that has a ferromagnetic core. NMR and Proton Precession Magnetometers (PPM) measure the resonance frequency of protons in the magnetic field to be measured. SQUID meters are very sensitive vector magnetometers, based on superconducting loops containing Josephson junctions. The magnetometer may be Lorentz-force-based MEMS sensor, relying on the mechanical motion of the MEMS structure due to the Lorentz force acting on the current-carrying conductor in the magnetic field.

Alternatively or in addition, the sensor 32 may be a blink detector, thus forming a closed control loop allowing the controller 39 to verify that the determined settings applied as part of the "Apply Settings" step 66 are indeed provided and the required blinking rate or closure is indeed achieved. Further, such sensor 32 may be used to indicate whether the electrodes are indeed properly attached to a person body and the system functions properly. Any sensor herein may be used for detecting eye blinking or as part of a blink sensor or detector.

Accidents due to drowsiness can be controlled and prevented with the help of eye blink sensor using IR rays, as described in an article entitled: "A Microcontroller Based Car-Safety System: Implementing Drowsiness Detection And Vehicle-Vehicle Distance Detection In Parallel" by Pragyaditya Das. and S. Pragadeesh, published 2015 in INTERNATIONAL JOURNAL OF SCIENTIFIC & TECHNOLOGY RESEARCH VOLUME 4, ISSUE 12, DECEMBER 2015 ISSN 2277-8616 161 IJSTR©2015, which is incorporated in its entirety for all purposes as if fully set forth herein. It consists of IR transmitter and an IR receiver. The transmitter transmits IR rays into the eye. If the eye is shut, then the output is high. If the eye is open, then the output is low. This output is interfaced with an alarm inside and outside the vehicle. This module can be connected to the braking system of the vehicle and can be used to reduce the speed of the vehicle. The alarm inside the vehicle will go on for a period of time until the driver is back to his senses. If the driver is unable to take control of the vehicle after that stipulated amount of time, then the alarm outside the vehicle will go on to warn and tell others to help the driver.

Facial paralysis remains one of the most challenging conditions to effectively manage, often causing life-altering deficits in both function and appearance. Facial rehabilitation via pacing and robotic technology has great yet unmet potential. A critical first step towards reanimating symmetrical facial movement in cases of unilateral paralysis is the detection of healthy movement to use as a trigger for stimulated movement. Testing a blink detection system that can be attached to standard eyeglasses and used as part of a closed-loop facial pacing system is described in a paper entitled: *"INFRARED-BASED BLINK DETECTING GLASSES FOR FACIAL PACING: TOWARDS A BIONIC BLINK"* by Alice Frigerio, Tessa A. Hadlock, Elizabeth H Murray, and James T Heaton, published 2014 [JAMA Facial Plast Surg. 2014; 16(3): 211-218. doi:10.1001/jamafacial.2014.1], which is incorporated in its entirety for all purposes as if fully set forth herein. Standard safety glasses were equipped with an infrared (IR) emitter/detector pair oriented horizontally across the palpebral fissure, creating a monitored IR beam that became interrupted when the eyelids closed.

A real-time online prototype driver-fatigue monitor is described in a paper entitled: *"Accident Prevention Using Eye Blinking and Head Movement"* by Abhi R. Varma, Seema V. Arote, Chetna Bharti, and Kuldeep Singh (all of Pravara Rural Engineering College, Loni). Published 2012 in "Emerging Trends in Computer Science and Information Technology—2012(ETCSIT2012) Proceedings published in International Journal of Computer Applications (IJCA)", which is incorporated in its entirety for all purposes as if fully set forth herein. It uses remotely located charge-coupled-device cameras equipped with active infrared illuminators to acquire video images of the driver. Various visual cues that typically characterize the level of alertness of a person are extracted in real time and systematically combined to infer the fatigue level of the driver. The visual cues employed characterize eyelid movement, gaze movement, head movement, and facial expression. A probabilistic model is developed to model human fatigue and to predict fatigue based on the visual cues obtained. The simultaneous use of multiple visual cues and their systematic combination yields a much more robust and accurate fatigue characterization than using a single visual cue. This system was validated under real-life fatigue conditions with human subjects of different ethnic backgrounds, genders, and ages; with/without glasses; and under different illumination conditions. It was found to be reasonably robust, reliable, and accurate in fatigue characterization.

In one example, the sensor 32 may include an environment sensor, for monitoring the environment in, or around, the device 31. Such sensor output may be used, as part of "Sensor Output" step 64 to adapt or optimize the device 31 operation to the environmental condition. For example, in case of high temperature or low humidity, the blinking rate may be increased to better water the eye.

An appropriate sensor 32 may be adapted for a specific physical phenomenon, such as a sensor responsive to temperature, humidity, pressure, audio, vibration, light, motion, sound, proximity, flow rate, electrical voltage, and electrical current. The sensor 32 may be thermoelectric sensor, for measuring, sensing or detecting the temperature (or the temperature gradient) of an object, which may be solid, liquid or gas. Such sensor may be a thermistor (either PTC or NTC), a thermocouple, a quartz thermometer, or an RTD. The sensor 32 may be based on a Geiger counter for detecting and measuring radioactivity or any other nuclear radiation. Light, photons, or other optical phenomena may be measured or detected by a photosensor or photodetector, used for measuring the intensity of visible or invisible light (such as infrared, ultraviolet, X-ray or gamma rays). A photosensor may be based on the photoelectric or the photovoltaic effect, such as a photodiode, a phototransistor, solar cell or a photomultiplier tube. A photosensor may be a photoresistor based on photoconductivity, or a CCD where a charge is affected by the light.

The sensor 32 may be an image sensor for providing digital camera functionality, allowing an image (either as still images or as a video) to be captured, stored, manipulated and displayed. The image capturing hardware integrated with the sensor unit may contain a photographic lens (through a lens opening) focusing the required image onto a photosensitive image sensor array disposed approximately at an image focal point plane of the optical lens, for capturing the image and producing electronic image information representing the image. The image sensor may be based on Charge-Coupled Devices (CCD) or Complementary Metal-Oxide-Semiconductor (CMOS). The image may be converted into a digital format by an image sensor AFE (Analog Front End) and an image processor, commonly including an analog to digital (A/D) converter coupled to the image sensor for generating a digital data representation of the image. The unit may contain a video compressor, coupled between the analog to digital (A/D) converter and the transmitter for compressing the digital data video before transmission to the communication medium. The compressor may be used for lossy or non-lossy compression of the image information, for reducing the memory size and reducing the data rate required for the transmission over the communication medium. The compression may be based on a standard compression algorithm such as JPEG (Joint Photographic Experts Group) and MPEG (Moving Picture Experts Group), ITU-T H.261, ITU-T H.263, ITU-T H.264, or ITU-T COR 601.

The sensor 32 may be a strain gauge, used to measure the strain, or any other deformation, of an object. The sensor may be based on deforming a metallic foil, semiconductor strain gauge (such as piezoresistors), measuring the strain along an optical fiber, capacitive strain gauge, and vibrating or resonating of a tensioned wire. Any sensor herein may be a tactile sensor, being sensitive to force or pressure, or being sensitive to a touch by an object, typically a human touch. A tactile sensor may be based on a conductive rubber, a lead zirconate titanate (PZT) material, a polyvinylidene fluoride (PVDF) material, a metallic capacitive element, or any combination thereof. A tactile sensor may be a tactile switch, which may be based on the human body conductance, using measurement of conductance or capacitance.

The sensor 32 may be a piezoelectric sensor, where the piezoelectric effect is used to measure pressure, acceleration, strain or force, and may use transverse, longitudinal, or shear effect mode. A thin membrane may be used to transfer and measure pressure, while mass may be used for acceleration measurement. A piezoelectric sensor element material may be a piezoelectric ceramics (such as PZT ceramic) or a single crystal material. A single crystal material may be gallium phosphate, quartz, tourmaline, or Lead Magnesium Niobate-Lead Titanate (PMN-PT).

The sensor 32 may be a motion sensor, and may include one or more accelerometers, which measures the absolute acceleration or the acceleration relative to freefall. The accelerometer may be piezoelectric, piezoresistive, capacitive, MEMS or electromechanical switch accelerometer, measuring the magnitude and the direction the device acceleration in a single-axis, 2-axis or 3-axis (omnidirectional). Alternatively or in addition, the motion sensor may be based on electrical tilt and vibration switch or any other electromechanical switch.

The sensor 32 may be a force sensor, a load cell, or a force gauge (a.k.a. force gage), used to measure a force magnitude and/or direction, and may be based on a spring extension, a strain gauge deformation, a piezoelectric effect, or a vibrating wire. Any sensor herein may be a driving or passive dynamometer, used to measure torque or any moment of force.

Any sensor herein may be a pressure sensor (a.k.a. pressure transducer or pressure transmitter/sender) for measuring a pressure of gases or liquids, and for indirectly measuring other parameters such as fluid/gas flow, speed, water-level, and altitude. A pressure sensor may be a pressure switch. A pressure sensor may be an absolute pressure sensor, a gauge pressure sensor, a vacuum pressure sensor, a differential pressure sensor, or a sealed pressure sensor. The changes in pressure relative to altitude may be used for an altimeter, and the Venturi effect may be used to measure flow by a pressure sensor. Similarly, the depth of a submerged body or the fluid level on contents in a tank may be measured by a pressure sensor.

A pressure sensor may be of a force collector type, where a force collector (such a diaphragm, piston, bourdon tube, or bellows) is used to measure strain (or deflection) due to applied force (pressure) over an area. Such sensor may be a based on the piezoelectric effect (a piezoresistive strain gauge), may be of a capacitive or of an electromagnetic type. A pressure sensor may be based on a potentiometer, or may be based on using the changes in resonant frequency or the thermal conductivity of a gas, or may use the changes in the flow of charged gas particles (ions).

The sensor 32 may be a position sensor for measuring linear or angular position (or motion). A position sensor may be an absolute position sensor, or may be a displacement (relative or incremental) sensor, measuring a relative position, and may be an electromechanical sensor. A position sensor may be mechanically attached to the measured object, or alternatively may use a non-contact measurement.

A position sensor may be an angular position sensor, for measuring involving an angular position (or the rotation or motion) of a shaft, an axle, or a disk. Absolute angular position sensor output indicates the current position (angle) of the shaft, while incremental or displacement sensor provides information about the change, the angular speed or the motion of the shaft. An angular position sensor may be of optical type, using reflective or interruption schemes, or may be of magnetic type, such as based on variable-reluctance (VR), Eddy-current killed oscillator (ECKO), Wiegand sensing, or Hall-effect sensing, or may be based on a rotary potentiometer. An angular position sensor may be transformer based such as a RVDT, a resolver or a synchro. An angular position sensor may be based on an absolute or incremental rotary encoder, and may be a mechanical or optical rotary encoder, using binary or gray encoding schemes.

The sensor 32 may be a mechanical or electrical motion detector (or an occupancy sensor), for discrete (on/off) or magnitude-based motion detection. A motion detector may be based on sound (acoustic sensors), opacity (optical and infrared sensors and video image processors), geomagnetism (magnetic sensors, magnetometers), reflection of transmitted energy (infrared laser radar, ultrasonic sensors, and microwave radar sensors), electromagnetic induction (inductive-loop detectors), or vibration (triboelectric, seismic, and inertia-switch sensors). Acoustic sensors may use electric effect, inductive coupling, capacitive coupling, triboelectric effect, piezoelectric effect, fiber optic transmission, or radar intrusion sensing. An occupancy sensor is typically a motion detector that may be integrated with hardware or software-based timing device.

A motion sensor may be a mechanically-actuated switch or trigger, or may use passive or active electronic sensors, such as passive infrared sensors, ultrasonic sensors, microwave sensor or tomographic detector. Alternatively or in addition, motion can be electronically identified using infrared (PIR) or laser optical detection or acoustical detection, or may use a combination of the technologies disclosed herein.

The sensor 32 may be a humidity sensor, such as a hygrometer or a humidistat, and may respond to an absolute, relative, or specific humidity. The measurement may be based on optically detecting condensation, or may be based on changing the capacitance, resistance, or thermal conductivity of materials subjected to the measured humidity.

The sensor 32 may be a clinometer for measuring angle (such as pitch or roll) of an object, typically with respect to a plane such as the earth ground plane. A clinometer may be based on an accelerometer, a pendulum, or on a gas bubble in liquid, or may be a tilt switch such as a mercury tilt switch for detecting inclination or declination with respect to a determined tilt angle.

The sensor 32 may be a gas or liquid flow sensor, for measuring the volumetric or mass flow rate via a defined area or a surface. A liquid flow sensor typically involves measuring the flow in a pipe or in an open conduit. A flow measurement may be based on a mechanical flow meter, such as a turbine flow meter, a Woltmann meter, a single jet meter, or a paddle wheel meter. Pressure-based meters may be based on measuring a pressure or a pressure differential based on Bernoulli's principle, such as a Venturi meter. The sensor may be an optical flow meter or be based on the Doppler-effect.

A flow sensor may be an air flow sensor, for measuring the air or gas flow, such as through a surface (e.g., through a tube) or a volume, by actually measuring the air volume passing, or by measuring the actual speed or air flow. In some cases, a pressure, typically differential pressure, may be measured as an indicator for the air flow measurements. An anemometer is an air flow sensor primarily for measuring wind speed, and may be cup anemometer, a windmill anemometer, hot-wire anemometer such as CCA (Constant-Current Anemometer), CVA (Constant-Voltage Anemometer) and CTA (Constant-Temperature Anemometer). Sonic anemometers use ultrasonic sound waves to measure wind velocity. Air flow may be measured by a pressure anemometer that may be a plate or tube class.

The sensor 32 may be a gyroscope, for measuring orientation in space, such as the conventional mechanical type, a MEMS gyroscope, a piezoelectric gyroscope, a FOG, or a VSG type. A sensor may be a nanosensor, a solid-state, or an ultrasonic based sensor. Any sensor herein may be an eddy-current sensor, where the measurement may be based on producing and/or measuring eddy-currents. Sensor may be a proximity sensor, such as metal detector. Any sensor herein may be a bulk or surface acoustic sensor, or may be an atmospheric sensor. While the apparatus and method herein are described involving deterministic operation, the operation may be based on, or associated with, randomness based on random numbers. For example, using continuous and steady blinking rate of the person 25, which corresponds to the period T 41d of the bursts train 41, may be visualized as 'mechanical' or 'robotic' behavior, in contrast to the normal variable blinking rate. As such, the period T 41d of the bursts train 41 may be randomized, such as between minimum and maximum values, such as between 4 and 6 seconds, trying to mimic a normal blinking behavior.

Figure 4A:
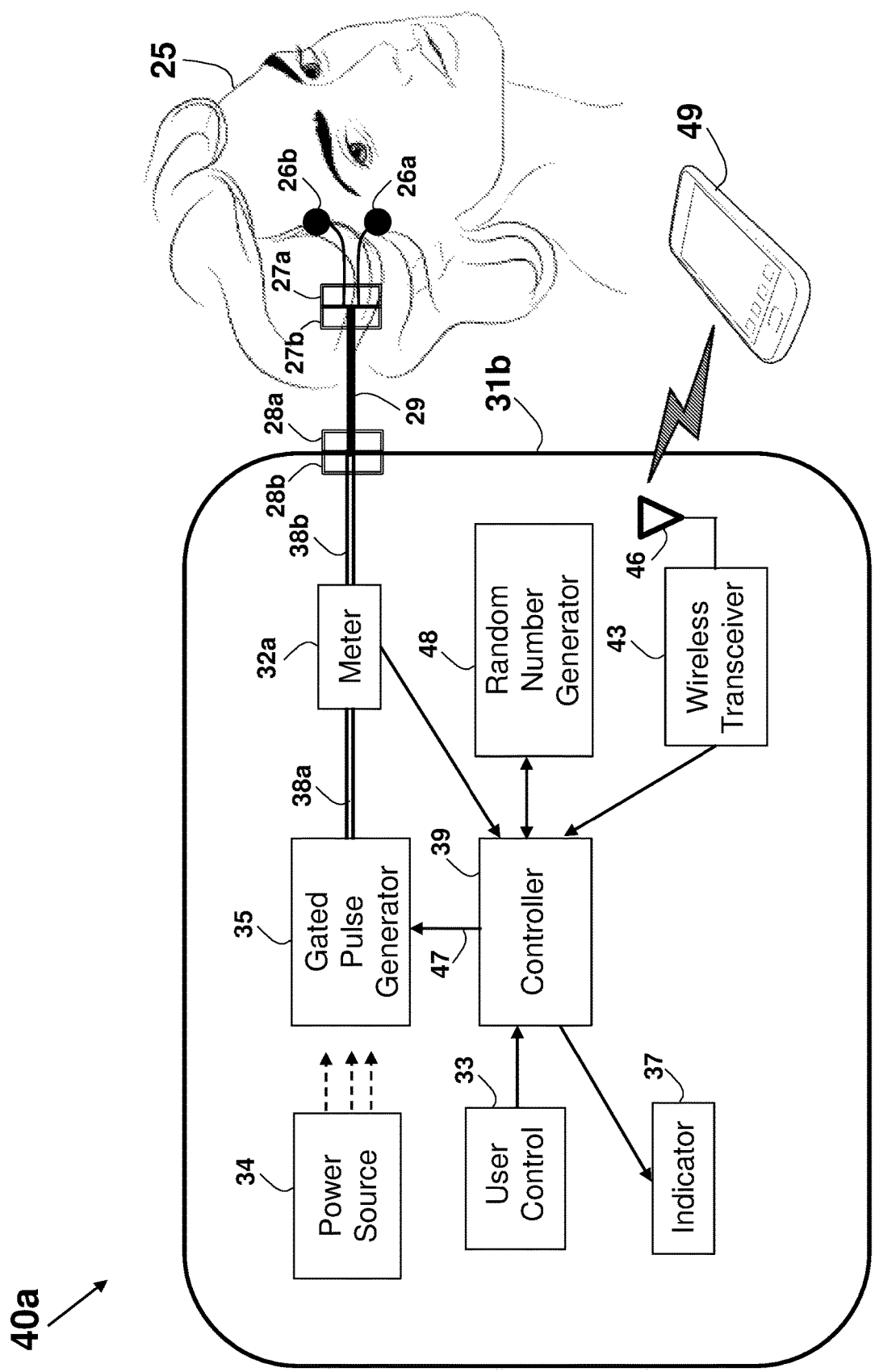
FIG. 4a illustrates schematically a block diagram of a battery-powered stimulating device that includes a random number generator and an electric meter.

In such a case, a stimulating device 31b shown as part of an arrangement 40a illustrated in FIG. 4a may comprise a random number generator 48 for generating random numbers that may be hardware-based using thermal noise, shot noise, nuclear decaying radiation, photoelectric effect, or quantum phenomena. Alternatively or in addition, the random number generator 48 may be software-based and may execute an algorithm for generating pseudo-random numbers.

Figure 4B:
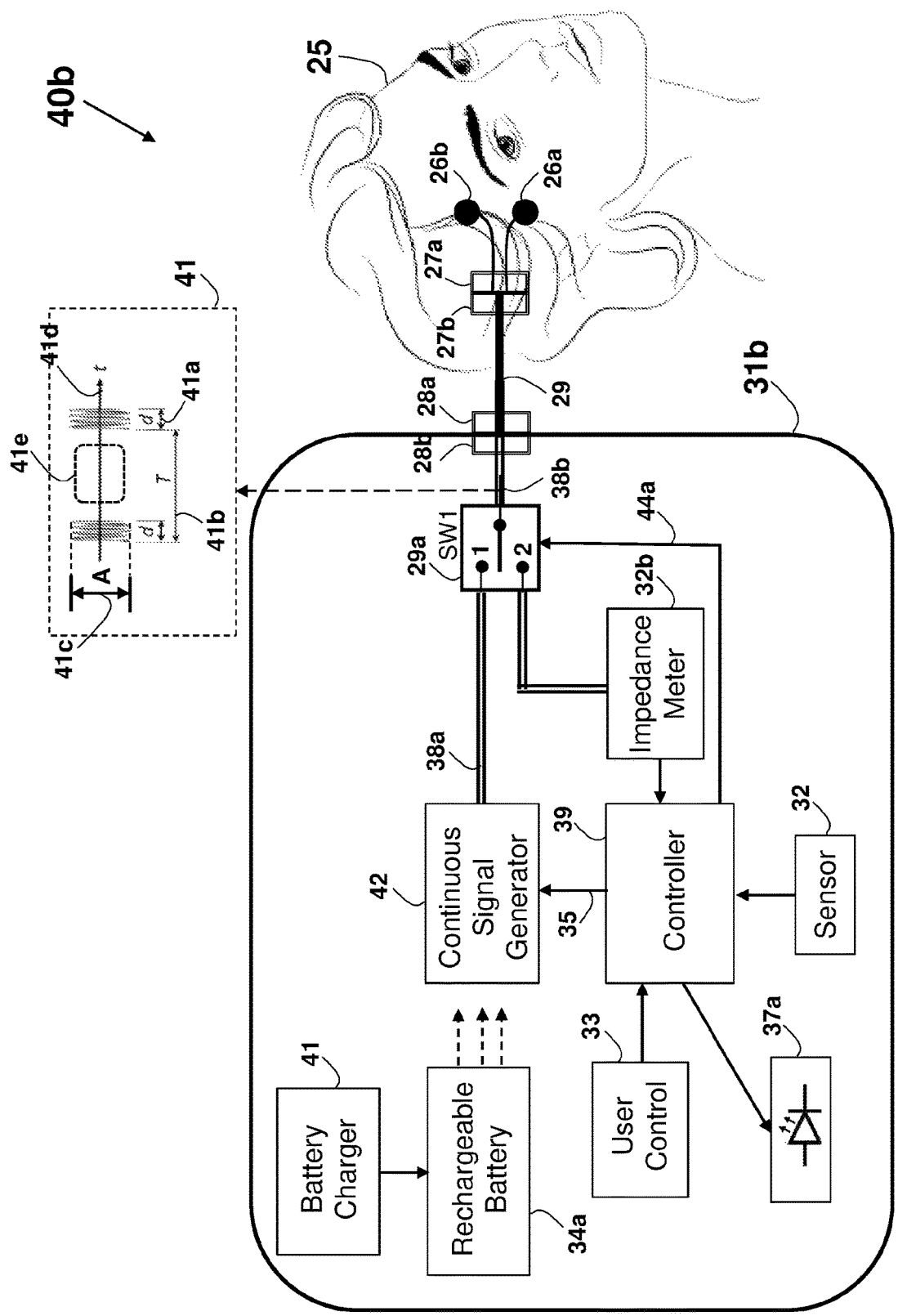
FIG. 4b illustrates schematically a block diagram of a battery-powered stimulating device that includes an impedance meter and having two states.

In one example, during the period between consecutive bursts 41a when no energy is transmitted to the electrodes 26a and 26b, the electrodes are used for electrical measurement of the human body, such as for measuring the impedance of the skin. Such a stimulator device 31b is shown as part of an arrangement 40b illustrated in FIG. 4b. A Single-Pole-Double-Throw (SPDT) two-way switch 29a is added between the signal generator 42 and the electrodes 26a and 26b. The switch 29a is controlled by the controller 39 via a port or connection 44a. In one state of the switch 29a, shown as state '1' of the switch, the cable or wires 38b is connected to the signal generator 42 via the connection 38a, reverting to the operation is described in the arrangement 40 shown in FIG. 4 or as described in the arrangement 40a shown in FIG. 4a, where electric pulses or bursts are transmitted to the human body 25 via the electrodes 26a and 26b. In another state of the switch 29a, shown as state '2' of the switch, the cable or wires 38b is connected to an impedance meter 32b for measuring an impedance of the human skin via the electrodes 26a and 26b. The measurement result is output to the controller 39 to be used thereof. For example, the impedance measuring may be performed during a period 41e (during which the switch 29a is in state '2') between two consecutive bursts 41a (during which the switch 29a is in state '1') connecting the busts 41a to the electrodes 26a and 26b.

The impedance meter 32b serves as an electrical sensor and may be an ohmmeter measuring the electrical resistance, commonly measured in ohms (Ω), milliohms, kiloohms or megohms, or conductance measured in Siemens (S) units. Low-resistance measurements commonly use micro-ohmmeter, while megohmmeter (a.k.a. Megger) measures large value of resistance. Common ohmmeter passes a constant known current through the measured unknown resistance (or conductance), while measuring the voltage across the resistance, and deriving the resistance (or conductance) value from Ohm's law (R=V/I). A Wheatstone bridge may also be used as a resistance sensor, by balancing two legs of a bridge circuit, where one leg includes the unknown resistance (or conductance) component. Variations of Wheatstone bridge may be used to measure capacitance, inductance, impedance, and other electrical or non-electrical quantities.

The electrical sensor 32b may be a capacitance meter for measuring capacitance, commonly using units of picofarads, nanofarads, microfarads, and Farads (F). The meter 32b may be an inductance meter for measuring inductance, commonly using SI units of Henry (H), such as microHenry, milliHenry, and Henry. Further, a sensor may be an impedance meter for measuring an impedance of a device or a circuit. The sensor 32a may be an LCR meter, used to measure inductance (L), capacitance (C), and resistance (R). The meter 32a may use sourcing an AC voltage, and use the ratio of the measured voltage and current (and their phase difference) through the tested device according to Ohm's law to calculate the impedance. Alternatively or in addition, a meter may use a bridge circuit (Similar to Wheatstone bridge concept), where variable calibrated elements are adjusted to detect a null. The measurement may be in a single frequency, or over a range of frequencies.

The output of the impedance meter 32b, wither alone or in conjunction with other sensors, such as sensor 32, may be part of the "Sensor Output" step 64, and as such may be used to determine any of the device settings as part of the "Determine Settings" step 65, as described above, and as such may impact, change, or affect the device operation as part of the "Apply Settings" step 66, such as any of the signal 41 parameters, such as the burst duration 'd' 41a, the repetition period 'T' 41b, the amplitude A 41c, the burst internal frequency 41d, or any combination thereof. For example, a low resistance measured may indicate that the person 25 is sweating, suggesting in physical action such as walking or running, and increasing the blinking rate.

The impedance meter 32b may use, may be based on, or may comprise, any of the circuits or techniques described in an Application Note entitled: "*Keysight Technologies—Impedance Measurement Handbook—A guide to measurement technology and techniques—6$^{th}$ Edition*", published Nov. 2, 2016 by Keysight Technologies, Inc. [5950-3000], which is incorporated in its entirety for all purposes as if fully set forth herein. Alternatively or in addition, the impedance meter 32b may use, may be based on, or may comprise, any of the circuits or techniques described in an Application Note AN-1302 Revision A entitled: "*Optimizing the ADuCM350 for 4-Wire, Bioisolated Impedance Measurement Applications*", published 2018 by Analog Devices, Inc. [AN12168-0-2/18(A)], which is incorporated in its entirety for all purposes as if fully set forth herein.

Figure 6:
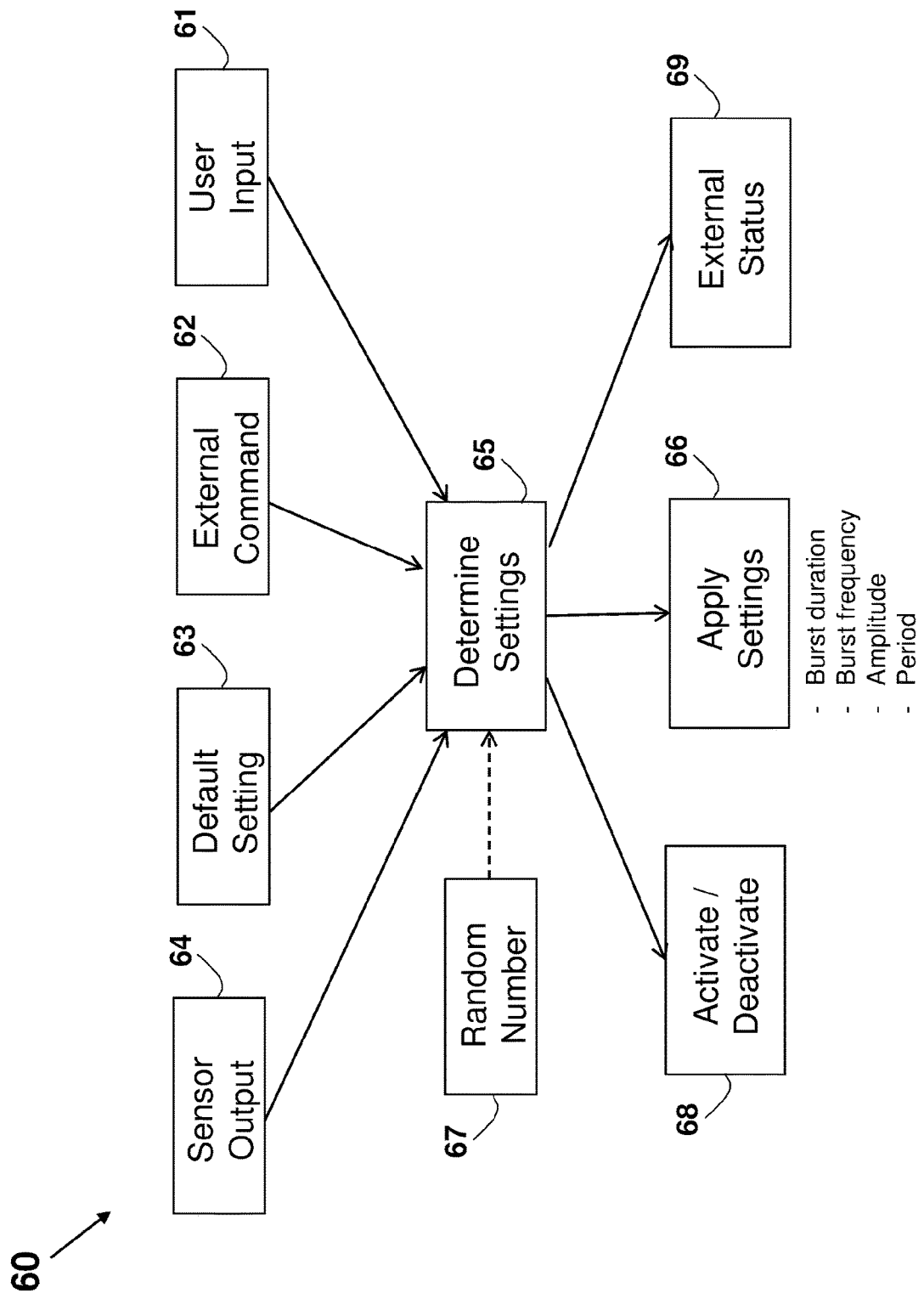
FIG. 6 illustrates schematically a simplified flowchart of a stimulator device operation.

The device 31 operation may be according to a general flow chart 60 shown in FIG. 6, as controlled by the controller 39. The controller 39 may determine as part of a "Determine Settings" step 65, if the generator 35 may be activated or deactivated as part of a "Activate/Deactivate" step 68, such as by directly controlling the generator 35 or by an actuating or de-actuating the switch 29 by the control port 45 via the connection 44. Alternatively or in addition, the controller 39 may set the bursts train 41 parameters as part of an "Apply Settings" step 66, such as via the control port of connection 47. The burst train parameters that may be set as part of the "Apply Settings" step 66 include the peak-to-peak amplitude 'A' 41c (or the nominal value, or effective value, of the signal 41), the burst duration d 41a, the frequency 'f' of the signal in the burst 41d, and the period T 41b. The activation as part of the "Activate/Deactivate" step 68 or the settings of the bursts train 41 parameters as part of an "Apply Settings" step 66 may be determined, as part of the "Determine Settings" step 65, in a deterministic way. Alternatively or in addition, the operation may involve randomness based on random number generated as part of a "Random Number" step 67, which may use the random number generator 48 shown as part of the device 31b in the arrangement 40a.

The device 31 may store "Default Setting" 63 that may include various settings that are used or assumed when no other input or command is available, such as upon power up before any other input or command is obtained or received. The activation (or deactivation) as part of the "Activate/Deactivate" step 68 or the settings of the bursts train 41 parameters as part of an "Apply Settings" step 66 may be determined, as part of the "Determine Settings" step 65, based on, or using, an input from the user as part of a "User Input" step 61, which may use, or may be based on, the user control 33 functionality. For example, a human user, such as the treated person 25, may activate the deice 31 when not needed (e.g., while sleeping), or may adjust the amplitude A 41c to a level that minimize pain or discomfort. Alternatively or in addition, the activation (or deactivation) as part of the "Activate/Deactivate" step 68 or the settings of the bursts train 41 parameters as part of an "Apply Settings" step 66 may be determined, as part of the "Determine Settings" step 65, based on, or using, an external command or input received, as part of an "External Command" step 62, from an external network via the communication interface 36.

Alternatively or in addition, the activation (or deactivation) as part of the "Activate/Deactivate" step 68 or the settings of the bursts train 41 parameters as part of an "Apply Settings" step 66 may be determined, as part of the "Determine Settings" step 65, based on, or using, the sensor 32 output, as part of a "Sensor Output" step 64. For example, the blinking rate (corresponding to the period T 41b) maybe optimized to the environment, such as higher blinking rate in case of higher temperature when the sensitivity to dry eye may be increased. In one example, a minimum or maximum threshold is defined associated with the sensor 32 output value, so that the device 31 is activated (or deactivated) in case where the sensor output is below the minimum threshold or is above the maximum threshold.

In one example, the controller 39 transmits over the external network, as part of a "External Status" step 69 using the communication interface 36 the device 31 status, such as activating/deactivating status, power source 34 (such as the battery 34a) status, sensor value, settings used, or any other information available in the device 31. Further, the device 31 status, such as activating/deactivating status, power source 34 (such as the battery 34a) status, sensor value, settings used, or any other information available in the device 31, may be indicated to a human user via the indicator 37.

As part of the "External Status" step 69, a message may be sent that may include identification of the device 31, such as its IP address, the time of sending the message, and the status. A notifying message may be sent periodically, such as every 1, 2, 5, or 10 seconds, every 1, 2, 5, or 10 minutes, every 1, 2, 5, or 10 hours, or every 1, 2, 5, or 10 days. Alternatively or in addition, the user may be notified by using an event-driven messaging. For example, a message may be transmitted upon a change in any parameter or characteristic in the device 31. Alternatively or in addition, a message may be transmitted upon the sensor 32 output exceeding a set maximum threshold, or upon measuring a sensor output below a set minimum threshold. Further, a message may be sent as a response to a received message, such as for acknowledgement. The message may be sent using XMPP, SIMPLE, Apple Push Notification Service (APNs), or IMPS. The message may be a text-based message, such as by using SMS, or Twitter services, as well as social marketing service such as Facebook. Alternatively or in addition, the message may include an audio or video message, and sent using MMS or Enhanced Messaging Service (EMS). Other services such as e-mail, Viber, or Whatsapp may be used.

The notification or data sent as part of "External Status" step 69 may be text based, such as an electronic mail (e-mail), website content, fax, or a Short Message Service (SMS). Alternatively or in addition, the notification or alert to the user device may be voice based, such as a voicemail, a voice message to a telephone device. Alternatively or in addition, the notification or the data to the user device may activate a vibrator, causing vibrations that are felt by human body touching, or may be based on a Multimedia Message Service (MMS) or Instant Messaging (IM). The messaging, alerting, and notifications may be based on, include part of, or may be according to U.S. Patent Application No. 2009/0024759 to McKibben et al. entitled: "System and Method for Providing Alerting Services", U.S. Pat. No. 7,653,573 to Hayes, Jr. et al. entitled: "Customer Messaging Service", U.S. Pat. No. 6,694,316 to Langseth. et al. entitled: "System and Method for a Subject-Based Channel Distribution of Automatic, Real-Time Delivery of Personalized Informational and Transactional Data", U.S. Pat. No. 7,334,001 to Eichstaedt et al. entitled: "Method and System for Data Collection for Alert Delivery", U.S. Pat. No. 7,136,482 to Wille entitled: "Progressive Alert Indications in a Communication Device", U.S. Patent Application No. 2007/0214095 to Adams et al. entitled: "Monitoring and Notification System and Method", U.S. Patent Application No. 2008/0258913 to Busey entitled: "Electronic Personal Alert System", or U.S. Pat. No. 7,557,689 to Seddigh et al. entitled: "Customer Messaging Service", which are all incorporated in their entirety for all purposes as if fully set forth herein.

Figure 7:
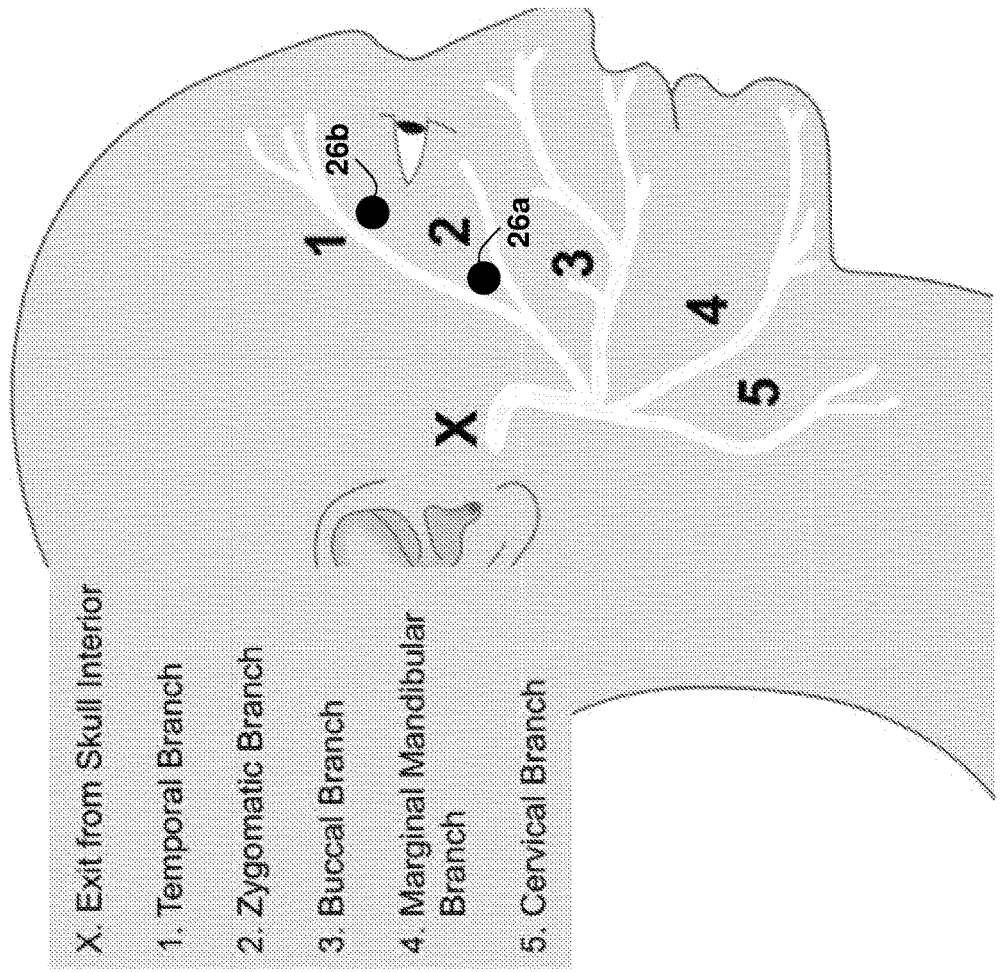
FIG. 7 depicts pictorially facial nerve branches external to the skull.

Major facial nerve branches outside of the skull is illustrated in a view 70 shown in FIG. 7. The point (X) in the illustration 70 is pointing the approximate location where the nerve extends outside of the skull, before branching to the different parts of the face. The facial nerve branches off to smaller nerves and muscles that go to 5 different parts of the face. Therefore, when the nerve is damaged those smaller veins are not supplied with enough blood for circulation which is necessary for muscles in the different areas of the face to move. Each nerve branch affects the movement of different muscles. The Temporal Branch (Frontal Branch), marked '1' in FIG. 7, affects the muscles in the Forehead, and the Zygomatic Branch (Malar Branches), marked '2' in FIG. 7, affects the Upper Cheek. The Temporal and the Zygomatic Branch together affect the muscles control opening and closure of the Eye. The Buccal Branch (Infraorbital Branches), marked '3' in FIG. 7, affects the cheek and above the mouth muscles, the Marginal Mandibular Branch, marked '4' in FIG. 7, affects the chin muscles, and the Cervical Branch, marked '5' in FIG. 7, affects some of the neck muscles. Facial nerve damage may affect the eyes, where the nerves from the Zygomatic Branch results in eyelid problems. This nerve controls the ability or lack thereof to either; 1) Blinking, or 2) Tear Production, but it can also cause 3) Ptosis (Droopy Eyelid). Dry eye can help as a warning of facial nerve damage. Other facial nerve damage may affect eating, since without the ability to move the Buccal branch and the Marginal Mandibular Branch, holding food in your mouth becomes very frustrating, and awkward. Drinking with a straw is often necessary. Similarly, talking may be affected since the same nerves that make eating difficult can also make proper or clear pronunciation of certain letters/sounds; B, P, M, and W. Facial nerve damage may affect a Droopy Face, due to lack of complete eyelid closure and a fallen smile, and nasal issues, such as a runny nose or congestion. Further, lack of control of wrinkled forehead symmetry, as well as saliva and tooth decay/dry mouth may be affected, since anything that diminishes the flow of saliva will dramatically increase the incidence of tooth decay. Although medications that stimulate Salivary Glands secretion are available, their side effects (nausea and diarrhea) often make them poorly tolerated. There are a variety of "artificial saliva" products that are available for purchase over the counter. But there is no substitute for prescription-strength topical fluoride preparations, whether; 1) applied in the dental office with fluoride varnishes, or 2) as prescription fluoride products for home use.

An optimal location of electrodes for eliciting blinking would provide closure of both lower and upper eye lid muscles, while using minimum current (or energy) thus minimizing pain or discomfort. Preferably, both the Zygomatic branch (for lower eye lid closure) and the Temporal branch (for higher eye lid closure) are stimulated, providing maximum or full closure of the eye when blinking is stimulated. Similarly, other bundle of nerves may be stimulated, simultaneously triggering few nerves that cooperate to form an action. Conventional locating of electrodes involves horizontal locating of the electrodes. However, various experiments suggest that such optimal location is locating a first electrode 26b near the Temporal Branch close to, and above, the eye, while the other electrode 26a is located near the Zygomatic branch split point, close to, and below, the eye, as shown in the illustration 70.

Figure 7A:
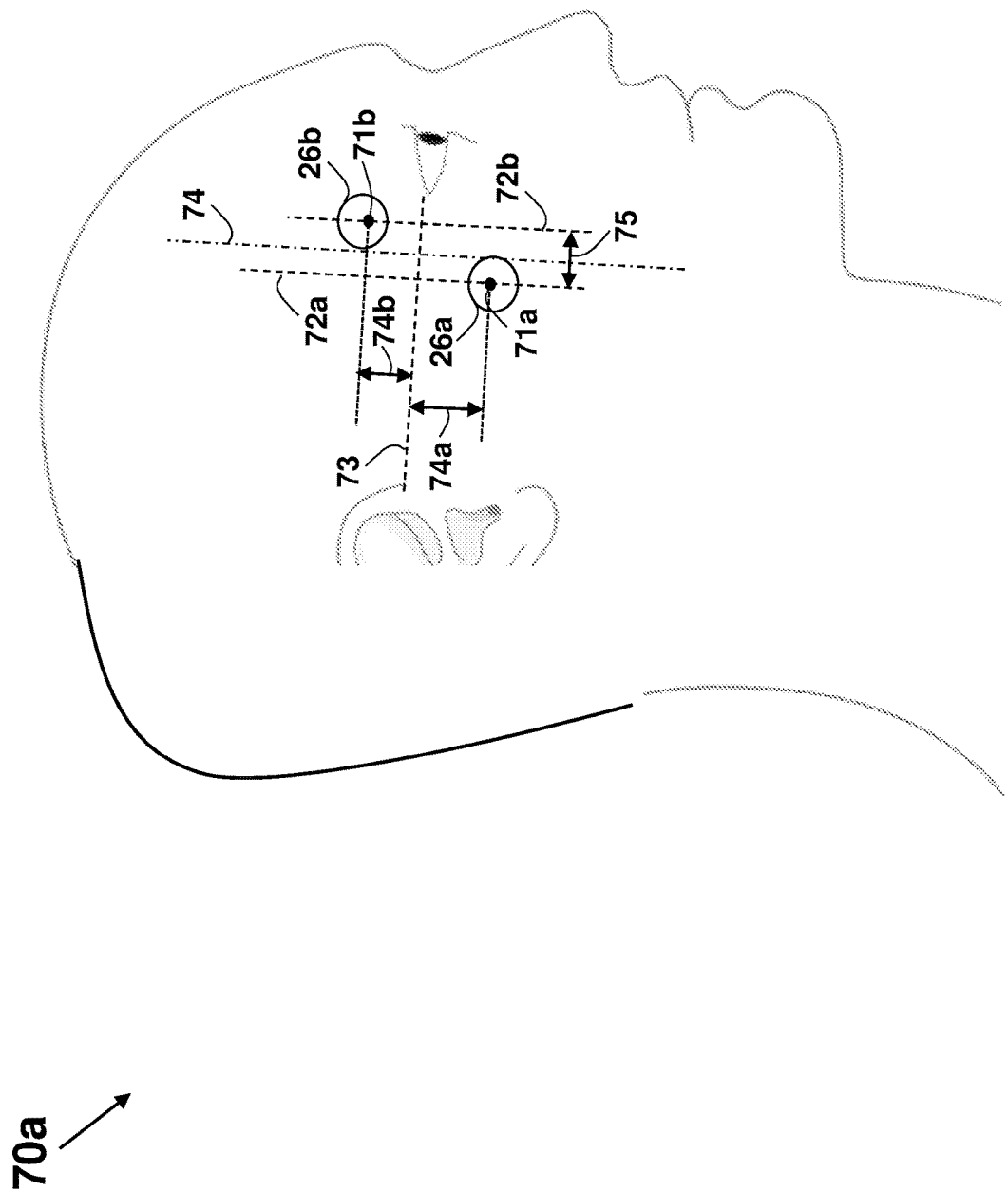
FIG. 7a depicts pictorially electrodes location for stimulating facial nerve branches external to the skull.

An example of locating electrodes is shown in a view 70a shown in FIG. 7a. As a reference, measurements use an imaginary line 73 which is the shortest line connecting the eye (where blinking is to be felicitated) and the ear of the same face side (either right eye and right ear, or left eye and left ear). The center of the conductive area of the electrode 26b is assumed to be point 71b, and the center of the conductive area of the electrode 26a is assumed to be point 71a. Preferably, part of, most of, or all of, the conductive area of the electrode 26b may be above the imaginary line 73. Similarly, preferably part of, most of, or all of, the conductive area of the electrode 26a may be below the imaginary line 73.

The center point 71b of the conductive area of the electrode 26b may be at a distance 74b above the imaginary line 73. The distance 74b may be at least 1 millimeter (mm), 2 mm, 3 mm, 5 mm, 7 mm, 10 mm, 12 mm, 15 mm, 20 mm, 25 mm, 30 mm, 40 mm, 50 mm, 70 mm, or 100 mm. Alternatively or in addition, the distance 74b may be less than 2 millimeter (mm), 3 mm, 5 mm, 7 mm, 10 mm, 12 mm, 15 mm, 20 mm, 25 mm, 30 mm, 40 mm, 50 mm, 70 mm, 100 mm, or 120 mm. Similarly, the center point 71a of the conductive area of the electrode 26a may be at a distance 74a above the imaginary line 73. The distance 74a may be at least 1 millimeter (mm), 2 mm, 3 mm, 5 mm, 7 mm, 10 mm, 12 mm, 15 mm, 20 mm, 25 mm, 30 mm, 40 mm, 50 mm, 70 mm, or 100 mm. Alternatively or in addition, the distance 74a may be less than 2 millimeter (mm), 3 mm, 5 mm, 7 mm, 10 mm, 12 mm, 15 mm, 20 mm, 25 mm, 30 mm, 40 mm, 50 mm, 70 mm, 100 mm, or 120 mm.

In one example, the center points 71a and 71b may be along a same line that is perpendicular to the imaginary line 73. Alternatively or in addition, the center point 71a may be along a line 72a that is perpendicular to the imaginary line 73, while the center point 71b may be along a different line 72b that is perpendicular to the imaginary line 73. In one example, a line 74 may be in the middle of the two lines 72a and 72b. The centers of the electrodes may be at a distance 75 (measured between the closest points along the imaginary line 73) as shown in the illustration 70a in FIG. 7a. The distance 75 may be at least 0 mm, 1 millimeter (mm), 2 mm, 3 mm, 5 mm, 7 mm, 10 mm, 12 mm, 15 mm, 20 mm, 25 mm, 30 mm, 40 mm, 50 mm, 70 mm, or 100 mm. Alternatively or in addition, the distance 75 may be less than 1 millimeter (mm), 2 mm, 3 mm, 5 mm, 7 mm, 10 mm, 12 mm, 15 mm, 20 mm, 25 mm, 30 mm, 40 mm, 50 mm, 70 mm, 100 mm, or 120 mm.

The term 'center' of an electrode herein refers to a centerpoint relating to the conductive area of the electrode that is touching, or is configured or designed to touch, the skin of a person, where every straight line in the area that goes through this point equally divides the area into two equal areas. In a case of circular shaped electrodes, the circle center is the center point.

Any device herein, such as the device 31 shown in FIG. 3, may be addressable in a network or the Internet using a digital address that may be a MAC layer address that may be MAC-48, EUI-48, or EUI-64 address type. Alternatively or in addition, the digital address may be a layer 3 address and may be static or dynamic IP address that may be IPv4 or IPv6 type address.

The device 31 may communicate over a network using the communication interface 36. In one example, the network is a wireless network that uses an antenna 46 and a wireless transceiver 43, which may part of the device 31a as shown in FIG. 4. In one example, as shown for the device 31b in the arrangement 40a, the wireless networking is used for communication with a smartphone 49. The wireless network may be a Wireless Wide Area Network (WWAN), such as WiMAX network or a cellular telephone network (such as Third Generation (3G) or Fourth Generation (4G) network). Alternatively or in addition, the wireless network may be a BAN (Body Area Network) or Wireless Personal Area Network (WPAN) that may be according to, may be compatible with, or may be based on, Bluetooth™ or IEEE 802.15.1-2005 standards, or may be according to, or may be based on, ZigBee™, IEEE 802.15.4-2003, or Z-Wave™ standard. Alternatively or in addition, the wireless network may be a Wireless Local Area Network (WLAN) that may be according to, may be compatible with, or may be based on, IEEE 802.11-2012, IEEE 802.11a, IEEE 802.11b, IEEE 802.11g, IEEE 802.11n, or IEEE 802.11ac.

Further, any device herein, such as the device 31a shown in FIG. 4, may be operative to communicate in an ad-hok scheme or for use with an intermediary device, where the wireless transceiver may be operative to communicate with the intermediary device using an infrastructure scheme. The intermediary device may be a Wireless Access Point (WAP), a wireless switch, or a wireless router. The wireless transceiver may be operative to wirelessly communicate and a wireless device, such as a hand-held or portable wireless device that may consist of, or comprise, a Personal Digital Assistant (PDA), a tablet computer, or a smartphone.

The Device

The device 31 may serve as a client device and may access data, such as retrieving data from, or sending data to, over the Internet. In the case of wireless networking, the wireless network may use any type of modulation, such as Amplitude Modulation (AM), a Frequency Modulation (FM), or a Phase Modulation (PM). Further, the wireless network may be a control network (such as ZigBee or Z-Wave), a home network, a WPAN (Wireless Personal Area Network), a WLAN (wireless Local Area Network), a WWAN (Wireless Wide Area Network), or a cellular network. An example of a Bluetooth-based wireless controller that may be included in a wireless transceiver is SPBT2632C1A Bluetooth module available from STMicroelectronics NV and described in the data sheet Doc1D022930 Rev. 6 dated April 2015 entitled: "*SPBT2632C1A—Bluetooth® technology class*-1 *module*", which is incorporated in its entirety for all purposes as if fully set forth herein.

Some embodiments may be used in conjunction with one or more types of wireless communication signals and/or systems, for example, Radio Frequency (RF), Infra-Red (IR), Frequency-Division Multiplexing (FDM), Orthogonal FDM (OFDM), Time-Division Multiplexing (TDM), Time-Division Multiple Access (TDMA), Extended TDMA (E-TDMA), General Packet Radio Service (GPRS), extended GPRS, Code-Division Multiple Access (CDMA), Wideband CDMA (WCDMA), CDMA 2000, single-carrier CDMA, multi-carrier CDMA, Multi-Carrier Modulation (MDM), Discrete Multi-Tone (DMT), Bluetooth®, Global Positioning System (GPS), Wi-Fi, Wi-Max, ZigBee™, Ultra-Wideband (UWB), Global System for Mobile communication (GSM), 2G, 2.5G, 3G, 3.5G, Enhanced Data rates for GSM Evolution (EDGE), or the like. Further, a wireless communication may be based on, or may be compatible with, wireless technologies that are described in Chapter 20: *"Wireless Technologies"* of the publication number 1-587005-001-3 by Cisco Systems, Inc. (July 1999) entitled: *"Internetworking Technologies Handbook"*, which is incorporated in its entirety for all purposes as if fully set forth herein.

Alternatively or in addition, the networking or the communication with the of the over the wireless network may be using, may be according to, may be compatible with, or may be based on, Near Field Communication (NFC) using passive or active communication mode, and may use the 13.56 MHz frequency band, and data rate may be 106 Kb/s, 212 Kb/s, or 424 Kb/s, and the modulation may be Amplitude-Shift-Keying (ASK), and may be according to, may be compatible with, or based on, ISO/IEC 18092, ECMA-340, ISO/IEC 21481, or ECMA-352. In such a case, the wireless transceiver 43 may be an NFC transceiver and the respective antenna 46 may be an NFC antenna.

Alternatively or in addition, the networking or the communication with the of the wireless-capable device 31*a* over the wireless network may be using, may be according to, may be compatible with, or may be based on, a Wireless Personal Area Network (WPAN) that may be according to, may be compatible with, or based on, Bluetooth™ or IEEE 802.15.1-2005 standards, and the wireless transceiver 43 may be a WPAN modem, and the respective antenna 46 may be a WPAN antenna. The WPAN may be a wireless control network according to, may be compatible with, or based on, ZigBee™ or Z-Wave™ standards, such as IEEE 802.15.4-2003.

Alternatively or in addition, the networking or the communication with the of the wireless-capable device 31*a* over the wireless network may be using, may be according to, may be compatible with, or may be based on, a Wireless Local Area Network (WLAN) that may be according to, may be compatible with, or based on, IEEE 802.11a, IEEE 802.11b, IEEE 802.11g, IEEE 802.11n, or IEEE 802.11ac standards, and the wireless transceiver 43 may be a WLAN modem, and the respective antenna 46 may be a WLAN antenna.

Alternatively or in addition, the networking or the communication with the of the wireless-capable device 31*a* over the wireless network may be using, may be according to, may be compatible with, or may be based on, a wireless broadband network or a Wireless Wide Area Network (WWAN), and the wireless transceiver 43 may be a WWAN modem, and the respective antenna 46 may be a WWAN antenna. The WWAN may be a WiMAX network such as according to, may be compatible with, or based on, IEEE 802.16-2009, and the wireless transceiver 43 may be a WiMAX modem, and the respective antenna 46 may be a WiMAX antenna. Alternatively or in addition, the WWAN may be a cellular telephone network and the wireless transceiver 43 may be a cellular modem, and the respective antenna 46 may be a cellular antenna. The WWAN may be a Third Generation (3G) network and may use UMTS W-CDMA, UMTS HSPA, UMTS TDD, CDMA2000 1×RTT, CDMA2000 EV-DO, or GSM EDGE-Evolution. The cellular telephone network may be a Fourth Generation (4G) network and may use HSPA+, Mobile WiMAX, LTE, LTE-Advanced, MBWA, or may be based on, or may be compatible with, IEEE 802.20-2008.

Alternatively or in addition, the networking or the communication with the of the wireless-capable device 31*a* over the wireless network may be using, may be according to, may be compatible with, or may be based on, a licensed or an unlicensed radio frequency band, such as the Industrial, Scientific and Medical (ISM) radio band.

The sensor 32 provides an electrical output signal in response to a physical, chemical, biological or any other phenomenon, serving as a stimulus to the sensor. The sensor may serve as, or be, a detector, for detecting the presence of the phenomenon. Alternatively or in addition, a sensor may measure (or respond to) a parameter of a phenomenon or a magnitude of the physical quantity thereof. For example, the sensor 32 may be a thermistor or a platinum resistance temperature detector, a light sensor, a pH probe, or a piezoelectric bridge. Similarly, the sensor 32 may be used to measure pressure, flow, force or other mechanical quantities. A signal conditioning circuit is typically coupled to the sensor 32 output, for adapting and preparing the output signal for further processing. For example, the conditioning circuit may include an amplifier connected to the sensor output. Other signal conditioning may also be applied in order to improve the handling of the sensor output or adapting it to the next stage or manipulating, such as attenuation, delay, current or voltage limiting, level translation, galvanic isolation, impedance transformation, linearization, calibration, filtering, amplifying, digitizing, integration, derivation, and any other signal manipulation. Some sensors conditioning involves connecting them in a bridge circuit. In the case of conditioning, the conditioning circuit may added to manipulate the sensor output, such as filter or equalizer for frequency related manipulation such as filtering, spectrum analysis or noise removal, smoothing or de-blurring in case of image enhancement, a compressor (or de-compressor) or coder (or decoder) in the case of a compression or a coding/decoding schemes, modulator or demodulator in case of modulation, and extractor for extracting or detecting a feature or parameter such as pattern recognition or correlation analysis. In case of filtering, passive, active or adaptive (such as Wiener or Kalman) filters may be used. The conditioning circuits may apply linear or non-linear manipulations. Further, the manipulation may be time-related such as analog or digital delay-lines, integrators, or rate-based manipulation. A sensor 32 may have analog output, requiring an A/D to be connected thereto, or may have digital output. Further, the conditioning may be based on the book entitled: "Practical Design Techniques for Sensor Signal Conditioning", by Analog Devices, Inc., 1999 (ISBN-0-916550-20-6), which is incorporated in its entirety for all purposes as if fully set forth herein. The signal conditioning may further use the any one of the schemes, components, circuits, interfaces, or manipulations described in an handbook published 2004-2012 by Measurement Computing Corporation entitled: *"Data Acquisition Handbook—A Reference For DAQ And Analog & Digital Signal Conditioning"*, which is incorporated in its entirety for all purposes as if fully set forth herein.

Hence, the sensor 32 output signal may be conditioned by the signal conditioning circuit. The signal conditioner converts the sensor signals into a form that can be converted to digital values, and may use or comprise time, frequency, or magnitude related manipulations. The signal conditioner may be linear or non-linear, and may include an operation or an instrument amplifier, a multiplexer, a frequency converter, a frequency-to-voltage converter, a voltage-to-frequency converter, a current-to-voltage converter, a current loop converter, a charge converter, an attenuator, a sample-and-hold circuit, a peak-detector, a voltage or current limiter, a delay line or circuit, a level translator, a galvanic isolator, an impedance transformer, a linearization circuit, a calibrator, a passive or active (or adaptive) filter, an integrator, a deviator, an equalizer, a spectrum analyzer, a compressor or a de-compressor, a coder (or decoder), a modulator (or demodulator), a pattern recognizer, a smoother, a noise remover, an average or RMS circuit, or any combination thereof. In the case of an analog sensor, the analog to digital (A/D) converter may be used to convert the conditioned sensor output signal to a digital sensor data.

Any element capable of measuring or responding to a physical phenomenon may be used as the sensor 32. An appropriate sensor may be adapted for a specific physical phenomenon, such as a sensor responsive to temperature, humidity, pressure, audio, vibration, light, motion, sound, proximity, flow rate, electrical voltage, and electrical current. The sensor 32 may measure the amount of a property or of a physical quantity, or the magnitude relating to a physical phenomenon, body, or substance. Alternatively or in addition, the sensor 32 may be used to measure the time derivative thereof, such as the rate of change of the amount, the quantity or the magnitude. In the case of space related quantity or magnitude, a sensor may measure the linear density, surface density, or volume density, relating to the amount of property per volume. Alternatively or in addition, the sensor 32 may measure the flux (or flow) of a property through a cross-section or surface boundary, the flux density, or the current. In the case of a scalar field, a sensor may measure the quantity gradient. The sensor 32 may measure the amount of property per unit mass or per mole of substance. A single sensor may be used to measure two or more phenomena.

The sensor 32 may directly or indirectly measure the rate of change of the physical quantity (gradient) versus the direction around a particular location, or between different locations. For example, a temperature gradient may describe the differences in the temperature between different locations. Further, the sensor 32 may measure time-dependent or time-manipulated values of the phenomenon, such as time-integrated, average or Root Mean Square (RMS or rms), relating to the square root of the mean of the squares of a series of discrete values (or the equivalent square root of the integral in a continuously varying value). Further, a parameter relating to the time dependency of a repeating phenomenon may be measured, such as the duty-cycle, the frequency (commonly measured in Hertz—Hz) or the period. A sensor may be based on the Micro Electro-Mechanical Systems—MEMS (a.k.a. Micro-mechanical electrical systems) technology. The sensor 32 may respond to environmental conditions such as temperature, humidity, noise, vibration, fumes, odors, toxic conditions, dust, and ventilation.

The sensor 32 may be an active sensor, requiring an external source of excitation. For example, resistor-based sensors such as thermistors and strain gages are active sensors, requiring a current to pass through them in order to determine the resistance value, corresponding to the measured phenomenon. Similarly, a bridge circuit based sensors are active sensors depending or external electrical circuit for their operation. A sensor may be a passive sensor, generating an electrical output without requiring any external circuit or any external voltage or current. Thermocouples and photodiodes are examples or passive sensors.

The sensor 32 may measure the amount of a property or of a physical quantity or the magnitude relating to a physical phenomenon, body or substance. Alternatively or in addition, a sensor may be used to measure the time derivative thereof, such as the rate of change of the amount, the quantity or the magnitude. In the case of space related quantity or magnitude, a sensor may measure the linear density, relating to the amount of property per length, a sensor may measure the surface density, relating to the amount of property per area, or a sensor may measure the volume density, relating to the amount of property per volume. Alternatively or in addition, a sensor may measure the amount of property per unit mass or per mole of substance. In the case of a scalar field, the sensor 32 may further measure the quantity gradient, relating to the rate of change of property with respect to position. Alternatively or in addition, the sensor 32 may measure the flux (or flow) of a property through a cross-section or surface boundary. Alternatively or in addition, the sensor 32 may measure the flux density, relating to the flow of property through a cross-section per unit of the cross-section, or through a surface boundary per unit of the surface area. Alternatively or in addition, the sensor 32 may measure the current, relating to the rate of flow of property through a cross-section or a surface boundary, or the current density, relating to the rate of flow of property per unit through a cross-section or a surface boundary. The sensor 32 may include or consists of a transducer, defined herein as a device for converting energy from one form to another for the purpose of measurement of a physical quantity or for information transfer. Further, a single sensor may be used to measure two or more phenomena. For example, two characteristics of the same element may be measured, each characteristic corresponding to a different phenomenon.

A sensor output may have multiple states, where the sensor state is depending upon the measured parameter of the sensed phenomenon. The sensor 32 may be based on a two state output (such as '0' or '1', or 'true' and 'false'), such as an electric switch having two contacts, where the contacts can be in one of two states: either "closed" meaning the contacts are touching and electricity can flow between them, or "open", meaning the contacts are separated and the switch is non-conducting. The sensor 32 may be a threshold switch, where the switch changes its state upon sensing that the magnitude of the measured parameter of a phenomenon exceeds a certain threshold. For example, the sensor 32 may be a thermostat is a temperature-operated switch used to control a heating process. Another example is a voice operated switch (a.k.a. VOX), which is a switch that operates when sound over a certain threshold is detected. It is usually used to turn on a transmitter or recorder when someone speaks and turn it off when they stop speaking. Another example is a mercury switch (also known as a mercury tilt switch), which is a switch whose purpose is to allow or interrupt the flow of electric current in an electrical circuit in a manner that is dependent on the switch's physical position or alignment relative to the direction of the "pull" of earth's gravity, or other inertia. The threshold of a threshold based switch may be fixed or settable. Further, an actuator may be used in order to locally or remotely set the threshold level.

The sensor 32 may be an analog sensor having an analog signal output such as analog voltage or current, or may have continuously variable impedance. Alternatively on in addition, the sensor 32 may have a digital signal output. A sensor may serve as a detector, notifying only the presence of a phenomenon, such as by a switch, and may use a fixed or settable threshold level. The sensor 32 may measure time-dependent or space-dependent parameters of a phenomenon. The sensor 32 may measure time-dependencies or a phenomenon such as the rate of change, time-integrated or time-average, duty-cycle, frequency or time between events. The sensor 32 may be a passive sensor, or an active sensor requiring an external source of excitation. The sensor 32 may be semiconductor-based, and may be based on MEMS technology.

In some cases, the sensor 32 operation is based on generating a stimulus or an excitation to generate influence or create a phenomenon. The entire or part of the generating or stimulating mechanism may be in this case an integral part of the sensor 32, or may be regarded as independent actuators, and thus may be controlled by the controller. Further, the sensor 32 and an actuator, independent or integrated, may be cooperatively operating as a set, for improving the sensing or the actuating functionality. For example, a light source, treated as an independent actuator, may be used to illuminate a location, in order to allow an image sensor to faithfully and properly capture an image of that location. In another example, where a bridge is used to measure impedance, the excitation voltage of the bridge may be supplied from a power supply treated and acting as an actuator.

The sensor 32 may respond to chemical process or may be involved in fluid handling, such as measuring flow or velocity. The sensor 32 may be responsive to the location or motion such as navigational instrument, or be used to detect or measure position, angle, displacement, distance, speed or acceleration. The sensor 32 may be responsive to mechanical phenomenon such as pressure, force, density or level. The environmental related sensor may respond to humidity, air pressure, and air temperature. Similarly, any sensor used to detect or measure a measurable attribute and converts it into an electrical signal may be used. Further, the sensor 32 may be a metal detector, which detects metallic objects by detecting their conductivity.

In one example, the sensor 32 is used to measure, sense or detect the temperature of an object, that may be solid, liquid or gas (such as the air temperature), in a location. Such sensor 32 may be based on a thermistor, which is a type of resistor whose resistance varies significantly with temperature, and is commonly made of ceramic or polymer material. A thermistor may be a PTC (Positive Temperature Coefficient) type, where the resistance increases with increasing temperatures, or may be an NTC (Negative Temperature Coefficient) type, where the resistance decreases with increasing temperatures. Alternatively (or in addition), a thermoelectric sensor may be based on a thermocouple, consisting of two different conductors (usually metal alloys), that produce a voltage proportional to a temperature difference. For higher accuracy and stability, an RTD (Resistance Temperature Detector) may be used, typically consisting of a length of fine wire-wound or coiled wire wrapped around a ceramic or glass core. The RTD is made of a pure material whose resistance at various temperatures is known (R vs. T). A common material used may be platinum, copper, or nickel. A quartz thermometer may be used as well for high-precision and high-accuracy temperature measurement, based on the frequency of a quartz crystal oscillator. The temperature may be measured using conduction, convection, thermal radiation, or by the transfer of energy by phase changes. The temperature may be measured in degrees Celsius (° C.) (a.k.a. Centigrade), Fahrenheit (° F.), or Kelvin (° K). In one example, the temperature sensor (or its output) is used to measure a temperature gradient, providing in which direction and at what rate the temperature changes the most rapidly around a particular location. The temperature gradient is a dimensional quantity expressed in units of degrees (on a particular temperature scale) per unit length, such as the SI (International System of Units) unit Kelvin per meter (K/m).

In some embodiments, a measurement of affective response of a user comprises, and/or is based on, a behavioral cue of the user. A behavioral cue of the user is obtained by monitoring the user in order to detect things such as facial expressions of the user, gestures made by the user, tone of voice, and/or other movements of the user's body (e.g., fidgeting, twitching, or shaking). The behavioral cues may be measured utilizing various types of sensors. Some non-limiting examples include an image capturing device (e.g., a camera), a movement sensor, a microphone, an accelerometer, a magnetic sensor, and/or a pressure sensor. In one example, a behavioral cue may involve prosodic features of a user's speech such as pitch, volume, tempo, tone, and/or stress (e.g., stressing of certain syllables), which may be indicative of the emotional state of the user. In another example, a behavioral cue may be the frequency of movement of a body (e.g., due to shifting and changing posture when sitting, laying down, or standing). In this example, a sensor embedded in a device such as accelerometers in a smartphone or smartwatch may be used to take the measurement of the behavioral cue.

In some embodiments, a measurement of affective response of a user may be obtained by capturing one or more images of the user with an image-capturing device, such as a camera. Optionally, the one or more images of the user are captured with an active image-capturing device that transmits electromagnetic radiation (such as radio waves, millimeter waves, or near visible waves) and receives reflections of the transmitted radiation from the user. Optionally, the one or more captured images are in two dimensions and/or in three dimensions. Optionally, the one or more captured images comprise one or more of the following: a single image, sequences of images, a video clip. In one example, images of a user captured by the image capturing device may be utilized to determine the facial expression and/or the posture of the user. In another example, images of a user captured by the image capturing device depict an eye of the user. Optionally, analysis of the images can reveal the direction of the gaze of the user and/or the size of the pupils. Such images may be used for eye tracking applications, such as identifying what the user is paying attention to, and/or for determining the user's emotions (e.g., what intentions the user likely has). Additionally, gaze patterns, which may involve information indicative of directions of a user's gaze, the time a user spends gazing at fixed points, and/or frequency at which the user changes points of interest, may provide information that may be utilized to determine the emotional response of the user.

In some embodiments, a measurement of affective response of a user may include a physiological signal derived from a biochemical measurement of the user. For example, the biochemical measurement may be indicative of the concentration of one or more chemicals in the body of the user (e.g., electrolytes, metabolites, steroids, hormones, neurotransmitters, and/or products of enzymatic activity). In one example, a measurement of affective response may describe the glucose level in the bloodstream of the user. In another example, a measurement of affective response may describe the concentration of one or more stress-related hormones such as adrenaline and/or cortisol. In yet another example, a measurement of affective response may describe the concentration of one or more substances that may serve as inflammation markers such as C-reactive protein (CRP). In one embodiment, a sensor that provides a biochemical measurement may be an external sensor (e.g., a sensor that measures glucose from a blood sample extracted from the user). In another embodiment, a sensor that provides a biochemical measurement may be in physical contact with the user (e.g., contact lens in the eye of the user that measures glucose levels). In yet another embodiment, a sensor that provides a biochemical measurement may be a sensor that is in the body of the user (an "in vivo" sensor). Optionally, the sensor may be implanted in the body (e.g., by a chirurgical procedure), injected into the bloodstream, and/or enter the body via the respiratory and/or digestive system.

Sensors used to take measurements of affective response may be considered, in some embodiments, to be part of a Body Area Network (BAN) also called a Body Sensor Networks (BSN). Such networks enable monitoring of user physiological signals, actions, health status, and/or motion patterns. Further discussion about BANs may be found in Chen et al., "Body area networks: A survey" in Mobile networks and applications 16.2 (2011): 171-193.

The aforementioned examples involving sensors and/or measurements of affective response represent an exemplary sample of possible physiological signals and/or behavioral cues that may be measured. Embodiments described in this disclosure may utilize measurements of additional types of physiological signals and/or behavioral cues, and/or types of measurements taken by sensors, which are not explicitly listed above. Additionally, in some examples given above some of the sensors and/or techniques may be presented in association with certain types of values that may be obtained utilizing those sensors and/or techniques. This is not intended to be limiting description of what those sensors and/or techniques may be used for. In particular, a sensor and/or a technique listed above, which is associated in the examples above with a certain type of value (e.g., a certain type of physiological signal and/or behavioral cue) may be used, in some embodiments, in order to obtain another type of value, not explicitly associated with the sensor and/or technique in the examples given above.

A wirelessly communicating device 31b is described in the arrangement 40a shown in FIG. 4a, and comprises the wireless transceiver 43, which is typically a wireless modem, connected to the antenna 46, controlled by the controller 39, and powered from the power source 34. The antenna 46 is used for transmitting and receiving over-the-air Radio-Frequency (RF) based communication signals. Commands received over the air are received by the antenna 46, processed by the wireless transceiver 43, and transmitted to the controller 39. Similarly, data to be wirelessly transmitted is received at the wireless transceiver 43 from the controller 39, and transmitted via the antenna 46 by the wireless transceiver 43. For example, data may be wirelessly sent to, and commands may be received from, the smartphone 49 over the wireless connection (or link), as shown in an arrangement 40a in FIG. 4a.

The smartphone 49 may be replaced with any device having wireless functionality, and such device may consist of, be part of, or include, a Personal Computer (PC), a desktop computer, a mobile computer, a laptop computer, a notebook computer, a tablet computer, a server computer, a handheld computer, a handheld device, a Personal Digital Assistant (PDA) device, or a cellular handset. Alternatively or in addition, such a device may consist of, be part of, or include, a handheld PDA device, an on-board device, an off-board device, a hybrid device, a vehicular device, a non-vehicular device, a mobile device, or a portable device.

Any function, discrete or continuous, monotonic or non-monotonic, may be applied to the sensor output for further handling or processing. The function may be an elementary function that is built from basic operations (e.g. addition, exponentials, and logarithms) such as an Algebraic function that can be expressed as the solution of a polynomial equation with integer coefficients, Polynomials that may be addition, multiplication, and exponentiation, such as Linear function (First degree polynomial, graph is a straight line), Quadratic function (Second degree polynomial, graph is a parabola), Cubic function (Third degree polynomial), Quartic function (Fourth degree polynomial), Quintic function (Fifth degree polynomial), Sextic function (Sixth degree polynomial), or Rational functions (A ratio of two polynomials). Similarly, the function may be an Nth root based, such as a Square root or a Cube root. Alternatively or in addition, a non algebraic function may be used, such as a Transcendental function, that may be Exponential function that raises a fixed number to a variable power, Hyperbolic functions that uses trigonometric functions, Logarithmic function, or a Power function that raises a variable number to a fixed power. The function may be a periodic function such as a trigonometric functions, that may use or include sine, cosine, tangent, cotangent, secant, cosecant, exsecant, excosecant, versine, coversine, vercosine, covercosine, haversine, hacoversine, havercosine, or hacovercosine, typically used in geometry.

The devices, systems, and methods described herein may be integrated with, or may be part of, a smartphone, or any device having wireless functionality, and such device may consist of, be part of, or include, a Personal Computer (PC), a desktop computer, a mobile computer, a laptop computer, a notebook computer, a tablet computer, a server computer, a handheld computer, a handheld device, a Personal Digital Assistant (PDA) device, or a cellular handset. Alternatively or in addition, such a device may consist of, be part of, or include, a handheld PDA device, an on-board device, an off-board device, a hybrid device, a vehicular device, a non-vehicular device, a mobile device, or a portable device. When integrated with a smartphone or any other wireless device, any part of, or whole of, any of the devices or systems described herein, or any part of, or whole of, any of the circuits of functionalities described herein, may be added to or integrated with the smartphone or the other wireless device, such as sharing the same enclosure, sharing the same power supply or power source (such as a battery), sharing the same user interface (such as a button, a display, or a touch-screen), or sharing the same processor.

Eye blink and smile are critically important facial movements, and have traditionally represented primary targets for functional restoration in patients experiencing facial paralysis, with eye closure generally regarded as the top functional priority. Surgical manipulation of the periocular complex does provide benefit; however, it does not restore high-quality, synchronous, dynamic movement, and it remains invasive. In one example, any of the methods and devices described herein may be used to artificially stimulate eye blink and smile, spanning from rudimentary conceptual work to indwelling stimulating electrodes, such as for treating patients with acute facial paralysis by delivering transcutaneous facial nerve stimulation to induce eye closure. Further, the discomfort of using such a method may be mitigated or eliminated when using such external blink restoration system. Furthermore, the vast majority of facial paralysis is unilateral, and facial expressions are typically symmetric, movements of the nonparalyzed side may be used to initiate corresponding movements of the paralyzed side. Any of the devices or methods herein may be used to detect movements on the healthy side of the face, and drive activation of contralateral paralyzed muscles, to elicit symmetric facial expressions, replacing or complementing surgical facial reanimation procedures by means of facial pacing technology.

Pain is a warning and diagnostics system and the human body's method of notifying that something is wrong, serving as a warning signal of a trauma or malfunction in the body. The pain typically travels from the injured area or organ along the small nerves leading to the spinal cord, where it travels up the spinal cord to the brain, where it is then interpreted causing the pain to be felt. In one example, any of the methods and devices described herein may be used as non-invasive, drug-free method for controlling pain. Comfortable electrical impulses are transmitted to the human body through the skin and to the nerves in a non-invasive way, in order to modify the pain perspective. While not curing the physiological problem that causes the pain, it may help and be effective, at least in some persons, in reducing or eliminating the pain, allowing for a return to normal activity.

While exampled herein for stimulating blinking or other eye related functionalities, any apparatus and method herein may equally be used for patients that suffer from Dry Eye Syndrome (DES). A study that investigates the association between partial blinking during spontaneous blinking as measured by interferometry and ocular exams for the assessment of dry eye disease (DED) is described in a paper entitled: *"Evaluation of incomplete blinking as a measurement of dry eye disease"* by Jie Y, Sella R, Feng J, Gomez M L, and Afshari N A, available at https://www.ncbi.nlm.nih.gov/pubmed/31152804 [Ocul Surf. 2019 May 29. pii: S1542-0124(19)30104-1. doi: 10.1016/j.jtos.2019.05.007], published 2019 by Elsevier Inc. This retrospective study included 58 eyes of patients previously diagnosed with DED. Ocular surface assessment included ocular surface disease index (OSDI) score, tear film osmolarity, tear breakup time (TBUT), grading of corneal fluorescein staining, Schirmer I test, and dry eye parameters by the LipiView™ interferometer (TearScience, Morrisville, NC, USA), including lipid layer thickness of the tear film (LLT), meibomian gland dropout (MGd), number of incomplete and complete blinks per 20 s and the partial blinking rate (PBR). Generalized estimation equations (GEE) were used for association testing between each variable of interest. The working correlation for each GEE model was selected using the Corrected Quasi-likelihood under the Independence Model Criterion.

The number of incomplete blinks was significantly associated with TBUT (P=0.006), OSDI (P=0.000) and MGd (P=0.000). PBR was significantly associated with OSDI (P=0.032) and MGd (P=0.000). The number of complete blinks was significantly associated with TBUT (P=0.032), but not with other ocular surface parameters. MGd was significantly associated with TBUT (P=0.002) and OSDI (P=0.001). LLT was significantly associated with tear film osmolarity (P=0.007), and tear film osmolarity was significantly associated with LLT (P=0.000). Incomplete blinking is associated with decreased TBUT, increased OSDI, and increased MGd possibly through its contribution to meibomian gland obstruction and subsequent loss of tear film homeostasis. It may therefore be considered an additive measure for mild-to-moderate DED assessment.

This retrospective study included 58 eyes of patients previously diagnosed with DED. Ocular surface assessment included ocular surface disease index (OSDI) score, tear film osmolarity, tear breakup time (TBUT), grading of corneal fluorescein staining, Schirmer I test, and dry eye parameters by the LipiView™ interferometer (TearScience, Morrisville, NC, USA), including lipid layer thickness of the tear film (LLT), meibomian gland dropout (MGd), number of incomplete and complete blinks per 20 s and the partial blinking rate (PBR). Generalized estimation equations (GEE) were used for association testing between each variable of interest. The working correlation for each GEE model was selected using the Corrected Quasi-likelihood under the Independence Model Criterion.

The number of incomplete blinks was significantly associated with TBUT (P=0.006), OSDI (P=0.000) and MGd (P=0.000). PBR was significantly associated with OSDI (P=0.032) and MGd (P=0.000). The number of complete blinks was significantly associated with TBUT (P=0.032), but not with other ocular surface parameters. MGd was significantly associated with TBUT (P=0.002) and OSDI (P=0.001). LLT was significantly associated with tear film osmolarity (P=0.007), and tear film osmolarity was significantly associated with LLT (P=0.000). Conclusions—Incomplete blinking is associated with decreased TBUT, increased OSDI, and increased MGd possibly through its contribution to meibomian gland obstruction and subsequent loss of tear film homeostasis. It may, therefore, be considered an additive measure for mild-to-moderate DED assessment.

While exampled herein for aesthetics and dry-eye purposes, any apparatus and method herein may equally be used for physiographic purposes, where the stimulated blinking may be used to strengthen the facial (or other) muscles, for example to elongate the time for ALS patients to communicate.

Further, while exampled herein for stimulating blinking or other eye related functionalities, any apparatus and method herein may equally be used for stimulating other human body muscles, such as other facial muscles. For example, such as by using different electrodes location, any apparatus and method herein may be used to elicit a smile, such as by stimulating the mouth related muscles by applying electrical current to the respective nerves. The loss of facial expression and the disfigurement of facial paralysis have serious implications for a patient's physical and psychological well-being. Numerous aetiologies of facial paralysis exist but once nerve recovery has been static for two years, interventional surgery is required to improve the situation. Facial paralysis is often treated as an aesthetic problem but can also have real physical and psychological problems. These include difficulty with speech, low self-esteem, poor social interaction, oral incontinence, and dental problems; caries may develop due to the lack of food progression through the oral cavity and repeated trauma and ulceration caused by biting of the inside of the paralysed cheek. Poor understanding of the treatment modalities available and an element of 'postcode lottery' have an impact on the service a patient may receive. Smile Restoration is described in a paper entitled: "*Smile Restoration for Permanent Facial Paralysis*", by Jonathan Leckenby and Adriaan Grobbelaar (both of the Department of Plastic Surgery, The Royal Free Hospital, University of London, London, UK), Published 2013 by The Korean Society of Plastic and Reconstructive Surgeons, [pISSN: 2234-6163●eISSN: 2234-6171, http://dx.doi.org/10.5999/aps.2013.40.5.633, Arch Plast Surg 2013; 40:633-638], which is incorporated in its entirety for all purposes as if fully set forth herein.

While exampled herein for stimulating blinking or other eye related functionalities for overcoming temporary or permanent facial nerve acute, such as Bell's palsy, any apparatus and method herein may equally be used for patients where stimulated blinking may be beneficial, such as for blinking deficiency or dry eye that results from Parkinson's Disease (PD), ALS (Amyotrophic Lateral Sclerosis), Stroke, Lyme disease, Ramsay Hunt syndrome type 2, also known as herpes zoster oticus, Moebius syndrome, Melkersson-Rosenthal syndrome, Guillain-Barré Syndrome (GBS), Sarcoidosis, or Sjögren syndrome (SjS, SS), as explained below.

a. Parkinson's Disease (PD). Parkinson's Disease (PD) belongs to a group of conditions called motor system disorders, which are the result of the loss of dopamine-producing brain cells. The four primary symptoms of PD are tremor, or trembling in hands, aims, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 60. Symptoms of PD are subtle and occur gradually. In some people the disease progresses more quickly than in others. As the disease progresses, the shaking, or tremor, which affects the majority of people with PD may begin to interfere with daily activities. Other symptoms may include depression and other emotional changes; difficulty in swallowing, chewing, and speaking; urinary problems or constipation; skin problems; and sleep disruptions. There are currently no blood or laboratory tests that have been proven to help in diagnosing sporadic PD. Therefore the diagnosis is based on medical history and a neurological examination. The disease can be difficult to diagnose accurately. Doctors may sometimes request brain scans or laboratory tests in order to rule out other diseases.

Hypomimia is a common and early symptom of Parkinson's disease (PD), which reduces the ability of PD patients in manifesting emotions, and it is visually evaluated by the neurologist during neurological examinations for PD diagnosis as described in task 3.2 of the Movement Disorder Society—Unified Parkinson's Disease Rating Scale (MDS-UPDRS). A paper entitled: "*Objective assessment of blinking and facial expressions in Parkinson's disease using vertical electrooculogram and facial surface electromyography*" by Carlo Maremmani, Roberto Monastero, Giovanni Orlandi, Stefano Salvadori, Aldo Pieroni, Roberta Baschi, Alessandro Pecori, Cristina Dolciotti, Giulia Berchina, Erika Rovini, Flavia Cuddemi and Filippo Cavallo [Accepted Manuscript online 24 Apr. 2019 at https://www.ncbi.nlm-.nih.gov/m/pubmed/31018181/?i=5&from=eye%20blink%20and%20disease] aims to measure physiological parameters related to eye blink and facial expressions extracted from vertical electrooculogram (VEOG) and facial surface electromyography (fsEMG) for differentiating PD patients from healthy control subjects (HC), since such evaluation is semi-quantitative and affected by inter-variability. The spontaneous eye blink rate-minute (sEBR), its maximum amplitude (BMP), and facial cutaneous muscles activity were measured in 24 PD patients and 24 HC while the subjects looked at a visual-tester composed by three main parts: static vision, dynamic vision, and reading silently. Specificity and sensitivity for each parameter were calculated. The VEOG and the fsEMG allowed identifying some parameters related to eye blink and facial expressions (i.e., sEBR, BMP, frontal and peribuccal muscular activities) able to distinguish between PD patients and HC with high sensitivity and specificity. Significance—The demonstration that the combination of parameters related to eye blink and facial expressions can discriminate with high accuracy PD patients versus HC, thus resulting in a useful tool to support the neurologist in objective assessment of hypomimia for improving PD diagnosis A study that provides preliminary evidence regarding the utility of continuous EBR monitoring for the non-invasive evaluation of the motor status in patients with PD, is described in a paper entitled: "*Using Spontaneous Eye-blink Rates to Predict the Motor Status of Patients with Parkinson's Disease*" by Hirotaka Iwaki, Hiroyuki Sogo, Haruhiko Morita, Noriko Nishikawa, Rina Ando, Noriyuki Miyaue, Satoshi Tada, Hayato Yabe, Masahiro Nagai and Masahiro Nomoto, published 2019 in Internal Medicine [doi: 10.2169/internalmedicine.1960-18 Intern Med 58: 1417-1421, 2019], which is incorporated in its entirety for all purposes as if fully set forth herein. Assessing daily motor fluctuations is an important part of the disease management for patients with Parkinson's disease (PD). However, the frequent recording of subjective and/or objective assessments is not always feasible, and easier monitoring methods have been sought. Previous studies have reported that the spontaneous eye-blink rate (EBR) is correlated with the dopamine levels in the brain. Thus, the continuous monitoring of the EBR may be useful for predicting the motor status in patients with PD. Methods Electrooculograms (EOGs) were recorded for up to 7.5 hours from three PD patients using a wearable device that resembled ordinary glasses. A receiver operating characteristic (ROC) analysis was performed to compare the ability of the EBR estimates at each time-point (Blink Index) and the plasma levodopa levels to predict the motor status. Results—The Blink Index was correlated with the plasma levodopa levels. When an indicator for the first hour of the observation period was included in the model, the Blink Index discerned wearing-off and dyskinesia as accurately as the plasma levodopa level.

Dry eye is an important problem in Parkinson's disease (PD) with a potential to affect life quality. Tear osmolarity, accepted as the gold standard in dry eye diagnosis, has not been studied in this subset of patients so far. A study that evaluates tear osmolarity, Schirmer's test scores and tear film break-up time (TBUT) in PD patients is described in a paper entitled: "Tear Osmolarity, Break-up Time and Schirmer's Scores in Parkinson's Disease" by Turk J. Ophthalmol Published online Aug. 5, 2015 [doi: 10.4274/tjo.46547, 2015 August; 45(4): 142-145 PMC—US National Library of Medicine National Institutes of Health], which is incorporated in its entirety for all purposes as if fully set forth herein. The results show that BR and Schirmer's scores decreased significantly in PD patients. Although not significant, the demonstrated tear osmolarity increment might be important to document the dry eye and inflammatory process of the ocular surface in PD patients. Materials and Methods—PD patients with a minimum follow-up of 1 year and healthy controls who admitted for refractive abnormalities were enrolled to the study. Subjects using any systemic medication with a possibility to affect tear tests were not included in the study. The presence of any ocular surface disorder, previous ocular surgery, previous dry eye diagnosis, any topical ophthalmic medication or contact lens use were other exclusion criteria. Age, gender, disease duration, and Hoehn and Yahr (H&Y) score for disease severity were noted, and blink rate (BR), Schirmer's test score, TBUT and tear osmolarity of the right eye were measured in both groups. Results—Thirty-seven PD patients and 37 controls were enrolled to the study. The groups were age and gender matched. The mean disease duration and H&Y score were 5.70±2.64 years and 1.70±0.93, respectively. H&Y staging and disease duration were not correlated to BR, Schirmer's scores, TBUT, or tear osmolarity (p>0.05). The mean BR was 8.54±4.99 blinks/minute in PD patients and 11.97±6.36 blinks/minute in the control group. Mean Schirmer's scores, TBUT and osmolarity values were 9.08±4.46 mm, 11.38±4.05 seconds and 306.43±12.63 mOsm/L in the PD group and 17.16±9.57 mm, 12.81±3.66 seconds and 303.81±16.13 mOsm/L in the control group. The differences were significant only in BR and Schirmer's scores.

b. ALS. Amyotrophic Lateral Sclerosis (ALS), also known as motor neurone disease (MND) or Lou Gehrig's disease, is a specific disease that causes the death of neurons controlling voluntary muscles. Some also use the term motor neuron disease for a group of conditions of which ALS is the most common. ALS is characterized by stiff muscles, muscle twitching, and gradually worsening weakness due to muscles decreasing in size. It may begin with weakness in the arms or legs, or with difficulty speaking or swallowing. About half of the people affected develop at least mild difficulties with thinking and behavior and most people experience pain. Most eventually lose the ability to walk, use their hands, speak, swallow, and breathe. The cause is not known in 90% to 95% of cases, but is believed to involve both genetic and environmental factors. The remaining 5-10% of cases are inherited from a person's parents. About half of these genetic cases are due to one of two specific genes. The underlying mechanism involves damage to both upper and lower motor neurons. The diagnosis is based on a person's signs and symptoms, with testing done to rule out other potential causes.

No cure for ALS is known. The goal of treatment is to improve symptoms. A medication called riluzole may extend life by about two to three months. Non-invasive ventilation may result in both improved quality and length of life. Mechanical ventilation can prolong survival but does not stop disease progression. A feeding tube may help. The disease can affect people of any age, but usually starts around the age of 60 and in inherited cases around the age of 50. The average survival from onset to death is two to four years, though this can vary. About 10% survive longer than 10 years. Most die from respiratory failure. In Europe, the disease affects about two to three people per 100,000 per year. Rates in much of the world are unclear. In the United States, it is more common in white people than black people. ALS patients may communicate via a dedicated communication computer that is based on eye focusing, blinking, and other eye tracking functions.

Apps are beginning to appear that take advantage of Apple's True Depth camera to provide eye gaze control on the latest iPhone or iPad Pro. There are actually two cameras; your usual selfie camera and an infrared camera that maps your face. Eye gaze for Apple devices has been a long wished for accessibility feature. Eye gaze bars that hook up to a computer usually cost around $2000, so that access to eye gaze and face tracking on the iPad is a big deal. News of this new technology came out at Apple's WWDC in June of 2018. Apple's ARKit 2.0 introduced an eye tracking feature. Folks quickly realized that this tool was not just for advertisers, but could really benefit people with disabilities, such as ALS. It took a few months for the first apps to follow.

An apparatus, system, and method for a mobile, low-cost headset for 3D point of gaze estimation is described in U.S. Patent Application No. 2015/0070470 to McMURROUGH entitled: "*Apparatus, System, and Method for Mobile, Low-Cost Headset for 3D Point of Gaze Estimation*", which is incorporated in its entirety for all purposes as if fully set forth herein. A point of gaze apparatus may include an eye tracking camera configured to track the movements of a user's eye and a scene camera configured to create a three-dimensional image and a two-dimensional image in the direction of the user's gaze. The point of gaze apparatus may include an image processing module configured to identify a point of gaze of the user and identify an object located at the user's point of gaze by using information from the eye tracking camera and the scene camera.

Biosensor, communicator, and/or controller apparatus, systems, and methods for monitoring movement of a person's eye are provided in U.S. Patent Application No. 2011/0077548 to Torch entitled: "Biosensors, communicators, and controllers monitoring eye movement and methods for using them", which is incorporated in its entirety for all purposes as if fully set forth herein. The apparatus includes a device configured to be worn on a user's head, a light source for directing light towards one or both eyes of the user, one or more image guides on the device for viewing one or both eyes of the user, and one or more cameras carried on the device and coupled to the image guides for acquiring images of the eyes and/or the user's surroundings. The apparatus may include a cable and/or a transmitter for transmitting image data from the camera to a remote location, e.g., to processor and/or display for analyzing and/or displaying the image data. A system including the apparatus may be used to monitor one or more oculometric parameters, e.g., pupillary response, and/or to control a computer using the user's eyes instead of a mouse.

c. Stroke. A stroke is a medical condition in which poor blood flow to the brain results in cell death. There are two main types of stroke: ischemic, due to lack of blood flow, and hemorrhagic, due to bleeding. Both result in parts of the brain not functioning properly. Signs and symptoms of a stroke may include an inability to move or feel on one side of the body, problems understanding or speaking, dizziness, or loss of vision to one side. Signs and symptoms often appear soon after the stroke has occurred. If symptoms last less than one or two hours it is known as a transient ischemic attack (TIA) or mini-stroke. A hemorrhagic stroke may also be associated with a severe headache. The symptoms of a stroke can be permanent. Long-term complications may include pneumonia or loss of bladder control.

The main risk factor for stroke is high blood pressure. Other risk factors include tobacco smoking, obesity, high blood cholesterol, diabetes mellitus, a previous TIA, and atrial fibrillation. An ischemic stroke is typically caused by blockage of a blood vessel, though there are also less common causes. A hemorrhagic stroke is caused by either bleeding directly into the brain or into the space between the brain's membranes. Bleeding may occur due to a ruptured brain aneurysm. Diagnosis is typically based on a physical exam and supported by medical imaging such as a CT scan or MRI scan. A CT scan can rule out bleeding, but may not necessarily rule out ischemia, which early on typically does not show up on a CT scan. Other tests such as an electrocardiogram (ECG) and blood tests are done to determine risk factors and rule out other possible causes. Low blood sugar may cause similar symptoms. Prevention includes decreasing risk factors, as well as possibly aspirin, statins, surgery to open up the arteries to the brain in those with problematic narrowing, and warfarin in those with atrial fibrillation. A stroke or TIA often requires emergency care. An ischemic stroke, if detected within three to four and half hours, may be treatable with a medication that can break down the clot. Aspirin should be used. Some hemorrhagic strokes benefit from surgery. Treatment to try to recover lost function is called stroke rehabilitation and ideally takes place in a stroke unit; however, these are not available in much of the world.

In 2013 approximately 6.9 million people had an ischemic stroke and 3.4 million people had a hemorrhagic stroke. In 2015 there were about 42.4 million people who had previously had a stroke and were still alive. Between 1990 and 2010 the number of strokes which occurred each year decreased by approximately 10% in the developed world and increased by 10% in the developing world. In 2015, stroke was the second most frequent cause of death after coronary artery disease, accounting for 6.3 million deaths (11% of the total). About 3.0 million deaths resulted from ischemic stroke while 3.3 million deaths resulted from hemorrhagic stroke. About half of people who have had a stroke live less than one year. Overall, two thirds of strokes occurred in those over 65 years old. Other stroke statistics may be found at http://www.strokecenter.org/patients/about-stroke/stroke-statistics/. Post stroke conditions are described in https://www.stroke.org/we-can-help/survivors/stroke-recovery/post-stroke-conditions/physical/.

d. Lyme disease. Lyme disease, also known as Lyme borreliosis, is an infectious disease caused by a bacterium named Borrelia spread by ticks. The most common sign of infection is an expanding area of redness on the skin, known as erythema migrans, that appears at the site of the tick bite about a week after it occurred. The rash is typically neither itchy nor painful. Approximately 70-80% of infected people develop a rash. Other early symptoms may include fever, headache and tiredness. If untreated, symptoms may include loss of the ability to move one or both sides of the face, joint pains, severe headaches with neck stiffness, or heart palpitations, among others. Months to years later, repeated episodes of joint pain and swelling may occur. Occasionally, people develop shooting pains or tingling in their arms and legs. Despite appropriate treatment, about 10 to 20% of people develop joint pains, memory problems, and tiredness for at least six months.

Lyme disease is transmitted to humans by the bites of infected ticks of the genus *Ixodes*. In the United States, ticks of concern are usually of the *Ixodes scapularis* type, and must be attached for at least 36 hours before the bacteria can spread. In Europe ticks of the *Ixodes ricinus* type may spread the bacteria more quickly. In North America, *Borrelia burgdorferi* and *Borrelia mayonii* are the cause. In Europe and Asia, the bacteria *Borrelia afzelii* and *Borrelia garinii* are also causes of the disease. The disease does not appear to be transmissible between people, by other animals, or through food. Diagnosis is based upon a combination of symptoms, history of tick exposure, and possibly testing for specific antibodies in the blood. Blood tests are often negative in the early stages of the disease. Testing of individual ticks is not typically useful.

Prevention includes efforts to prevent tick bites such as by wearing clothing to cover the arms and legs, and using DEET-based insect repellents. Using pesticides to reduce tick numbers may also be effective. Ticks can be removed using tweezers. If the removed tick was full of blood, a single dose of doxycycline may be used to prevent development of infection, but is not generally recommended since development of infection is rare. If an infection develops, a number of antibiotics are effective, including doxycycline, amoxicillin, and cefuroxime. Standard treatment usually lasts for two or three weeks. Some people develop a fever and muscle and joint pains from treatment which may last for one or two days. In those who develop persistent symptoms, long-term antibiotic therapy has not been found to be useful.

Lyme disease is the most common disease spread by ticks in the Northern Hemisphere. It is estimated to affect 300,000 people a year in the United States and 65,000 people a year in Europe. Infections are most common in the spring and early summer. Lyme disease was diagnosed as a separate condition for the first time in 1975 in Old Lyme, Connecticut. It was originally mistaken for juvenile rheumatoid arthritis. The bacterium involved was first described in 1981 by Willy Burgdorfer. Chronic symptoms following treatment are well described and are known as post-treatment Lyme disease syndrome (PTLDS). PTLDS is different from chronic Lyme disease; a term no longer supported by the scientific community and used in different ways by different groups. Some healthcare providers claim that PTLDS is caused by persistent infection, but this is not believed to be true because of the inability to detect infectious organisms after standard treatment. A vaccine for Lyme disease was marketed in the United States between 1998 and 2002, but was withdrawn from the market due to poor sales. Research is ongoing to develop new vaccines.

e. Ramsay Hunt syndrome type 2. Ramsay Hunt syndrome type 2, also known as herpes zoster oticus, is a disorder that is caused by the reactivation of varicella zoster virus in the geniculate ganglion, a nerve cell bundle of the facial nerve. Ramsay Hunt syndrome type 2 typically presents with inability to move many facial muscles, pain in the ear, taste loss on the front of the tongue, dry eyes and mouth, and a vesicular rash. The symptoms and signs include acute facial nerve paralysis, pain in the ear, taste loss in the front two-thirds of the tongue, dry mouth and eyes, and an erythematous vesicular rash in the ear canal, the tongue, and/or hard palate. Since the vestibulocochlear nerve is in proximity to the geniculate ganglion, it may also be affected, and patients may also suffer from tinnitus, hearing loss, and vertigo. Involvement of the trigeminal nerve can cause numbness of the face. Ramsay Hunt syndrome type 2 refers to shingles of the geniculate ganglion. After initial infection, varicella zoster virus lies dormant in nerve cells in the body, where it is kept in check by the immune system. Given the opportunity, for example during an illness that suppresses the immune system, the virus travels to the end of the nerve cell, where it causes the symptoms described above.

The affected ganglion is responsible for the movements of facial muscles, the touch sensation of a part of ear and ear canal, the taste function of the frontal two-thirds of the tongue, and the moisturization of the eyes and the mouth. The syndrome specifically refers to the combination of this entity with weakness of the muscles activated by the facial nerve. In isolation, the latter is called Bell's palsy. However, as with shingles, the lack of lesions does not definitely exclude the existence of a herpes infection. Even before the eruption of vesicles, varicella zoster virus can be detected from the skin of the ear. Shingles is prevented by immunizing against the causal virus, varicella zoster, for example through Zostavax, a stronger version of chickenpox vaccine.

f. Moebius syndrome. Moebius syndrome is a rare neurological condition that primarily affects the muscles that control facial expression and eye movement. The signs and symptoms of this condition are present from birth. Weakness or paralysis of the facial muscles is one of the most common features of Moebius syndrome. Affected individuals lack facial expressions; they cannot smile, frown, or raise their eyebrows. The muscle weakness also causes problems with feeding that become apparent in early infancy. Many people with Moebius syndrome are born with a small chin (micrognathia) and a small mouth (microstomia) with a short or unusually shaped tongue. The roof of the mouth may have an abnormal opening (cleft palate) or be high and arched. These abnormalities contribute to problems with speech, which occur in many children with Moebius syndrome. Dental abnormalities, including missing and misaligned teeth, are also common. Moebius syndrome also affects muscles that control back-and-forth eye movement. Affected individuals must move their head from side to side to read or follow the movement of objects. People with this disorder have difficulty making eye contact, and their eyes may not look in the same direction (strabismus). Additionally, the eyelids may not close completely when blinking or sleeping, which can result in dry or irritated eyes.

Other features of Moebius syndrome can include bone abnormalities in the hands and feet, weak muscle tone (hypotonia), and hearing loss. Affected children often experience delayed development of motor skills (such as crawling and walking), although most eventually acquire these skills. Some research studies have suggested that children with Moebius syndrome are more likely than unaffected children to have characteristics of autism spectrum disorders, which are a group of conditions characterized by impaired communication and social interaction. However, recent studies have questioned this association. Because people with Moebius syndrome have difficulty with eye contact and speech due to their physical differences, autism spectrum disorders can be difficult to diagnose in these individuals. Moebius syndrome may also be associated with a somewhat increased risk of intellectual disability; however, most affected individuals have normal intelligence.

g. Melkersson-Rosenthal syndrome. Melkersson-Rosenthal syndrome is a rare neurological disorder characterized by recurring facial paralysis, swelling of the face and lips (usually the upper lip—cheilitis granulomatosis) and the development of folds and furrows in the tongue (fissured tongue). Onset is in childhood or early adolescence. After recurrent attacks (ranging from days to years in between), swelling may persist and increase, eventually becoming permanent. The lip may become hard, cracked, and fissured with a reddish-brown discoloration. The cause of Melkersson-Rosenthal syndrome is unknown, but there may be a genetic predisposition. It has been noted to be especially prevalent among certain ethnic groups in Bolivia. It can be symptomatic of Crohn's disease or sarcoidosis. Approximately 400 cases have been reported worldwide.

Diagnosis is mainly based on clinical features. However, biopsy has been useful in diagnosis as well as in differentiating between the different types of the disease. Treatment is symptomatic and may include nonsteroidal anti-inflammatory drugs (NSAIDs) and corticosteroids to reduce swelling, antibiotics and immunosuppressants. Surgery may be indicated to relieve pressure on the facial nerves and reduce swelling, but its efficacy is uncertain. Massage and electrical stimulation may also be prescribed. Melkersson-Rosenthal syndrome may recur intermittently after its first appearance. It can become a chronic disorder. Follow-up care should exclude the development of Crohn's disease or sarcoidosis.

h. Guillain-Barré Syndrome (GBS). Guillain-Barré syndrome (GBS) is a rapid-onset muscle weakness caused by the immune system damaging the peripheral nervous system. The initial symptoms are typically changes in sensation or pain along with muscle weakness, beginning in the feet and hands. This often spreads to the arms and upper body, with both sides being involved. The symptoms develop over hours to a few weeks. During the acute phase, the disorder can be life-threatening, with about 15% developing weakness of the breathing muscles requiring mechanical ventilation. Some are affected by changes in the function of the autonomic nervous system, which can lead to dangerous abnormalities in heart rate and blood pressure. The cause is unknown. The underlying mechanism involves an autoimmune disorder in which the body's immune system mistakenly attacks the peripheral nerves and damages their myelin insulation. Sometimes this immune dysfunction is triggered by an infection or, less commonly by surgery and rarely by vaccination. The diagnosis is usually made based on the signs and symptoms, through the exclusion of alternative causes, and supported by tests such as nerve conduction studies and examination of the cerebrospinal fluid. There are a number of subtypes based on the areas of weakness, results of nerve conduction studies and the presence of certain antibodies. It is classified as an acute polyneuropathy.

In those with severe weakness, prompt treatment with intravenous immunoglobulins or plasmapheresis, together with supportive care, will lead to good recovery in the majority of people. Recovery may take weeks to years. About a third have some permanent weakness. Globally, death occurs in about 7.5% of those affected. Guillain-Barré syndrome is rare, at one or two cases per 100,000 people every year. Both sexes and all parts of the world have similar rates of disease. The first symptoms of Guillain-Barré syndrome are numbness, tingling, and pain, alone or in combination. This is followed by weakness of the legs and arms that affects both sides equally and worsens over time. The weakness can take half a day to over two weeks to reach maximum severity, and then becomes steady. In one in five people, the weakness continues to progress for as long as four weeks. The muscles of the neck may also be affected, and about half experience involvement of the cranial nerves which supply the head and face; this may lead to weakness of the muscles of the face, swallowing difficulties and sometimes weakness of the eye muscles. In 8%, the weakness affects only the legs (paraplegia or paraparesis). Involvement of the muscles that control the bladder and anus is unusual. In total, about a third of people with Guillain-Barré syndrome continue to be able to walk. Once the weakness has stopped progressing, it persists at a stable level ("plateau phase") before improvement occurs. The plateau phase can take between two days and six months, but the most common duration is a week. Pain-related symptoms affect more than half, and include back pain, painful tingling, muscle pain and pain in the head and neck relating to irritation of the lining of the brain.

Many people with Guillain-Barré syndrome have experienced the signs and symptoms of an infection in the 3-6 weeks prior to the onset of the neurological symptoms. This may consist of upper respiratory tract infection (rhinitis, sore throat) or diarrhea. In children, particularly those younger than six years old, the diagnosis can be difficult and the condition is often initially mistaken (sometimes for up to two weeks) for other causes of pains and difficulty walking, such as viral infections, or bone and joint problems. On neurological examination, characteristic features are the reduced strength of muscles and reduced or absent tendon reflexes (hypo- or areflexia, respectively). However, a small proportion have normal reflexes in affected limbs before developing areflexia, and some may have exaggerated reflexes. In the Miller Fisher variant of Guillain-Barré syndrome (see below), a triad of weakness of the eye muscles, abnormalities in coordination, as well as absent reflexes can be found. The level of consciousness is normally unaffected in Guillain-Barré syndrome, but the Bickerstaff brainstem encephalitis subtype may feature drowsiness, sleepiness, or coma Directly assessing nerve conduction of electrical impulses can exclude other causes of acute muscle weakness, as well as distinguish the different types of Guillain-Barré syndrome. Needle electromyography (EMG) and nerve conduction studies may be performed. In the first two weeks, these investigations may not show any abnormality. Neurophysiology studies are not required for the diagnosis. Formal criteria exist for each of the main subtypes of Guillain-Barré syndrome (AIDP and AMAN/AMSAN, see below), but these may misclassify some cases (particularly where there is reversible conduction failure) and therefore changes to these criteria have been proposed. Sometimes, repeated testing may be helpful.

i. Sarcoidosis. Sarcoidosis is a disease involving abnormal collections of inflammatory cells that form lumps known as granulomas. The disease usually begins in the lungs, skin, or lymph nodes. Less commonly affected are the eyes, liver, heart, and brain. Any organ, however, can be affected. The signs and symptoms depend on the organ involved. Often, no, or only mild, symptoms are seen. When it affects the lungs, wheezing, coughing, shortness of breath, or chest pain may occur. Some may have Lofgren syndrome with fever, large lymph nodes, arthritis, and a rash known as erythema nodosum.

The cause of sarcoidosis is unknown. Some believe it may be due to an immune reaction to a trigger such as an infection or chemicals in those who are genetically predisposed. Those with affected family members are at greater risk. Diagnosis is partly based on signs and symptoms, which may be supported by biopsy. Findings that make it likely include large lymph nodes at the root of the lung on both sides, high blood calcium with a normal parathyroid hormone level, or elevated levels of angiotensin converting enzyme in the blood. The diagnosis should only be made after excluding other possible causes of similar symptoms such as tuberculosis.

Sarcoidosis may resolve without any treatment within a few years. However, some people may have long-term or severe disease. Some symptoms may be improved with the use of anti-inflammatory drugs such as ibuprofen. In cases where the condition causes significant health problems, steroids such as prednisone are indicated. Medications such as methotrexate, chloroquine, or azathioprine may occasionally be used in an effort to decrease the side effects of steroids. The risk of death is 1-7%. The chance of the disease returning in someone who has had it previously is less than 5%. In 2015, pulmonary sarcoidosis and interstitial lung disease affected 1.9 million people globally and they resulted in 122,000 deaths. It is most common in Scandinavians, but occurs in all parts of the world. In the United States risk is greater among black as opposed to white people. It usually begins between the ages of 20 and 50. It occurs more often in women than men. Sarcoidosis was first described in 1877 by the English doctor Jonathan Hutchinson as a nonpainful skin disease.

Sarcoidosis is a systemic inflammatory disease that can affect any organ, although it can be asymptomatic and is discovered by accident in about 5% of cases. Common symptoms, which tend to be vague, include fatigue (unrelieved by sleep; occurs in 66% of cases), lack of energy, weight loss, joint aches and pains (which occur in about 70% of cases),arthritis (14-38% of persons), dry eyes, swelling of the knees, blurry vision, shortness of breath, a dry, hacking cough, or skin lesions. Less commonly, people may cough up blood. The cutaneous symptoms vary, and range from rashes and noduli (small bumps) to erythema nodosum, granuloma annulare, or lupus pernio. Sarcoidosis and cancer may mimic one another, making the distinction difficult. The combination of erythema nodosum, bilateral hilar lymphadenopathy, and joint pain is called Lofgren syndrome, which has a relatively good prognosis. This form of the disease occurs significantly more often in Scandinavian patients than in those of non-Scandinavian origin.

Any of the components of the nervous system can be involved. Sarcoidosis affecting the nervous system is known as neurosarcoidosis. Cranial nerves are most commonly affected, accounting for about 5-30% of neurosarcoidosis cases, and peripheral facial nerve palsy, often bilateral, is the most common neurological manifestation of sarcoidosis. It occurs suddenly and is usually transient. The central nervous system involvement is present in 10-25% of sarcoidosis cases. Other common manifestations of neurosarcoidosis include optic nerve dysfunction, papilledema, palate dysfunction, neuroendocrine changes, hearing abnormalities, hypothalamic and pituitary abnormalities, chronic meningitis, and peripheral neuropathy. Myelopathy, that is spinal cord involvement, occurs in about 16-43% of neurosarcoidosis cases and is often associated with the poorest prognosis of the neurosarcoidosis subtypes. Whereas facial nerve palsies and acute meningitis due to sarcoidosis tend to have the most favourable prognosis, another common finding in sarcoidosis with neurological involvement is autonomic or sensory small-fiber neuropathy. Neuroendocrine sarcoidosis accounts for about 5-10% of neurosarcoidosis cases and can lead to diabetes insipidus, changes in menstrual cycle and hypothalamic dysfunction. The latter can lead to changes in body temperature, mood, and prolactin (see the endocrine and exocrine section for details).

j. Sjögren syndrome. Sjögren syndrome (SjS, SS) is a long-term autoimmune disease that affects the body's moisture-producing glands. Primary symptoms are a dry mouth and dry eyes. Other symptoms can include dry skin, vaginal dryness, a chronic cough, numbness in the arms and legs, feeling tired, muscle and joint pains, and thyroid problems. Those affected are at an increased risk (5%) of lymphoma. While the exact cause is unclear, it is believed to involve a combination of genetics and an environmental trigger such as exposure to a virus or bacteria. It can occur independently of other health problems (primary Sjögren syndrome) or as a result of another connective tissue disorder (secondary Sjögren syndrome).The inflammation that results progressively damages the glands. Diagnosis is by biopsy of moisture-producing glands and blood tests looking for specific antibodies. On biopsy there are typically lymphocytes within the glands. Treatment is directed at the person's symptoms. For dry eyes artificial tears, medications to reduce inflammation, punctal plugs, or surgery to shut the tear ducts, may be tried. For a dry mouth, chewing gum (preferably sugar free), sipping water, or a saliva substitute may be used. In those with joint or muscle pain, ibuprofen may be used. Medications that can cause dryness, such as antihistamines, may also be stopped.

The disease was described in 1933 by Henrik Sjögren, after whom it is named; however, a number of earlier descriptions of people with the symptoms exist. Between 0.2% and 1.2% of the population are affected, with half having the primary form and half the secondary form. Females are affected about ten times as often as males and it commonly begins in middle age; however, anyone can be affected. Among those without other autoimmune disorders, life expectancy is unchanged.

The hallmark symptom of SS is dry mouth and kerato-conjunctivitis sicca (dry eyes).Vaginal dryness and dry skin and dry nose may also occur. Other organs of the body may also be affected including kidneys, blood vessels, lungs, liver, pancreas, and brain. Skin dryness in some people with SS may be the result of lymphocytic infiltration into skin glands. The symptoms may develop insidiously, with the diagnosis often not considered for several years, because the complaints of sicca may be otherwise attributed to medications, a dry environment, aging, or may be regarded as not of severity warranting the level of investigation necessary to establish the presence of the specific underlying autoimmune disorder. SS can damage vital organs of the body with symptoms that may plateau or worsen, or go into remission as with other autoimmune diseases. Some people may experience only the mild symptoms of dry eyes and mouth, while others have symptoms of severe disease. Many patients can treat problems symptomatically. Others experience blurred vision, constant eye discomfort, recurrent mouth infections, swollen parotid glands, dysphonia (vocal disorders including hoarseness), and difficulty in swallowing and eating. Debilitating fatigue and joint pain can seriously impair quality of life. Some patients can develop renal (kidney) involvement (autoimmune tubulointerstitial nephritis) leading to proteinuria (excess protein in urine), urinary concentrating defect, and distal renal tubular acidosis.

Moisture replacement therapies such as artificial tears may ease the symptoms of dry eyes. Some patients with more severe problems use goggles to increase local humidity or have punctal plugs inserted to help retain tears on the ocular surface for a longer time. Additionally, cyclosporine (Restasis) is available by prescription to help treat chronic dry eye by suppressing the inflammation that disrupts tear secretion. Prescription drugs are also available that help to stimulate salivary flow, such as cevimeline (Evoxac) and pilocarpine. Salagen, a manufactured form of pilocarpine, can be used to help produce tears, as well as saliva in the mouth and intestines. It is derived from the jaborandi plant.

Any apparatus herein, which may be any of the systems, devices, modules, or functionalities described herein, may be integrated with a smartphone. The integration may be by being enclosed in the same housing, sharing a power source (such as a battery), using the same processor, or any other integration functionality. In one example, the functionality of any apparatus herein, which may be any of the systems, devices, modules, or functionalities described here, is used to improve, to control, or otherwise be used by the smartphone. In one example, a measured or calculated value by any of the systems, devices, modules, or functionalities described herein, is output to the smartphone device or functionality to be used therein. Alternatively or in addition, any of the systems, devices, modules, or functionalities described herein is used as a sensor for the smartphone device or functionality.

A 'nominal' value herein refers to a designed, expected, or target value. In practice, a real or actual value is used, obtained, or exists, which varies within a tolerance from the nominal value, typically without significantly affecting functioning. Common tolerances are 20%, 15%, 10%, 5%, or 1% around the nominal value.

Discussions herein utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

Throughout the description and claims of this specification, the word "couple", and variations of that word such as "coupling", "coupled", and "couplable", refers to an electrical connection (such as a copper wire or soldered connection), a logical connection (such as through logical devices of a semiconductor device), a virtual connection (such as through randomly assigned memory locations of a memory device) or any other suitable direct or indirect connections (including combination or series of connections), for example for allowing the transfer of power, signal, or data, as well as connections formed through intervening devices or elements.

The arrangements and methods described herein may be implemented using hardware, software or a combination of both. The term "integration" or "software integration" or any other reference to the integration of two programs or processes herein refers to software components (e.g., programs, modules, functions, processes etc.) that are (directly or via another component) combined, working or functioning together or form a whole, commonly for sharing a common purpose or a set of objectives. Such software integration can take the form of sharing the same program code, exchanging data, being managed by the same manager program, executed by the same processor, stored on the same medium, sharing the same GUI or other user interface, sharing peripheral hardware (such as a monitor, printer, keyboard and memory), sharing data or a database, or being part of a single package. The term "integration" or "hardware integration" or integration of hardware components herein refers to hardware components that are (directly or via another component) combined, working or functioning together or form a whole, commonly for sharing a common purpose or set of objectives. Such hardware integration can take the form of sharing the same power source (or power supply) or sharing other resources, exchanging data or control (e.g., by communicating), being managed by the same manager, physically connected or attached, sharing peripheral hardware connection (such as a monitor, printer, keyboard and memory), being part of a single package or mounted in a single enclosure (or any other physical collocating), sharing a communication port, or used or controlled with the same software or hardware. The term "integration" herein refers (as applicable) to a software integration, a hardware integration, or any combination thereof.

The term "port" refers to a place of access to a device, electrical circuit or network, where energy or signal may be supplied or withdrawn. The term "interface" of a networked device refers to a physical interface, a logical interface (e.g., a portion of a physical interface or sometimes referred to in the industry as a sub-interface—for example, such as, but not limited to a particular VLAN associated with a network interface), and/or a virtual interface (e.g., traffic grouped together based on some characteristic—for example, such as, but not limited to, a tunnel interface). As used herein, the term "independent" relating to two (or more) elements, processes, or functionalities, refers to a scenario where one does not affect nor preclude the other. For example, independent communication such as over a pair of independent data routes means that communication over one data route does not affect nor preclude the communication over the other data routes.

As used herein, the term "Integrated Circuit" (IC) shall include any type of integrated device of any function where the electronic circuit is manufactured by the patterned diffusion of trace elements into the surface of a thin substrate of semiconductor material (e.g., Silicon), whether single or multiple die, or small or large scale of integration, and irrespective of process or base materials (including, without limitation Si, SiGe, CMOS and GAs) including, without limitation, applications specific integrated circuits (ASICs), field programmable gate arrays (FPGAs), digital processors (e.g., DSPs, CISC microprocessors, or RISC processors), so-called "system-on-a-chip" (SoC) devices, memory (e.g., DRAM, SRAM, flash memory, ROM), mixed-signal devices, and analog ICs.

The circuits in an IC are typically contained in a silicon piece or in a semiconductor wafer, and commonly packaged as a unit. The solid-state circuits commonly include interconnected active and passive devices, diffused into a single silicon chip. Integrated circuits can be classified into analog, digital and mixed signal (both analog and digital on the same chip). Digital integrated circuits commonly contain many of logic gates, flip-flops, multiplexers, and other circuits in a few square millimeters. The small size of these circuits allows high speed, low power dissipation, and reduced manufacturing cost compared with board-level integration. Further, a multi-chip module (MCM) may be used, where multiple integrated circuits (ICs), the semiconductor dies, or other discrete components are packaged onto a unifying substrate, facilitating their use as a single component (as though a larger IC).

The term "computer-readable medium" (or "machine-readable medium") as used herein is an extensible term that refers to any medium or any memory, that participates in providing instructions to a processor, (such as the processor in the controller 39) for execution, or any mechanism for storing or transmitting information in a form readable by a machine (e.g., a computer). Such a medium may store computer-executable instructions to be executed by a processing element and/or software, and data that is manipulated by a processing element and/or software, and may take many forms, including but not limited to, non-volatile medium, volatile medium, and transmission medium. Transmission media includes coaxial cables, copper wire and fiber optics. Transmission media can also take the form of acoustic or light waves, such as those generated during radio-wave and infrared data communications, or other form of propagating signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

The term "computer" is used generically herein to describe any number of computers, including, but not limited to personal computers, embedded processing elements and systems, software, ASICs, chips, workstations, mainframes, etc. Any computer herein may consist of, or be part of, a handheld computer, including any portable computer that is small enough to be held and operated while holding in one hand or fit into a pocket. Such a device, also referred to as a mobile device, typically has a display screen with touch input and/or miniature keyboard. Non-limiting examples of such devices include Digital Still Camera (DSC), Digital video Camera (DVC or digital camcorder), Personal Digital Assistant (PDA), and mobile phones and Smartphones. The mobile devices may combine video, audio and advanced communication capabilities, such as PAN and WLAN. A mobile phone (also known as a cellular phone, cell phone and a hand phone) is a device which can make and receive telephone calls over a radio link whilst moving around a wide geographic area, by connecting to a cellular network provided by a mobile network operator. The calls are to and from the public telephone network, which includes other mobiles and fixed-line phones across the world. The Smartphones may combine the functions of a personal digital assistant (PDA), and may serve as portable media players and camera phones with high-resolution touch-screens, web browsers that can access, and properly display, standard web pages rather than just mobile-optimized sites, GPS navigation, Wi-Fi and mobile broadband access. In addition to telephony, the Smartphones may support a wide variety of other services such as text messaging, MMS, email, Internet access, short-range wireless communications (infrared, Bluetooth), business applications, gaming and photography.

Some embodiments may be used in conjunction with various devices and systems, for example, a Personal Computer (PC), a desktop computer, a mobile computer, a laptop computer, a notebook computer, a tablet computer, a server computer, a handheld computer, a handheld device, a Personal Digital Assistant (PDA) device, a cellular handset, a handheld PDA device, an on-board device, an off-board device, a hybrid device, a vehicular device, a non-vehicular device, a mobile or portable device, a non-mobile or non-portable device, a wireless communication station, a wireless communication device, a wireless Access Point (AP), a wired or wireless router, a wired or wireless modem, a wired or wireless network, a Local Area Network (LAN), a Wireless LAN (WLAN), a Metropolitan Area Network (MAN), a Wireless MAN (WMAN), a Wide Area Network (WAN), a Wireless WAN (WWAN), a Personal Area Network (PAN), a Wireless PAN (WPAN), devices and/or networks operating substantially in accordance with existing IEEE 802.11, 802.11a, 802.11b, 802.11g, 802.11k, 802.11n, 802.11r, 802.16, 802.16d, 802.16e, 802.20, 802.21 standards and/or future versions and/or derivatives of the above standards, units and/or devices which are part of the above networks, one way and/or two-way radio communication systems, cellular radio-telephone communication systems, a cellular telephone, a wireless telephone, a Personal Communication Systems (PCS) device, a PDA device which incorporates a wireless communication device, a mobile or portable Global Positioning System (GPS) device, a device which incorporates a GPS receiver or transceiver or chip, a device which incorporates an RFID element or chip, a Multiple Input Multiple Output (AMMO) transceiver or device, a Single Input Multiple Output (SIMO) transceiver or device, a Multiple Input Single Output (MISO) transceiver or device, a device having one or more internal antennas and/or external antennas, Digital Video Broadcast (DVB) devices or systems, multi-standard radio devices or systems, a wired or wireless handheld device (e.g., BlackBerry, Palm Treo), a Wireless Application Protocol (WAP) device, or the like.

Any system, device, module, or circuit herein may be addressable in a wireless network (such as the Internet) using a digital address that may be a MAC layer address that may be MAC-48, EUI-48, or EUI-64 address type, or may be a layer 3 address and may be static or dynamic IP address that may be IPv4 or IPv6 type address. Any system, device, or module herein may be further configured as a wireless repeater, such as a WPAN, WLAN, or a WWAN repeater.

As used herein, the terms "program", "programmable", and "computer program" are meant to include any sequence or human or machine cognizable steps, which perform a function. Such programs are not inherently related to any particular computer or other apparatus, and may be rendered in virtually any programming language or environment, including, for example, C/C++, Fortran, COBOL, PASCAL, assembly language, markup languages (e.g., HTML, SGML, XML, VoXML), and the likes, as well as object-oriented environments such as the Common Object Request Broker Architecture (CORBA), Java™ (including J2ME, Java Beans, etc.) and the like, as well as in firmware or other implementations. Generally, program modules include routines, programs, objects, components, data structures, etc., that perform particular tasks or implement particular abstract data types.

The terms "task" and "process" are used generically herein to describe any type of running programs, including, but not limited to a computer process, task, thread, executing application, operating system, user process, device driver, native code, machine or other language, etc., and can be interactive and/or non-interactive, executing locally and/or remotely, executing in foreground and/or background, executing in the user and/or operating system address spaces, a routine of a library and/or standalone application, and is not limited to any particular memory partitioning technique. The steps, connections, and processing of signals and information illustrated in the figures, including, but not limited to, any block and flow diagrams and message sequence charts, may typically be performed in the same or in a different serial or parallel ordering and/or by different components and/or processes, threads, etc., and/or over different connections and be combined with other functions in other embodiments, unless this disables the embodiment or a sequence is explicitly or implicitly required (e.g., for a sequence of reading the value, processing the value: the value must be obtained prior to processing it, although some of the associated processing may be performed prior to, concurrently with, and/or after the read operation). Where certain process steps are described in a particular order or where alphabetic and/or alphanumeric labels are used to identify certain steps, the embodiments of the invention are not limited to any particular order of carrying out such steps. In particular, the labels are used merely for convenient identification of steps, and are not intended to imply, specify or require a particular order for carrying out such steps. Furthermore, other embodiments may use more or less steps than those discussed herein. The invention may also be practiced in distributed computing environments where tasks are performed by remote processing devices that are linked through a communications network. In a distributed computing environment, program modules may be located in both local and remote memory storage devices.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. The present invention should not be considered limited to the particular embodiments described above, but rather should be understood to cover all aspects of the invention as fairly set out in the attached claims. Various modifications, equivalent processes, as well as numerous structures to which the present invention may be applicable, will be readily apparent to those skilled in the art to which the present invention is directed upon review of the present disclosure.

Each of the methods or steps herein, may consist of, include, be part of, be integrated with, or be based on, a part of, or the whole of, the steps, functionalities, or structure (such as software) described in the publications that are incorporated in their entirety herein. Further, each of the components, devices, or elements herein may consist of, integrated with, include, be part of, or be based on, a part of, or the whole of, the components, systems, devices or elements described in the publications that are incorporated in their entirety herein.

All publications, standards, patents, and patent applications cited in this specification are incorporated herein by reference as if each individual publication, patent, or patent application were specifically and individually indicated to be incorporated by reference and set forth in its entirety herein.

The invention claimed is:

1. A device (31a) for artificially stimulating a facial nerve or muscle at a temporal skin (70) in a human body scalp (25) for eliciting eye blinking as a substitute to brain stimulating signal, for use with a network, the device comprising:
    a controllable pulse generator (42) for generating a bursts train signal (41);
    a sensor (32) that outputs a sensor signal in response to a physical phenomenon;
    an antenna (46);
    a transceiver (43) coupled to the antenna for transmitting digital data to, and for receiving digital data from, the network;
    a single structure comprising two electrodes (26a, 26b),
        wherein the surface area of the two electrodes is more than 30 mm$^2$ and less than 100 mm$^2$,
        wherein each of the two electrodes includes a conductive area, and wherein each conductive area comprises a center point, wherein a distance between the center point of each conductive area is between 15 mm and 20 mm, wherein each conductive area is attachable to the human body scalp at the temporal skin and connected to the pulse generator for coupling bursts train signal to the human body for periodically stimulating the facial nerve or muscle, so that when attached the two electrodes elicit eye blinking by stimulating the facial nerve or muscle;

software and a processor (39) for executing the software, the processor is coupled to the sensor for receiving the sensor signal therefrom, to the transceiver for receiving the digital data from the network therefrom, and to control and activate the controllable pulse generator;

a power source (34, 34a) for supplying Direct Current, DC, power to the controllable pulse generator, the sensor, the transceiver, and the processor; and a single wearable enclosure housing the pulse generator, the sensor, the transceiver, the antenna, the processor, and the power source, wherein the pulse generator is controlled or activated in response to the sensor signal or the received digital data from the network, wherein each burst of the bursts train signal is the same, wherein each burst of the bursts train signal has a duration and a pulse signal frequency, wherein the duration of each burst of the bursts train signal is more than 7 ms and less than 300 ms, wherein the pulse signal frequency in each burst of the bursts train signal is more than 250 Hz and less than 1000 Hz, and wherein the bursts train signal has at least two consecutive bursts, and wherein a period between the at least two consecutive bursts is more than 2,000 ms and less than 9,500 ms.

2. The device according to claim 1, wherein the sensor is configured to measure the amount of a property or of a physical quantity or the magnitude relating to the physical phenomenon.

3. The device according to claim 1, wherein the two electrodes are mechanically attached or coupled to each other.

4. The device according to claim 1, wherein a parameter or a characteristic of the bursts train signal is set in response to the sensor signal.

5. The device according to claim 1, wherein the network comprises, uses, or consists of, a wireless network, and the transceiver comprises, uses, or consists of, a wireless transceiver coupled to the antenna for wirelessly transmitting and receiving the digital data over the air using the wireless network, wherein the antenna is configured to transmit and receive Radio Frequency, RF, signals over the air.

6. The device according to claim 1, wherein the sensor is a physiological sensor that responds to parameters associated with the human body, and is external to the sensed body, implanted inside the sensed body, attached to the sensed body, or wearable on the sensed body.

7. The device according to claim 1, further integrated with at least one of a wireless device, a notebook computer, a laptop computer, a media player, a Digital Still Camera (DSC), a Digital video Camera (DVC or digital camcorder), a Personal Digital Assistant (PDA), a cellular telephone, a digital camera, a video recorder, or a smartphone.

8. The device according to claim 1, further comprising an electric sensor connectable to the two electrodes for measuring an electrical parameter by the two electrodes.

* * * * *